US011085081B2

(12) United States Patent
Diatchenko et al.

(10) Patent No.: US 11,085,081 B2
(45) Date of Patent: Aug. 10, 2021

(54) METHODS AND MATERIALS FOR DETERMINING PAIN SENSITIVITY AND PREDICTING AND TREATING RELATED DISORDERS

(71) Applicant: The University of North Carolina at Chapel Hill, Chapel Hill, NC (US)

(72) Inventors: Luda B. Diatchenko, Chapel Hill, NC (US); William Maixner, Chapel Hill, NC (US); Gary D. Slade, Chapel Hill, NC (US); Andrea Gail Neely, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 95 days.

(21) Appl. No.: 15/968,438

(22) Filed: May 1, 2018

(65) Prior Publication Data

US 2019/0010548 A1  Jan. 10, 2019

Related U.S. Application Data

(60) Continuation of application No. 13/624,608, filed on Sep. 21, 2012, now abandoned, which is a division of application No. 11/632,141, filed as application No. PCT/US2005/026201 on Jul. 25, 2005, now abandoned.

(60) Provisional application No. 60/671,855, filed on Apr. 15, 2005, provisional application No. 60/590,792, filed on Jul. 23, 2004.

(51) Int. Cl.
| | |
|---|---|
| *C12Q 1/6883* | (2018.01) |
| *C12Q 1/6881* | (2018.01) |
| *G16B 20/00* | (2019.01) |
| *C12N 15/113* | (2010.01) |

(52) U.S. Cl.
CPC ......... *C12Q 1/6883* (2013.01); *C12Q 1/6881* (2013.01); *C12Y 201/01006* (2013.01); *C12N 15/1137* (2013.01); *C12N 15/1138* (2013.01); *C12N 2310/14* (2013.01); *C12Q 2600/106* (2013.01); *C12Q 2600/156* (2013.01); *C12Q 2600/158* (2013.01); *C12Q 2600/172* (2013.01); *G16B 20/00* (2019.02)

(58) Field of Classification Search
None
See application file for complete search history.

(56) References Cited

U.S. PATENT DOCUMENTS

| | | | |
|---|---|---|---|
| 4,736,866 A | 4/1988 | Leder et al. | |
| 5,162,215 A | 11/1992 | Bosselman et al. | |
| 5,234,933 A | 8/1993 | Marnett et al. | |
| 5,326,902 A | 7/1994 | Seipp et al. | |
| 5,449,754 A | 9/1995 | Nishioka | |
| 5,489,742 A | 2/1996 | Hammer et al. | |
| 5,550,316 A | 8/1996 | Mintz | |
| 5,573,933 A | 11/1996 | Seamark et al. | |
| 5,614,396 A | 3/1997 | Bradley et al. | |
| 5,625,125 A | 4/1997 | Bennett et al. | |
| 5,648,061 A | 7/1997 | Bernstein et al. | |
| 5,741,957 A | 4/1998 | Deboer et al. | |
| 5,807,522 A | 9/1998 | Brown et al. | |
| 6,171,797 B1 | 1/2001 | Perbost | |
| 6,180,082 B1 | 1/2001 | Woltering et al. | |
| 6,180,351 B1 | 1/2001 | Cattell | |
| 6,232,072 B1 | 5/2001 | Fisher | |
| 6,242,266 B1 | 6/2001 | Schleifer et al. | |
| 6,475,736 B1 | 11/2002 | Stanton, Jr. | |
| 2002/0106734 A1 | 8/2002 | Soppet | |
| 2003/0069316 A1 | 4/2003 | Aho et al. | |
| 2004/0014111 A1 | 1/2004 | Li et al. | |
| 2010/0132058 A1 | 5/2010 | Diatchenko et al. | |

FOREIGN PATENT DOCUMENTS

| | | |
|---|---|---|
| WO | 93/25521 | 12/1993 |
| WO | 95/25116 | 9/1995 |
| WO | 98/41531 | 9/1998 |
| WO | 99/37761 | 7/1999 |
| WO | 01/68083 | 9/2001 |

OTHER PUBLICATIONS

Nicholl et al. Ann Rheum Dis 2010. 69: 2009-2012.*
Lee et al BMC Rheumatology. 2018. 2: 38, p. 1-9.*
Aaron et al. "Overlapping Conditions Among Patients With Chronic Fatigue Syndrome, Fibromya/gla, and Temporomandibular Disorder" Archives of Internal Medicine, 160(2):221-227 (2000).
Abiola et al. "The nature and identification of quantitative trait loci: a community's view" Nature Reviews Genetics, 4 (11):911-916 (2003).
Aley et al. "Nociceptor sensitization by extracellular signal-regulated kinases" The Journal of Neuroscience, 21 (17):6933-6939 (2001).
Altschul et al. "Gapped BLAST and PSI-BLAST: a new generation of protein database search programs" Nucleic Acids Research, 25(17):3389-3402 (1997).

(Continued)

*Primary Examiner* — Carla J Myers
(74) *Attorney, Agent, or Firm* — Myers Bigel, P.A.

(57) ABSTRACT

Methods of treating somatosensory disorders and modulating production of proinflammatory cytokines by administering to a subject an effective amount of a COMT modulator, ADRB2 modulator, ADRB3 modulator or combinations thereof are provided. Methods of predicting effective pharmacological therapies for a subject afflicted with a somatosensory disorder by determining a genotype of the subject with regard to a gene selected from the group consisting of COMT, ADRB2, ADRB3, and combinations thereof are further provided. Methods of determining pain responses or pain perception and predicting susceptibility of a subject to develop related disorders, such as somatosensory disorders and somatization, by determining a genotype of the subject with regard to a gene selected from the group consisting of COMT, ADRB2, ADRB3, and combinations thereof are further provided.

3 Claims, 25 Drawing Sheets

Specification includes a Sequence Listing.

(56) References Cited

OTHER PUBLICATIONS

Andiappan et al. "Evaluating the transferability of Hapmap SNPs to a Singapore Chinese population" BMC Genetics, 11(36):1-16 (2010).
Armero et al. "COMT (Val158Met) polymorphism is not associated to neuropathic pain in a Spanish population" European Journal of Pain, 9(3):229-232 (2005).
Arruda et al. "Increase of interleukin-6 mRNA in the spinal cord following peripheral nerve injury in the rat: potential role of IL-6 in neuropathic pain" Molecular Brain Research, 62(2):228-235 (1998).
Aston-Jones et al. "Role of locus coeruleus in attention and behavioral flexibility" Biological Psychiatry, 46 (9):1309-1320 (1999).
Belfer et al. "Haplotype structure of the beta adrenergic receptor genes in US Caucasians and African Americans" European Journal of Human Genetics, 13(3):341-351 (2005).
Belfer et al. "Pain modality- and sex-specific effects of COMT genetic functional variants" Pain, 154(8):1368-1376 (2013).
Bolan et al. "Functional analysis of MOR-1 splice variants of the mouse mu opioid receptor gene Oprm" Synapse, 51 (1):11-18 (2004).
Bond et al. "Single-nucleotide polymorphism in the human mu opioid receptor gene alters beta-endorphin binding and activity: possible implications for opiate addiction" Proceedings of the National Academy of Sciences USA, 95 (16):9608-9613 (1998).
Bortoluzzi et al. "Towards an in silico analysis of transcription patterns" Trends in Genetics, 15(3):118-119 (1999).
Bouchard et al. "Genetic and environmental influences on human psychological differences" Journal of Neurobiology, 54(1):4-45 (2003).
Bradley et al. "Central nervous system mechanisms of pain in fibromyalgia and other musculoskeletal disorders: behavioral and psychologic treatment approaches" Current Opinion in Rheumatology, 14:45-51 (2002).
Bragdon et al. "Group differences in pain modulation: pain-free women compared to pain-free men and to women with TMD" Pain, 96(3):227-237 (2002).
Bray et al. "Positional genomic analysis identifies the β2-adrenergic receptor gene as a susceptibility locus for human hypertension" Circulation, 101(25):2877-2882 (2000).
Bray et al. "A haplotype implicated in schizophrenia susceptibility is associated with reduced COMT expression in human brain" American Journal of Human Genetics, 73(1):152-161 (2003).
Bruehl et al. "Interactions between the cardiovascular and pain regulatory systems: an updated review of mechanisms and possible alterations in chronic pain" Neuroscience and Biobehavioral Reviews, 28(4):395-414 (2004).
Burge et al. "Prediction of complete gene structures in human genomic DNA" Journal of Molecular Biology, 268 (1):78-94 (1997).
Busjahn et al. "β-2 adrenergic receptor gene variations and coping styles in twins" Biological Psychology, 61 (1-2):97-109 (2002).
Cadet et al. "Molecular identification and functional expression of mu 3, a novel alternatively spliced variant of the human mu opiate receptor gene" The Journal of Immunology, 170(10):5118-5123 (2003).
Caspi et al. "Influence of life stress on depression: moderation by a polymorphism in the 5-HTT gene" Science, 301 (5631):386-389 (2003).
Chandra et al. "Cyclic AMP signaling pathways are important in IL-1 beta transcriptional regulation" The Journal of Immunology, 155(10):4535-4543 (1995).
Chaplan et al. "Quantitative assessment of tactile allodynia in the rat paw" Journal of Neuroscience Methods, 53 (1):55-63 (1994).
Chaplan et al. "Role of voltage-dependent calcium channel subtypes in experimental tactile allodynia" The Journal of Pharmacology and Experimental Therapeutics, 269(3):1117-1123 (1994).
Cherny et al. "Strategies to manage the adverse effects of oral morphine: an evidence-based report" Journal of Clinical Oncology, 19(9):2542-2554 (2001).
Comeron, J.M. "Selective and mutational patterns associated with gene expression in humans: influences on synonymous composition and intron presence" Genetics, 167(3):1293-1304 (2004).
Comings et al. "Comparison of the role of dopamine, serotonin, and noradrenaline genes in ADHD, ODD and conduct disorder: multivariate regression analysis of 20 genes" Clinical Genetics, 57(3):178-196 (2000).
Coppack, S.W. "Pro-inflammatory cytokines and adipose tissue" Proceedings of the Nutrition Society, 60(3):349-356 (2001).
Cunha et al. "A cascade of cytokines mediates mechanical inflammatory hypernociception in mice" Proceedings of the National Academy of Sciences USA, 102(5):1755-1760 (2005).
Dao et al. "The efficacy of oral splints in the treatment of myofascial pain of the jaw muscles: a controlled clinical trial" Pain, 56(1):85-94 (1994).
Deckert et al. "Excess of high activity monoamine oxidase A gene promoter alleles in female patients with panic disorder" Human Molecular Genetics, 8(4):621-624 (1999).
Demille et al. "Population variation in linkage disequilibrium across the COMT gene considering promoter region and coding region variation" Human Genetics, 111(6):521-537 (2002).
Diatchenko et al. "COMT haplotypes contributing to pain sensitivity and painful TMD" IADR/AADR/CADR 82nd General Session, Mar. 10-13, 2004 https://iadr.abstractarchives.com/abstract/2004Hawaii-47884/comt-haplotypes-contributing-to-pain-sensitivity-and-painful-tmd.
Diatchenko et al. "Genetic basis for individual variations in pain perception and the development of a chronic pain condition" Human Molecular Genetics, 14(1):135-143 (2005).
Diatchenko et al. "Idiopathic pain disorders—pathways of vulnerability" Pain, 123(3):226-230 (2006).
Diatchenko et al. "Three major haplotypes of the beta2 adrenergic receptor define psychological profile, blood pressure, and the risk for development of a common musculoskeletal pain disorder" American Journal of Medical Genetics B Neuropsychiatric Genetics, 141B(5):449-462 (2006).
Drysdale et al. "Complex promoter and coding region beta 2-adrenergic receptor haplotypes alter receptor expression and predict in vivo responsiveness" Proceedings of the National Academy of Sciences USA, 97 (19):10483-10488 (2000).
Duan et al. "Synonymous mutations in the human dopamine receptor D2 (DRD2) affect mRNA stability and synthesis of the receptor" Human Molecular Genetics, 12(3):205-216 (2003).
Duguay et al. "A novel functional polymorphism in the uridine diphosphate-glucuronosyltransferase 2B7 promoter with significant impact on promoter activity" Clinical Pharmacology and Therapeutics, 75(3):223-233 (2004).
Edwards et al. "Basal heat pain thresholds predict opioid analgesia in patients with postherpetic neuralgia" Anesthesiology, 104(6):1243-1248 (2006).
Eid et al. "Sociability and positive emotionality: genetic and environmental contributions to the covariation between different facets of extraversion" Journal of Personality, 71(3):319-346 (2003).
Elenkov et al. "The Sympathetic Nerve—An Integrative Interface between Two Supersystems: The Brain and the Immune System" Pharmacological Reviews, 52(4):596-638 (2000).
Enoch et al. "Genetic origins of anxiety in women: a role for a functional catechol-O-methyltransferase polymorphism" Psychiatric Genetics, 13(1):33-41 (2003).
Estevez et al. "Update on the genetics of migraine" Human Genetics, 114(3):225-235 (2004).
Examination Report corresponding to European Patent Application No. 12000245.6 (dated Mar. 20, 2013).
Extended European Search Report corresponding to European Patent Application No. 12000245.6 (10 pages) (dated Jul. 11, 2012).
Exton et al. "G protein beta3 subunit 825T allele is associated with depression in young, healthy subjects" NeuroReport, 14(3):531-533 (2003).
Fillingim et al. "Pain Sensitivity in Patients with Temporomandibular Disorders: Relationship to Clinical and Psychosocial Factors" The Clinical Journal of Pain, 12(4):260-269 (1996).
Fillingim et al. "The influence of resting blood pressure and gender on pain responses" Psychosomatic Medicine, 58 (4):326-332 (1996).

(56) References Cited

OTHER PUBLICATIONS

Fillingim et al. "Resting blood pressure and thermal pain responses among females: effects on pain unpleasantness but not pain intensity" International Journal of Psychophysiology, 30(3):313-318 (1998).
Fillingim et al. "The A118G single nucleotide polymorphism of the mu-opioid receptor gene (OPRM1) is associated with pressure pain sensitivity in humans" The Journal of Pain, 6(3):159-167 (2005).
Flores et al. "The pharmacogenetics of analgesia: toward a genetically-based approach to pain management" Pharmacogenetics, 2(3):177-194 (2001).
Fruhstorfer et al. "Method for quantitative estimation of thermal thresholds in patients" Journal of Neurology, Neurosurgery & Psychiatry, 39(11):1071-1075 (1976).
Gabriel et al. "The structure of haplotype blocks in the human genome" Science, 296(5576):2225-2229 (2002).
Gaiddon et al. "Brain-derived neurotrophic factor exerts opposing effects on beta2-adrenergic receptor according to depolarization status of cerebellar neurons" Journal of Neurochemistry, 73(4):1467-1476 (1999).
Galer et al. "Individual variability in the response to different opioids: report of five cases" Pain, 49(1):87-91 (1992).
Garofalo et al. "Predicting chronicity in acute temporomandibular joint disorders using the research diagnostic criteria" Journal of the American Dental Association, 129(4):438-447 (1998).
Glatt et al. "Association between a functional catechol O-methyltransferase gene polymorphism and schizophrenia: meta-analysis of case-control and family-based studies" American Journal of Psychiatry, 160(3):469-476 (2003).
Goldman et al. "COMT VAL158MET: Linkage to Pain/Stress Response, Anxiety, and Cognition" Alcoholism Clinical and Experimental Research, 27(5 Suppl):9A (2003).
Goldstein, F. J. "Adjuncts to opioid therapy" Journal of the American Osteopathic Association, 102(9 Suppl. 3):S15-S21 (2002).
Gordon et al. "Genetic approaches to the study of anxiety" Annual Review of Neuroscience, 27:193-222 (2004).
Gracely et al. "Pain catastrophizing and neural responses to pain among persons with fibromyalgia" Brain, 127(Pt. 4):835-843 (2004).
Gratze et al. "beta-2 Adrenergic receptor variants affect resting blood pressure and agonist-induced vasodilation in young adult Caucasians" Hypertension, 33(6):1425-1430 (1999).
Gursoy et al. "Significance of catechol-O-methyltransferase gene polymorphism in fibromyalgia syndrome" Rheumatology International, 23(3):104-107 (2003).
Hagen et al. "Does hypertension protect against chronic musculoskeletal complaints? The Nord-Trøndelag Health Study" Archives of Internal Medicine, 165(8):916-922 (2005).
Halushka et al. "Patterns of single-nucleotide polymorphisms in candidate genes for blood-pressure homeostasis" Nature Genetics, 22(3):239-247 (1999).
Han et al. "A possible genetic mechanism underlying individual and interstrain differences in opioid actions: focus on the mu opioid receptor gene" Annals of the New York Academy of Sciences, 1025:370-375 (2004).
Hargreaves et al. "A new and sensitive method for measuring thermal nociception in cutaneous hyperalgesia" Pain, 32(1):77-88 (1988).
Hemminger et al. "TAMAL: an integrated approach to choosing SNPs for genetic studies of human complex traits" Bioinformatics, 22(5):626-627 (2006).
Herken et al. "Possible association of temporomandibular joint pain and dysfunction with a polymorphism in the serotonin transporter gene" American Journal of Orthodontics and Dentofacial Orthopedics, 120(3):308-313 (2001).
Hirota et al. "Sequence variability and candidate gene analysis in two cancer patients with complex clinical outcomes during morphine therapy" Drug Metabolism and Disposition, 31(5):677-680 (2003).
Hirschhorn et al. "A comprehensive review of genetic association studies" Genetics in Medicine, 4(2):45-61 (2002).

Hocking et al. "Genetic variation in the beta2-adrenergic receptor but not catecholamine-O-methyltransferase predisposes to chronic pain: Results from the 1958 British Birth Cohort Study" Pain, 149(1):143-151 (2010).
Hoit et al. "beta2-adrenergic receptor polymorphisms at amino acid 16 differentially influence agonist-stimulated blood pressure and peripheral blood flow in normal individuals" American Hearth Journal, 139(3):537-542 (2000).
Iaccarino et al. "β2-Adrenergic Receptor Gene Delivery to the Endothelium Corrects Impaired Adrenergic Vasorelaxation in Hypertension" Circulation, 106:349-355 (2002).
Ikeda et al. "How individual sensitivity to opiates can be predicted by gene analyses" Trends in Pharmacological Sciences, 26(6):311-317 (2005).
International Preliminary Report on Patentability corresponding to International Patent Application No. PCT/US05/26201 (dated Oct. 25, 2007).
International Search Report and the Written Opinion of the International Searching Authority corresponding to International Patent Application No. PCT/US2006/45757 (dated Sep. 25, 2007).
Jaeger et al. "Quantification of changes in myofascial trigger point sensitivity with the pressure algometer following passive stretch" Pain, 27(2):203-210 (1986).
Jakobi et al. "Catechol-O-Methyltransferase Gene Polymorphisms Are Not Associated with Multisomatoform Disorder in a Group of German Multisomatoform Disorder Patients and Healthy Controls" Genetic Testing & Molecular Biomarkers, 14(3):293-297 (2010).
Johansson et al. "Variation in the adiponutrin gene influences its expression and associates with obesity" Diabetes, 55(3):826-833 (2006).
John et al. "Widespread pain as a risk factor for dysfunctional temporomandibular disorder pain" Pain, 102(3):257-263 (2003).
Kato et al. "Chronic widespread pain and its comorbidities: a population-based study" Archives of Internal Medicine, 166(15):1649-1654 (2006).
Keefe et al. "Pain behavior and pain coping strategies in low back pain and myofascial pain dysfunction syndrome patients" Pain, 24(1):49-56 (1986).
Khasar et al. "Epinephrine produces a beta-adrenergic receptor-mediated mechanical hyperalgesia and in vitro sensitization of rat nociceptors" Journal of Neurophysiology, 81(3):1104-1112 (1999).
Khasar et al. "Vagal modulation of nociception is mediated by adrenomedullary epinephrine in the rat" The European Journal of Neuroscience, 17(4):909-915 (2003).
Kiefer et al. "The role of macrophages in immune-mediated damage to the peripheral nervous system" Progress in Neurobiology, 64(2):109-127 (2001).
Kim et al. "Genetics, Pain, and Analgesia" Pain: Clinical Updates, 13(3):1-4 (2005).
Klepstad et al. "The 118 A > G polymorphism in the human mu-opioid receptor gene may increase morphine requirements in patients with pain caused by malignant disease" Acta Anaesthesiologica Scandinavica, 48 (10):1232-1239 (2004).
Kotanko et al. "Essential hypertension in African Caribbeans associates with a variant of the beta2-adrenoceptor" Hypertension, 30(4):773-776 (1997).
Langdahl et al. "Osteoporotic Fractures Are Associated with an 86-Base Pair Repeat Polymorphism in the Interleukin-1-Receptor Antagonist Gene But Not with Polymorphisms in the Interleukin-1b Gene" Journal of Bone & Mineral Research, 15(3):402-414 (2000).
Lawford et al. "D2 dopamine receptor gene polymorphism: paroxetine and social functioning in posttraumatic stress disorder" European Neuropsychopharmacology, 13(5):313-320 (2003).
Lesch, K. P. "Gene-environment interaction and the genetics of depression" Journal of Psychiatry & Neuroscience, 29(3):174-184 (2004).
Li et al. "The 341C/T polymorphism in the GSTP1 gene is associated with increased risk of oesophageal cancer" BMC Genetics, 11(47):1-9 (2010).
Lötsch et al. "The polymorphism A118G of the human mu-opioid receptor gene decreases the pupil constrictory effect of morphine-6-glucuronide but not that of morphine" Pharmacogenetics, 12(1):3-9 (2002).

(56) References Cited

OTHER PUBLICATIONS

Lötsch et al. "Are mu-opioid receptor polymorphisms important for clinical opioid therapy?" Trends in Molecular Medicine, 11(2):82-89 (2005).

Magliozzi et al. "Lymphocyte beta-adrenoreceptor density in patients with unipolar depression and normal controls" Biological Psychiatry, 26(1):15-25 (1989).

Maixner et al. "Cardiovascular and sensory responses to forearm ischemia and dynamic hand exercise" American Journal of Physiology. Regulatory, Integrative and Comparative Physiology, 259(6 Pt. 2):R1156-R1163 (1990).

Maixner et al. "Relationship between pain sensitivity and resting arterial blood pressure in patients with painful temporomandibular disorders" Psychosomatic Medicine, 59(5):503-511 (1997).

Maixner et al. "Sensitivity of patients with painful temporomandibular disorders to experimentally evoked pain: evidence for altered temporal summation of pain" Pain, 76(1-2):71-81 (1998).

Männistö et al. "Catechol-O-methyltransferase (COMT): Biochemistry, Molecular Biology, Pharmacology, and Clinical Efficacy of the New Selective COMT Inhibitors" Pharmacological Reviews, 51(4):593-628 (1999).

Matthes et al. "Loss of morphine-induced analgesia, reward effect and withdrawal symptoms in mice lacking the mu-opioid-receptor gene" Nature, 383(6603):819-823 (1996).

Mcbeth et al. "Features of somatization predict the onset of chronic widespread pain: results of a large population-based study" Arthritis and Rheumatism, 44(4):940-946 (2001).

Mccubbin et al. "Do endogenous opioids mediate the relationship between blood pressure and pain sensitivity in normotensives?" Pain, 57(1):63-67 (1994).

Mcdermid et al. "Generalized hypervigilance in fibromyalgia: evidence of perceptual amplification" Pain, 66(2-3) 133-144 (1996).

Mcgraw et al. "Polymorphisms of the 5' leader cistron of the human beta2-adrenergic receptor regulate receptor expression" The Journal of Clinical Investigation, 102(11):1927-1932 (1998).

Mense, S. "Nociception from skeletal muscle in relation to clinical muscle pain" Pain, 54(3):241-289 (1993).

Mogil, Jeffrey S. "The genetic mediation of individual differences in sensitivity to pain and its inhibition" Proceedings of the National Academy of Sciences USA, 96(14):7744-7751 (1999).

Mogil et al. "The melanocortin-1 receptor gene mediates female-specific mechanisms of analgesia in mice and humans" Proceedings of the National Academy of Sciences USA, 100(8):4867-4872 (2003).

Mohamed-Ali et al. "β-Adrenergic Regulation of IL-6 Release from Adipose Tissue: In Vivo and in Vitro Studies" The Journal of Clinical Endocrinology & Metabolism, 86(12):5864-5869 (2001).

Munoz-Valle et al. "Polymorphism of the beta3-adrenergic receptor and lipid profile in patients with rheumatoid arthritis and systemic lupus erythematosus treated with chloroquine" Rheumatology International, 23(3):99-103 (2003).

Narita et al. "Reduced expression of a novel µ-opioid receptor (MOR) subtype MOR-1B in CXBK mice: Implications of MOR-1B in the expression of MOR-mediated responses" European Journal of Neuroscience, 18(12):3193-3198 (2003).

O'Donnell et al. "Involvement of beta-1 and beta-2 adrenergic receptors in the antidepressant-like effects of centrally administered isoproterenol" The Journal of Pharmacology & Experimental Therapeutics, 271(1):246-254 (1994).

Ogurtsov et al. "Owen: aligning long collinear regions of genomes" Bioinformatics, 18(12):1703-1704 (2002).

Orozi et al. "Alcoholism: genes and mechanisms" Pharmacogenomics, 5(8):1037-1048 (2004).

Pan, Y. X. "Diversity and complexity of the mu opioid receptor gene: alternative pre-mRNA splicing and promoters" DNA & Cell Biology, 24(11):736-750 (2005).

Pan et al. "Identification and characterization of six new alternatively spliced variants of the human mu opioid receptor gene, Oprm" Neuroscience, 133(1):209-220 (2005).

Pasternak, G. W. "Incomplete cross tolerance and multiple mu opioid peptide receptors" Trends in Pharmacological Sciences, 22(2):67-70 (2001).

Pasternak, G. W. "Multiple opiate receptors: déjà vu all over again" Neuropharmacology, 47(Suppl. 1):312-323 (2004).

Price, D. D. "Selective activation of A-delta and C nociceptive afferents by different parameters of nociceptive heat stimulation: a tool for analysis of central mechanisms of pain" Pain, 68(1):1-3 (1996).

Pritchard, Jonathan K. "Are rare variants responsible for susceptibility to complex diseases?" American Journal of Human Genetics, 69(1):124-137 (2001).

Pritchard, Jonathan K. "Deconstructing maize population structure" Nature Genetics, 28:203-204 (2001).

Rakvåg et al. "The Val158Met polymorphism of the human catechol-O-methyltransferase (COMT) gene may influence morphine requirements in cancer pain patients" Pain, 116(1-2):73-78 (2005).

Rao et al. "Cardiovascular responses to central administration of mu and kappa opioid receptor agonist and antagonist in normal rats" Peptides, 24(5):745-754 (2003).

Raphael et al. "Widespread pain and the effectiveness of oral splints in myofascial face pain" Journal of the American Dental Association, 132(3):305-316 (2001).

Risch, N. J. "Searching for genetic determinants in the new millennium" Nature, 405(6788):847-856 (2000).

Roach et al. "Differential activation of the transcription factor cyclic AMP response element binding protein (CREB) in macrophages following infection with pathogenic and nonpathogenic mycobacteria and role for CREB in tumor necrosis factor alpha production" Infection & Immunity, 73(1):514-522 (2005).

Rockman et al. "Abundant raw material for cis-regulatory evolution in humans" Molecular Biology & Evolution, 19 (11):1991-2004 (2002).

Romberg et al. "Pharmacokinetic-Pharmacodynamic Modeling of Morphine-6-glucuronide-induced Analgesia in Healthy Volunteers: Absence of Sex Differences" Anesthesiology, 100:120-133 (2004).

Saavedra "Naloxone reversible decrease in pain sensitivity in young and adult spontaneously hypertensive rats" Brain Research, 209(1):245-249 (1981).

Sarlani et al. "Evidence for generalized hyperalgesia in temporomandibular disorders patients" Pain, 102(3):221-226 (2003).

Schuller et al. "Retention of heroin and morphine-6 beta-glucuronide analgesia in a new line of mice lacking exon 1 of MOR-1" Nature Neuroscience, 2(2):151-156 (1999).

Shagin et al. "A novel method for SNP detection using a new duplex-specific nuclease from crab hepatopancreas" Genome Research, 12(12):1935-1942 (2002).

Sheffield et al. "Race and sex differences in cutaneous pain perception" Psychosomatic Medicine, 62(4):517-523 (2000).

Shifman et al. "A highly significant association between a COMT haplotype and schizophrenia" American Journal of Human Genetics, 71(6):1296-1302 (2002).

Skarke et al. "Analgesic effects of morphine and morphine-6-glucuronide in a transcutaneous electrical pain model in healthy volunteers" Clinical Pharmacology & Therapeutics, 73(1):107-121 (2003).

Slade et al. "Influence of Psychological Factors on Risk of Temporomandibular Disorders" Journal of Dental Research, 86(11):1120-1125 (2007).

Small et al. "Pharmacology and physiology of human adrenergic receptor polymorphisms" Annual Review of Pharmacology & Toxicology, 43:381-411 (2003).

Smoller et al. "Genetic association analysis of behavioral inhibition using candidate loci from mouse models" American Journal of Medical Genetics, 105(3):226-235 (2001).

Snapir et al. "Effects of common polymorphisms in the α1A-, α2B-, β1- and β2-adrenoreceptors on haemodynamic responses to adrenaline" Clinical Science, 104:509-520 (2003).

Sommer et al. "Recent findings on how proinflammatory cytokines cause pain: peripheral mechanisms in inflammatory and neuropathic hyperalgesia" Neuroscience Letters, 361(1-3):184-187 (2004).

(56) References Cited

OTHER PUBLICATIONS

Sora et al. "Opiate receptor knockout mice define µ receptor roles in endogenous nociceptive responses and morphine-induced? analgesia" Proceedings of the National Academy of Sciences USA, 94(4):1544-1549 (1997).

Stefano et al. "Endogenous morphine" Trends in Neurosciences, 23(9):436-442 (2000).

Stephens et al. "A new statistical method for haplotype reconstruction from population data" American Journal of Human Genetics, 68(4):978-989 (2001).

Stephens et al. "A comparison of bayesian methods for haplotype reconstruction from population genotype data" American Journal of Human Genetics, 73(5):1162-1169 (2003).

Strosberg, A. D. "Structure and function of the beta 3-adrenergic receptor" Annual Review of Pharmacology & Toxicology, 37:421-450 (1997).

Supplementary European Search Report corresponding to European Patent Application No. 05858041 (dated Oct. 7, 2009).

Svensson et al. "Analysis of stimulus-evoked pain in patients with myofascial temporomandibular pain disorders" Pain, 92(3):399-409 (2001).

Tattersfield et al. "Are beta2-adrenoceptor polymorphisms important in asthma—an unravelling story" The Lancet, 364(9444):1464-1466 (2004).

Thiessen et al. "Increased prescribing of antidepressants subsequent to beta-blocker therapy" Archives of Internal Medicine, 150(11):2286-2290 (1990).

Thompson et al. "Opiate-induced analgesia is increased and prolonged in mice lacking P-glycoprotein" Anesthesiology, 92(5):1392-1399 (2000).

Tsujii et al. "A beta-3 adrenergic agonist (BRL-37,344) decreases food intake" Physiology & Behavior, 63(4):723-728 (1998).

Uhl et al. "The mu opiate receptor as a candidate gene for pain: polymorphisms, variations in expression, nociception, and opiate responses" Proceedings of the National Academy of Sciences USA, 69(14):7752-7755 (1999).

Vandvik et al. "Prevalence, comorbidity and impact of irritable bowel syndrome in Norway" Scandinavian Journal of Gastroenterology, 41(6):650-656 (2006).

Vassend et al. "Negative affectivity, somatic complaints, and symptoms of temporomandibular disorders" Journal of Psychosomatic Research, 39(7):889-899 (1995).

Verne et al. "Hypersensitivity to visceral and cutaneous pain in the irritable bowel syndrome" Pain, 93(1):7-14 (2001).

Wacholder et al. "Assessing the probability that a positive report is false: an approach for molecular epidemiology studies" Journal of the National Cancer Institute, 96(6):434-442 (2004).

Wall et al. "Haplotype blocks and linkage disequilibrium in the human genome" Nature Reviews Genetics, 4:587-597 (2003).

Wand et al. "The mu-opioid receptor gene polymorphism (A118G) alters HPA axis activation induced by opioid receptor blockade" Neuropsychopharmacology, 26(1):106-114 (2002).

Ward-Routledge et al. "Involvement of central alpha- and beta-adrenoceptors in the pressor response to electrical stimulation of the rostral ventrolateral medulla in rats" British Journal of Pharmacology, 94(2):609-619 (1988).

Wetmur et al. "Kinetics of renaturation of DNA" Journal of Molecular Biology, 31(3):349-370 (1968).

Wilson et al. "Somatization and pain dispersion in chronic temporomandibular disorder pain" Pain, 57(1):55-61 (1994).

Wolozin et al. "Classification of multiple morphine and enkephalin binding sites in the central nervous system" Proceedings of the National Academy of Sciences USA, 78(10):6181-6185 (1981).

Wüst et al. "Common polymorphisms in the glucocorticoid receptor gene are associated with adrenocortical responses to psychosocial stress" The Journal of Clinical Endocrinology & Metabolism, 89(2):565-573 (2004).

Xie et al. "Characterization and implications of estrogenic down-regulation of human catechol-O-methyltransferase gene transcription" Molecular Pharmacology, 56(1):31-38 (1999).

Xu et al. "b2 Adrenoceptor gene single nucleotide polymorphisms are associated with rheumatoid arthritis in northern Sweden" Annals of the Rheumatic Diseases, 64:773-776 (2005).

Yeomans et al. "Nociceptive responses to high and low rates of noxious cutaneous heating are mediated by different nociceptors in the rat: behavioral evidence" Pain, 68(1):133-140 (1996).

Yu et al. "Association study of the interleukin-1 beta (C-511T) genetic polymorphism with major depressive disorder, associated symptomatology, and antidepressant response" Neuropsychopharmacology, 28(6):1182-1185 (2003).

Zhang et al. "Synthesis of interleukin 6 (interferon-beta 2/B cell stimulatory factor 2) in human fibroblasts is triggered by an increase in intracellular cyclic AMP" The Journal of Biological Chemistry, 263(13):6177-6182 (1988).

Zhang et al. "Antagonism of the antidepressant-like effects of clenbuterol by central administration of beta-adrenergic antagonists in rats" Psychopharmacology, 170(1):102-107 (2003).

Zill et al. "SNP and haplotype analysis of a novel tryptophan hydroxylase isoform (TPH2) gene provide evidence for association with major depression" Molecular Psychiatry, 9(11):1030-1036 (2004).

Zolnoun et al. "A conceptual model for the pathophysiology of vulvar vestibulitis syndrome" Obstetrical & Gynecological Survey, 61(6):395-401 (2006).

Zondervan et al. "The complex interplay among factors that influence allelic association" Nature Reviews Genetics, 5(2):89-100 (2004).

Zubieta et al. "COMT val158met genotype affects mu-opioid neurotransmitter responses to a pain stressor" Science, 299(5610):1240-1243 (2003).

* cited by examiner

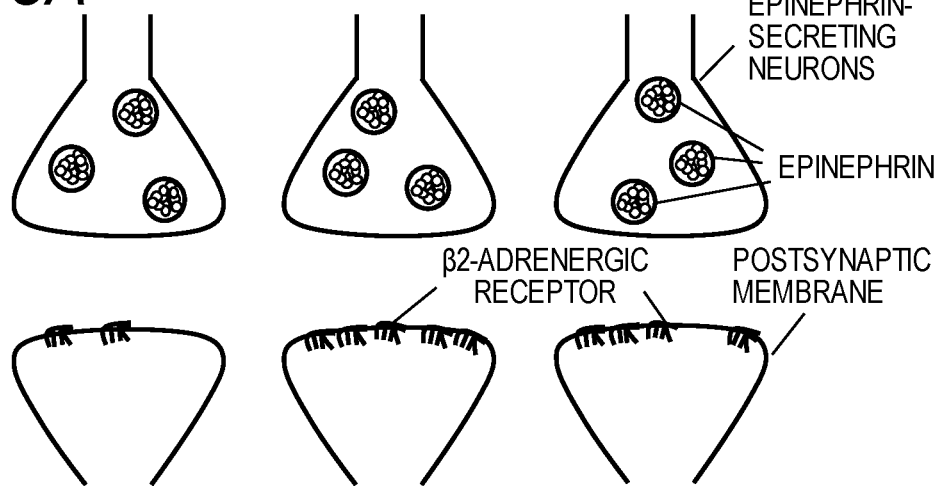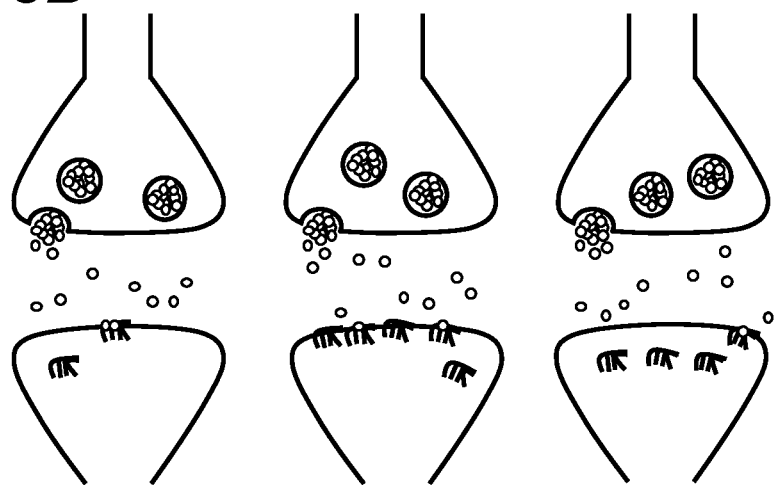

FIG. 6A
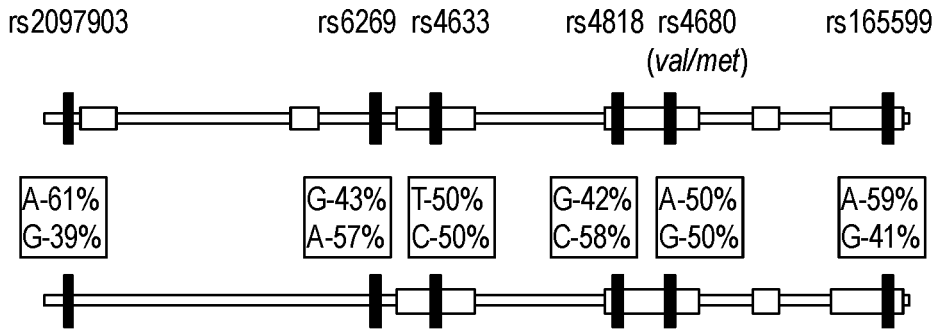
FIG. 6B
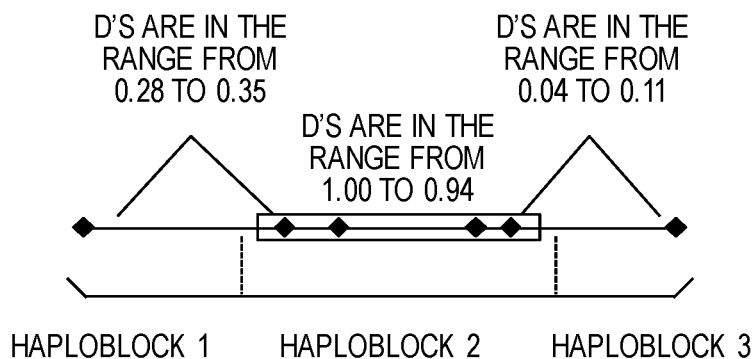
FIG. 6C
| HAPLOTYPE SEQUENCE | FREQUENCY, % |
|---|---|
| G---C--------------G---G | 36.5 |
| A---T--------------C---A | 48.7 |
| A---C--------------C---G | 10.7 |
| G---C--------------C---G | 1.2 |
| A---T--------------G---G | 1.0 |
| A---C--------------G---G | 1.0 |
| G---C--------------C---A | 0.7 |

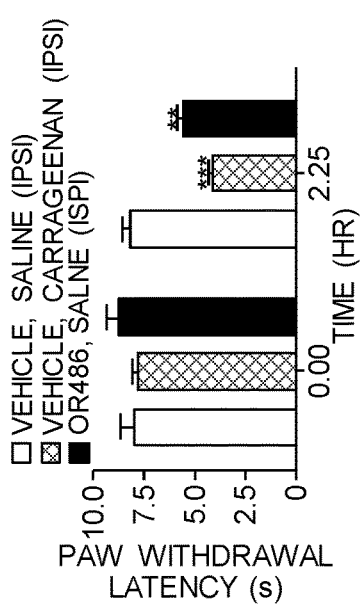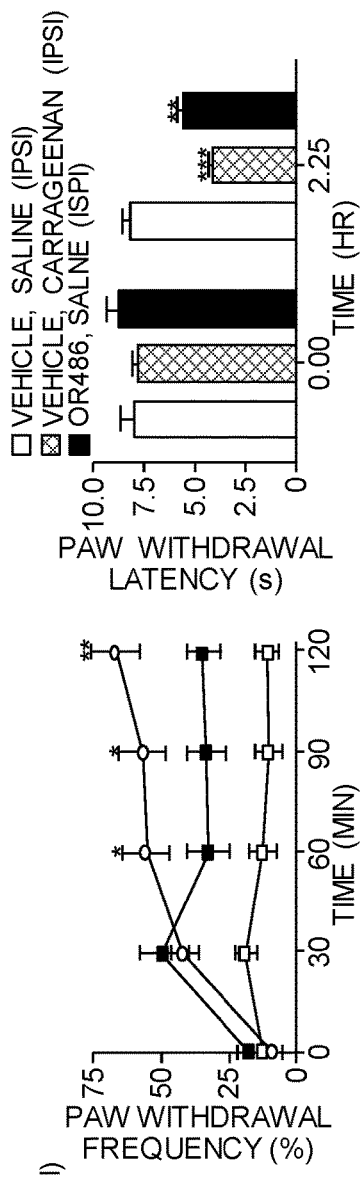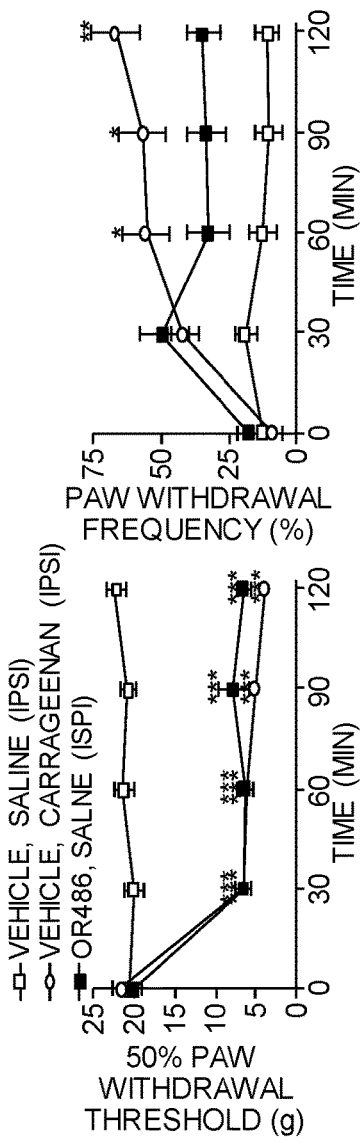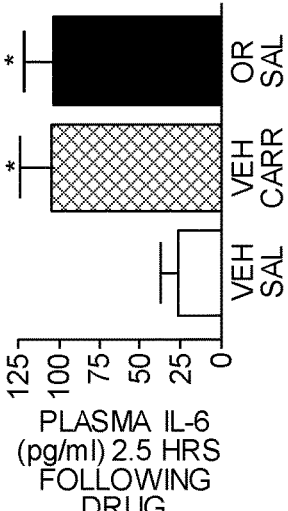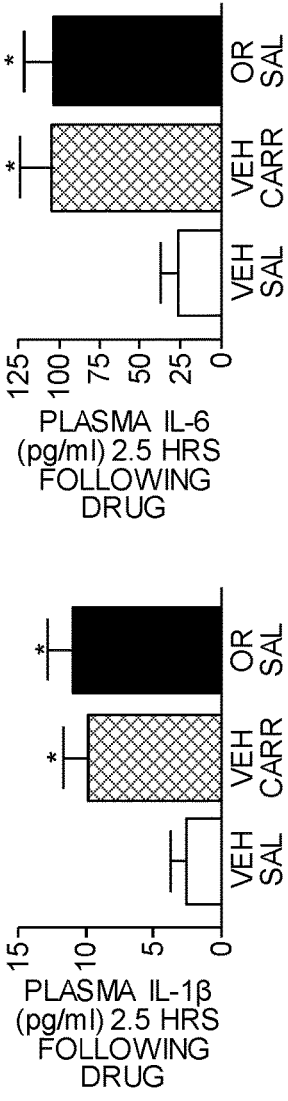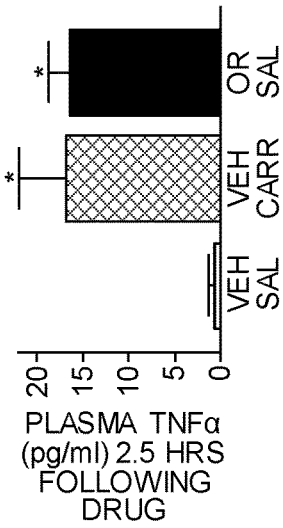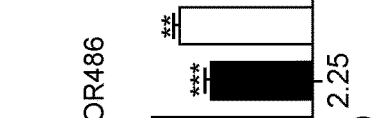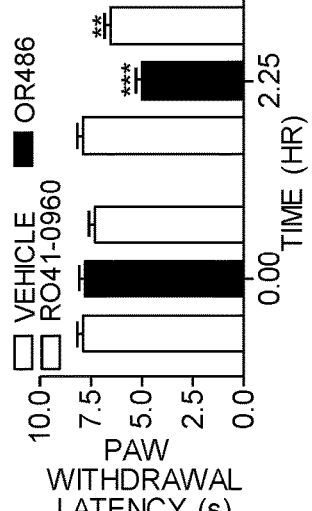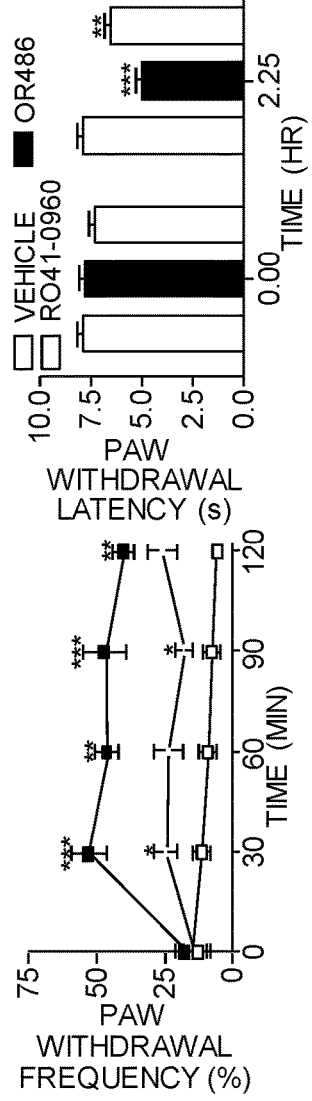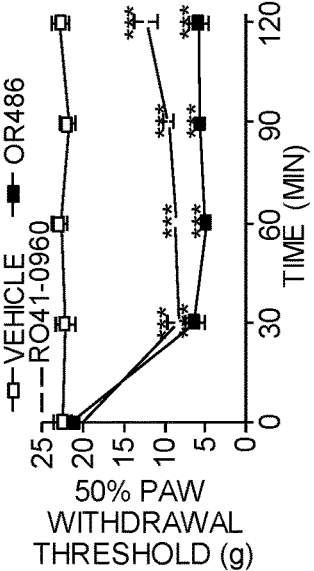

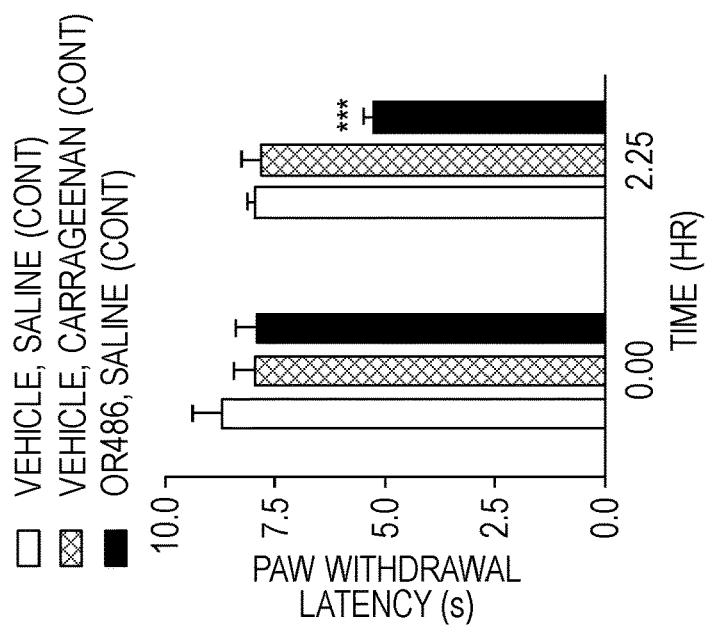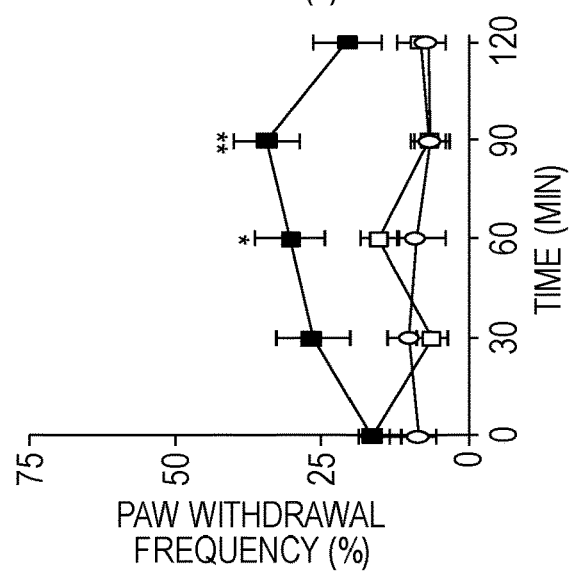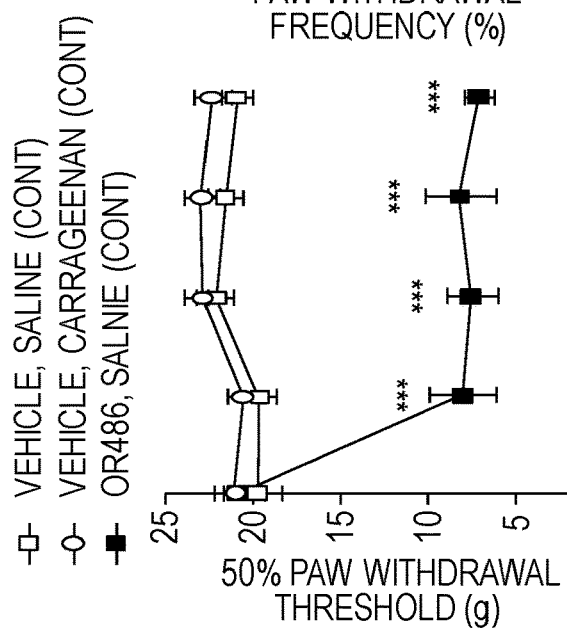

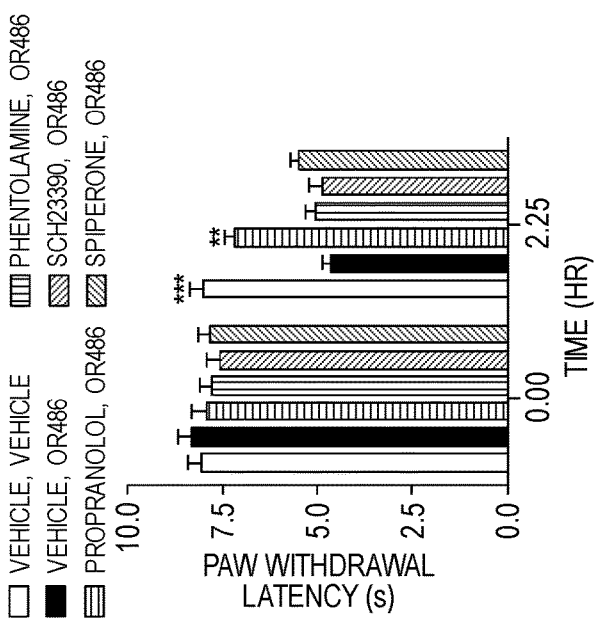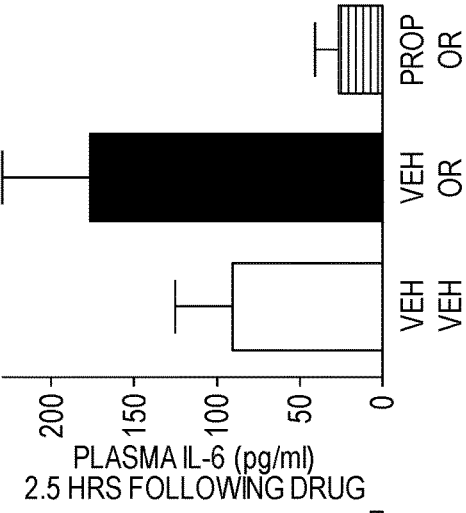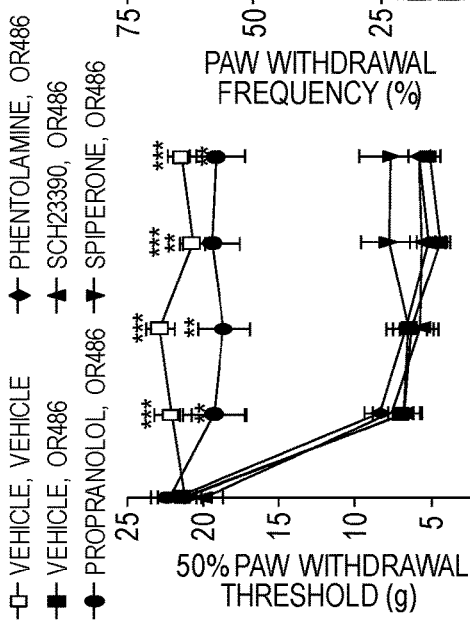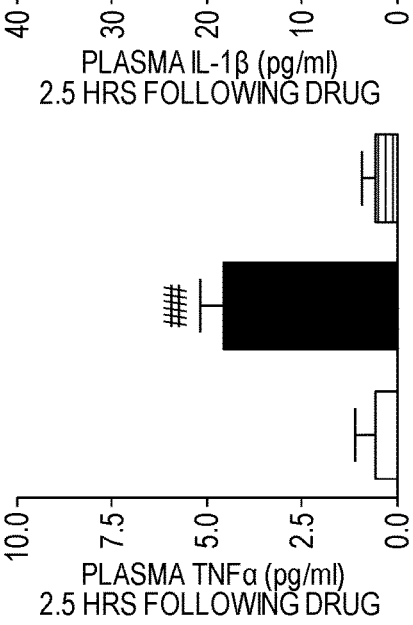

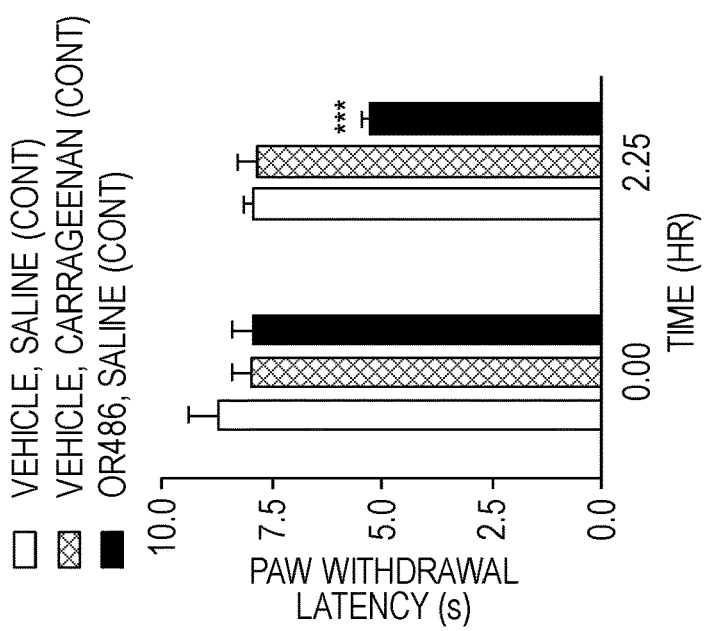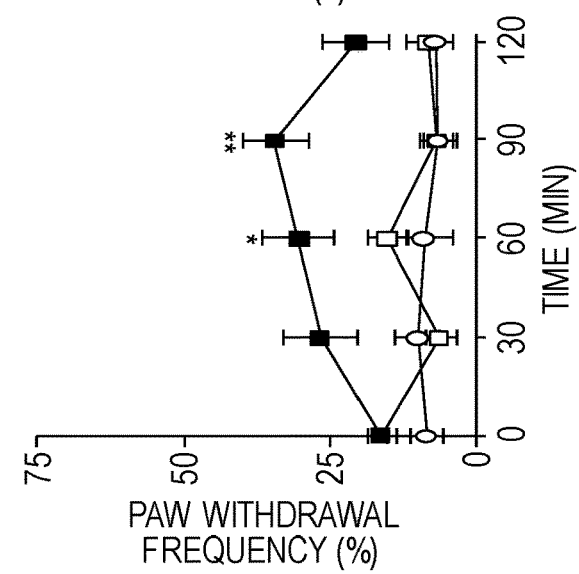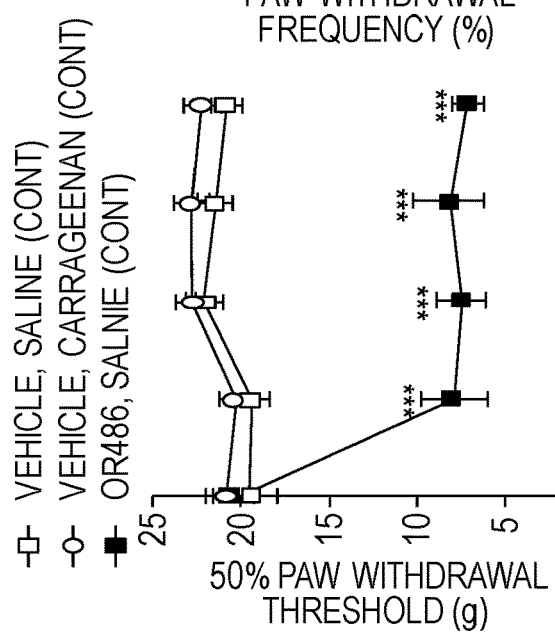

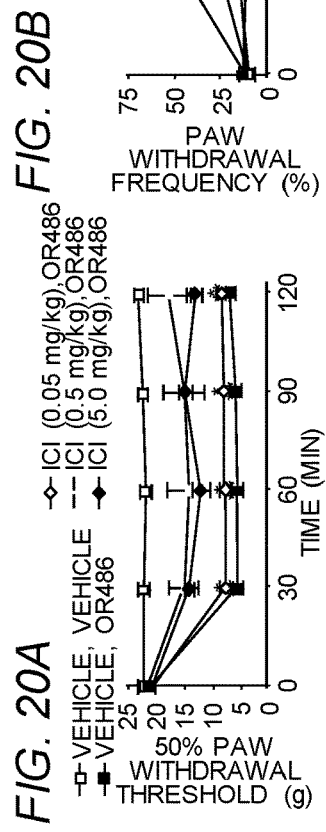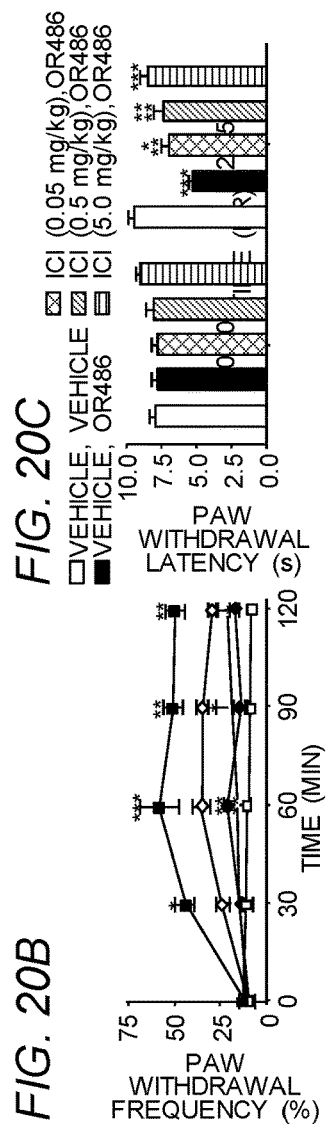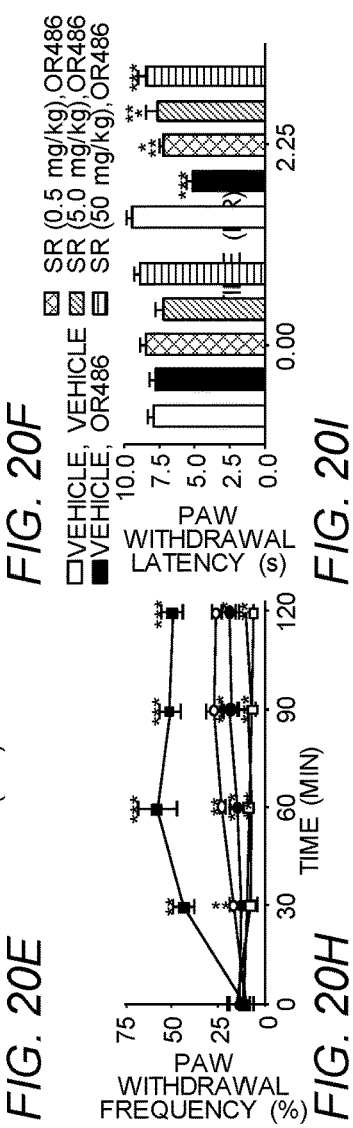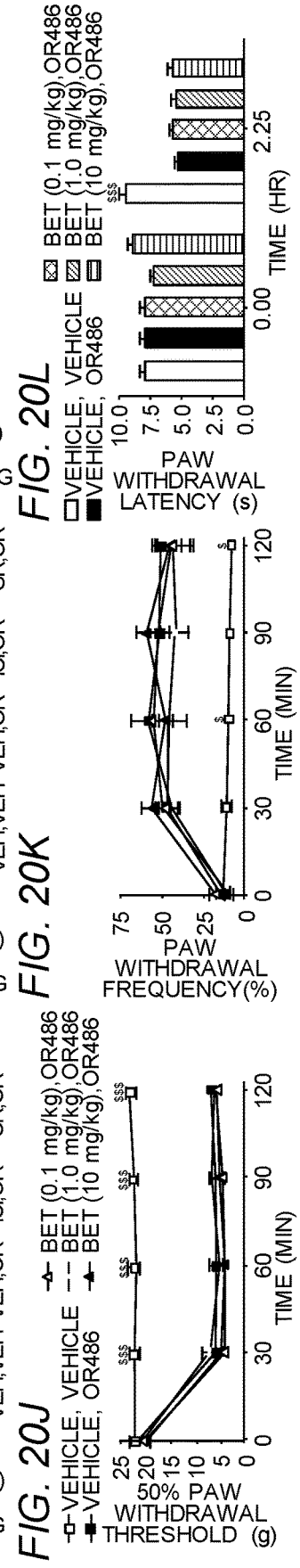

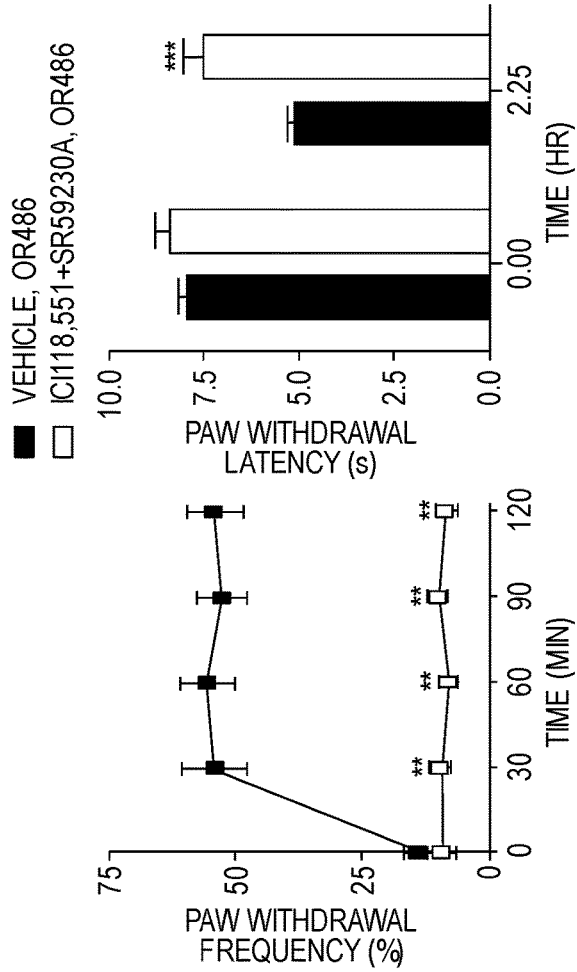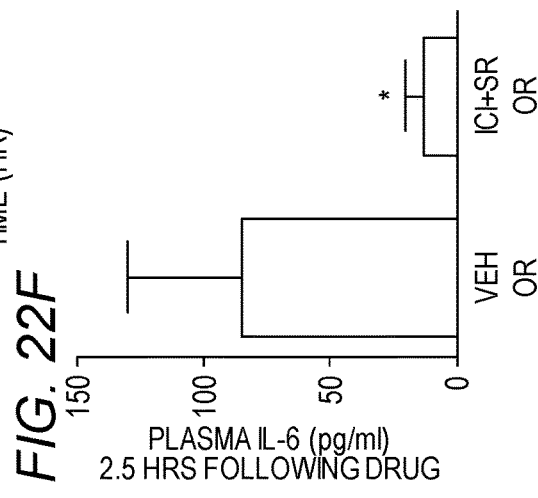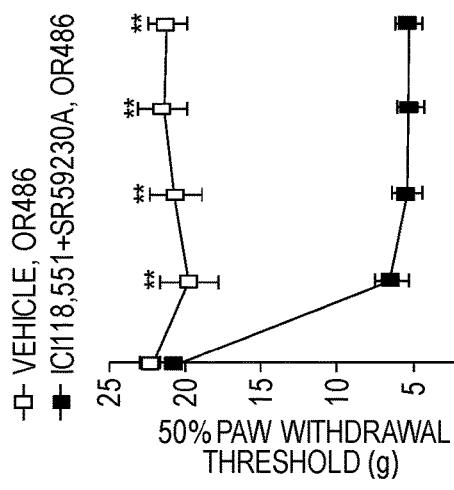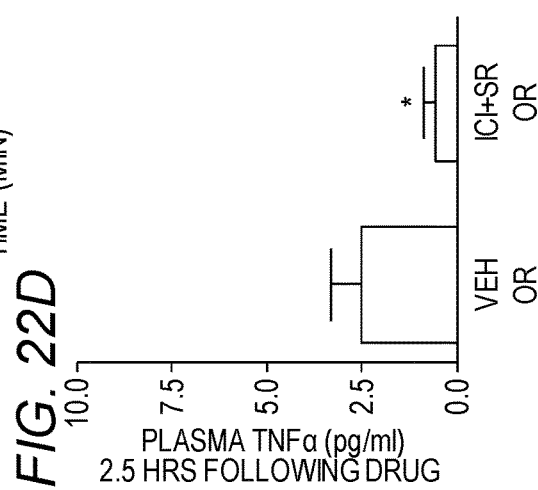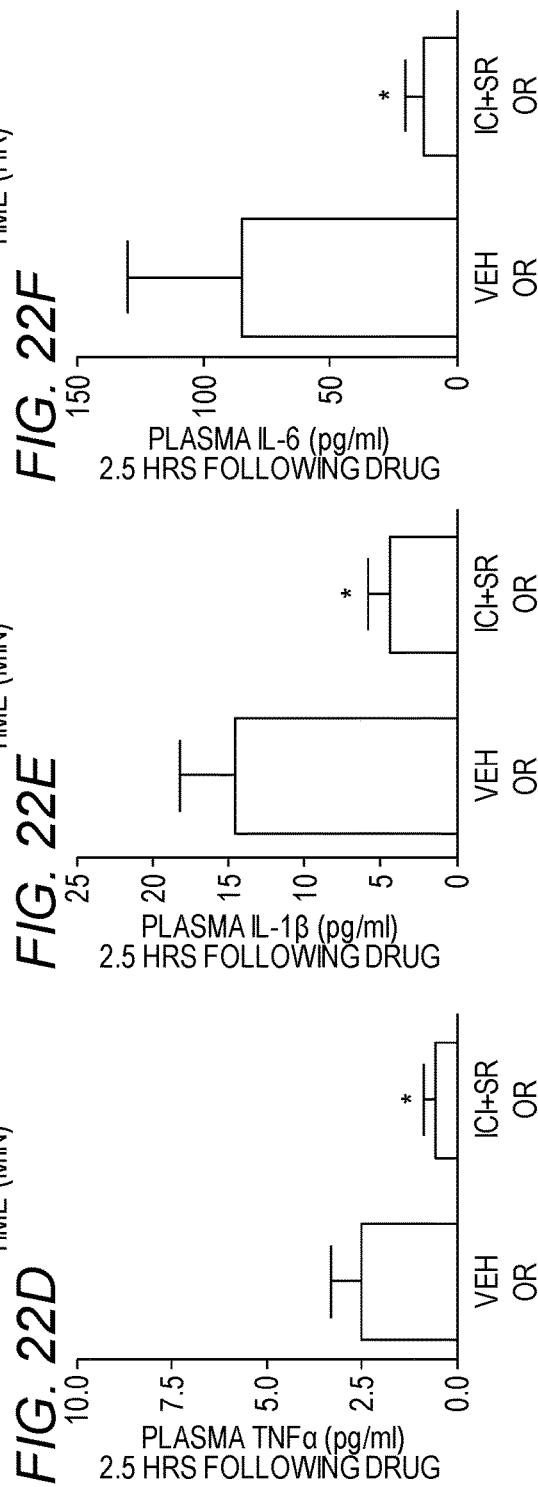
FIG. 22A, FIG. 22B, FIG. 22C, FIG. 22D, FIG. 22E, FIG. 22F

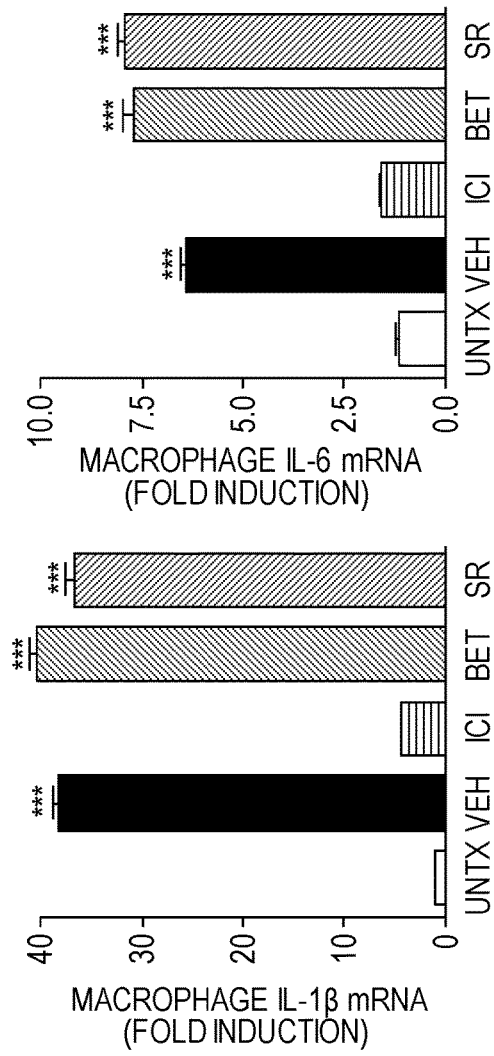
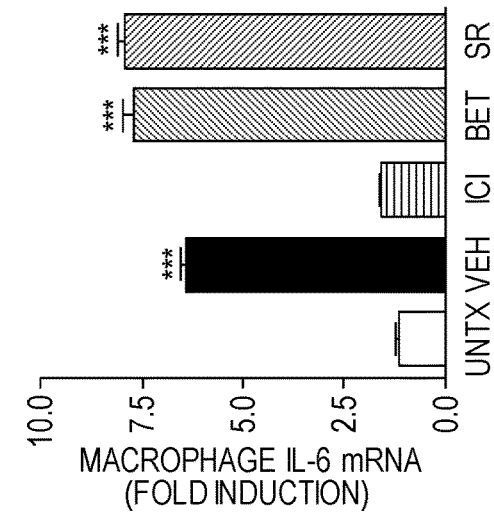
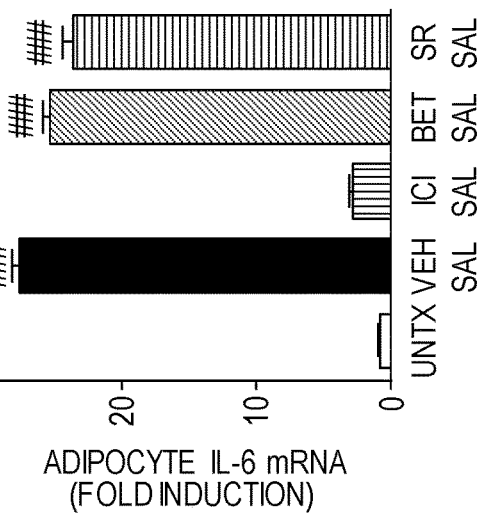
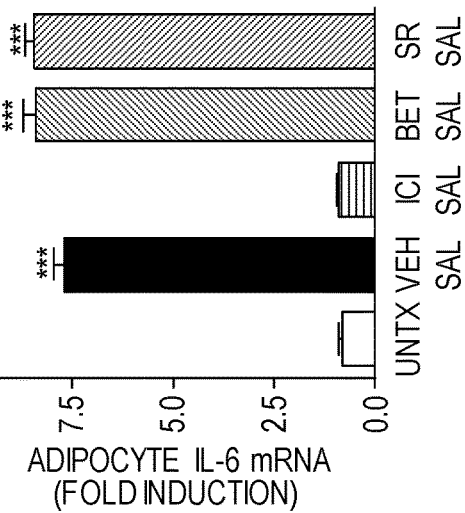
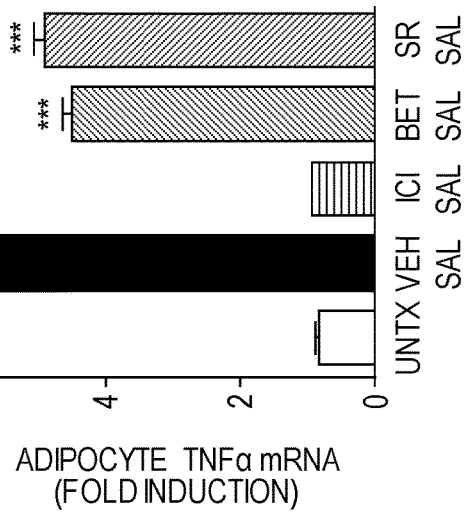

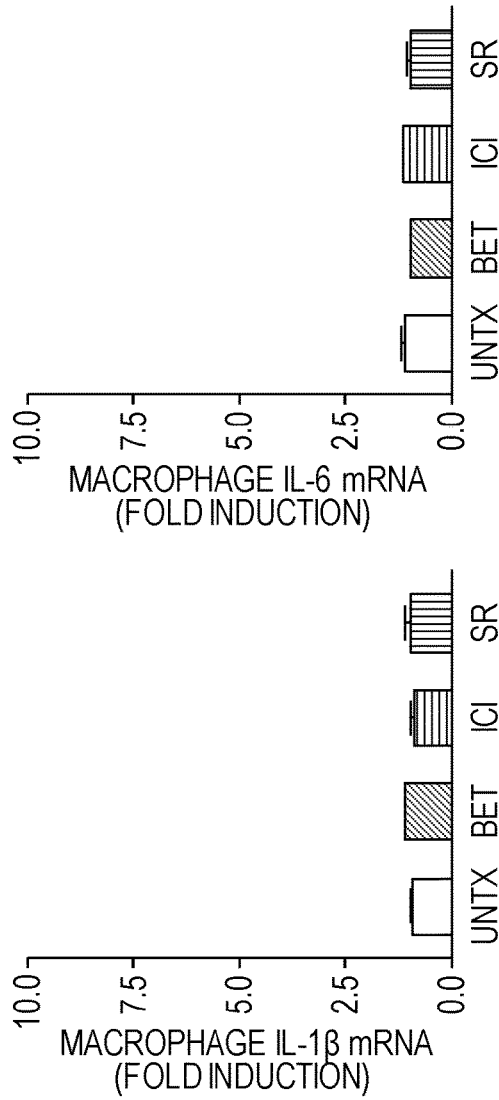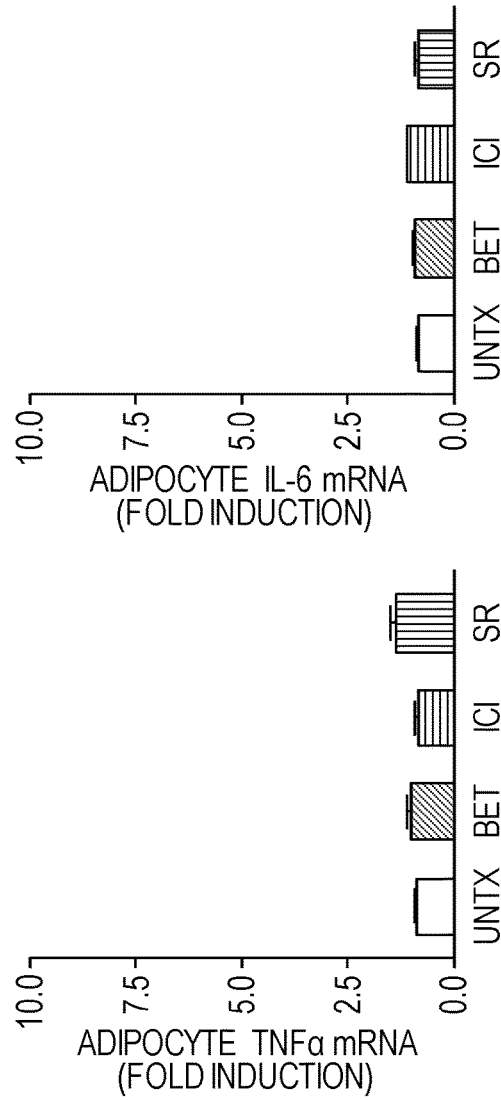

FIG. 25

| POSITION OF NUCLEOTIDE VARIATION* | MINOR ALLELE COUNT | SNP RS NUMBER | QUERY NUCLEOTIDE | BI911023.1 | BP266348.1 | BP347785.1 | BE245562.1 | C18250.1 | BI915042.1 | BI767888.1 | CN83762.1 | CV575184.1 | BI907638.1 | BP215171.1 | CO955925.1 | BU149301.1 | AL553611.3 | BI820274.1 | BG284879.1 | BP366282.1 | BP305076.1 | BP267840.1 | BP267306.1 | BP304134.1 | BP380312.1 | AV647785.1 | BO372763.1 |
|---|---|---|---|---|---|---|---|---|---|---|---|---|---|---|---|---|---|---|---|---|---|---|---|---|---|---|---|
| HIT STARTS | | | | 29 | 0 | 0 | 0 | 0 | 32 | 24 | 187 | 271 | 39 | 19 | 217 | 38 | 35 | 25 | 10 | 55 | 10 | 25 | 25 | 10 | 25 | 23 | 336 |
| HIT ENDS | | | | 671 | 581 | 559 | 402 | 573 | 879 | 850 | 954 | 871 | 693 | 593 | 620 | 326 | 992 | 840 | 691 | 636 | 594 | 597 | 595 | 591 | 579 | 449 | 766 |
| 173 | 15 | RS1042711 | C | C | C | C | C | | | | | | | | | | | | | | | | | | | | | |
| 200 | 4 | RS1801704 | T | T | T | T | T | | | | | | | | | | | | | | | | | | | | | |
| 265 | 15 | RS1042713 | A | G | G | G | G | | A | A | A | A | A | A | A | A | A | A | A | A | A | A | A | A | A | A | A | A |
| 298 | 5 | RS1042714 | C | G | G | G | G | | C | C | C | C | C | C | C | C | C | C | C | C | C | C | C | C | C | C | C | |
| 471 | 10 | RS1042717 | G | G | G | G | G | G | G | G | G | G | G | G | G | | | G | G | G | G | G | G | G | G | G | G | |
| 742 | 3 | RS1042718 | C | C | C | C | C | | C | C | C | | | | | | | | | | | | | | | | | | |
| | | | | H1 SPECIFIC | | | | | | | H2 SPECIFIC | | | | | | | | | | H3 SPECIFIC | | | | | | | |
| EST QUANTITY | | | | 5 | | | | | | | 8 | | | | | | | | | | 11 | | | | | | | |
| OBSERVED EST QUANTITY / HAPLOTYPE FREQUENCY x 24** | | | | 0.496 | | | | | | | 0.877 | | | | | | | | | | 2.182 | | | | | | | |
| EXPRESSION LEVEL RELATIVE TO HAPLOTYPE 1 | | | | 1 | | | | | | | 1.8 | | | | | | | | | | 4.4 | | | | | | | |

METHODS AND MATERIALS FOR DETERMINING PAIN SENSITIVITY AND PREDICTING AND TREATING RELATED DISORDERS

RELATED APPLICATIONS

This application is a continuation of U.S. application Ser. No. 13/624,608, filed on Sep. 21, 2012, which is a divisional of U.S. application Ser. No. 11/632,141, filed on Jul. 2, 2009, which is a 35 U.S.C. 371 national phase application of International Application No. PCT/US05/26201, filed on Jul. 25, 2005, which claims the benefit of U.S. Provisional Patent Application Ser. No. 60/590,792, filed Jul. 23, 2004 and U.S. Provisional patent Application Ser. No. 60/671,855 filed Apr. 15, 2005; the disclosures of each of which are incorporated herein by reference in their entireties.

STATEMENT OF FEDERAL SUPPORT

This invention was made with government support under Grant Nos. DE016558, DE007509, and NS045685 awarded by the National Institutes of Health. The government has certain rights in the invention.

STATEMENT REGARDING ELECTRONIC FILING OF A SEQUENCE LISTING

A sequence Listing in ASCII text format, submitted under 37 C.F.R. § 1.821, entitled 5470-605TSDVCT_ST25.txt, 53,431 bytes in size, generated on Apr. 30, 2018 and filed via EFS-Web, is provided in lieu of a paper copy. This Sequence Listing is incorporated by reference into the specification for its disclosures.

TECHNICAL FIELD

The presently disclosed subject matter relates to selecting and administering effective therapies for treatment of somatosensory and related disorders to a subject. Further, the presently disclosed subject matter provides for selecting the effective therapy for treating a somatosensory disorder based upon the determined genotype of the subject. In particular, the presently disclosed subject matter relates to selecting the effective therapy for treating a somatosensory disorder of a subject based upon the determination of COMT, ADRB2, or ADRB3 genotypes or combinations thereof of the subject. The presently disclosed subject matter further relates in some embodiments to predicting the susceptibility of a subject to develop somatosensory and related disorders based upon determined genotypes of the subject.

BACKGROUND

An individual's sensitivity to pain is influenced by a variety of environmental and genetic factors (Mogil (1999)). Although the relative importance of genetic versus environmental factors in human pain sensitivity remains unclear, reported heritability for nociceptive and analgesic sensitivity in mice is estimated to range from 28% to 76% (Mogil (1999)). Even though animal studies have provided a list of candidate "pain genes," only a few genes have been identified that are associated with the perception of pain in humans.

An understanding of the underlying neurobiological and psychological processes that contribute to enhanced pain sensitivity and the risk of developing somatosensory disorders are beginning to emerge (FIG. 1). The ability of central nociceptive pathways to show enhanced responses to peripheral input depends not only on the activity of peripheral primary afferents, but also on the activity of central pain regulatory systems. The interplay between peripheral afferent input and central nervous system regulatory systems modulates the activity of central neural networks and produces dynamic, time-dependent alterations in the excitability and response characteristics of spinal and supraspinal neural and glia cells that respond to noxious stimuli. Thus, aberrant neural processing of noxious stimuli and psychological dysfunction can result in enhanced pain sensitivity and increase the risk of developing somatosensory disorders that result from multiple etiologies and which are difficult to clinically categorize and treat effectively (FIG. 1).

The biological and psychological determinants of pain sensitivity and somatosensory disorders are influenced by both genetic factors, including heritable genetic variation, and environmental circumstances that determine an individual's biological and psychological profiles or phenotypes. As such, a better understanding of the underlying genetic factors is needed in order to provide effective treatments. In particular, there is an unmet need for a better understanding of genetic variation on molecular pathways that mediate variations in pain sensitivity. Such understanding would provide valuable insights useful for diagnosing and treating disorders involving pain perception.

SUMMARY

In one embodiment of the presently disclosed subject matter, methods of treating a somatosensory disorder in a subject are provided. In some embodiments, the method comprises administering to the subject an effective amount of a COMT modulator, an ADRB2 modulator, an ADRB3 modulator, or combinations thereof.

In some embodiments, both the ADRB2 antagonist and the ADRB3 antagonist are administered to the subject.

In some embodiments, the methods further comprise determining a genotype of the subject with respect to a gene selected from the group consisting of ADRB2, ADRB3, COMT, and combinations thereof and administering to the subject the effective amount of the COMT modulator, the ADRB2 modulator, the ADRB3 modulator, or combinations thereof based on determined genotype of the subject.

In some embodiments, the determined genotype of the subject with respect to ADRB2 is selected from the group consisting of two copies of Haplotype 2, two copies of Haplotype 3, one copy of both Haplotype 2 and Haplotype 3, and at least one copy of Uncommon and the somatosensory disorder is treated by administering the ADRB2 modulator, the COMT modulator, or combinations thereof to the subject.

In some embodiments, the determined genotype of the subject with respect to ADRB3 is selected from the group consisting of two copies of Haplotype 1, and at least one copy of Uncommon and the somatosensory disorder is treated by administering the ADRB3 modulator, the COMT modulator, or combinations thereof to the subject.

In some embodiments, the determined genotype of the subject with respect to COMT is selected from the group consisting of two copies of APS, two copies of HPS, and one copy of both APS and HPS and the somatosensory disorder is treated by administering the COMT modulator, the ADRB2 modulator, the ADRB3 modulator, or combinations thereof to the subject.

In another embodiment, a method of predicting susceptibility of a subject to develop a somatosensory disorder is provided. In some embodiments, the method comprises determining a genotype of the subject with respect to a gene selected from the group consisting of ADRB2, ADRB3, COMT, and combinations thereof; and comparing the genotype of the subject with at least one reference genotype associated with the susceptibility to develop the somatosensory disorder, wherein the reference genotype is selected from the group consisting of an ADRB2 genotype, an ADRB3 genotype, a COMT genotype, and combinations thereof, whereby susceptibility of the subject to develop the somatosensory disorder is predicted.

In some embodiments, the determined genotype of the subject with respect to ADRB2 is selected from the group consisting of two copies of Haplotype 1, two copies of Haplotype 2, two copies of Haplotype 3, one copy of both Haplotype 2 and Haplotype 3, and at least one copy of Uncommon and the subject is predicted to be susceptible to develop the somatosensory disorder.

In some embodiments, the determined genotype of the subject with respect to ADRB3 is selected from the group consisting of two copies of Haplotype 1, and at least one copy of Uncommon and the subject is predicted to be susceptible to develop the somatosensory disorder.

In some embodiments, the determined genotype of the subject with respect to COMT is selected from the group consisting of two copies of APS, two copies of HPS, and one copy of both APS and HPS and the subject is predicted to be susceptible to develop the somatosensory disorder.

In one embodiment, methods of predicting a pain response in a subject are provided. In some embodiments, the method comprises determining a genotype of the subject with respect to a gene selected from the group consisting of ADRB2, ADRB3, COMT, and combinations thereof; and comparing the genotype of the subject with at least one reference genotype associated with pain response variability, wherein the reference genotype is selected from the group consisting of an ADRB2 genotype, an ADRB3 genotype, a COMT genotype, and combinations thereof, whereby pain response in the subject is predicted.

In some embodiments, the determined genotype of the subject with respect to ADRB2 is only one copy of Haplotype 1, and the subject is predicted to have a decreased sensitivity to pain as compared to a population norm.

In some embodiments, the determined genotype of the subject with respect to ADRB3 is selected from the group consisting of at least one copy of Haplotype 2 and at least one copy of Haplotype 3 and the subject is predicted to have decreased sensitivity to pain as compared to a population norm.

In some embodiments, the determined genotype of the subject with respect to COMT is selected from the group consisting of two copies of APS, two copies of HPS, and one copy of both APS and HPS and the subject is predicted to have an increased sensitivity to pain as compared to a population norm.

In one embodiment, methods of predicting somatization in a subject are provided. In some embodiments, the method comprises determining a genotype of the subject with respect to a gene selected from the group consisting of ADRB2, ADRB3, COMT, and combinations thereof; and comparing the genotype of the subject with at least one reference genotype associated with somatization, wherein the reference genotype is selected from the group consisting of an ADRB2 genotype, an ADRB3 genotype, a COMT genotype, and combinations thereof.

In some embodiments, the determined genotype of the subject with respect to ADRB2 is two copies of Haplotype 2, and the subject is predicted to have increased somatization as compared to a population norm.

In some embodiments, the determined genotype of the subject with respect to ADRB3 is at least one copy of Haplotype 3, and the subject is predicted to have a decreased somatization as compared to a population norm.

In some embodiments, the determined genotype of the subject with respect to COMT is selected from the group consisting of two copies of APS, two copies of HPS, and one copy of both APS and HPS and the subject is predicted to have an increased somatization as compared to a population norm.

In one embodiment, methods of selecting a therapy for a subject having a somatosensory disorder are provided. In some embodiments, the method comprises determining a genotype of the subject with respect to a gene selected from the group consisting of ADRB2, ADRB3, COMT, and combinations thereof; and selecting a therapy based on the determined genotype of the subject.

In some embodiments, the therapy is selected from the group consisting of a pharmacological therapy, a behavioral therapy, a psychotherapy, a surgical therapy, and combinations thereof.

In some embodiments, the therapy is a pharmacological therapy comprising administering to the subject an effective amount of an ADRB2 modulator, an ADRB3 modulator, a COMT modulator, or combinations thereof.

In some embodiments, the determined genotype of the subject with respect to ADRB2 is selected from the group consisting of two copies of Haplotype 2, two copies of Haplotype 3, one copy of both Haplotype 2 and Haplotype 3, and an effective amount of an ADRB2 modulator, a COMT modulator, or combinations thereof is selected as a therapy.

In some embodiments, the determined genotype of the subject with respect to ADRB3 is two copies of Haplotype 1, and an effective amount of an ADRB2 modulator, a COMT modulator, or combinations thereof is selected as a therapy.

In some embodiments, the determined genotype of the subject with respect to COMT is selected from the group consisting of two copies of APS, two copies of HPS, and one copy of both APS and HPS and an effective amount of an ADRB2 modulator, an ADRB3 modulator, a COMT modulator, or combinations thereof is selected as a therapy.

In some embodiments, both the ADRB2 antagonist and the ADRB3 antagonist are selected.

In one embodiment, methods of classifying a somatosensory disorder afflicting a subject are provided. In some embodiments, the method comprises determining a genotype of the subject with respect to a gene selected from the group consisting of ADRB2, ADRB3, COMT, and combinations thereof; and classifying the somatosensory disorder into a genetic subclass somatosensory disorder based on the determined genotype of the subject.

In some embodiments, classifying the somatosensory disorder into the genetic subclass somatosensory disorder is utilized to select an effective therapy for use in treating the genetic subclass somatosensory disorder.

In one embodiment, methods of modulating production of proinflammatory cytokines in a subject are provided. In some embodiments, the method comprises administering to the subject an effective amount of a COMT modulator, an ADRB2 modulator, an ADRB3 modulator, or combinations thereof. In some embodiments, the proinflammatory cytokines are selected from the group consisting of IL-6, IL-1α, IL-1β, TNF-α, and combinations thereof. In some embodiments, modulating production of proinflammatory cytokines comprises inhibiting production of proinflammatory cytokines.

In some embodiments, both the ADRB2 antagonist and the ADRB3 antagonist are administered to the subject.

In some embodiments, determining a genotype of the subject with respect to a gene selected from the group consisting of ADRB2, ADRB3, COMT, and combinations thereof and administering to the subject the effective amount of the COMT modulator, the ADRB2 modulator, the ADRB3 modulator, or combinations thereof based on the determined genotype of the subject.

In some embodiments, the determined genotype of the subject with respect to ADRB2 is selected from the group consisting of two copies of Haplotype 2, two copies of Haplotype 3, one copy of both Haplotype 2 and Haplotype 3, and the production of proinflammatory cytokines in the subject is modulated by administering the ADRB2 modulator, the COMT modulator, or combinations thereof to the subject.

In some embodiments, the determined genotype of the subject with respect to ADRB3 is selected from the group consisting of two copies of Haplotype 1, and the production of proinflammatory cytokines in the subject is modulated by administering the ADRB3 modulator, the COMT modulator, or combinations thereof to the subject.

In some embodiments, the determined genotype of the subject with respect to COMT is selected from the group consisting of two copies of APS, two copies of HPS, and one copy of both APS and HPS and the production of proinflammatory cytokines in the subject is modulated by administering the COMT modulator, the ADRB2 modulator, the ADRB3 modulator, or combinations thereof to the subject.

In one embodiment, methods of producing non-human animal models of a human somatosensory disorder are provided. In some embodiments, the method comprises modulating COMT activity, ADRB2 activity, ADRB3 activity, or combinations thereof in the non-human animal model to produce the non-human animal model of the human somatosensory disorder.

In some embodiments, the non-human animal model is a rodent.

In some embodiments, modulating COMT activity in the non-human animal model comprises inhibiting COMT activity in the non-human animal model.

In some embodiments, inhibiting COMT activity comprises administering a COMT inhibitor to the non-human animal model.

In some embodiments, the non-human animal model exhibits an increase in production of proinflammatory cytokines.

In some embodiments, the proinflammatory cytokines are selected from the group consisting of IL-6, IL-1β, TNF-α, IL-1α and combinations thereof.

In one embodiment, a non-human animal possessing modulated COMT activity, modulated ADRB2 activity, modulated ADRB3 activity, or combinations thereof, wherein the non-human animal exhibits characteristics of a somatosensory disorder is provided.

In some embodiments, the non-human animal is a genetically modified animal.

In some embodiments, the non-human animal transgenic animal overexpresses ADRB2, ADRB3, or both ADRB2 and ADRB3.

In some embodiments, the non-human animal is a COMT knockout or knockdown animal.

In one embodiment, methods of predicting COMT activity, ADRB2 activity, ADRB3 activity, or combinations thereof in a subject are provided. In some embodiments, the method comprises determining a genotype of the subject with respect to a gene selected from the group consisting of ADRB2, ADRB3, COMT, and combinations thereof; and comparing the genotype of the subject with at least one reference genotype associated with activity of ADRB2, ADRB3, COMT, and combinations thereof, wherein the reference genotype is selected from the group consisting of an ADRB2 genotype, an ADRB3 genotype, a COMT genotype, and combinations thereof, whereby activity of COMT activity, ADRB2 activity, ADRB3 activity, or combinations thereof is predicted.

In some embodiments, the COMT genotype of the reference genotype is selected from the group consisting of low pain sensitive haplotype (LPS), average pain sensitive haplotype (APS), and high pain sensitive haplotype (HPS); the ADRB2 genotype of the reference genotype is selected from the group consisting of Haplotype 1, Haplotype 2, Haplotype 3, and Uncommon; and the ADRB3 genotype of the reference genotype is selected from the group consisting of Haplotype 1, Haplotype 2, Haplotype 3, and Uncommon.

In some embodiments, the determined genotype of the subject with respect to COMT is selected from the group consisting of two copies of APS, two copies of HPS, and one copy of both APS and HPS and the subject is predicted to have low COMT activity.

In some embodiments, the determined genotype of the subject with respect to ADRB2 is selected from the group consisting of two copies of Haplotype 1 and the subject is predicted to have low ADRB2 activity.

In some embodiments, the determined genotype of the subject with respect to ADRB2 is selected from the group consisting of two copies of Haplotype 2, two copies of Haplotype 3, and one copy of both Haplotype 2 and Haplotype 3, and the subject is predicted to have high ADRB2 activity.

In some embodiments, the determined genotype of the subject with respect to ADRB2 is selected from the group consisting of two copies of Haplotype 3, and the subject is predicted to have high ADRB2 activity in the resting stage and low ADRB2 activity in response to agonist, including but not restricted to epinephrine.

In some embodiments, the determined genotype of the subject with respect to ADRB3 is selected from the group consisting of at least one copy of Haplotype 2, at least one copy of Haplotype 3 and the subject is predicted to have low ADRB3 activity.

In some embodiments, an effective dosage of a therapeutic compound metabolized by COMT is determined for the subject on the basis of the determined COMT genotype.

In some embodiments, example drugs include, but are not limited to: Steroid sex hormones such as estrogen; Drugs that inhibit COMT enzyme such as tolcapone; Drugs that influence the bioavailability of norepinephrine and dopamine such as methylphenidate and L-DOPA; Drugs that influence the reuptake of norepinephrine such as antidepressants; drugs that influence α-adrenergic receptors such as clonidine and mirtazapine; drugs that influence dopamine receptors such as antipsychotics.

In some embodiments, an adverse biological side effect to the subject by a compound metabolized by COMT can be predicted on the basis of the determined COMT genotype.

In some embodiments, the somatosensory disorder is selected from the group consisting of chronic pain conditions, fibromyalgia syndrome, tension headache, migraine headache, irritable bowel syndrome, chronic lower back pain, chronic fatigue, multiple chemical sensitivities, temporomandibular joint disorder, post-traumatic stress disorder, chronic idiopathic pelvic pain, Gulf War Syndrome, vulvar vestibulitis, osteoarthritis, rheumatoid arthritis, and angina pectoris.

In some embodiments the ADRB2 modulator is an ADRB2 antagonist, the ADRB3 modulator is an ADRB3 antagonist, and the COMT modulator is a COMT activator.

In some embodiments, determining the genotype of the subject comprises identifying at least one haplotype of ADRB2, ADRB3, COMT, or combinations thereof; identifying at least one polymorphism unique to at least one haplotype of ADRB2, ADRB3, COMT, or combinations thereof; identifying at least one polymorphism exhibiting high linkage disequilibrium to at least one polymorphism unique to the at least one ADRB2 haplotype, ADRB3 haplotype, COMT haplotype, or combinations thereof; or identifying at least one polymorphism exhibiting high linkage disequilibrium to at least one ADRB2 haplotype, ADRB3 haplotype, COMT haplotype, or combinations thereof.

In some embodiments, the ADRB2 genotype is selected from the group consisting of Haplotype 1, Haplotype 2, Haplotype 3, and Uncommon; the ADRB3 genotype is selected from the group consisting of Haplotype 1, Haplotype 2, Haplotype 3, and Uncommon; and the COMT genotype is selected from the group consisting of low pain sensitive haplotype (LPS), average pain sensitive haplotype (APS), and high pain sensitive haplotype (HPS).

Accordingly, it is an object of the presently disclosed subject matter to provide novel methods and materials for predicting and treating somatosensory disorders. This and other objects are achieved in whole or in part by the presently disclosed subject matter.

An object of the presently disclosed subject matter having been stated hereinabove, other aspects and objects will become evident as the description proceeds when taken in connection with the accompanying Drawings and Examples as best described herein below.

BRIEF DESCRIPTION OF THE DRAWINGS

FIGS. 3A and 3B show a model of proposed functional variants of ADRB2 corresponding to the three major haplotypes (H1, H2, and H3). Putative haplotype-specific expression of ADRB2 on the postsynaptic membrane of CNS neurons at (FIG. 3A) resting state and (FIG. 3B) following stimulation with an agonist. In the periphery, epinephrine is released from adrenal glands and binds ADRB2 expressed on smooth muscle.

FIG. 6A is a schematic diagram of COMT genomic organization and SNP positions and percentage distribution. COMT gene locus (chromosome 22, band q11.21) spans for 27,221 bases.

FIG. 6B is a schematic diagram of linkage disequilibrium between six SNP markers. Four SNPs, rs6269, rs4633, rs4818 and rs4680 (val[158]met), which occur within the central region of the COMT gene, were found to exhibit strong LDs with the strongest associations found between SNPs rs6269 and rs4818 (D'=0.94, $R^2$=0.88) and between SNPs rs4633 and rs4680 (D'=0.96, $R^2$=0.91). In contrast, SNP rs2097903, located in the 5' promoter region, and rs165599, located in the 3'UTR, did not show strong LDs. Thus, LD analysis demonstrated that the COMT locus covers 3 haploblocks. SNP rs2097903 is situated on the first haploblock, SNPs rs6269, rs4633, rs4818 and rs4680 are situated on the second haploblock and SNP rs165599 is situated on the third haploblock.

FIG. 6C shows the estimated frequencies of the COMT haplotypes. The sequence of alleles in each haplotype for haploblock 2 reflects the order of occurrence from 5' to 3' in the COMT gene (SNPs: rs6269, rs4633, rs4818 and rs4680 respectively). Seven haplotypes out of possible 16 were detected for these 4 SNPs with the most frequent haplotype (48.7%) composed of the most frequent alleles for all 4 markers (A_T_C_A for SNPs rs6269, rs4633, rs4818 and rs4680, respectively). The second major haplotype (36.5%) was composed of the least frequent alleles for all 4 markers (G_C_G_G). The third haplotype (10.5%) was composed of a combination of the most frequent alleles for SNPs rs4633 and rs4680 and the least frequent alleles for SNPs rs6269 and rs4818 (A_C_C_G). These three haplotypes accounted for 95.9% of all detected haplotypes. These findings are consistent with previously reported LD analysis of COMT SNPs that each haploblock within human genomic DNA is usually represented by three to five major haplotypes.

IG. 7A is a schematic diagram of ADRB3 genomic organization, SNP positions and distribution percentages. The human ADRB3 consists of 2 exons and spans ~5 kb on chromosome 6p12. The protein coding region is shown as break blocks.

Figures 7A, 7B:
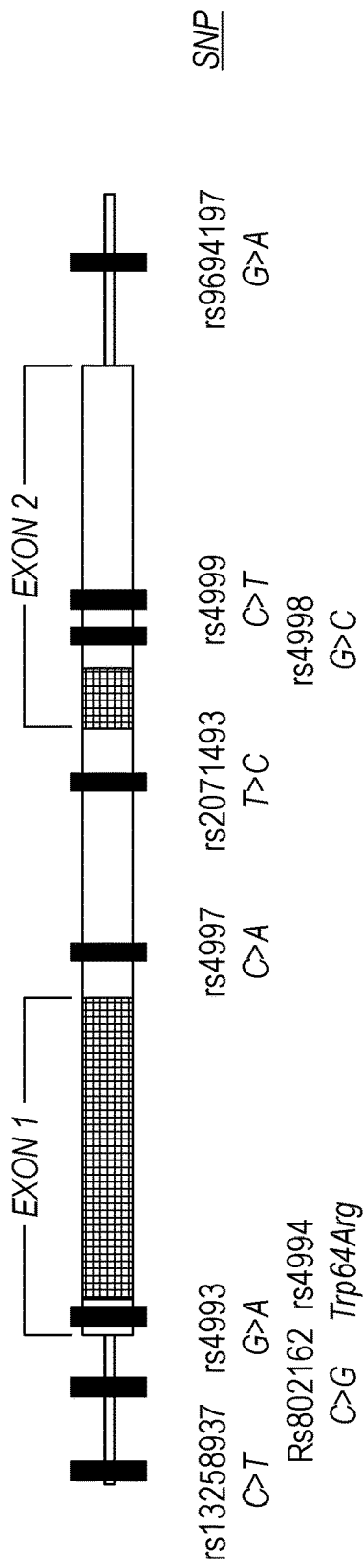

FIG. 7B shows estimated frequencies of the ADRB3 haplotypes. The sequence of alleles in each haplotype reflects the order of occurrence from 5' to 3' in the ADRB3 gene locus (SNPs: rs4994, rs4994, rs4997, rs2071493, rs4998, rs4999 and rs9694197, respectively). Minor alleles are shown in bold.

Figure 8:
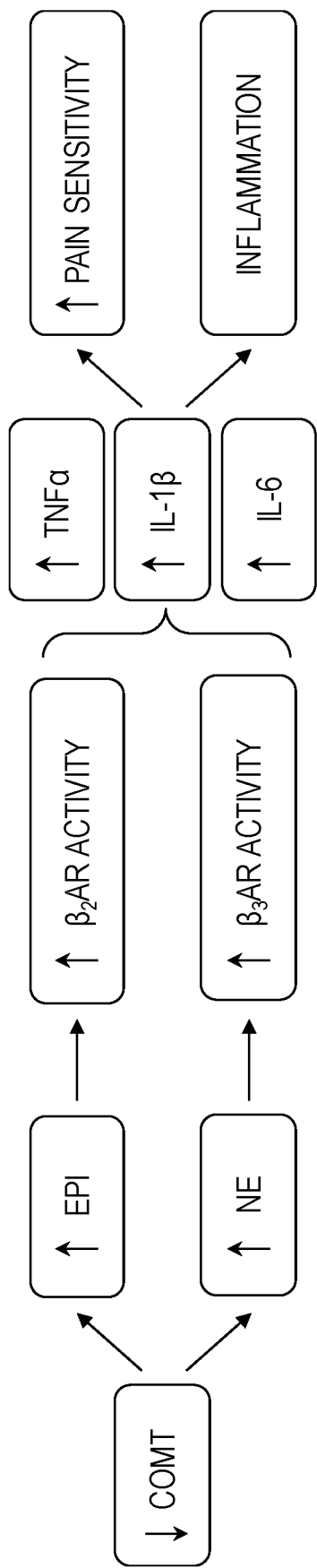

FIG. 8 is a schematic diagram showing interactions of COMT, ADRB2 ($\beta_2$AR), and ADRB3 ($\beta_3$AR) affecting pain sensitivity and inflammation via modulation of proinflammatory cytokine production.

Figure 9:
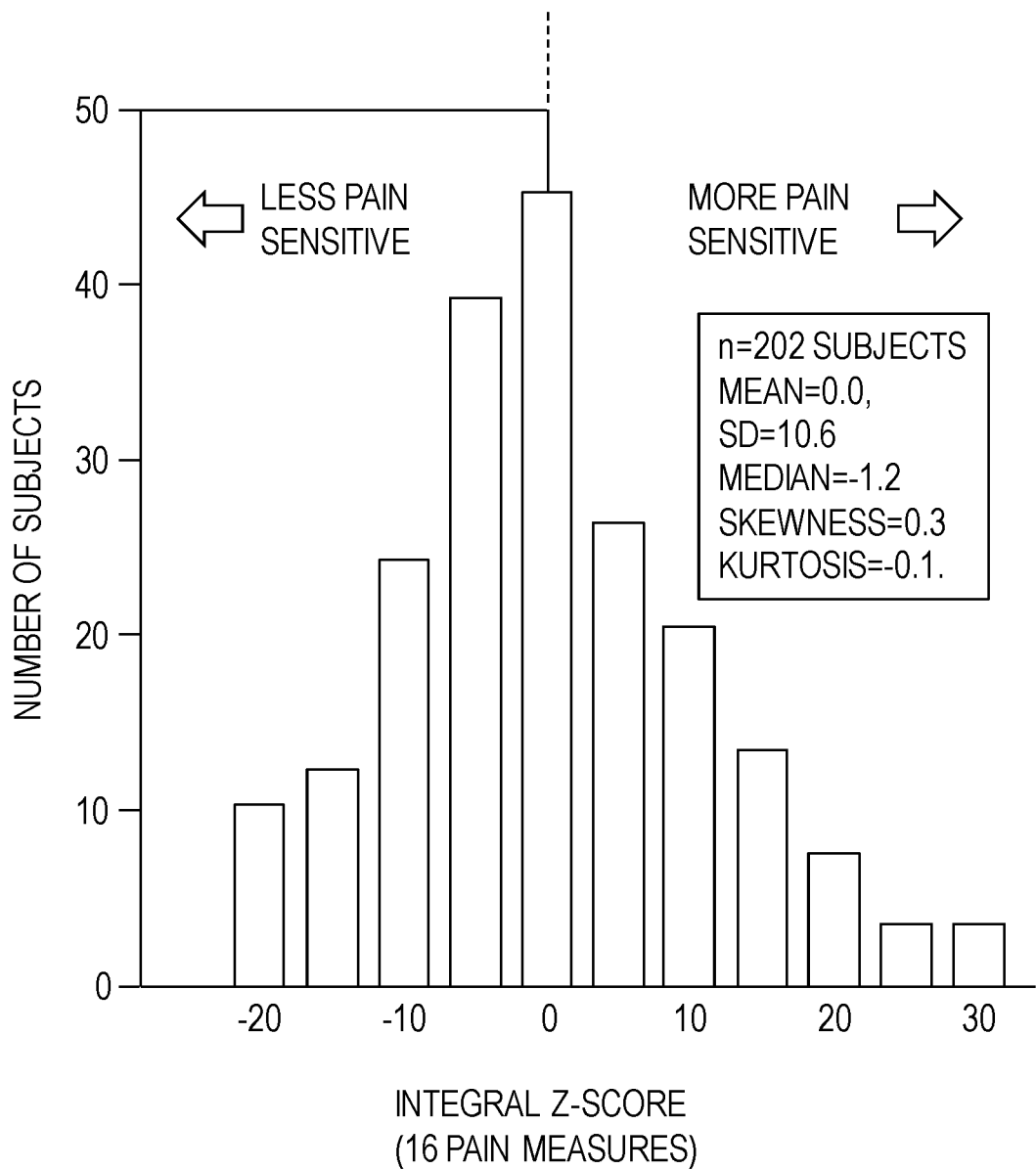

FIG. 9 is a graph showing distribution of a summary measure of pain sensitivity. A summary measure of pain sensitivity was derived from 16 individual pain measures, each standardized to unit normal deviates (z-scores) with a mean of zero and standard deviation of one. The 16 pain measures were: thermal pain threshold conveyed by A$\delta$ afferents and both threshold and tolerance conveyed by C-fiber afferents, all measured in ° C. at each of three anatomical sites (arm, cheek and foot); tolerance to temporal summation of C-fiber mediated pain (as reported on 0-100 visual analog scale); right arm ischemic pain onset and tolerance (seconds); and mechanical pain thresholds (kg) assessed over the temporalis and masseter muscles, the temporomandibular joint and the ventral surfaces of wrists. Individuals represented at the extreme left-side of the figure are resistant to pain evoking procedures while individuals represented at the extreme right-side of the figure are most sensitive to pain evoking pain procedures.

Figure 10:
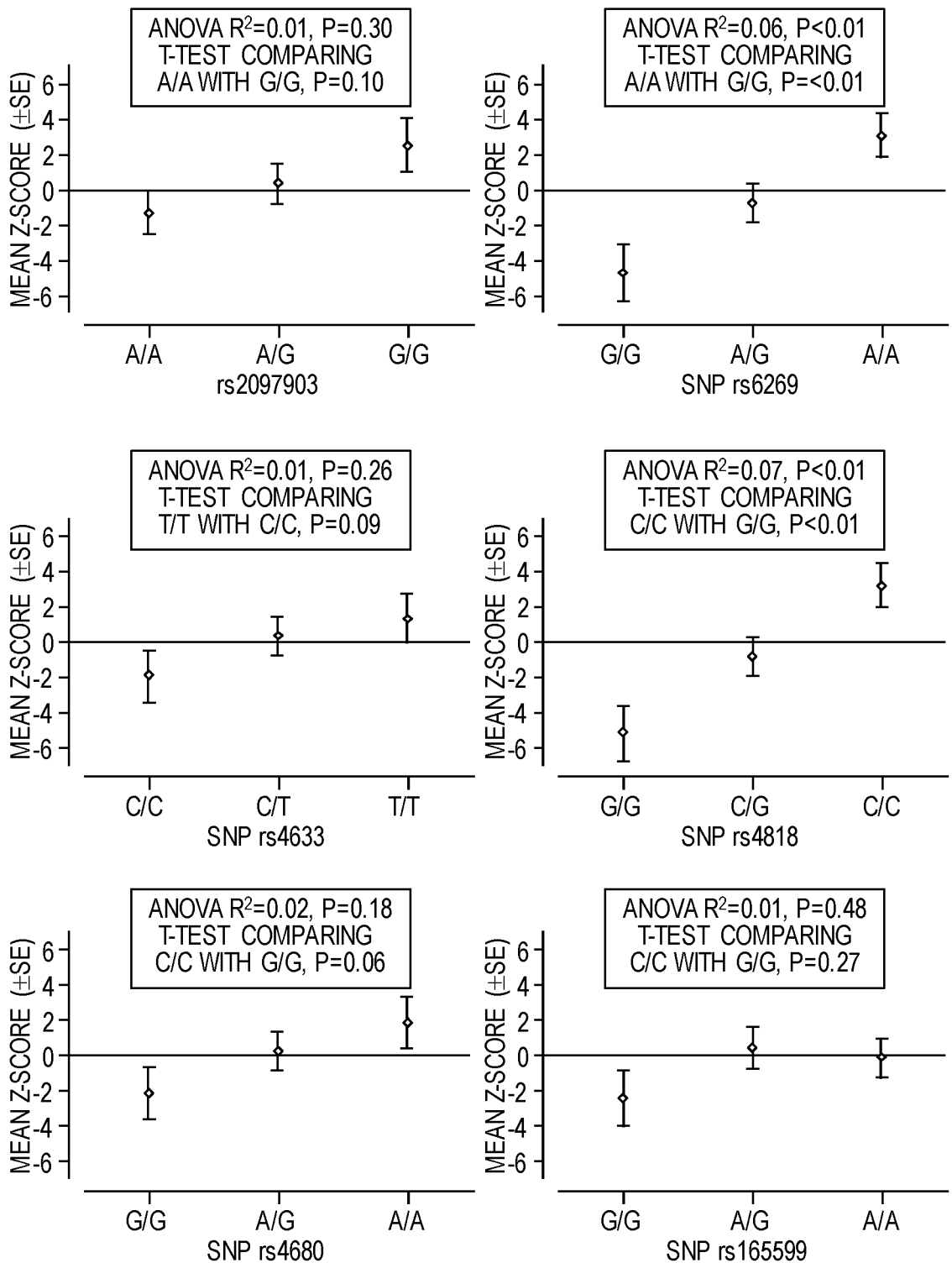

FIG. 10 is a series of graphs showing variations in pain tolerance associated with individual SNPs. The first presented allele in each plot is associated with the least pain sensitivity. Differences among all three allele combinations were assessed by analysis of variance (ANOVA) using z-score as the dependent variable. The significance of the difference in the mean z-scores associated with each homozygous genotype was determined via the Students t-test. Each value represents the mean z-score with associated s.e.m.

Figure 11:
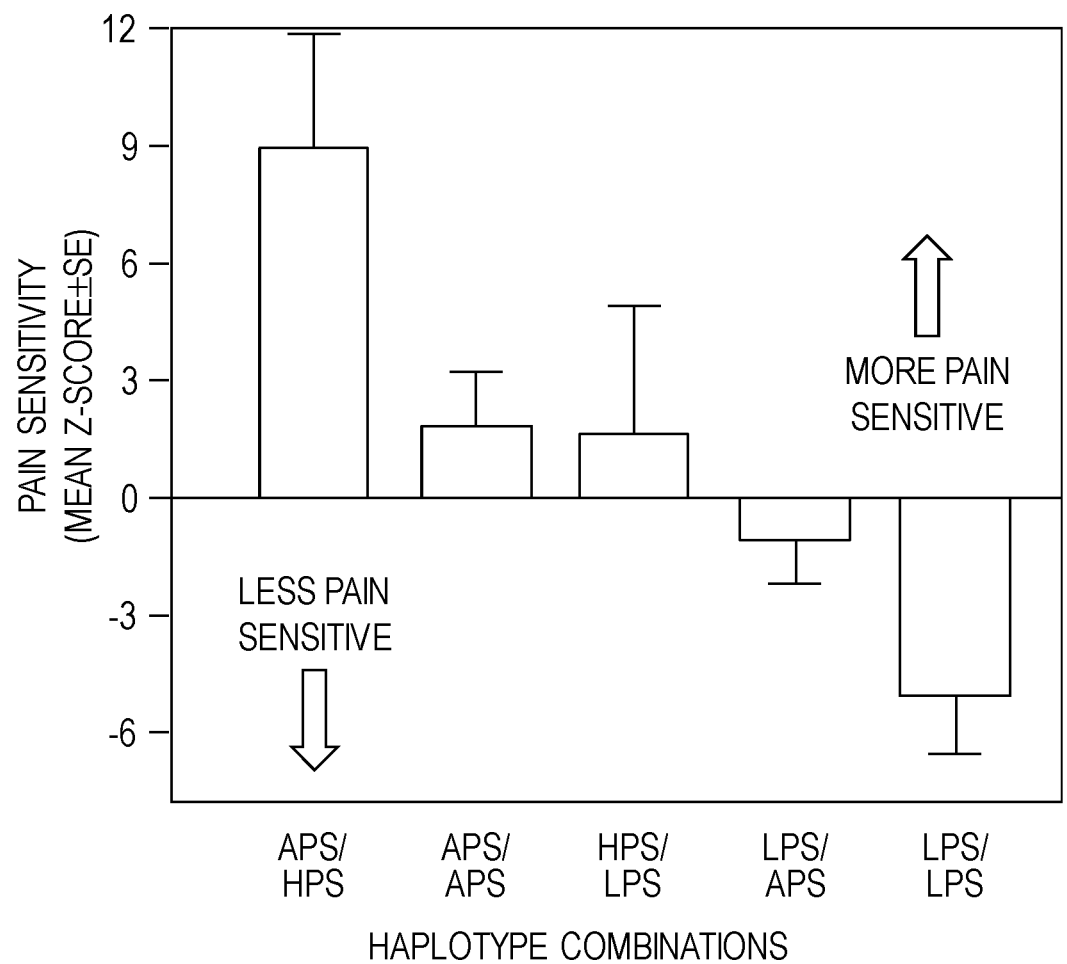

FIG. 11 is a graph showing pain responsiveness categorized by three major COMT haplotype combinations. LPS—haplotype G_C_G_G, APS—haplotype A_T_C_A, HPS—haplotype A_C_C_G. The greater values reflect greater pain sensitivity. Each value represents the mean z-score with associated s.e.m.

Figure 12A:
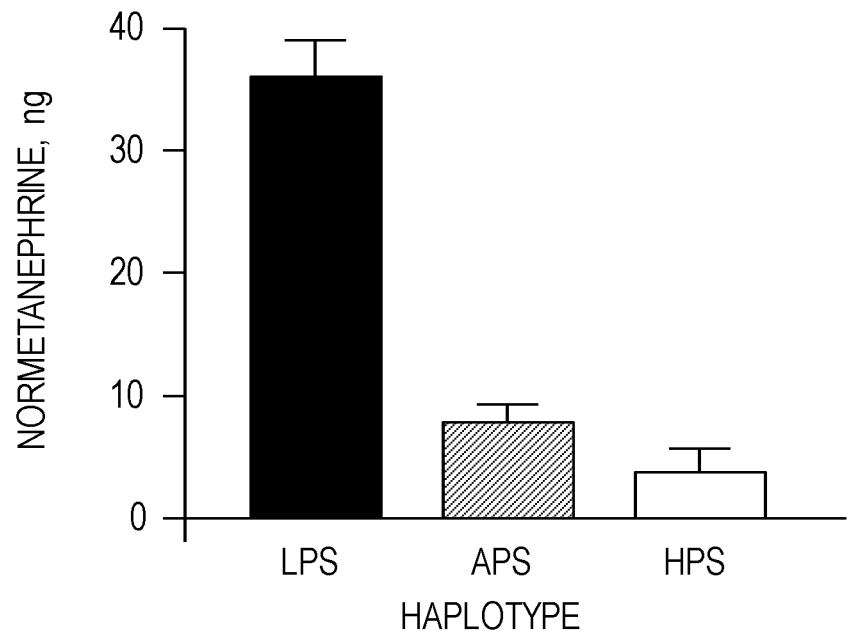
Figure 12B:
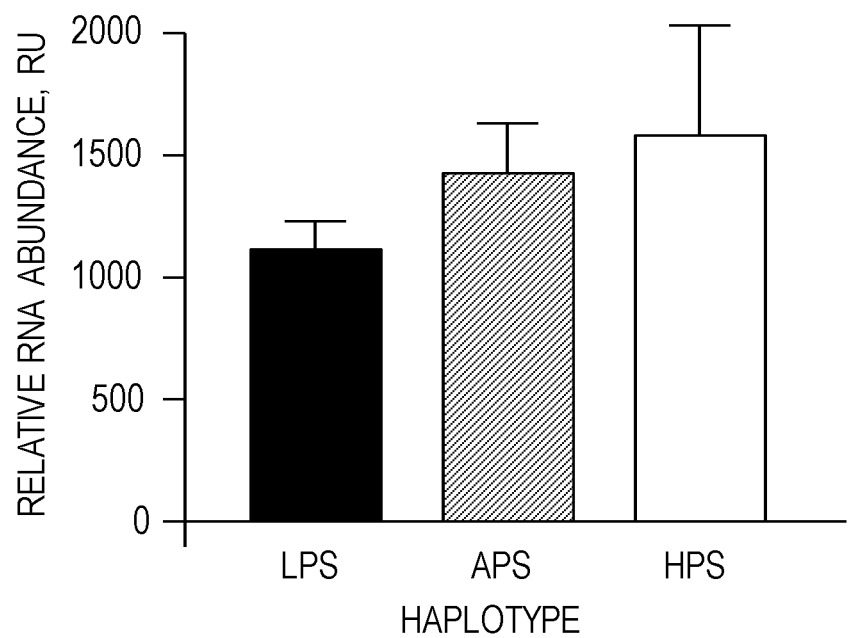

FIGS. 12A and 12B are graphs showing the effect of haplotype on COMT activity in transfected HEK 293 cells. HEK 293 cells were transiently transfected with 6 full-length COMT cDNA clones that corresponded to the three major haplotypes (LPS, APS, HPS). The expression of COMT protein was assessed by measurement COMT enzymatic activity (FIG. 12A) in the lysate from transfected cells. COMT activity was assessed from 2 independent clones for each haplotype. Two independent ELISAs for each of the 2 independent transfections were performed for each clone. The graph shows the average values for the 8 measurements for each haplotype. The COMT activity was calculated as ng of normetanephrine (NMN), synthesized during 1 hour at 37° C. under described enzymatic condition per $10^5$ transfected cells. The highest COMT activity was observed for LPS haplotypes ([NMN]=34.3±3.0 ng per $10^5$ cells; FIG. 12A), the lower activity was observed for APS haplotype ([NMN]=7.2±1.53 ng per $10^5$ cells) while HPS haplotypes produced the lowest activity ([NMN]=3.0±2.20 ng per $10^5$ cells; FIG. 12A). The relative abundance of COMT RNA (FIG. 12B) was assessed by real-time PCR. Each value represents the mean value with associated s.e.m.

Figure 13A:
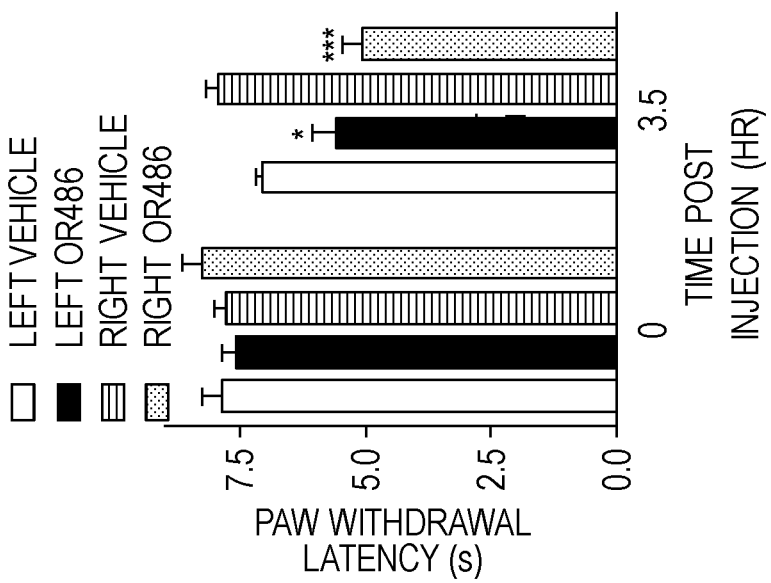
Figure 13B:
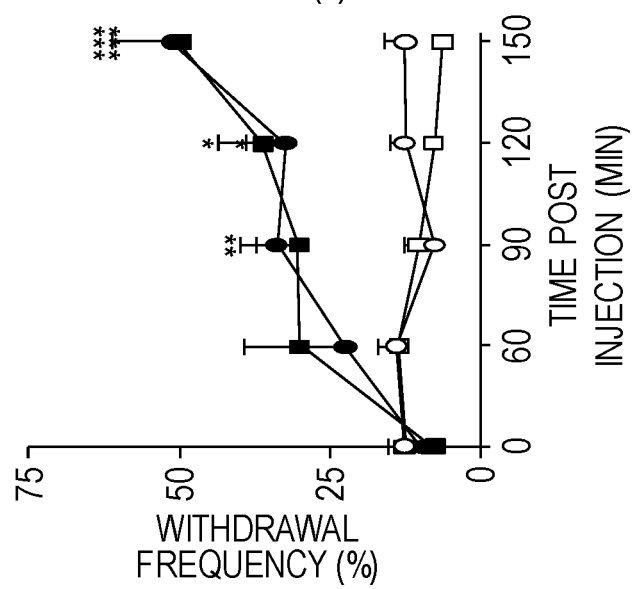
Figure 13C:
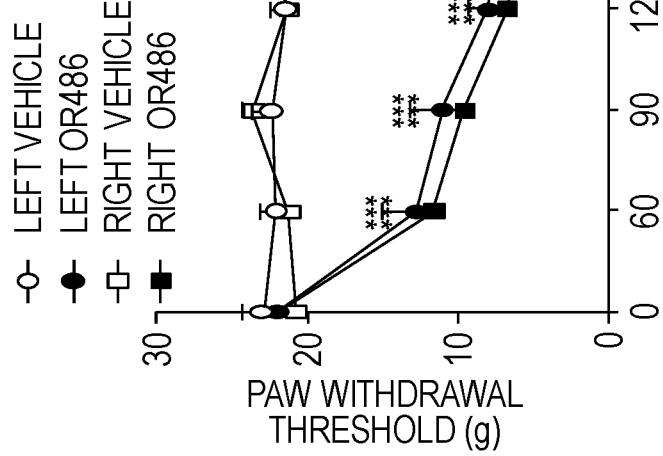

FIGS. 13A-13C are a series of graphs showing the effect of COMT inhibition on rat pain behavior. Baseline sensitivity to mechanical stimuli was estimated by measuring both threshold (FIG. 13A) and frequency (FIG. 13B) of paw withdrawal. Sensitivity to thermal stimuli was estimated by measuring latency of paw withdrawal (FIG. 13C). After establishing baseline sensitivity, animals received the COMT inhibitor OR486 (30 mg/kg i.p.) or vehicle one hour prior to testing. Data are expressed as Mean±SEM. *P<0.001, P<0.01, *P<0.05 different from control conditions by ANOVA and Bonferroni post hoc tests. N=8 rats per group.

Figure 14C:
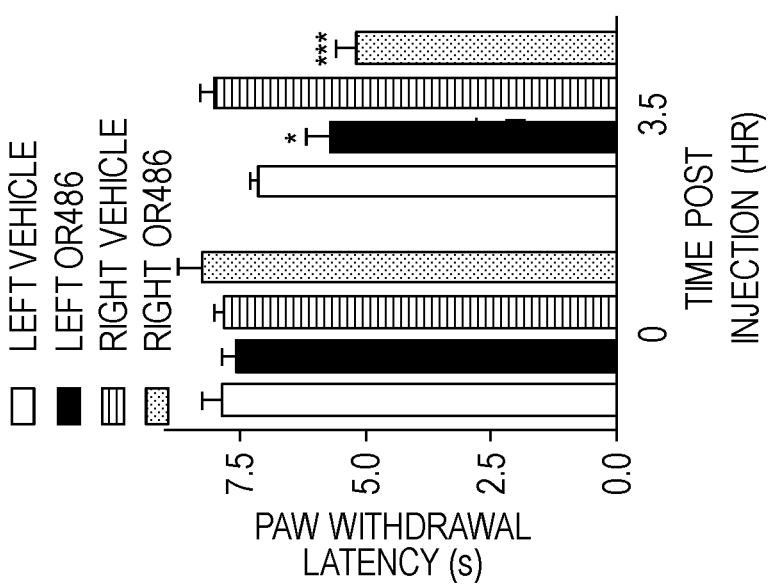
Figure 14B:
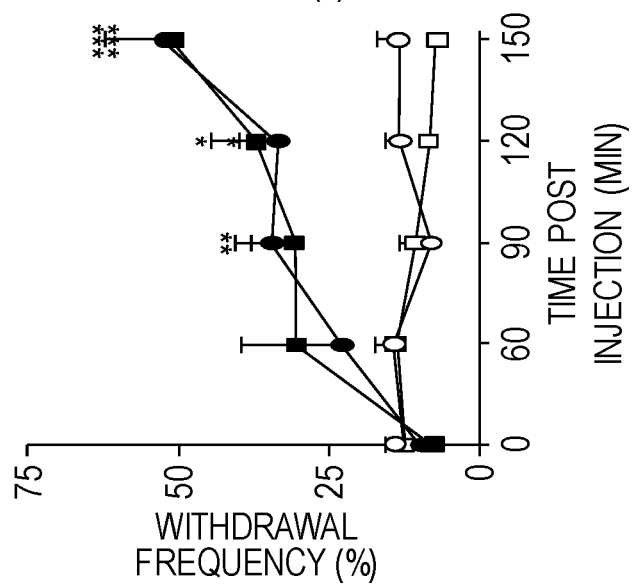
Figure 14A:
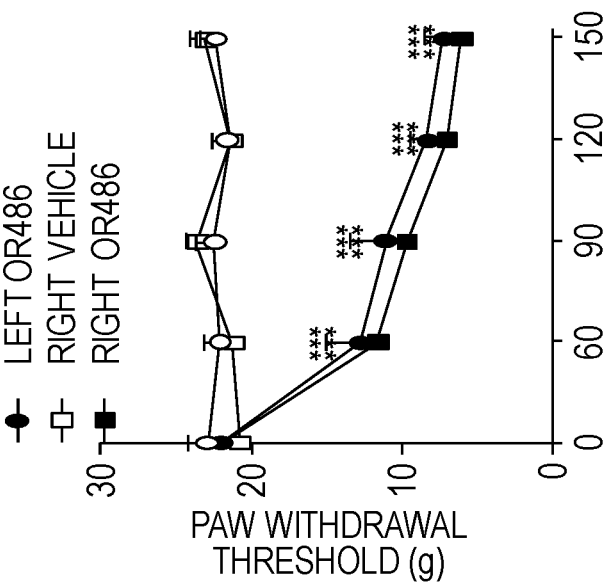

FIGS. 14A, 14B, and 14C are graphs showing pain sensitivity and TMD incidence by haplotype groupings. All subjects were subdivided to two groups: LPS and HPS/APS. Subjects were assigned to the LPS group if they carried at least one LPS haplotype. Subjects were assigned to the HPS/APS group if they carried only APS and HPS haplotypes. FIG. 14A shows that subjects from the LPS group demonstrated significantly lower pain responsiveness than those from the HPS/APS group (P=0.02, t-test). FIG. 14B shows the number of incidence case per 100 person years as a function of haplotype group. FIG. 14C is a graph of paw withdrawal latency.

FIGS. 15A-15I are a series of graphs demonstrating that COMT inhibition increases pain sensitivity and proinflammatory cytokine production. Separate groups of rats received i.p. injections of the COMT inhibitor OR486 (30 mg/kg) or vehicle 30 min prior to i.pl. saline (N=8 per group). The comparison group received i.p. injections of vehicle 30 min prior to i.pl. 3% carrageenan (N=8). Baseline responsiveness to von Frey monofilaments and radiant heat did not differ between groups prior to pharmacological manipulations. Administration of carrageenan or OR486 (FIG. 15A), decreased paw withdrawal threshold to mechanical stimuli ($F_{2,6}$=244.0, P<0.0001; P<0.001 per comparison) (FIG. 15B), increased paw withdrawal frequency to repeated presentation of a 25 g monofilament ($F_{2,6}$=20.26, P<0.003; P<0.01 and P<0.05, respectively), and (FIG. 15C) decreased paw withdrawal latency to thermal stimuli ($F_{2,21}$=48.07, P<0.0001; P<0.001 per comparison) relative to vehicle. Rats receiving carrageenan or OR486 had elevated levels of (FIG. 15D) TNF$\alpha$ ($F_{2,9}$=8.213, P<0.01) (FIG. 15E) IL-1$\beta$ ($F_{2,8}$=7.15, P<0.02) (FIG. 15F) and IL-6 ($F_{2,9}$=7.15, P<0.02). A second COMT inhibitor was then employed. Separate groups of rats received i.p. injections of OR486 (30 mg/kg), RO41-0960 (30 mg/kg), or vehicle (N=8 per group). Administration of RO41-0960 (FIG. 15G) decreased paw withdrawal threshold to mechanical stimuli ($F_{2,6}$=253.6, P<0.0001; P<0.001 per comparison), (FIG. 15H) increased paw withdrawal frequency to mechanical stimuli ($F_{2,8}$=120.1, P<0.0001; P<0.001 and P<0.01, respectively), and (FIG. 15I) decreased paw withdrawal latency to thermal stimuli ($F_{2,21}$=33.14, P<0.0001; P<0.001 and P<0.01, respectively) relative to vehicle. Data are 30 Mean±SEM. *P<0.001, P<0.01, *P≤0.05 different from vehicle+saline (a-f) or vehicle (g-i).

FIGS. 16A-16C are graphs showing COMT inhibition increases pain sensitivity in the non-inflamed paw. Separate groups of rats received i.p. injections of the COMT inhibitor OR486 (30 mg/kg) or vehicle 30 min prior to i.pl. administration of saline (N=8 per group). The comparison group received i.p. injections of vehicle 30 min prior to i.pl.

administration of 3% carrageenan in the right hindpaw (N=8). Administration of OR486 (FIG. 16A) decreased paw withdrawal threshold to mechanical stimuli ($F_{2,6}$=436.6, P<0.0001; P<0.001 per comparison), (FIG. 16B) increased paw withdrawal frequency to repeated presentation of a 25 g monofilament ($F_{2,6}$=30.31, P<0.0008; P<0.01 per comparison), and (FIG. 16C) decreased paw withdrawal latency to thermal stimuli ($F_{2,21}$=27.81, P<0.0001; P<0.001 per comparison) relative to administration of vehicle or carrageenan in the contralateral non-inflamed paw. Data are expressed as Mean±SEM. *P<0.001, P<0.01, *P<0.05 different from all comparison groups.

Figure 17C:
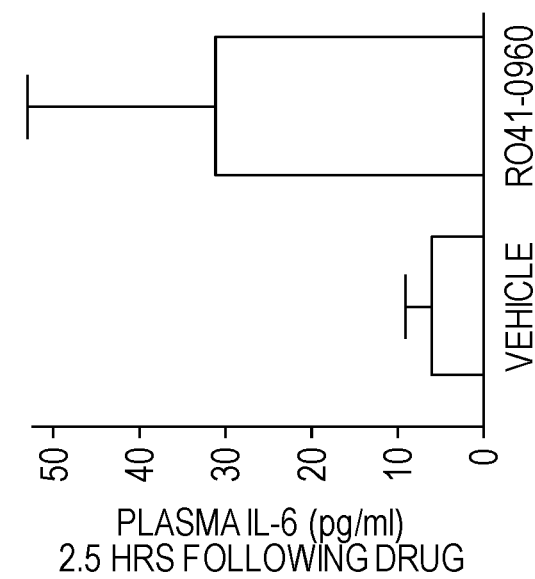
Figure 17B:
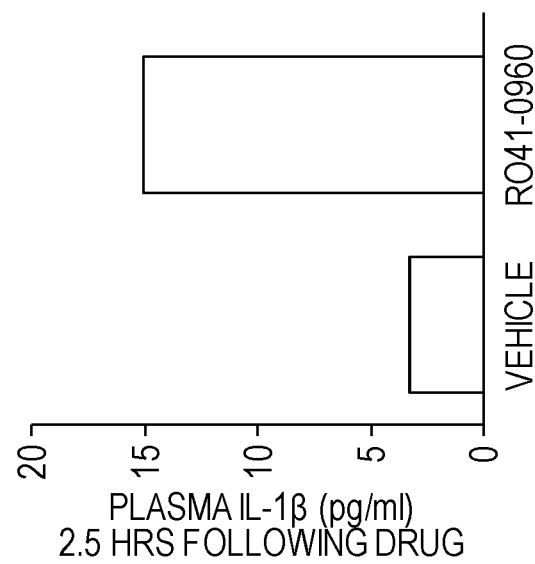
Figure 17A:
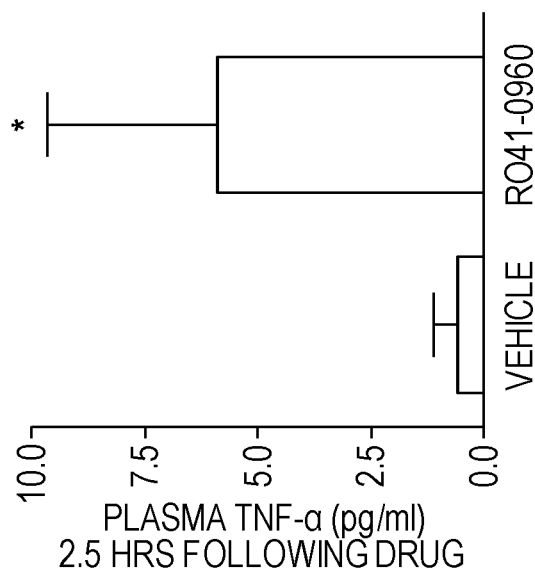

FIGS. 17A-17C are graphs showing that the COMT inhibitor RO41-0960 increases plasma proinflammatory cytokine levels. Separate groups of rats received RO41-0960 (30 mg/kg i.p.) or vehicle (N=8 per group). Rats receiving RO41-0960 exhibited (FIG. 17A) elevated plasma levels of TNFα ($t_{13}$=2.44, P<0.05). FIG. 17B shows animals receiving RO41-0960 also exhibited a 4.5 fold increase in plasma levels of IL-1β, however statistical analysis was not conducted because of inadequate sample size due to sample loss. FIG. 17C shows a trend towards elevated levels of IL-6 (P<0.06) was apparent. Data are expressed as Mean±SEM. *P<0.05 different from vehicle.

FIGS. 18A-18F are graphs showing that administration of the nonselective βAR antagonist propranolol completely blocks OR486-induced pain sensitivity and proinflammatory cytokine production. Separate groups of rats received i.p. injections of the αAR antagonist phentolamine (3 mg/kg), the βAR antagonist propranolol (3 mg/kg), the $D_1$-like dopamine antagonist SCH23390 (0.2 mg/kg), the $D_2$-like dopamine antagonist spiperone (0.2 mg/kg), or vehicle 10 minutes prior to i.p. administration of OR486 (N=8 per group). Baseline responsiveness to mechanical and thermal stimuli did not differ between groups prior to pharmacological manipulations. Administration of propranolol prior to OR486 normalized (FIG. 18A) paw withdrawal threshold to mechanical stimuli ($F_{5,15}$=305.9, P<0.0001; P<0.001 per comparison), (FIG. 18B) paw withdrawal frequency to mechanical stimuli ($F_{5,15}$=93.96, P<0.0001; P<0.001 per comparison), and FIG. 18C) paw withdrawal latency to radiant heat ($F_{5,42}$=24.47, P<0.0001; P<0.01 per comparison) relative to animals receiving phentolamine, SCH23390, spiperone, or vehicle prior to OR486. Preemptive administration of propranolol also decreased plasma levels of (FIG. 18D) TNFα ($F_{2,21}$=17.08, P<0.0001), (FIG. 18E) IL-1β ($F_{2,20}$=17.78, P<0.001), and (FIG. 18F) IL-6 ($F_{2,20}$=3.65, P<0.05) relative to administration of vehicle prior to OR486. Data are expressed as Mean±SEM. *P<0.001, P<0.01 different from vehicle+OR486, phentolamine+OR486, SCH23390+OR486, and spiperone+OR486. +P<0.05 different from vehicle+OR486. ####P<0.001 different from vehicle+vehicle and propranolol+OR486. $P<0.05 different from propranolol+OR486.

FIGS. 19A-19C are graphs showing adrenergic and dopaminergic antagonists administered in the absence of OR486 do not alter pain sensitivity. Separate groups of rats received the α-adrenergic antagonist phentolamine (3 mg/kg), the β-adrenergic antagonist propranolol (3 mg/kg), the $D_1$-like dopamine antagonist SCH23390 (0.2 mg/kg), the $D_2$-like dopamine antagonist spiperone (0.2 mg/kg), or vehicle 10 min prior to i.p. administration of vehicle (N=8 per group). Administration of phentolamine, propranolol, SCH23390, or spiperone failed to affect (FIG. 19A) paw withdrawal threshold to mechanical stimuli, (FIG. 19B) paw withdrawal frequency to mechanical stimuli, or (FIG. 19C) paw withdrawal latency to radiant heat relative to vehicle. Data are expressed as Meant±SEM.

FIGS. 20A-20L are graphs showing that administration of selective antagonists for $β_2$- or $β_3$ARs reduces OR486-induced pain sensitivity and proinflammatory cytokine production. Separate groups of rats received i.p. injections of the $β_1$ antagonist betaxolol (0.1, 1.0, and 10 mg/kg), the $β_2$ antagonist ICI118,551 (0.05, 0.5, and 5 mg/kg), the $β_3$ antagonist SR59230A (0.5, 5, and 50 mg/kg), or vehicle 10 min prior to i.p. administration of OR486 (N=6 per group). Baseline responsiveness to mechanical and thermal stimuli did not differ between groups prior to pharmacological manipulations. Administration of the middle (0.5 mg/kg) or high (5.0 mg/kg) dose of ICI118,551 prior to OR486 (FIG. 20A) increased paw withdrawal threshold ($F_{4,12}$=281.2, P<0.0001; P<0.001 per comparison) and (FIG. 20B) decreased paw withdrawal frequency ($F_{4,12}$=87.61, P<0.0001; P<0.05 per comparison) to mechanical stimuli relative to animals receiving vehicle or the low (0.05 mg/kg) dose of ICI118,551 prior to OR486. (FIG. 20C) Administration of the high (5.0 mg/kg) dose of ICI118,551 increased paw withdrawal latency to radiant heat relative to animals receiving vehicle prior to OR486 ($F_{4,25}$=9.87, P<0.0001; P<0.01). Administration of the middle (5 mg/kg) or high (50 mg/kg) dose of SR59230A prior to OR486 (FIG. 20D) increased paw withdrawal threshold to mechanical stimuli ($F_{4,12}$=151.4, P<0.0001; P<0.001 per comparison), (FIG. 20E) decreased paw withdrawal frequency ($F_{4,12}$=104.6, P<0.0001; P<0.001 per comparison) to mechanical stimuli, and (FIG. 20F) increased paw withdrawal latency to thermal stimuli ($F_{4,25}$=10.65, P<0.0001; P<0.05 per comparison) relative to animals receiving vehicle prior to OR486. Animals receiving selective $β_2$- or $β_3$ARs antagonists prior to OR486 also exhibited decreased levels of (FIG. 20G) TNFα ($F_{3,38}$=5.94, P<0.003), (FIG. 20H) IL-1β ($F_{3,43}$=20.02, P<0.001), and (FIG. 20I) IL-6 ($F_{3,44}$=9.17, P<0.0001) relative to those receiving vehicle prior to OR486. Cytokine data for animals receiving the low, middle, and high dose of ICI118,551 or SR59230A were pooled as they did not differ. Administration of the $β_1$AR antagonist betaxolol prior to OR486 failed to alter (FIG. 20J) paw withdrawal threshold to mechanical stimuli, (FIG. 20K) paw withdrawal frequency to mechanical stimuli, or (FIG. 20L) paw withdrawal latency to radiant heat relative to animals receiving vehicle prior to OR486. Data are expressed as Mean±SEM. +++P<0.001, ++P<0.01, +P<0.05 different from vehicle+OR486. *P<0.001, P<0.01, *P<0.05 different from vehicle+vehicle. ###P<0.001, ##P<0.01 different from vehicle+vehicle, ICI118,551+OR486, or ICI118,551+OR486. $$$P<0.001, $P<0.05 different from vehicle+OR486, betaxolol (0.1 mg/kg)+OR486, betaxolol (1.0 mg/kg)+OR486, and betaxolol (10 mg/kg)+OR486.

Figure 21A:
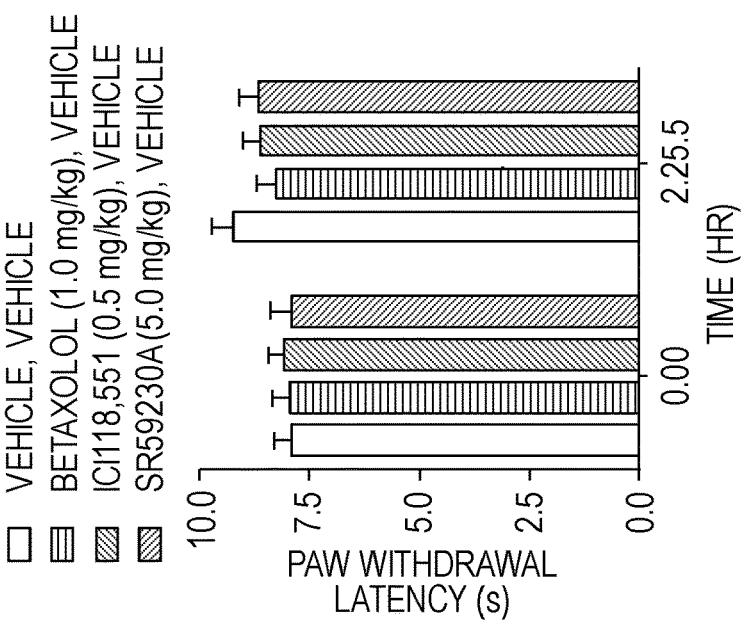
Figure 21B:
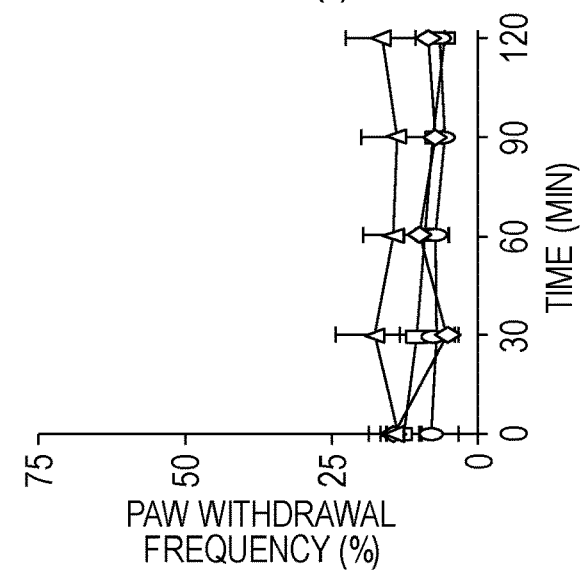
Figure 21C:
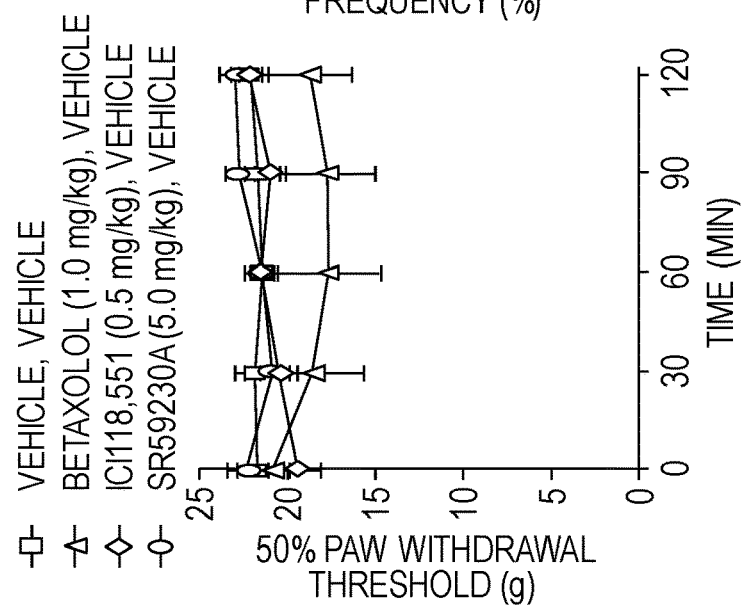

FIGS. 21A-21C are graphs showing that selective βAR antagonists administered in the absence of OR486 do not alter pain sensitivity. Separate groups of animals received i.p. injections of the $β_1$ antagonist betaxolol (1.0 mg/kg), the $β_2$ antagonist ICI118,551 (0.5 mg/kg), the $β_3$ antagonist SR59230A (5 mg/kg), or vehicle 10 min prior to i.p. administration of vehicle (N=6 per group). Administration of betaxolol, ICI118,551, or SR59230A failed to affect (FIG. 21A) paw withdrawal threshold to mechanical stimuli, (FIG. 21B) paw withdrawal frequency to mechanical stimuli, or (FIG. 21C) paw withdrawal latency to radiant heat relative to vehicle. Data are expressed as Mean±SEM.

FIGS. 22A-22F are graphs showing that coadministration of selective antagonists for $β_2$- and $β_3$ARs completely blocks OR486-induced pain sensitivity and proinflammatory cytokine production. Separate groups of rats received i.p. injections of ICI118,551 (0.5 mg/kg)+SR59230A (5.0 mg/kg) or vehicle prior to i.p. administration of OR486 (N=8 per group). Baseline responsiveness to mechanical and thermal stimuli did not differ between groups prior to pharmacological manipulations. Concurrent administration of ICI118,551 and SR59230A prior to OR486 completely normalized OR486-induced (FIG. 22A) mechanical allodynia ($t_3$=23.69, P<0.0003), (FIG. 22B) mechanical hyperalgesia ($t_3$=42.77, P<0.0001), and (FIG. 22C) thermal hyperalgesia ($t_7$=10.60, P<0.0001). Rats receiving concurrent administration of $\beta_2$- and $\beta_3$AR antagonists prior to OR486 also had decreased plasma levels of (FIG. 22D) TNFα ($t_{13}$=2.45, P<0.03), (FIG. 22E) IL-1β ($t_{14}$=2.63, P<0.02), and (FIG. 22F) IL-6 ($t_{14}$=1.75, P=0.05) relative to rats receiving vehicle prior to OR486. Data are expressed as Mean±SEM. *P<0.001, P<0.01, *P≤0.05 different from vehicle.

FIGS. 23A-23E are graphs showing that stimulation of $\beta_2$- and $\beta_3$AR in vitro leads to increased transcription of proinflammatory cytokines. Drug doses within one log unite of the ED50 or ID50 were selected based on a dose response curve (data are not shown). Cells were pretreated with the $\mu_1$ antagonist betaxolol (0.3 μM), the $\beta_2$ antagonist ICI118,551 (0.3 μM), the $\mu_3$ antagonist SR59230A (0.1 μM), or vehicle 30 min prior to 1 hr treatment with the $\beta_2$ agonist salmeterol (0.5 μM) or the $\beta_3$ agonist CL316243 (0.3 μM). In macrophages, stimulation of $\beta_2$ARs by salmeterol produced a (FIG. 23A) 38-fold increase in IL-1β ($F_{4,15}$=1068, P<0.0001) and (FIG. 23B) a 6.5-fold increase in IL-6 ($F_{4,15}$=462.6, P<0.0001) mRNA levels. In adipocytes, stimulation of $\beta_2$ARs by salmeterol produced a (FIG. 23C) 6-fold increase in TNFα ($F_{4,15}$=579.2, P<0.0001) and (FIG. 23D) an 8-fold increase in IL-6 ($F_{4,15}$=333.2, P<0.0001) mRNA levels. The salmeterol-induced increase in macrophage IL-1β and IL-6 transcript levels and adipocyte TNFα and IL-6 transcript levels was completely blocked by ICI118,551, but not by betaxolol or SR59230A. (FIG. 23E) Similarly, stimulation of $\beta_3$ARs in adipocytes by CL316243 produced a 28-fold increase in IL-6 mRNA levels ($F_{4,15}$=897.9, P<0.0001). The CL316243-induced increase in adipocyte IL-6 transcript levels was completely blocked by SR59230A, but not by betaxolol or ICI118,551. Data are expressed as Mean±SEM. ***P<0.001 different from untreated and ICI118,551+salmeterol. ####P<0.001 different from untreated and SR59230A+CL316243.

FIGS. 24A-24D are graphs showing that selective βAR antagonists administered in the absence of $\beta_2$AR stimulation by salmeterol or $\beta_3$AR stimulation by CL316243 do not meaningfully alter proinflammatory cytokine transcription. Macrophages and adipocytes received betaxolol (0.3 μM), ICI118,551 (0.3 μM), SR59230A (0.1 μM), or no treatment. Relative to untreated macrophages, administration of betaxolol, ICI118,551, or SR59230A resulted in a (FIG. 24A) 0.91-1.16 fold induction of IL-1β mRNA and (FIG. 24B) 0.81-0.96 fold induction of IL-6 mRNA. Relative to untreated adipocytes, administration of betaxolol, ICI118, 551, or SR59230A resulted in a (FIG. 24C) 0.84-1.47 fold induction of TNFα mRNA and (FIG. 24D) 0.91-1.22 fold induction of IL-6 mRNA. Data are expressed as Mean±SEM.

FIG. 25 is a table providing relative EST abundance. *BLAST search was performed using RefSeq sequence of ADRB2 NM_000024.3. **This number reflects the ratio between the amount of observed EST's and the amount expected if expression levels were equal between the three haplotypes.

DETAILED DESCRIPTION

Figure 1:
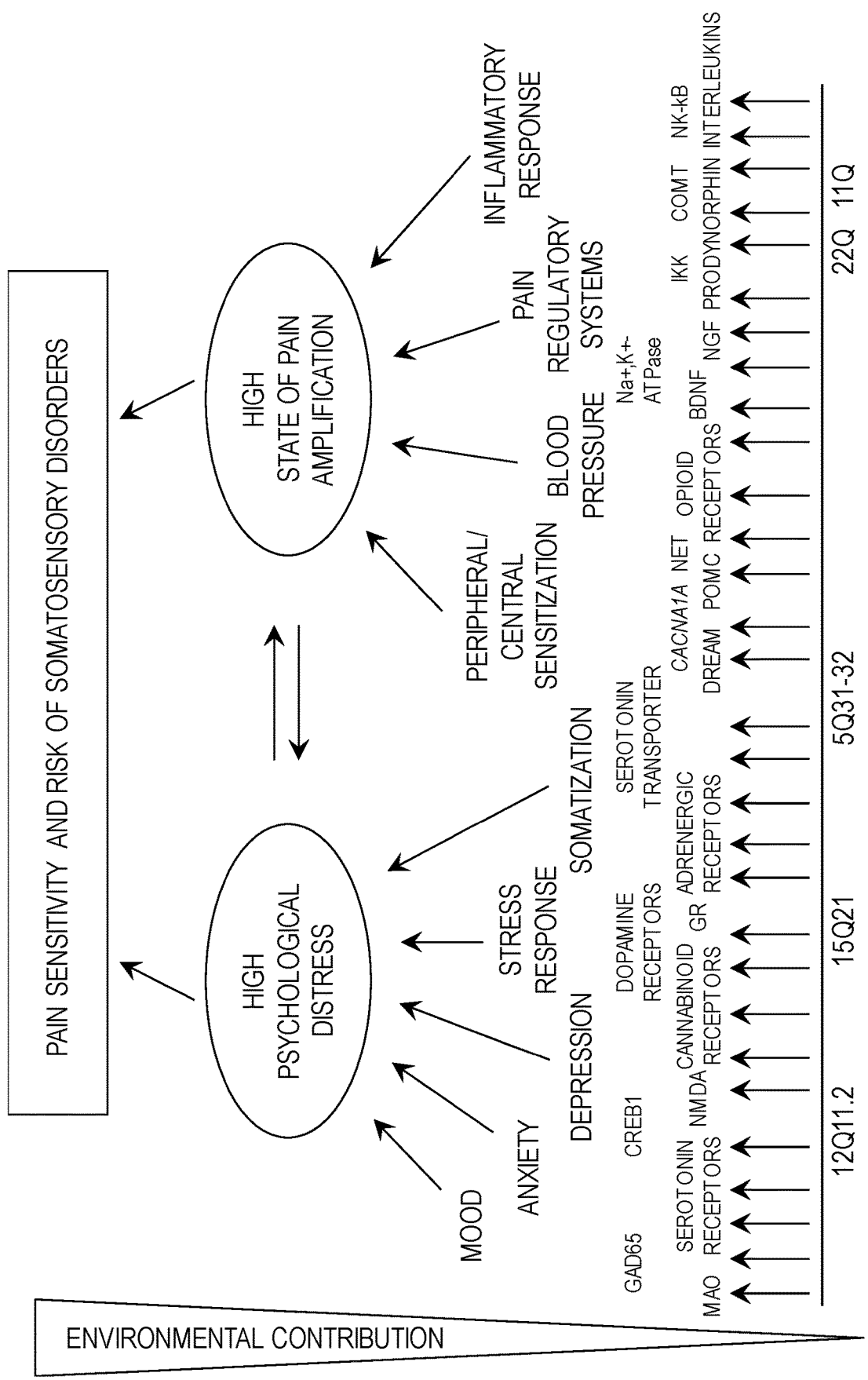
FIG. 1 shows a model of somatosensory disorder risk factors. The model displays likely biological and psychological determinants that contribute to the risk of somatosensory disorder onset and persistence.

Somatosensory disorders are comprised of several chronic clinical conditions that are characterized by the perception of persistent pain, unpleasantness or discomfort in various tissues and regions of the body. As one example, temporomandibular disorder (TMD), a prototypic somatosensory disorder, is associated with a state of pain amplification as well as psychological distress, which is characterized by high levels of somatization, depression, anxiety and perceived stress (FIG. 1). TMD alone impacts 5-15% of the population and has been estimated to incur approximately $1 billion in healthcare costs. A common feature of somatosensory disorders is that a given somatosensory disorder is often associated with other comorbid somatosensory conditions. It is generally accepted that impairments in CNS regulatory processes contribute to the pain amplification and psychological dysfunction associated with somatosensory disorders. However, details as to the specific molecular pathways resulting in the CNS regulatory process impairments and the exact role individual genetic variation play in the process are heretofore undetermined. Furthermore, a host of biological, psychological, and environmental factors also impact pain sensitivity and the risk of developing a somatosensory disorder. As shown in FIG. 1, a multitude of known factors can compound or interact to increase pain sensitivity and the risk of developing a somatosensory disorder. Thus, an individual with enhanced pain processing and/or psychological dysfunction (e.g., somatization), due to for example genetic variability affecting protein activity, as compared to a population norm, would be predicted to have a greater pain sensitivity and risk of developing a somatosensory disorder.

The presently disclosed subject matter provides new insights into the molecular pathways involved in the development of somatosensory disorders and further reveals genotypes, which can include specific genetic polymorphisms present in subjects that, when coupled with environmental factors such as physical or emotional stress, can produce a clinical phenotype that is vulnerable to the development of a somatosensory disorder. The genotypes (which can include specific genetic polymorphisms) identified herein are useful for predicting the susceptibility of a subject to develop a somatosensory disorder, or related condition, including for example increased pain sensitivity and predilection toward somatization.

The presently disclosed subject matter also provides methods for using the using the knowledge of the genotype (which can include the presence of specific polymorphisms) of a particular subject suffering from a somatosensory or related disorder to subclassify the disorder, thereby allowing for development of optimal treatments for treating the disorder based on the determination that subjects exhibiting a particular genotype (which can include the presence of particular polymorphisms, as disclosed herein) respond well or poorly to particular pharmacologic, behavioral, and surgical treatments.

In particular, the presently disclosed subject matter provides that the enzyme catecholamine—O-methyltransferase (COMT), which functions in part to metabolize catecholamines such as epinephrine and norepinephrine, the $\beta_2$-adrenergic receptor (ADRB2) and the $\beta_3$-adrenergic receptor (ADRB3), which are receptors for catecholamines, are components of a molecular pathway that plays a role in somatosensory disorders. The presently disclosed subject matter discloses pharmacotherapies that correct or improve the impairments in this pathway. Further, the presently disclosed subject matter provides insights into particular polymorphism patterns more prevalentin subjects suffering from somatosensory and related disorders.

Therefore, determining a subject's genotype for COMT, ADRB2, and/or ADRB3 can be used to predict the susceptibility of the subject to develop a somatosensory or related disorder, as disclosed herein. Further, determining a subject's genotype can be used to develop and/or provide an effective therapy for the subject, as it has been determined by the present co-inventors and is disclosed herein for the first time that particular genotypes of the COMT, ADRB2, and/or ADRB3 genes, result in gene products with different activities that make a subject more or less responsive to particular pharmacologic therapies. Thus, a subject's determined genotype with respect to COMT, ADRB2, and/or ADRB3 can be used to subclassify the particular somatosensory or related disorder and thereby direct treatment strategies.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

"$\beta_2$-adrenergic receptor" (ADRB2) and "$\beta_3$-adrenergic receptor (ADRB3)" as used herein refer to cellular macromolecular complexes that when stimulated by catecholamines such as epinephrine (ADRB2) and norepinephrine (ADRB3) produce biological or physiological effects. The core component of both ADRB2 and ADRB3 is a seven transmembrane domain protein that comprise several functional sites. These proteins are comprised of a ligand-binding domain, as well as an effector domain that permits the receptor to associate with other cellular proteins, such as G proteins and $\beta$-arrestin. Together, these molecules interact as a receptor unit to produce a biological response. These receptors are widely distributed on multiple tissues throughout the body. ADRB2 can be found on neuronal and glial tissues in the central nervous system and on smooth muscle, bone, cartilage, connective tissue, the intestines, lungs, bronchial glands, liver. ADRB2 receptors are present on macrophages and when stimulated produce proinflammatory and pro-pain producing cytokines such as IL1$\beta$, IL6, and TNF$\alpha$. ADRB3 are present on smooth muscle, white and brown adipose tissue and in several regions of the central nervous system including the hypothalamus, cortex, and hippocampus. ADRB3 receptors are highly enriched on adipocytes and when stimulated produce proinflammatory and pro-pain producing cytokines such as IL1$\beta$, IL6, and TNF$\alpha$.

"Catecholamine-O-methyltransferase" (COMT) as used herein refers to an enzyme that functions in part to metabolize catechols and catecholamines, such as epinephrine and norepinephrine by covalently attaching to the catecholamine one or more methyl moieties. The enzyme is widely distributed throughout the body, including the brain. The highest concentrations of COMT are found in the liver and kidney. Most of norepinephrine and epinephrine that is released from the adrenal medulla or by exocytosis from adrenergic fibers is methylated by COMT to metanephrine or normetanephrine, respectively.

As used herein, the term "expression" generally refers to the cellular processes by which an RNA is produced by RNA polymerase (RNA expression) or a polypeptide is produced from RNA (protein expression).

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

"ADRB2 gene" and "ADRB3 gene" are used to refer to gene loci related to the corresponding seven transmembrane domain proteins, which are the core component of the receptor complex.

As used herein, the term "DNA segment" means a DNA molecule that has been isolated free of total genomic DNA of a particular species. Included within the term "DNA segment" are DNA segments and smaller fragments of such segments, and also recombinant vectors, including, for example, plasmids, cosmids, phages, viruses, and the like.

As used herein, the term "genotype" means the genetic makeup of an organism. Expression of a genotype can give rise to an organism's phenotype, i.e. an organism's physical traits. The term "phenotype" each refers to any observable property of an organism, produced by the interaction of the genotype of the organism and the environment. A phenotype can encompass variable expressivity and penetrance of the phenotype. Exemplary phenotypes include but are not limited to a visible phenotype, a physiological phenotype, a susceptibility phenotype, a cellular phenotype, a molecular phenotype, and combinations thereof. Preferably, the phenotype is related to a pain response variability, including phenotypes related to somatosensory disorders and/or predictions of susceptibility to somatosensory disorders, or related pain sensitivity conditions. As such, a subject's genotype when compared to a reference genotype or the genotype of one or more other subjects can provide valuable information related to current or predictive phenotype.

"Determining the genotype" of a subject, as used herein, can refer to determining at least a portion of the genetic makeup of an organism and particularly can refer to determining a genetic variability in the subject that can be used as an indicator or predictor of phenotype. The genotype determined can be the entire genome of a subject, but far less sequence is usually required. The genotype determined can be as minimal as the determination of a single base pair, as in determining one or more polymorph isms in the subject. Further, determining a genotype can comprise determining one or more haplotypes. Still further, determining a genotype of a subject can comprise determining one or more polymorphisms exhibiting high linkage disequilibrium to at least one polymorphism or haplotype having genotypic value.

As used herein, the term "polymorphism" refers to the occurrence of two or more genetically determined alternative variant sequences (i.e., alleles) in a population. A polymorphic marker is the locus at which divergence occurs. Preferred markers have at least two alleles, each occurring at frequency of greater than 1%. A polymorphic locus may be as small as one base pair.

As used herein, "haplotype" means the collective characteristic or characteristics of a number of closely linked loci with a particular gene or group of genes, which can be inherited as a unit. For example, in some embodiments, a haplotype can comprise a group of closely related polymorphisms (e.g., single nucleotide polymorphisms (SNPs)). In some embodiments, the determined genotype of a subject can be particular haplotypes for COMT, ADRB2, and ADRB3, such as for example: with regard to the ADRB2 genotype, Haplotype 1, Haplotype 2, Haplotype 3, and Uncommon; with regard to the ADRB3 genotype, Haplotype 1, Haplotype 2, Haplotype 3, and Uncommon; and with regard to the COMT genotype, low pain sensitive haplotype (LPS), average pain sensitive haplotype (APS), and high pain sensitive haplotype (HPS). Each of these haplotypes is defined by specific SNP patterns, as disclosed in detail herein.

As used herein, "linkage disequilibrium" means a derived statistical measure of the strength of the association or co-occurrence of two independent genetic markers. Various statistical methods can be used to summarize LD between two markers but in practice only two, termed D' and r2, are widely used.

In some embodiments, determining the genotype of a subject can comprise identifying at least one haplotype of a gene, such as for example ADRB2, ADRB3, COMT or combinations thereof. In some embodiments, determining the genotype of a subject can comprise identifying at least one polymorphism unique to at least one haplotype of a gene, such as for example ADRB2, ADRB3, COMT, or combinations thereof. In some embodiments, determining the genotype of a subject can comprise identifying at least one polymorphism exhibiting high linkage disequilibrium to at least one polymorphism unique to at least one haplotype, such as for example ADRB2 haplotype, ADRB3 haplotype, COMT haplotype, or combinations thereof. In some embodiments, determining the genotype of a subject can comprise identifying at least one polymorphism exhibiting high linkage disequilibrium to at least one haplotype, such as for example ADRB2 haplotype, ADRB3 haplotype, COMT haplotype, or combinations thereof.

As used herein, the term "modulate" means an increase, decrease, or other alteration of any, or all, chemical and biological activities or properties of a wild-type or mutant polypeptide, such as for example COMT, ADRB2, ABRB3 or combinations thereof. A peptide can be modulated at either the level of expression, e.g., modulation of gene expression (for example, anti-sense therapy, siRNA or other similar approach, gene therapy, including exposing the subject to a gene therapy vector encoding a gene of interest or encoding a nucleotide sequence that influences expression of a gene of interest), or at the level of protein activity, e.g., administering to a subject an agonist or antagonist of a receptor macromolecule, such as ADRB2 and/or ADRB3, or an activator or inactivator of an enzyme polypeptide, such as for example COMT. The term "modulation" as used herein refers to both upregulation (i.e., activation or stimulation) and downregulation (i.e. inhibition or suppression) of a response.

As used herein, the term "mutation" carries its traditional connotation and means a change, inherited, naturally occurring or introduced, in a nucleic acid or polypeptide sequence, and is used in its sense as generally known to those of skill in the art.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably herein when referring to a gene product.

"Somatization" as used herein refers to an individual's report of distress arising from the perception of bodily dysfunction. Complaints typically focus on cardiovascular, gastrointestinal, respiratory and other systems with strong autonomic mediation. Aches and pain, and discomfort are frequently present and localized in the gross musculatures of the body.

"Somatosensory disorder" as used herein refers to clinical conditions characterized by the perception of persistent pain, discomfort or unpleasantness in various regions of the body. These conditions are generally, but not always, associated with enhanced sensitivity to pain. On occasion, these conditions are observed without currently known measures of tissue pathology. Exemplary somatosensory disorders include, but are not limited to chronic pain conditions, idiopathic pain conditions, fibromyalgia syndrome, myofascial pain disorders, tension headache, migraine headache, phantom limb sensations, irritable bowel syndrome, chronic lower back pain, chronic fatigue syndrome, multiple chemical sensitivities, temporomandibular joint disorder, post-traumatic stress disorder, chronic idiopathic pelvic pain, Gulf War Syndrome, vulvar vestibulitis, osteoarthritis, rheumatoid arthritis, and angina pectoris. A general characteristic of a specific somatosensory disorder is that it can be associated with at least one additional or multiple co-morbid somatosensory disorders.

"Treatment" as used herein refers to any treatment of a somatosensory disorder and includes: (i) preventing the disorder from occurring in a subject which may be predisposed to the disorder, but has not yet been diagnosed as having it; (ii) inhibiting the disorder, i.e., arresting its development; or (iii) relieving the disorder, i.e., causing regression of clinical symptoms of the disorder.

II. Methods of Predicting Enhanced Pain Sensitivity and Risk of Developing Somatosensory Disorders The presently disclosed subject matter provides for determining a genotype of a subject with respect to particular genes having a role in determining pain sensitivity in the subject. Thus, determining the genotype of the subject can elucidate pain processing and psychological phenotypes in the subject, which in turn can be used to predict a subject's pain sensitivity and risk for develop a somatosensory disorder (FIG. 1). The present subject matter discloses for the first time that the COMT, ADRB2, and ADRB3 genes encode for proteins that each, and in combination with one another, play an important role in pain perception or sensitivity. Thus, genotyping one or more of these genes can provide valuable information related to pain sensitivity useful for predicting responses to pain, susceptibility to develop pain disorders and even insights into effective therapies to treat sensory disorders and related conditions.

II.A. COMT Genotypes

As disclosed herein, COMT genotype is highly associated with human pain perception. As further discussed in the Examples herein below, there are three major COMT haplotypes (low pain sensitivity (LPS), average pain sensitivity (APS) and high pain sensitivity (HPS)) that determine COMT enzymatic activity, encompassing ~96% of the examined genotypes. As indicated by the nomenclature, the LPS haplotype is associated with low pain sensitivity, APS is associated with higher pain sensitivity, and HPS with the highest sensitivity to pain. Collectively, these three haplotypes account for about ~11% of the variability in pain perception. Given the inevitably polygenic nature of pain perception, the magnitude of the effect of COMT haplotypes on pain sensitivity is substantial. Indeed, quantitative trait locus (QTL) mapping studies for related traits in mice have shown that each single QTL usually accounts for 5 to 25% of the overall variance in nociceptive sensitivity (Mogil et al. (2003); Abiola et al. (2003)).

The combination of synonymous and nonsynonymous SNPs within COMT haplotypes can produce effects on protein function that exceed the effects of individual SNPs. The presently disclosed subject matter provides evidence to show that genomic variations in the COMT gene do not alter the amount of COMT mRNA, suggesting that the differences in enzymatic activity result from differences in protein translation. The fact that expressed cDNA constructs, which differed in only three SNPs rs4633, rs4818, and rs4680 (val$^{158}$met), showed more than an 11-fold difference in expressed enzyme activity, confirms that the observed association between haplotypes and pain sensitivity can be caused by combinations of these three SNPs and not necessarily by other SNPs in the haploblock situated in the 5' or intronic region of the COMT gene that can affect RNA transcription. Without desiring to be limited by theory, interactions between SNPs can possibly have profound effects on the secondary mRNA structure, which controls the efficacy of protein translation. The identification of new functional haplotypes disclosed herein suggests that haplotype reconstruction can provide important insights into relationship between COMT polymorphism, human pain sensitivity, and somatosensory disorders.

Furthermore, COMT inhibition in rodents results in a robust increase in pain sensitivity. The presently disclosed subject matter provides evidence that COMT activity regulates pain sensitivity and strongly suggests that the observed association between COMT genotype and pain perception in humans is not epiphenomenal.

The presently disclosed subject matter represents the first demonstration of an association between a genetic polymorphism that impacts pain sensitivity and the risk for myogenous temporomandibular disorder (TMD), which is a highly prevalent musculoskeletal pain condition (i.e, somatosensory disorder). The presence of even a single high COMT activity (LPS) haplotype diminishes by as much as 2.3 times, the risk of developing TMD. The risk ratio of 2.3 is of a magnitude comparable to genetic risk factors for other multifactorial conditions such as schizophrenia and is similar to other predictors of TMD, such as a history of chronic pain at other body sites. The clinical relevance of this novel finding is best quantified by the measure of population attributable risk for having HPS and/or APS, which was 29% in the particular cohort of women subjects studied in the Example presented below, indicating that nearly one third of new TMD cases can be attributed to this COMT genotype.

Without desiring to be limited by theory, a possible mechanism by which diminished COMT activity influences pain perception and the development of somatosensory disorders is that reduced COMT activity results in elevated levels of catecholamines such as epinephrine, which promote the production of persistent pain states via the stimulation of ADRB2 and ADRB3 in the peripheral and central nervous system. The data disclosed herein supports this proposed mechanism. The novel clinical, animal and molecular data presented herein are in complete agreement with the conclusion that COMT activity substantially influences pain sensitivity, and that the three major haplotypes determine COMT activity in humans in a fashion that inversely correlates with pain sensitivity and the risk of developing somatosensory disorders, including for example TMD. Thus, determination of a genotype of COMT in a subject can be used to identify a pain sensitivity phenotype in the subject, which in turn can be utilized to predict pain sensitivity and/or susceptibility of the subject to develop a condition related to hypersensitivity to pain, such as for example a somatosensory disorder.

The novel insights disclosed herein with regard to determining and predicting pain sensitivity and risk of development of somatosensory disorders is not limited to COMT genotypes, but further extends to ADRB2 and ADRB3, individually and in combination with each other.

II.B. ADRB2 Genotypes

The presently disclosed subject matter provides that common genetic variants of ADRB2, comparable to COMT, also influence human psychological traits such as somatization, anxiety, and depression that influence pain sensitivity and the risk of developing a somatosensory disorder (FIG. 1). The presently disclosed subject matter provides in some embodiments three major ADRB2 haplotypes (H1, H2, H3) that determine ADRB2 expression and activity, as well as other rare haplotypes, referred to collectively herein as "Uncommon".

Figures 2A, 2B, 2C:
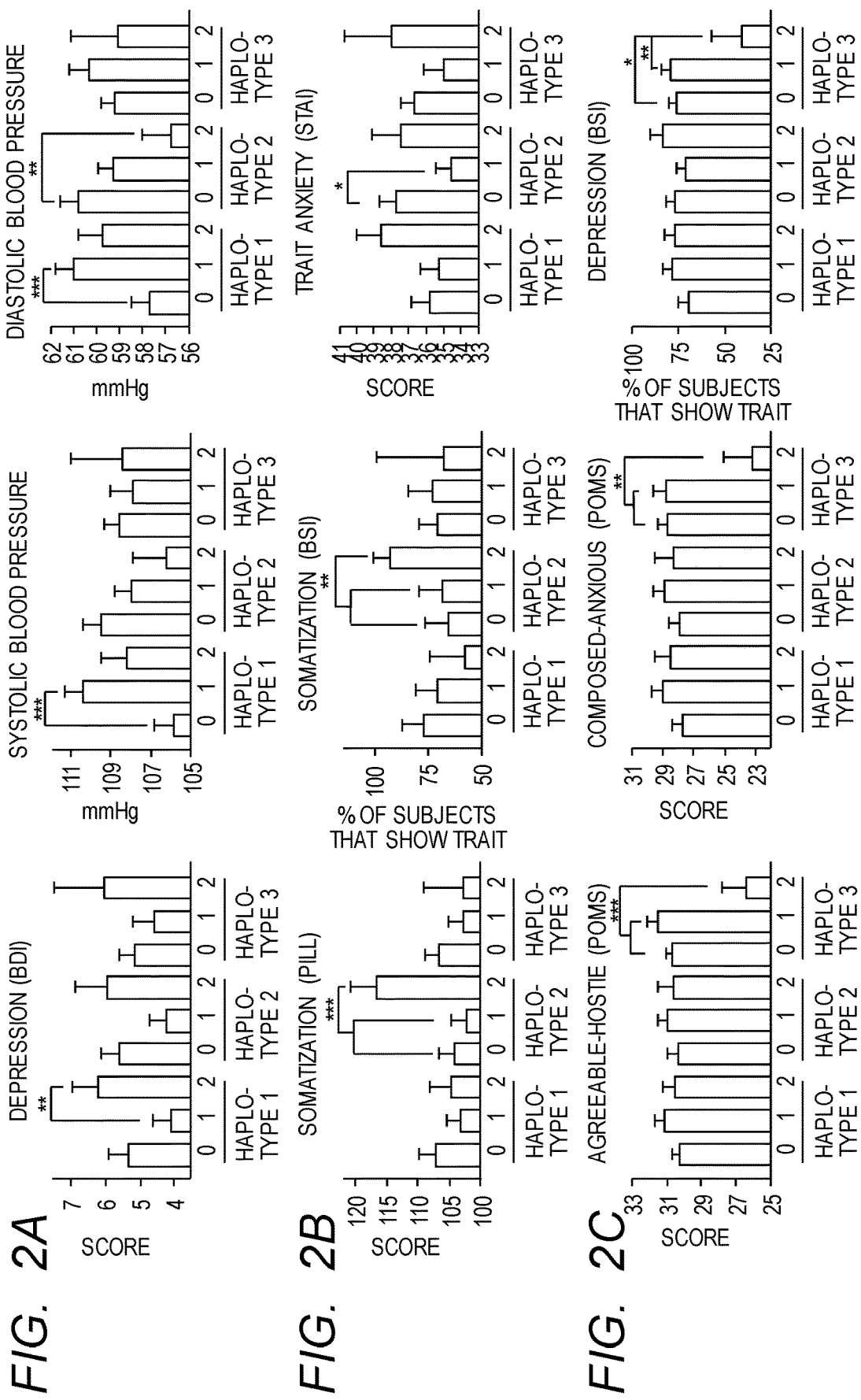
FIGS. 2A-2C are a series of graphs showing the effect of ADRB2 haplotypes on psychological scores and resting arterial blood pressure. The major effects of the number of copies of haplotype 1 (FIG. 2A), haplotype 2 (FIG. 2B) or haplotype 3 (FIG. 2C) are presented. The following haplotype dose-effects are shown: no corresponding haplotype (0), one copy (1) or two copies (2) of the corresponding haplotype. Each value represents the mean of each variable with associated SEM. Greater positive values for BDI, PILL, BSI and Trait Anxiety scores reflect more negative psychological characteristics. The greater values for measured obtained from the POMS scale reflect more positive psychological characteristics: agreeable or composed, different from the indicated groups. BDI, PILL, STAI and POMS scores were measured in relative unites, blood pressure was measured in mm of mercury (mmHg), BSI depression and somatization presented as percent of subjects that show trait (subjects, scored at 30 and corresponded to individuals that answered all questions negatively, were treated as a group that showed no signs of depression or somatization). *$P<0.01$, $P<0.05$ and *$P<0.1$.

In the cohort studied and disclosed in the Examples herein below, H1 homozygotes had the highest BDI depression and trait anxiety scores (FIGS. 2A-2B and Table 8). Previously published animal studies, which have examined the physiology of ADRB2, provide evidence that low levels of the receptor can lead to depression and anxiety and that direct stimulation of central ADRB2 produces antidepressant-like effects in rats (Zhanq et al. (2003)). Furthermore, reductions in the density of ADRB in humans is associated with depression and panic-anxiety (Magliozzi et al. (1989)). Based on these results, related association studies and analysis of the EST databases, it can be stated that H1 codes for low levels of receptor (Lo expressers), at least in the CNS, as depicted in FIGS. 3A-3B.

The H2 haplotype showed a strong association with somatization (see BSI and PILL scores in the Examples herein below and FIG. 2B) and H2 homozygotes showed significantly higher somatization score (Table 8). This observation is in agreement with the EST expression analysis data suggesting that H2 codes for high levels of receptor (Hi expressers—FIGS. 3A-3B). In human studies, stimulation of ADR82 was shown to be associated with enhanced epinephrine-mediated physiological arousal and increased somatic awareness across multiple systems (e.g., gastrointestinal, cardiorespiratory, etc.) (Kopin, I. J (1984); Easton et al. (1976); Lader. M. (1988)). In the data disclosed herein in the Examples, H2 demonstrated a protective role against elevated trait anxiety because subjects without H2 reported the highest trait anxiety scores (FIG. 2B and Table 8).

Haplotype H3 was associated with the highest state- and mood-dependent anxiety and hostility scores (Table 8). These observations suggest a rapid stress-evoked reduction in the amount of functionally available ADR82 in H3 homozygotes (FIGS. 3A-3B). These results are in agreement with the presence of the G allele at SNP rs1042713 (Arg$^{16}$Gly) that codes for Gly16 (FIGS. 4A-4B), which is responsible for agonist-dependent internalization of the receptor and is consistent with the EST expression analysis data disclosed in the Examples, which indicates that H3 codes for high basal levels of receptor (Hi expressers). Furthermore, H3 homozygotes report the lowest level of depression (BSI), which is in agreement with the high psychological reactivity observed in these subjects.

Resting arterial diastolic blood pressure is associated with the number of copies of H2 (FIG. 2A). H2 homozygotes (high expression/slow internalization) had the lowest resting diastolic pressure and subjects without a H2 haplotype (subjects with combinations of H1 and H3, rapid receptor internalization) had the greatest resting diastolic pressures (Table 8, FIG. 2A). An even stronger effect was observed for H1 (Table 8, FIG. 2A). Subjects with no H1 (subjects with combinations of H2 and H3, high receptor expression) had the lowest systolic and diastolic blood pressure (FIG. 2A, Table 8). Although homozygotes for H1 had higher resting arterial blood pressure, the highest resting arterial systolic and diastolic blood pressures were seen with H1-H2 and H1-H3 heterozygotes (Table 9), suggesting a H1 overdominance. It is noteworthy that these same subjects were less likely to develop TMD (Table 10), which is consistent with the substantial literature that pain sensitivity and the risk of developing chronic musculoskeletal conditions is inversely related to resting arterial blood pressure (Maixner et al. (1997); Bruehl et al. (2004); Fillingim et al. (1998); Pfleeger et al. (1997); Maixner, W. (1991); Randich et al. (1984); Sheps et al. (1992); Hagen et al. (2005)).

The analysis of EST databases disclosed herein suggests that H1 codes for a lower amount of RNA expression compared to H2 and H3. The outcomes of the association study, and known effects of genetic variations in ADRB2 on various physiological functions such as blood pressure (Bray et al. (2000)) and airway resistance (Tattersfield et al. (2004)), support this conclusion. Two cell biology-based studies, which sought to determine the relationship between ADRB2 expression and common polymorphisms, did not reach consistent conclusions on this subject (Drysdale et al. (2000); McGaw et al. (1998)), which may be due to tissue specific effects on haplotype expression. Although cell culture studies can be designed for an accurate assessment of haplotype-specific expression in different tissue-specific cell lines and under different conditions of transcription stimulation, it is believed that the data and analysis provided in the Examples herein below that H1 codes for a lower level of expression of the receptor compared to H2 and H3, particularly in the CNS.

While it is not desired to be bound by any particular theory of operation, based on the data and analysis provided in the Examples below, the analysis of EST frequencies, and known data related to ADRB2 cell biology, a model that explains how different haplotypes produce different psychological phenotypes (FIGS. 3A-3B) is provided herein. In the resting physiological state, H1 homozygotes express several times fewer receptors than either H2 or H3 homozygous (FIG. 3A). Chronically diminished ADRB2 function in the CNS, as proposed for H1 homozygotes, would produce psychological traits such as depression and anxiety, which has been observed in some patients treated with non-selective ADRB2 receptor blockers (Thiessen et al. (1990). In contrast, chronically enhanced ADRB2 function, as proposed for H2 homozygotes, would display psychological characteristics of physiological arousal and enhanced awareness of bodily functions (i.e., somatization) evoked by stimulation of central ADRB2 and a reduction in arterial blood pressure by ADRB2 stimulation on peripheral blood vessels.

Epinephrine released from the adrenal glands in response to a stressful situation should lead to a rapid internalization of receptor variants H1 and H3. For the H3 homozygotes, but not H1 homozygotes, this would lead to a significant reduction in receptor density producing a stress-evoked state-dependent anxiety (FIG. 3B). Based on this model, and without wishing to be limited by theory, it is proposed that the relative rank order of ADRB2 receptor function in response to agonist stimulation is the following: H2 (high expression/low down regulation) similar to H3 (high expression/high down regulation), both of which are greater than H1 (low expression/high down regulation).

The presently disclosed subject matter can thus provide and advantage in considering haplotypes rather than single SNPs. Each haplotype of ADRB2 codes for two basic receptor properties—the level of expression and the internalization responses produced by agonist stimulation. Both of these properties influence physiological responses and phenotypes associated with ADRB2.

An overdominance of H1 over H2 and H3 is another feature of ADRB2 genetics that can complicate the interpretation of association studies. Individuals heterozygous for H1-H2 and H1-H3 show the highest level of resting arterial blood pressure and lowest BDI depression score (FIG. 2A). Although the H1-H2 and H1-H3 heterozygotes represented almost half of the initially tested cohort, only one TMD case was observed in this group, yielding significantly elevated risk of developing TMD for both "Lo" and "Hi" homozygotes and suggests that the presence of one H1 haplotype is protective against TMD onset. An overdominance was further confirmed by linear models that investigated the interactions between haplotypes. The best-fit model for resting blood pressure revealed interactions between the H1 haplotype and H2 and H3, but only the H1-H3 interaction revealed a significant overdominance, which was probably due to the limited sample size. The H1-H3 interaction also showed overdominance when associated with BSI depression phenotype (Table 9): H1-H3 heterozygotes showed the highest BSI depression score while H3 homozygotes showed the lowest BSI depression score (Table 8). Importantly, H1-H3 heterozygotes showed the highest score for both mood phenotypes (POMS agreeable-hostile, POMS composed-anxious; Table 8), which probably reflects the low psychological reactivity, associated with the H1-H3 heterozygotes.

The data provided herein with regard to ADRB2 genotypes are of considerable clinical significance and are the first to demonstrate an association between a genetic polymorphism that correlates with psychological traits, resting blood pressure, and pain sensitivity determination, which in turn is associated with the susceptibility of developing a somatosensory disorder or somatization or predicting a subject's pain sensitivity. For example, the observed genetic risk for developing TMD associated with ADRB2 polymorphism is substantially greater than that reported for other putative risk factors such as estrogen exposure or history of chronic pain at other body sites (John et al. (2003); Von Korff et al. (1993)). The clinical relevance of these findings are best quantified by the measure of population attributable risk for being homozygous for either high or low expression of ADRB2, which was 82% in the cohort of women subjects (see Examples), indicating that more than eight in ten of the myogenous TMD cases can be attributed to the ADRB2 haplotypes disclosed herein.

Individuals with relatively high ADRB2 function (H2 and H3) had a high likelihood of developing TMD (Table 10). H2 homozygotes showed the highest TMD incidence rate (0.200). H2-H3 heterozygotes and H3 homozygotes, where ADRB2 function should be slightly diminished, showed TMD incidence rates of 0.125 and 0.100 respectively, which was still higher than the average TMD incidence rate of 0.083. Surprisingly, very low ADRB2 function appears to increase the risk for TMD development. An elevated TMD incidence rate of 0.105 for H1 homozygotes was observed. H1 heterozygotes, those who had one haplotype that coded for high ADRB2 expression (H2 or H3) and one haplotype that coded for low ADRB2 expression of low activity (H1), were protected from the development of TMD. Only one subject who was H1 heterozygote developed TMD, even though almost half of all the variants observed in the cohort were H1 heterozygotes (Table 10). Thus, the data disclosed herein (see Examples herein below) suggest that either positive or negative imbalances in ADRB2 function can increase the vulnerability to TMD. Collectively, 14 of 15 TMD (93%) patients were associated with a relative hyperfunction (10/15) or hypofunction of (4/15) of ADRB2 (Table 10).

The findings disclosed herein have important treatment implications. If ADRB2 hyperfunction contributes to somatosensory disorders, such as for example TMD, then a relatively high percentage of these patients (~60-70%) should respond to treatment with an ADRB2 antagonist, such as for example propranolol. In contrast, approximately 25 to 30% of some somatosensory disorders, such as for example TMD, should have a hypofunction of ADRB2 (H1/H1) and should not respond to treatment with an ADRB2 antagonist. In fact, treatment of this group with such an agent might actually worsen their signs and symptoms. Thus, the presently disclosed subject matter provides for predicting treatment outcomes to ADRB2 blockade by determining the specific haplotype profile for patients with somatosensory disorders, including, for example, TMD.

II.C. ADRB3 Genotypes

The presently disclosed subject matter also provides that common genetic variants of ADRB3, comparable to COMT and ADRB2, can also influence human psychological traits that influence pain sensitivity and the risk of developing a sensory disorder. Particularly, there are three major ADRB3 haplotypes (H1, H2, H3) that determine ADRB2 expression and activity, as well as other rare haplotypes, referred to collectively herein as "Uncommon".

By way of elaboration, the data presented herein based on the determined association analysis of ADRB3 haplotypes with pain responsiveness and somatization score, demonstrates that subjects bearing H2 or H3 haplotypes of ADRB3 can be predicted to have lower risk for developing somatosensory disorders, including TMD.

Figure 5:
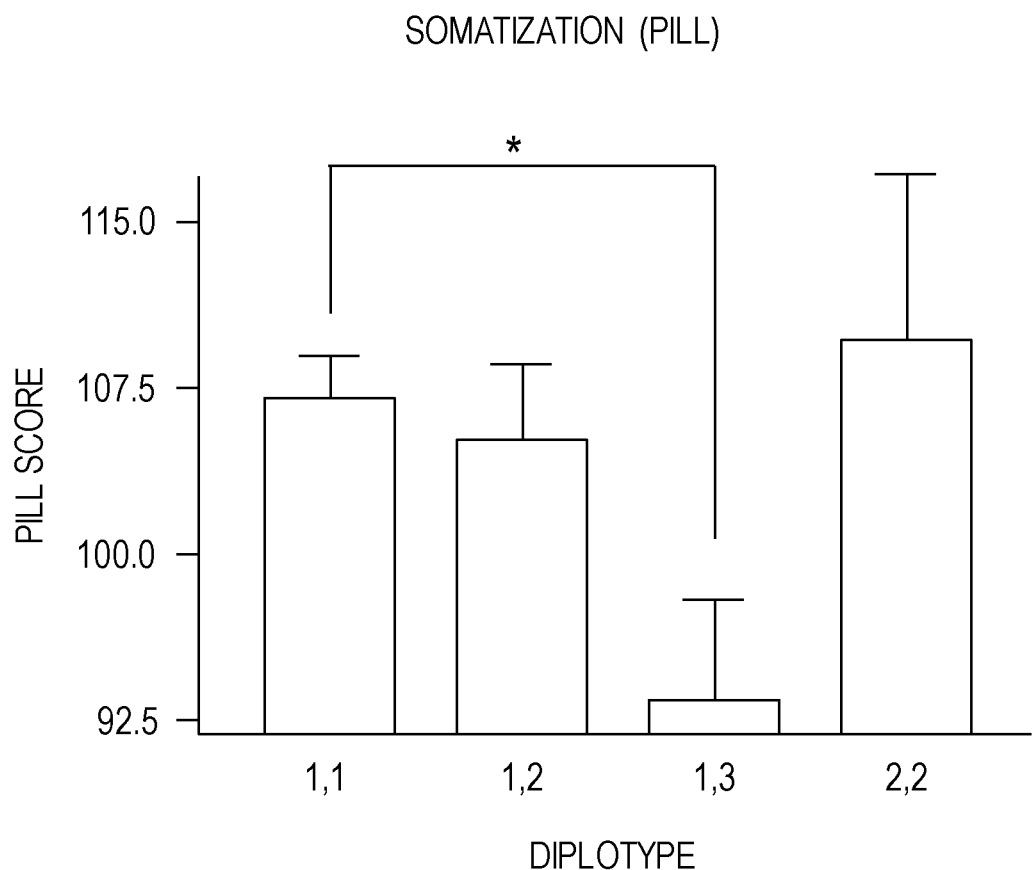
FIG. 5 is a graph showing the effect of ADRB3 haplotypes on PILL somatization score. The major effects of Haplotype 3 are presented. Each value represents the mean of PILL somatization score with associated SEM. Greater positive values reflect more negative psychological characteristics. *Student T-test, $P<0.05$.

Further, with regard to predicting somatization in a subject based on genotyping of the subject with regard to ADRB3 haplotype, subjects bearing a H3 haplotype have a lower PILL somatization score than those who do not carry a H3 allele (see FIG. 5). Consistent with this observation, H1/H3 heterozygotes also have low pain responsiveness (see Table 11).

The data presented in the Examples further indicates ADRB3 H1/H2 subjects (i.e., the subject possesses one copy of both Haplotype 1 and Haplotype 2 for ADRB3) or H2/H2 subjects (i.e., the subject possesses two copies of Haplotype 2 for ADRB3), who exhibit the lowest pain sensitivity, and ADRB3 H1/H3 subjects (i.e., the subject possesses one copy of both Haplotype 1 and Haplotype 3 for ADRB3), who have low pain sensitivity and the lowest somatization scores, each have lower risk of developing pain-related conditions, such as for example somatosensory disorders.

IID. Methods of Predicting Susceptibility to Develop Somatosensory Disorders

On the basis of the data disclosed herein and the discussion preceding regarding determining pain perception-related genotypes, the presently disclosed subject matter provides methods of predicting susceptibility of a subject, i.e. the predisposition of or risk of the subject, to develop a somatosensory disorder. In some embodiments, the method comprises determining a genotype of the subject with respect to a gene selected from the group consisting of ADRB2, ADRB3, COMT, and combinations thereof; and comparing the genotype of the subject with at least one reference genotype associated with susceptibility to develop the somatosensory disorder, wherein the reference genotype is selected from the group consisting of an ADRB2 genotype, an ADRB3 genotype, a COMT genotype, and combinations thereof, whereby susceptibility of the subject to develop the somatosensory disorder is predicted.

"Reference genotype" as used herein refers to a previously determined pattern of unique genetic variation associated with a particular phenotype, such as for example pain perception or sensitivity. The reference genotype can be as minimal as the determination of a single base pair, as in determining one or more polymorphisms in the subject. Further, the reference genotype can comprise one or more haplotypes. Still further, the reference genotype can comprise one or more polymorphisms exhibiting high linkage disequilibrium to at least one polymorphism or haplotype. In some particular embodiments, the reference genotype comprises one or more haplotypes of COMT, ADRB2, ADRB3, or combinations thereof determined to be associated with pain perception, including for example pain response prediction, susceptibility to a somatoform disorder, and/or somatization. In some embodiments, the haplotypes represent a particular collection of specific single nucleotide polymorphisms. For example, FIGS. 6A-6C shows haplotype sequences of COMT based on polymorphism patterns which determine haplotypes LPS, APS, and HPS, and when inherited in particular combinations (as described herein) are associated with differences in pain sensitivity. These combinations are reference genotypes for predicting susceptibility to somatosensory disorders and related conditions based on matching determined genotypes of a subject to the reference genotypes.

In particular embodiments, SNPs rs6269G/A (GCATTT CTGAACCTTGCCCCTCTGC[G/A]AACACAAGGGG G CGATGGTGGCACT (SEQ ID NO: 29)); rs4633C/T (CCAAGGAGCAGCGCATCCTGAACCA[C/T]GTGC TG CAGCATGCGGAGCCCGGGA (SEQ ID NO: 30)); rs4818G/C (GCCTGCTGTCACCAGGGGCGAGGCT[G/C]ATCACCATCGAGATCAACCCCGACT (SEQ ID NO: 31)); and rs4680G/A (CCAGCGGATGGTGGATTTCG CTGGC[G/A]TGAAGGACAAGGTGTGCATGCCTGA (SEQ ID NO: 32)) are used to determine the COMT haplotypes. Using the convention order rs6269_rs4633_rs4818_rs4680, haplotype G_C_G_G is referred to herein as LPS, haplotype A_T_C_A is referred to herein as APS, and haplotype A_C_C_G is referred to herein as HPS.

Figures 4A, 4B:
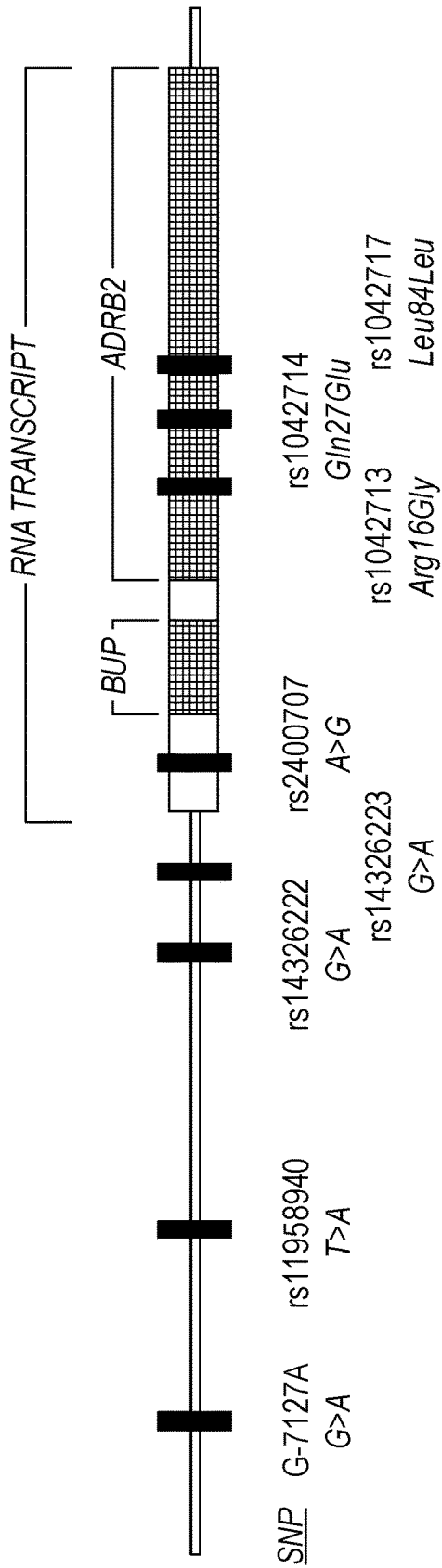
FIG. 4A is a schematic diagram of ADRB2 genomic organization, SNP positions and distribution percentages. The human ADRB2 is an intronless gene that spans ~5,500 kb on chromosome 5q31-32. ADRB2 transcript codes for two independent peptides showed as break blocks: $\beta_2$ adrenergic receptor protein (ADRB2) and $\beta_2$ adrenergic receptors upstream protein (BUP) that inhibits receptor translation.
FIG. 4B shows estimated frequencies of the main ADRB2 haplotypes. The sequence of alleles in each haplotype reflects the order of occurrence from 5' to 3' in the ADRB2 gene locus (SNPs: G-7127A, rs11958940, rs1432622, rs1432623, rs2400707, rs1042713, rs1042714 and rs1042717, respectively).

Likewise, FIG. 4B shows haplotypes H1, H2, and H3 of ADRB2 based on specific polymorphisms as shown in FIG. 4A and FIGS. 7A-7B shows haplotypes H1, H2, and H3 of ADRB3 based on specific polymorphisms.

In some embodiments, for ADRB2, SNPs G-7127AG/A (CAAGTTGTTGTGTAGGATATTGGCAATTTTTGCTT G TCAGCTCCATGGTACTTCTTC CGAATCA[G/A]AA ATTTATCTCCTCAGTGGCCCTCAAAGCACTTTCTT C CCACTATAG GCTTGTTCAGTTTAGAGTAGACAG (SEQ ID NO: 267)); rs11958940T/A (ACTCTCTAAGGT-CATGTGAACAGTAWGCAGTGCTACTCGAACTCC T CTGCT (SEQ ID NO:268)); rs1432622GC/T (GAAAAC-TATGTGAATATAATAGATC[C/T]TTAATTCATATTTG TGGATTTTATG) (SEQ ID NO:269)); rs1432623C/T (TTATGTAAACTTCGCTTACAAACTA[C/T]ACTTGT GTGACACTTATATGAGCAA (SEQ ID NO:270)); rs 2400707AIG (CCAGATGGTGGCAA TTTCACATGGC [A/G]CAACCCGAAAGATTAACAAACTATC (SEQ ID NO:271)); rs1042713G/A (CAGCGCCTTCTT GCTGGCA CCCAAT[G/A]GAAGCCATGCGCCGGACCACGACGT (SEQ ID NO:272)); rs1042714G/C(TGCGCCGGACCA CGACGTCACGCAG[G/C]AAAGGGACGAGGTGTG G GTGGTGGG (SEQ ID NO:273)); and rs1042717G/A (CCTGTGCTGATCTGGTCATGGGCCT[G/A]GCAGTG GTGCCCTTTGGGGCCGCCC (SEQ ID NO: 274)) are used to determine the ADRB2 haplotypes. Using the convention order G-7127A_rs11958940_rs14326222_rs14326223_rs2400707_rs1042713_rs1042714_rs10 427 17G/A haplotype G_A_A_A_G_G_G_G is referred to herein as Haplotype 1 (H1), haplotype A_T_G_G_A_A_C_G is referred to herein as Haplotype 2 (H2), and haplotype G_T_G_G_A_G_C_A is referred to herein as Haplotype 3 (H3).

In some embodiments, for ADRB3, rs4994T/C (CCTGC TGGTCATCGTGGCCATCGCC[T/C]GGACTCCGAGA CTCCAGACCATGAC (SEQ ID NO: 302)); rs4997C/A (ACGGCTCGACGGGTAGGTAACCGGG[C/A]CAGA GGGACCGGCGGCTCAGGGTCG (SEQ ID NO: 303)); rs2071493A/G (GTGCCCTGGCGTTTTTGTGTAACTA [A/G]ATATGCGTTCCAGGGTCTCTGATCT (SEQ ID NO: 304)); rs4998G/C (CTCCTCCCTCAGTGG TAGT GTCCAG[G/C]TGCCGTGGAGCAGCAGGCTGGCTTT (SEQ ID NO: 305)); and rs9694197G/A (CCAAGAAA TCTTGCACACCTCAGAC[G/A]CCAGAGATCTCACC CTGCCCTGGTT (SEQ ID NO: 306)) are used to determine the ADRB3 haplotypes. Using the convention order rs4994_rs4997_rs2071493_rs4998_rs9694197 haplotype T_C_T_G_G is referred to herein as Haplotype 1 (H1), haplotype T_A_T_G_G is referred to herein as Haplotype 2 (H2), and haplotype C_A_C_C_A is referred to herein as Haplotype 3 (H3).

In the Sequence Listing, the polymorphic nucleotide site of each sequence is represented by a one letter symbol as set forth in WI PO Standard ST.25 (1998), Appendix 2, Table 2, herein incorporated by reference. For example, "R" represents G or A ([G/A]) at the sequence site, "Y" represents C or T at the sequence site ([C/T]), etc.

In some embodiments of the methods of predicting susceptibility of a subject to develop a somatosensory disorder disclosed herein, determining the genotype of the subject comprises one or more of:

(i) identifying at least one haplotype of ADRB2, ADRB3, COMT or combinations thereof;

(ii) identifying at least one polymorphism unique to at least one haplotype of ADRB2, ADRB3, COMT, or combinations thereof;

(iii) identifying at least one polymorphism exhibiting high linkage disequilibrium to at least one polymorphism unique to at least one ADRB2 haplotype, ADRB3 haplotype, COMT haplotype, or combinations thereof; or (iv) identifying at least one polymorphism exhibiting high linkage disequilibrium to at least one ADRB2 haplotype, ADRB3 haplotype, COMT haplotype, or combinations thereof.

The determined genotype of the subject is then compared to one or more reference genotypes associated with susceptibility to develop a somatosensory disorder and if the determined genotype matches the reference genotype, the subject is predicted to be susceptible to a particular degree (as compared to a population norm) to develop a somatosensory disorder.

As indicated above, the determined genotype need not necessarily be determined based on a need to compare the determined genotype to the reference genotype in particular, but rather can be for example one or more polymorphisms exhibiting high linkage disequilibrium to a COMT, ADRB2, ADRB3 polymorphism or haplotype or combinations thereof, which can be equally predictive of susceptibility to develop a somatosensory disorder. For example, SEQ ID NOs: 29-266 are known SNPs for COMT. It is then determined, by art recognized techniques, if one or more of the known SNPs of COMT exhibit high linkage disequilibrium to one or more of the SNPs used to determine the reference haplotypes of COMT predictive of susceptibility to develop a somatosensory disorder. Thus, after a review of the guidance provided herein, one of ordinary skill would appreciate that any one or more polymorphisms exhibiting high linkage disequilibrium to a polymorphism or haplotype of the determined genotype with regard to COMT could likewise be effective as a substitute or additional component of or as a substitute for the determined genotype. Similarly, SEQ ID NOs: 267-301 and SEQ ID NOs: 302-330 are known SNPs for ADRB2 and ADRB3, respectively, and those SNPs exhibiting high linkage disequilibrium to one or more polymorphisms or haplotypes of the determined genotype with regard to ADRB2 or ADRB3 can also be used as a substitute or additional component of the determined genotype. Likewise, polymorphisms exhibiting high linkage disequilibrium to COMT, ADRB2, or ADRB3 (i.e. haplotypes and/or polymorphisms) could be used to supplement or replace components of the reference genotype.

In some embodiments of the presently disclosed methods, the ADRB2 genotype of the reference genotype is selected from the group consisting of H1, H2, H3, and Uncommon;

the ADRB3 genotype of the reference genotype is selected from the group consisting of H1, H2, H3, and Uncommon; and the COMT genotype of the reference genotype is selected from the group consisting of LPS, APS, and HPS. Further, in some embodiments, the determined genotype of the subject with respect to ADRB2 is selected from the group consisting of two copies of H1 (i.e., homozygous for H1), two copies of H2 (i.e., homozygous for H2), two copies of H3 (i.e., homozygous for H3), one copy of both H2 and H3 (i.e., heterozygous for H2/H3), and at least one copy of Uncommon (i.e., homozygous or heterozygous for Uncommon) and the subject is then predicted to be susceptible to develop the somatosensory disorder. Still further, in some embodiments, the determined genotype of the subject with respect to ADRB3 is selected from the group consisting of two copies of H1, and at least one copy of Uncommon and the subject is predicted to be susceptible to develop the somatosensory disorder. Even further, in some embodiments, the determined genotype of the subject with respect to COMT is selected from the group consisting of two copies of APS, two copies of HPS, and one copy of both APS and HPS and the subject is predicted to be susceptible to develop the somatosensory disorder.

In some embodiments, the presently disclosed subject matter provides methods of classifying a somatosensory disorder afflicting a subject. The methods comprise in some embodiments determining a genotype of the subject with respect to a gene selected from the group consisting of ADRB2, ADRB3, COMT, and combinations thereof and classifying the somatosensory disorder into a genetic subclass somatosensory disorder based on the determined genotype of the subject. Classifying the somatosensory disorder into a genetic subclass somatosensory disorder can be utilized to select an effective therapy for use in treating the genetic subclass somatosensory disorder.

In some embodiments of the methods, determining the genotype of the subject comprises one or more of:
 i. identifying at least one haplotype of ADRB2, ADRB3, COMT or combinations thereof;
 ii. identifying at least one polymorphism unique to at least one haplotype of ADRB2, ADRB3, COMT, or combinations thereof;
 iii. identifying at least one polymorphism exhibiting high linkage disequilibrium to at least one polymorphism unique to at least one ADRB2 haplotype, ADRB3 haplotype, COMT haplotype, or combinations thereof; or
 iv. identifying at least one polymorphism exhibiting high linkage disequilibrium to at least one ADRB2 haplotype, ADRB3 haplotype, COMT haplotype, or combinations thereof.

In some embodiments of the methods, the ADRB2 genotype is selected from the group consisting of Haplotype 1, Haplotype 2, Haplotype 3, and Uncommon; the ADRB3 genotype is selected from the group consisting of Haplotype 1, Haplotype 2, Haplotype 3, and Uncommon; and the COMT genotype is selected from the group consisting of low pain sensitive haplotype (LPS), average pain sensitive haplotype (APS), and high pain sensitive haplotype (HPS).

The presently disclosed subject matter further provides that pain sensitivity-related haplotypes, such as for example ADRB2 and COMT, can be used to guide pharmacological treatment decisions regarding the treatment of persistent or chronic pain and inflammatory conditions, such as for example somatosensory disorders. Specifically, subjects with low COMT activity (HPS/APS group) can be predicted to benefit from pharmacological therapy with ADRB2 antagonists or procedures that block or reduce ADRB2 function, with the best therapeutic effect observed for individuals who are either H2 or H3 homozygous. In contrast, subjects with high COMT activity (LPS group) can be predicted to be poor responders to ADRB2-antagonist therapy, except for subjects carrying H3/H3 and H2/H3 diplotypes.

As such, the presently disclosed subject matter provides in some embodiments methods for selecting a therapy for a subject having a somatosensory disorder. In some embodiments, the methods comprise determining a genotype of the subject with respect to a gene selected from the group consisting of ADRB2, ADRB3, COMT, and combinations thereof and selecting a therapy based on the determined genotype of the subject.

In some embodiments of the methods, determining the genotype of the subject comprises one or more of:
 (i) identifying at least one haplotype of ADRB2, ADRB3, COMT or combinations thereof;
 (ii) identifying at least one polymorphism unique to at least one haplotype of ADRB2, ADRB3, COMT, or combinations thereof;
 (iii) identifying at least one polymorphism exhibiting high linkage disequilibrium to at least one polymorphism unique to at least one ADRB2 haplotype, ADRB3 haplotype, COMT haplotype, or combinations thereof; or
 (iv) identifying at least one polymorphism exhibiting high linkage disequilibrium to at least one ADRB2 haplotype, ADRB3 haplotype, COMT haplotype, or combinations thereof.

In some embodiments, the therapy is selected from the group consisting of a pharmacological therapy, a behavioral therapy, a psychotherapy, a surgical therapy, and combinations thereof. In some embodiments the therapy is a pharmacological therapy comprising administering to the subject an effective amount of an ADRB2 modulator, an ADRB3 modulator, a COMT modulator, or combinations thereof. In some embodiments, the therapy is a behavioral therapy comprising treating the subject with biofeedback therapy and/or relaxation therapy. In some embodiments, the therapy is a surgical therapy, such as for example a back surgery, medical Implant procedures (e.g., CNS stimulators for pain relief), joint implant procedures, dental implant procedures (e.g., tooth implants), or cosmetic/plastic surgery.

In some embodiments of the method, the ADRB2 genotype is selected from the group consisting of Haplotype 1, Haplotype 2, Haplotype 3, and Uncommon; the ADRB3 genotype is selected from the group consisting of Haplotype 1, Haplotype 2, Haplotype 3, and Uncommon; and the COMT genotype is selected from the group consisting of low pain sensitive haplotype (LPS), average pain sensitive haplotype (APS), and high pain sensitive haplotype (HPS). Further, in some embodiments, the determined genotype of the subject with respect to ADRB2 is selected from the group consisting of two copies of H2, two copies of H3, and one copy of both H2 and H3 and an effective amount an effective amount of an ADRB2 modulator, a COMT modulator, or combinations thereof is selected as a therapy. Still further, in some embodiments, the determined genotype of the subject with respect to ADRB3 is selected from the group consisting of two copies of H1 and an effective amount of an ADRB3 modulator, a COMT modulator, or combinations thereof is selected as a therapy. Even further, in some embodiments, the determined genotype of the subject with respect to COMT is selected from the group consisting of two copies of APS, two copies of HPS, and one copy of both APS and HPS and an effective amount of an ADRB2 modulator, an ADRB3 modulator, a COMT modulator, or combinations thereof is selected as a therapy. In some embodiments, the ADRB2 modulator can be an ADRB2 antagonist. Further, in some embodiments, the ADRB3 modulator is an ADRB3 antagonist. The ADRB2 and ADRB3 antagonists can be selective or nonselective for ADRB2 and ADRB3, respectively and can be selected for administration either alone or in combination. Still further, in some embodiments, the COMT modulator is a COMT activator. Examples of nonselective ADRB2 antagonist include, but are not limited to: propranolol, sotalol, timolol, carteolol, carvedilol, nadolol, penbutolol, labetalol, and pindoloL Examples of relatively selective ADRB2 antagonists include, but are not limited to: butoxamine [DL-erythro-.alpha.-(2,5-dimethoxyphenyl)-.beta.-t-butyl aminopropanol hydrochloride], ICI 118,551 [(−)-1-(2,3-[dihydro-7-methyl-1H-inden-4-yl]oxy)-3-([1-methylethyl]-amino)-2-butanol], and H35/25 [1-(4'methylphenyl)-b 2,2-1-isopropylaminopropanol. Examples of relatively selective ADRB3 antagonists include, but are not limited to: L748337 [(S)—N-[4-[2-[[3-[3-(acetamidomethyl)phenoxy]-2-hydroxypropyl] ami-no] ethyl] phenyl] benzenesulfonamide], CL 316234 [disodium (R,R)-5-(2-[{2-(3-chlorophenyl)-2-hydroxyethyl}-amino]propyl)-1,3-benzodioxole-2,2, dicarboxylate], SR59230A [(1-(2-ethylphenoxy)-3-[[(1S)-1,2,3,4-tetrahydro-1-naphthalenyl]amino]-(2S)-2-propanol)]. A further example of a ADRB2 antagonist is estrogen, and its associated metabolites, which impair ADRB2 receptor transduction and signaling in response to agonist stimulation. An example of a COMT activator is, but is not limited to, progesterone, which induces the expression of COMT.

II.E. Methods of Predicting a Pain Response

The presently disclosed subject matter provides methods of predicting a pain response in a subject. In some embodiments, the methods comprise determining a genotype of the subject with respect to a gene selected from the group consisting of ADRB2, ADRB3, COMT, and combinations thereof and comparing the genotype of the subject with at least one reference genotype associated with pain response variability, wherein the reference genotype is selected from the group consisting of an ADRB2 genotype, an ADRB3 genotype, a COMT genotype, and combinations thereof, whereby pain response in the subject is predicted.

In some embodiments of the methods, determining the genotype of the subject comprises one or more of: (i) identifying at least one haplotype of ADRB2, ADRB3, COMT or combinations thereof; (ii) identifying at least one polymorphism unique to at least one haplotype of ADRB2, ADRB3, COMT, or combinations thereof; (iii) identifying at least one polymorphism exhibiting high linkage disequilibrium to at least one polymorphism unique to at least one ADRB2 haplotype, ADRB3 haplotype, COMT haplotype, or combinations thereof; or (iv) identifying at least one polymorphism exhibiting high linkage disequilibrium to at least one ADRB2 haplotype, ADRB3 haplotype, COMT haplotype, or combinations thereof.

In some embodiments, the ADRB2 genotype of the reference genotype is selected from the group consisting of H1, H2, and H3; the ADRB3 genotype of the reference genotype is selected from the group consisting of H1, H2, and H3; and the COMT genotype of the reference genotype is selected from the group consisting of LPS, APS, and HPS. Further, in some embodiments, the determined genotype of the subject with respect to ADRB2 is only one copy of Haplotype1, and the subject is predicted to have a decreased sensitivity to pain as compared to a population norm. Still further, in some embodiments, the determined genotype of the subject with respect to ADRB3 is selected from the group consisting of at least one copy of H2 and at least one copy of H3 and the subject is predicted to have decreased sensitivity to pain as compared to a population norm. Even further, in some embodiments of the methods, the determined genotype of the subject with respect to COMT is selected from the group consisting of two copies of APS, two copies of HPS, and one copy of both APS and HPS and the subject is predicted to have an increased sensitivity to pain as compared to a population norm.

II.F. Methods of Predicting Somatization

The presently disclosed subject matter provides methods of predicting somatization in a subject. In some embodiments, the methods comprise determining a genotype of the subject with respect to a gene selected from the group consisting of ADRB2, ADRB3, COMT, and combinations thereof and comparing the genotype of the subject with at least one reference genotype associated with pain response variability, wherein the reference genotype is selected from the group consisting of an ADRB2 genotype, an ADRB3 genotype, a COMT genotype, and combinations thereof, whereby somatization in the subject is predicted.

In some embodiments of the methods, determining the genotype of the subject comprises one or more of:
 (i) identifying at least one haplotype of ADRB2, ADRB3, COMT or combinations thereof;
 (ii) identifying at least one polymorphism unique to at least one haplotype of ADRB2, ADRB3, COMT, or combinations thereof;
 (iii) identifying at least one polymorphism exhibiting high linkage disequilibrium to at least one polymorphism unique to at least one ADRB2 haplotype, ADRB3 haplotype, COMT haplotype, or combinations thereof; or
 (iv) identifying at least one polymorphism exhibiting high linkage disequilibrium to at least one ADRB2 haplotype, ADRB3 haplotype, COMT haplotype, or combinations thereof.

In some embodiments, the ADRB2 genotype of the reference genotype is selected from the group consisting of H1, H2, and H3; the ADRB3 genotype of the reference genotype is selected from the group consisting of H1, H2, and H3; and the COMT genotype of the reference genotype is selected from the group consisting of LPS, APS, and HPS. Further, in some embodiments, the determined genotype of the subject with respect to ADRB2 is two copies of H2 and the subject is predicted to have increased somatization as compared to a population norm. Still further, in some embodiments, the determined genotype of the subject with respect to ADRB3 is at least one copy of H3 and the subject is predicted to have decreased somatization as compared to a population norm. Even further, in some embodiments of the methods, the determined genotype of the subject with respect to COMT is selected from the group consisting of two copies of APS, two copies of HPS, and one copy of both APS and HPS and the subject is predicted to have increased somatization as compared to a population norm.

II.G. Methods of Predicting Biological Activity of ADRB2, COMT and ADRB3

The presently disclosed subject matter provides methods of predicting biological activity of ADRB2, ADRB3, and COMT in a subject. In some embodiments, the methods comprise determining a genotype of the subject with respect to a gene selected from the group consisting of ADRB2, ADRB3, COMT, and combinations thereof and comparing the genotype of the subject with at least one reference genotype associated with variability in biological activity, wherein the reference genotype is selected from the group consisting of an ADRB2 genotype, an ADRB3 genotype, a COMT genotype, and combinations thereof, whereby biological activity of the proteins in the subject is predicted.

In some embodiments of the methods, determining the genotype of the subject comprises one or more of:
  (i) identifying at least one haplotype of ADRB2, ADRB3, COMT or combinations thereof;
  (ii) identifying at least one polymorphism unique to at least one haplotype of ADRB2, ADRB3, COMT, or combinations thereof;
  (iii) identifying at least one polymorphism exhibiting high linkage disequilibrium to at least one polymorphism unique to at least on ADRB2 haplotype, ADRB3 haplotype, COMT haplotype, or combinations thereof; or
  (iv) identifying at least one polymorphism exhibiting high linkage disequilibrium to at least one ADRB2 haplotype, ADRB3 haplotype, COMT haplotype, or combinations thereof.

In some embodiments, the ADRB2 genotype of the reference genotype is selected from the group consisting of H1, H2, and H3; the ADRB3 genotype of the reference genotype is selected from the group consisting of H1, H2, and H3; and the COMT genotype of the reference genotype is selected from the group consisting of LPS, APS, and HPS. Further, in some embodiments, the determined genotype of the subject with respect to ADRB2 is two copies of H1 and the subject is predicted to have low biological activity of ADRB2 as compared to a population norm. In some embodiments, the determined genotype of the subject with respect to ADRB2 is two copies of H2, two copies of H3, and one copy of each H2 and H3 and the subject is predicted to have high biological activity of a ADRB2 receptor as compared to a population norm. In some embodiments, the determined genotype of the subject with respect to ADRB2 is two copies of H3 and the subject is predicted to have high biological activity of a ADRB2 receptor as compared to a population norm in a resting state and low biological activity of a ADRB2 receptor as compared to a population norm in response to an agonist, including but not limited to epinephrine. Further, in some embodiments, the determined genotype of the subject with respect to ADRB3 is at least one copy of H2 or H3 and the subject is predicted to have low biological activity of ADRB3 as compared to a population norm. Even further, in some embodiments of the methods, the determined genotype of the subject with respect to COMT is selected from the group consisting of two copies of APS, two copies of HPS, and one copy of both APS and HPS and the subject is predicted to have low enzymatic activity of COMT as compared to a population norm.

Further, in some embodiments of the methods, the determined genotype of the subject with respect to COMT is selected from the group consisting of two copies of APS, two copies of HPS, and one copy of both APS and HPS and the subject is predicted to need a low effective dosage of a therapeutic compound metabolized by COMT and high adverse biological side effect to the subject by a compound metabolized by COMT, as compared to a population norm. Examples of the compounds include, but are not limited to: Steroid sex hormones such as estrogen; Drugs that inhibit COMT enzyme such as tolcapone; Drugs that influence the bioavailability of norepinephrine and dopamine such as methylphenidate and L-DOPA; Drugs that influence the reuptake of norepinephrine such as antidepressants; drugs that influence α-adrenergic receptors such as clonidine and mirtazapine; drugs that influence dopamine receptors such as antipsychotics.

III. Methods of Treatment

As disclosed herein, stimulation of ADRB2 and ADRB3 in vitro leads to increased transcription of proinflammatory cytokines (see Examples). In macrophages, the selective ADRB2 agonist salmeterol produces a 38-fold increase in IL-1β and a 6.5-fold increase in IL-6 mRNA levels. In adipocytes, salmeterol produces a 6-fold increase in TNFα and an 8-fold increase in IL-6 mRNA levels. The increased transcription of proinflammatory cytokines produced by salmeterol was completely blocked by the selective ADRB2 antagonist ICI118,551, but not by the ADRB1 antagonist betaxolol or the ADRB3 antagonist SR59230A. The selective ADRB3 agonist CL316243 produced a 28-fold increase in adipocyte IL-6 mRNA levels. The CL316243-induced increase in IL-6 transcription was completely blocked by the ADRB3 antagonist, but not by ADRB1 or ADRB2 antagonists. Further, COMT regulates activity of catecholamines, such as for example epinephrine and norepinephrine, and therefore decreased COMT activity can lead to elevated levels of epinephrine and norepinephrine. Increased activity in these catecholamines can further activate ADRB2 and/or ADRB3. As shown in FIG. 8, COMT, ADRB2 and ADRB3 act in concert and increased or decreased activity of each can result in increased or decreased levels of proinflammatory cytokines, which in turn can manifest as an increase in pain sensitivity and/or possibly result in inflammation.

Thus, taken together, these data demonstrate that stimulation of ADRB2 and ADRB3 located for example on macrophages and adipocytes can result in elevated levels of prototypical proinflammatory cytokines that are known to activate peripheral and central neural pathways that evoke the sensation of pain. Furthermore, reduction or blockade of ADRB2 and ADRB3 function (e.g., specific and/or non-specific antagonists), or the activation of COMT, can be used to treat persistent pain and associated inflammatory conditions by blocking pro-pain and proinflammatory cytokine production.

IIIA. Methods of Treating a Somatosensory Disorder

The presently disclosed subject matter provides methods of treating a somatosensory disorder in a subject. In some embodiments, the methods comprise administering to the subject an effective amount of a COMT modulator, an ADRB2 modulator, an ADRB3 modulator, or combinations thereof.

In some embodiments, the ADRB2 modulator can be an ADRB2 antagonist. In some embodiments the ADRB3 modulator can be an ADRB3 antagonist. In some embodiments, the COMT modulator is a COMT activator. The ADRB2 and ADRB3 antagonists can be specific or non-specific for ADRB2 and ADRB3, respectively and can be administered either alone or in combination. Examples of non-selective ADRB2 antagonist include, but are not limited to: propranolol, sotalol, timolol, carteolol, carvedilol, nadolol, penbutolol, labetalol, and pindolol. Examples of relatively selective ADRB2 antagonists include, but are not limited to: butoxamine [DL-erythro-.alpha.-(2,5-dimethoxyphenyl)-.beta.-t-butyl aminopropanol hydrochloride], ICI 118,551 [(−)-1-(2,3-[dihydro-7-methyl-1H-inden-4-yl]oxy)-3-([1-methylethyl]-amino)-2-butanol], and H35/25 [1-(4'-methylphenyl)-b 2,2-1-isopropylaminopropanol. Examples of relatively selective ADRB3 antagonists include, but are not limited to: L748337 [(S)—N-[4-[2-[[3-[3-(acetamidomethyl)phenoxy]-2-hydroxypropyl]ami-no]ethyl]phenyl] benzenesulfonamide], CL316234 [disodium(R,R)-5-(2-[{2-(3-chlorophenyl)-2-hydroxyethyl}-amino]propyl)-1,3-benzodioxole-2,2,dicarboxylate], SR59230A [(1-(2-ethylphenoxy)-3-[[(1S)-1,2,3,4-tetrahydro-1-naphthalenyl]amino]-(2S)-2-propanol)]. A further example of a ADRB2 antagonist is estrogen, and its associated metabolites, which impair ADRB2 receptor transduction and signaling in response to agonist stimulation. An example of a COMT activator is, but is not limited to, progesterone, which induces the expression of COMT.

The genotyping methods for predicting or determining pain sensitivity disclosed herein are applicable as well to the present methods of treating a somatosensory disorder. Determining a genotype of a subject with regard to pain perception or pain sensitivity genotypes, such as for example ADRB2, ADRB3, COMT genotypes and combinations thereof can be useful in selecting a particular therapy for use in treating the subject, for example as discussed herein above in particular with regard to ADRB2 and ADRB3 antagonist therapies.

As such, in some embodiments of the methods for treating a somatosensory disorder, the methods further comprise determining a genotype of the subject with respect to a gene selected from the group consisting of ADRB2, ADRB3, COMT, and combinations thereof and administering to the subject the effective amount of the COMT modulator, the ADRB2 modulator, the ADRB3 modulator, or combinations thereof based on the determined genotype of the subject.

In some embodiments of the methods, determining the genotype of the subject comprises one or more of:
  (i) identifying at least one haplotype of ADRB2, ADRB3, COMT or combinations thereof;
  (ii) identifying at least one polymorphism unique to at least one haplotype of ADRB2, ADRB3, COMT, or combinations thereof;
  (iii) identifying at least one polymorphism exhibiting high linkage disequilibrium to at least one polymorphism unique to at least one ADRB2 haplotype, ADRB3 haplotype, COMT haplotype, or combinations thereof; or
  (iv) identifying at least one polymorphism exhibiting high linkage disequilibrium to at least one ADRB2 haplotype, ADRB3 haplotype, COMT haplotype, or combinations thereof.

In some embodiments of the methods, the ADRB2 genotype is selected from the group consisting of Haplotype 1, Haplotype 2, Haplotype 3, and Uncommon; the ADRB3 genotype is selected from the group consisting of Haplotype 1, Haplotype 2, Haplotype 3, and Uncommon; and the COMT genotype is selected from the group consisting of low pain sensitive haplotype (LPS), average pain sensitive haplotype (APS), and high pain sensitive haplotype (HPS). Still further, in some embodiments, the determined genotype of the subject with respect to ADRB2 is selected from the group consisting of two copies of H2, two copies of H3, one copy of both H2 and H3, and at least one copy of Uncommon and the somatosensory disorder is treated by administering the ADRB2 modulator, the COMT modulator, or combinations thereof to the subject. Still further, in some embodiments, the determined genotype of the subject with respect to ADRB3 is selected from the group consisting of two copies of H1 and at least one copy of Uncommon and the somatosensory disorder is treated by administering the ADRB2 modulator, the COMT modulator, or combinations thereof to the subject. Even further, in some embodiments, the determined genotype of the subject with respect to COMT is selected from the group consisting of two copies of APS, two copies of HPS, and one copy of both APS and HPS and the somatosensory disorder is treated by administering the ADRB2 modulator, the COMT modulator, or combinations thereof to the subject.

III.B. Methods of Modulating Production of Proinflammatory Cytokines

The presently disclosed subject matter further provides methods of modulating production of proinflammatory cytokines in a subject (see FIG. 8). In some embodiments, the methods comprise administering to the subject an effective amount of a COMT modulator, an ADRB2 modulator, an ADRB3 modulator, or combinations thereof to thereby modulate production of proinflammatory cytokines.

Proinflammatory cytokines are cytokines that can induce, increase or maintain inflammation in vitro or in vivo in a subject. Exemplary proinflammatory cytokines include, but are not limited to of IL-6, IL-1α, IL-1β, TNF-α, and combinations thereof.

In some embodiments of the methods, modulating production of proinflammatory cytokines comprises inhibiting production of proinflammatory cytokines. As such, the ADRB2 modulator can be an ADRB2 antagonist, the ADRB3 modulator can be an ADRB3 antagonist, and the COMT modulator can be a COMT activator, as each of which can cause down regulation or inhibition of proinflammatory cytokines (see FIG. 8). In some embodiments, both the ADRB2 antagonist and the ADRB3 antagonist can be administered to the subject. In some embodiments, the COMT activator, the ADRB2 antagonist and the ADRB3 antagonist can be administered to the subject.

Chemical small molecular weight compounds can be used as ADRB2 and ADRB3 antagonists. However, any chemical or biological compound that inhibits function of the receptors can be used, such as antisense DNA, RNA or oligonucleotides, siRNA, inhibitory peptide or dominant-negative mutant. Furthermore, any chemical or biological compound that activates COMT can be used as COMT activator, for example, introduction of plasmid or viral DNA expressing COMT protein into a subject.

In some embodiments of the methods for modulating production of proinflammatory cytokines, the methods further comprise determining a genotype of the subject with respect to a gene selected from the group consisting of ADRB2, ADRB3, COMT, and combinations thereof and administering to the subject the effective amount of the COMT modulator, the ADRB2 modulator, the ADRB3 modulator, or combinations thereof based on the determined genotype of the subject.

In some embodiments of the methods, determining the genotype of the subject comprises:
  (i) identifying at least one haplotype of ADRB2, ADRB3, COMT or combinations thereof;
  (ii) identifying at least one polymorphism unique to at least one haplotype of ADRB2, ADRB3, COMT, or combinations thereof;
  (iii) identifying at least one polymorphism exhibiting high linkage disequilibrium to at least one polymorphism unique to at least one ADRB2 haplotype, ADRB3 haplotype, COMT haplotype, or combinations thereof; or
  (iv) identifying at least one polymorphism exhibiting high linkage disequilibrium to at least one ADRB2 haplotype, ADRB3 haplotype, COMT haplotype, or combinations thereof.

In some embodiments of the methods, the ADRB2 genotype is selected from the group consisting of Haplotype 1, Haplotype 2, Haplotype 3, and Uncommon; the ADRB3 genotype is selected from the group consisting of Haplotype 1, Haplotype 2, Haplotype 3, and Uncommon; and the COMT genotype is selected from the group consisting of low pain sensitive haplotype (LPS), average pain sensitive haplotype (APS), and high pain sensitive haplotype (HPS). Further, in some embodiments, the determined genotype of the subject with respect to ADRB2 is selected from the group consisting of two copies of H2, two copies of H3, and one copy of both H2 and H3 and the production of proinflammatory cytokines in the subject is modulated by administering the ADRB2 modulator, the COMT modulator, or combinations thereof to the subject. Still further, in some embodiments, the determined genotype of the subject with respect to ADRB3 is selected from the group consisting of two copies of Haplotype 1, and the production of proinflammatory cytokines in the subject is modulated by administering the ADRB3 modulator, the COMT modulator, or combinations thereof to the subject. Even further, in some embodiments, the determined genotype of the subject with respect to COMT is selected from the group consisting of two copies of APS, two copies of HPS, and one copy of both APS and HPS and the production of proinflammatory cytokines in the subject is modulated by administering the COMT modulator, the ADRB2 modulator, the ADRB3 modulator, or combinations thereof to the subject.

III.C. Representative Therapeutic Approaches

As noted herein above, the term "modulate" can refer to an increase, decrease, or other alteration of any, or all, chemical and biological activities or properties of a wild-type or mutant polypeptide, such as for example COMT, ADRB2, ADRB3 or combinations thereof. A peptide can be modulated at either the level of expression, e.g., modulation of gene expression (for example, antisense therapy, siRNA or other similar approach, gene therapy, including exposing the subject to a gene therapy vector encoding a gene of interest or encoding a nucleotide sequence that influences expression of a gene of interest), or at the level of the expressed protein, e.g., administering to a subject an agonist or antagonist of a receptor macromolecule, such as ADRB2 and/or ADRB3, or an activator or inactivator of an enzyme polypeptide, such as for example COMT. The term "modulation" as used herein refers to both upregulation (i.e., activation or stimulation) and down regulation (i.e. inhibition or suppression) of a response.

III.C.1. Gene Therapy

Thus, the presently disclosed subject matter also provides for gene, therapy compositions, methods, systems and approaches. Exemplary gene therapy methods, including liposomal transfection of nucleic acids into host cells, are described in U.S. Pat. Nos. 5,279,833; 5,286,634; 5,399, 346; 5,646,008; 5,651,964; 5,641,484; and 5,643,567, the contents of each of which are herein incorporated by reference.

Briefly, gene therapy directed toward modulation of polypeptide levels, to thereby affect or modulate the biological activity of, for example, COMT, ADRB2, ADRB3 or combinations thereof in a target cell is provided. In one embodiment, a therapeutic method of the present invention provides a process for modulation of polypeptide levels comprising: (a) delivering to the cell an effective amount of a DNA molecule comprising a polynucleotide that encodes a polypeptide; and (b) maintaining the cell under conditions sufficient for expression of said polypeptide.

A vehicle can be a cell transformed or transfected with the DNA molecule or a transfected cell derived from such a transformed or transfected cell. Approaches for transforming or transfecting a cell with a DNA molecule are disclosed herein and are known in the art.

Nonviral DNA delivery vehicles include polyamines and neutral polymers (synthetic or nonsynthetic, such as gelatin) capable of condensing DNA to nanoparticles with radii of 20-100 nm. Nanoparticles have great potential in providing sustained gene expression in cells and in providing simple and reproducible production, allowing for future up-scaling and commercial production. Thus, nanoparticles are suitable for use in combination with the nucleic acids of the presently disclosed subject matter. See generally Vijayanathan V, Thomas T, Thomas T J (2002) DNA Nanoparticles and Development of DNA Delivery Vehicles for Gene Therapy. *Biochemistry* 41 (48):14085-94; Brannon-Peppas L & Blanchette J O (2004) Nanoparticle and Targeted Systems for Cancer Therapy. *Adv Drug Deliv Rev* 56(11):1649-59.

Nonviral DNA delivery vehicles also include liposomes. Modern drug encapsulation methods allow efficient packing of therapeutic substances inside liposomes, thereby reducing the systemic toxicity of the drugs. Specific targeting can enhance the therapeutic effect of the drugs through their accumulation at the diseased site. Thus, liposomes are suitable for use in combination with the nucleic acids of the presently disclosed subject matter, and can serve to enhance the cancer-killing selectivity of the presently disclosed subject matter. See Felnerova D, Viret J F, Gluck R, Moser C (2004) Liposomes and Virosomes as Delivery Systems for Antigens, Nucleic Acids and Drugs. *Curr Opin Biotechnol* 15(6):518-29.

III.C.2. Viral Vectors

The vehicle can comprise a virus or an antibody that specifically infects or immunoreacts with an antigen of the target tissue or tumor. An advantage of a viral infection system is that it allows for a very high level of infection into the appropriate recipient cell. Also, antibodies have been used to target and deliver DNA molecules.

It is also envisioned that this embodiment of the present invention can be practiced using alternative viral or phage vectors, including retroviral vectors and vaccinia viruses whose genome has been manipulated in alternative ways so as to render the virus non-pathogenic. Methods for creating such a viral mutation are set forth in detail in U.S. Pat. No. 4,769,331, incorporated herein by reference.

Indeed, viral vectors have been widely used as systems for delivering nucleic acid sequences of interest to cells. Retrovirus, lentivirus, herpes virus, and parvovirus vectors have all been used, and each system has its advantages. Retroviruses have the advantage that they efficiently insert themselves into a host chromosome, ensuring long-term expression. "Pseudotyped" variants of retrovirus are available that will insert themselves into all cells or only into specific cells. However, the efficient insertion of retroviruses into host chromosomes is also a disadvantage, as random insertions can create mutations that are deleterious. Also, some retroviruses require that the host cell be in a state of replication before they can integrate into the host genome.

Lentiviruses, including human immunodeficiency virus (HIV), are a group of related retroviruses. Like other retrovirus vectors, lentivirus vectors can accommodate transgenes up to about 8 kb in length, and can be prevented from replicating by eliminating essential viral genes. Unlike other retrovirus vectors, lentivirus vectors are able to infect non-dividing cells.

Herpes simplex virus is a double-stranded DNA virus with a 152-kb genome. Its relatively large size means that it could be used for manipulation of larger transgenes and even multiple transgenes. Herpes simplex virus can infect a wide variety of cell types in both the dividing and the nondividing state.

Retrovirus, lentivirus, and herpes virus vectors are suitable for use in the methods, systems, and kits of the presently disclosed subject matter, and these vectors are particularly useful in the field of gene therapy, as reviewed in Lundstrom, K (2004) Gene Therapy Applications of Viral Vectors. *Techno/Cancer Res Treat* 3(5):467-77.

Parvoviruses, including adenoviruses, are small, single-stranded, non-enveloped DNA viruses between twenty to thirty nanometers in diameter. The genomes of parvoviruses are approximately 5000 nucleotides long, containing two open reading frames. The left-hand open reading frame encodes the proteins responsible for replication (Rep), while the right-hand open reading frame encodes the structural proteins of the capsid (Cap). All parvoviruses have virions with icosahedral symmetry composed of a major Cap protein, usually the smallest of the Cap proteins, and one or two minor Cap proteins. The Cap proteins are generated from a single gene that initiates translation from different start codons. These proteins have identical C-termini, but possess unique N-termini due to different initiation codons.

Most parvoviruses have narrow host ranges; the tropism of B19 is for human erythroid cells (Munshi et al., (1993) J. Virology 67:562), while canine parvovirus has a tropism for lymphocytes in adult dogs (Parrish et al., (1988) Virology 166:293; Chang et al., (1992) J. Virology 66:6858). Adena-associated virus (AAV), on the other hand, can replicate well in canine, mouse, chicken, bovine, monkey cells, as well as numerous human cells and cell lines, when the appropriate helper virus is present. In the absence of helper virus, AAV will infect and establish latency in all of these cell types, suggesting that the MV receptor is common and conserved among species. Several serotypes of AAV have been identified, including serotypes 1, 2, 3, 4, 5 and 6.

Adeno-associated virus (AAV) is a dependent parvovirus twenty nanometers in size that requires co-infection with another virus (either adenovirus or certain members of the herpes virus group) to undergo a productive infection in cells. In the absence of co-infection with helper virus, the AAV virion binds to a cellular receptor and enters the cell, migrates to the nucleus, and delivers a single-stranded DNA genome that can establish latency by integration into the host chromosome. The interest in AAV as a vector has centered around the biology of this virus. In addition to its unique life cycle, AAV has a broad host range for infectivity (human, mouse, monkey, dog, etc.), is ubiquitous in humans, and is completely nonpathogenic.

The finite packaging capacity of this virus (4.5 kb) has restricted the use of this vector in the past to small genes or cDNAs. To advance the prospects of AAV gene delivery, vectors sufficient to carry larger genes must be developed. In addition, virions that specifically and efficiently target defined cell types without transducing others are beneficial for clinical applications.

Parvovirus and AAV vectors are suitable for use in the methods, systems, and kits of the presently disclosed subject matter, and these vectors are particularly useful in the field of gene therapy. Representative vectors that can be employed in the methods, systems, and kits of the presently disclosed subject matter are described in U.S. Pat. Nos. 6,458,587; 6,489,162; 6,491,907; and 6,548,286, the contents of which are incorporated in their entireties by reference.

In some embodiments, an adenovirus vector of the presently disclosed subject matter is conditionally replication competent. That is, it contains one or more functional genes required for its replication placed under the transcriptional control of an inducible promoter. This inhibits uncontrolled replication in vivo and reduces undesirable side effects of viral infection. Replication competent self-limiting or self-destructing viral vectors can also be used, as can replication deficient viral vectors.

Incorporation of a nucleic acid construct into a viral genome can be optionally performed by ligating the construct into an appropriate restriction site in the genome of the virus. Viral genomes can then be packaged into viral coats or capsids by any suitable procedure. In particular, any suitable packaging cell line can be used to generate viral vectors of the presently disclosed subject matter. These packaging lines complement the conditionally replication deficient viral genomes of the presently disclosed subject matter, as they include, typically incorporated into their genomes, the genes which have been put under an inducible promoter deleted in the conditionally replication competent vectors. Thus, the use of packaging lines allows viral vectors of the presently disclosed subject matter to be generated in culture.

In some embodiments, the nucleic acids of the presently disclosed subject matter are packaged in a viral vector. For local administration of viral vectors, previous clinical studies have demonstrated that up to $10^{13}$ plaque forming units (pfu) of virus can be injected with minimal toxicity. In human patients, $1\times10^9$-$1\times10^{13}$ pfu are routinely used (see Habib N A, Hodgson H J, Lemoine N & Pignatelli M (1999) A Phase I/li Study of Hepatic Artery Infusion with wtp53-CMV-Ad in Metastatic Malignant Liver Tumours. *Hum Gene Ther* 10:2019-2034). To determine an appropriate dose within this range, preliminary treatments can begin with $1\times10^9$ pfu, and the dose level can be escalated in the absence of dose-limiting toxicity. Toxicity can be assessed using criteria set forth by the National Cancer Institute and is reasonably defined as any grade 4 toxicity or any grade 3 toxicity persisting more than 1 week. Dose is also modified to maximize analgesic activity. With replicative virus vectors, a dosage of about $1\times10^7$ to $1\times10^8$ pfu can be used in some instances.

III.C.3. Transcriptional Modulation

A method for transcriptionally modulating in a multicellular organism the expression of a gene encoding a target polypeptide to modulate polypeptide levels, to thereby affect or modulate the biological activity of, for example, COMT, ADRB2, ADRB3 or combinations thereof in a warm-blooded vertebrate subject is also contemplated in accordance with the present invention. This method comprises administering to the warm-blooded vertebrate subject a compound at a concentration effective to transcriptionally modulate expression of, for example, COMT, ADRB2, ADRB3 or combinations thereof.

In accordance with the presently disclosed subject matter, the compound can optionally comprise an antibody or polypeptide described above and which transcriptionally modulates expression of, for example, COMT, ADRB2, ADRB3 or combinations thereof. Optionally, the antibody or polypeptide directly binds to DNA or RNA, or directly binds to a protein involved in transcription.

Representative chemical entities (e.g., small molecule mimetics) for use in accordance with the presently disclosed subject matter do not naturally occur in any cell, whether of a multicellular or a unicellular organism. In some embodiments the chemical entity is not a naturally occurring molecule, e.g., it is a chemically synthesized entity. Optionally, the compound can bind a modulatable transcription sequence of the gene. For example, the compound can bind a promoter region upstream of a nucleic acid sequence encoding, for example, COMT, ADRB2, ADRB3 or combinations thereof.

In the methods above, modulation of transcription results in either upregulation or down regulation of expression of the gene encoding the protein of interest, depending on the identity of the molecule that contacts the cell.

III.C.4. Antisense Oligonucleotide Therapy

Expression can also be modulated in a subject through the administration of an antisense oligonucleotide derived from a nucleic acid molecule encoding, for example, COMT, ADRB2, ADRB3 or combinations thereof. Therapeutic methods utilizing antisense oligonucleotides have been described in the art, for example, in U.S. Pat. Nos. 5,627,158 and 5,734,033, the contents of each of which are herein incorporated by reference.

III.C.5. RNA Interference

The term "modulate" can also refer to a change in the expression level of a gene, or a level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit" or "suppress", but the use of the word "modulate" is not limited to this definition.

The term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an siRNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

The terms "small interfering RNA", "short interfering RNA", "small hairpin RNA", "siRNA", and shRNA are used interchangeably and refer to any nucleic acid molecule capable of mediating RNA interference (RNAi) or gene silencing. See e.g., Bass, *Nature* 411:428-429, 2001; Elbashir et al., *Nature* 411:494-498, 2001 a; and PCT International Publication Nos. WO00/44895, WO01/36646, WO99/32619, WO00/01846, WO01/29058, WO99/07409, and WO00/44914. In one embodiment, the siRNA comprises a double stranded polynucleotide molecule comprising complementary sense and antisense regions, wherein the antisense region comprises a sequence complementary to a region of a target nucleic acid molecule (for example, a nucleic acid molecule encoding COMT, ADRB2, or ADRB3). In another embodiment, the siRNA comprises a single stranded polynucleotide having self-complementary sense and antisense regions, wherein the antisense region comprises a sequence complementary to a region of a target nucleic acid molecule. In another embodiment, the siRNA comprises a single stranded polynucleotide having one or more loop structures and a stem comprising self-complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

The presently disclosed subject matter takes advantage of the ability of short, double stranded RNA molecules to cause the down regulation of cellular genes, a process referred to as RNA interference. As used herein, "RNA interference" (RNAi) refers to a process of sequence-specific posttranscriptional gene silencing mediated by a small interfering RNA (siRNA). See generally Fire et al., *Nature* 391:806-811, 1998. The process of posttranscriptional gene silencing is thought to be an evolutionarily conserved cellular defense mechanism that has evolved to prevent the expression of foreign genes (Fire, *Trends Genet* 15:358-363, 1999).

RNAi might have evolved to protect cells and organisms against the production of double stranded RNA (dsRNA) molecules resulting from infection by certain viruses (particularly the double stranded RNA viruses or those viruses for which the life cycle includes a double stranded RNA intermediate) or the random integration of transposon elements into the host genome via a mechanism that specifically degrades single stranded RNA or viral genomic RNA homologous to the double stranded RNA species.

The presence of long dsRNAs in cells stimulates the activity of the enzyme Dicer, a ribonuclease III. Dicer catalyzes the degradation of dsRNA into short stretches of dsRNA referred to as small interfering RNAs (siRNA) (Bernstein et al., *Nature* 409:363-366, 2001). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., *Genes Dev* 15:188-200, 2001b).

RNAi has been described in several cell type and organisms. Fire et al., 1998 described RNAi in *C. elegans*. Wianny & Zernicka-Goetz, *Nature Cell Biol* 20 2:70-75, 1999 disclose RNAi mediated by dsRNA in mouse embryos. Hammond et al, *Nature* 404:293-296, 2000 were able to induce RNAi in *Drosophila* cells by transfecting dsRNA into these cells. Elbashir et al. *Nature* 411:494-498, 2001 a demonstrated the presence of RNAi in cultured mammalian cells including human embryonic kidney and Hela cells by the introduction of duplexes of synthetic 21 nucleotide RNAs.

Other studies have indicated that a 5'-phosphate on the target complementary strand of a siRNA duplex facilitate siRNA activity and that ATP is utilized to maintain the 5'-phosphate moiety on the siRNA (Nykanen et al., *Cell* 107:309-321, 2001). Other modifications that might be tolerated when introduced into an siRNA molecule include modifications of the sugar-phosphate backbone or the substitution of the nucleoside with at least one of a nitrogen or sulfur heteroatom (PCT International Publication Nos. WO00/44914 and WO01/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2,359,180).

Other references disclosing the use of dsRNA and RNAi include PCT International Publication Nos. WO01/75164 (in vitro RNAi system using cells from *Drosophila* and the use of specific siRNA molecules for certain functional genomic and certain therapeutic applications); WO01/36646 (methods for inhibiting the expression of particular genes in mammalian cells using dsRNA molecules); WO99/32619 (methods for introducing dsRNA molecules into cells for use in inhibiting gene expression); WO01/92513 (methods for mediating gene suppression by using factors that enhance RNAi); WO02/44321 (synthetic siRNA constructs); WO00/63364 and WO01/04313 (methods and compositions for inhibiting the function of polynucleotide sequences); and WO02/055692 and WO02/055693 (methods for inhibiting gene expression using RNAi).

In some embodiments, the presently disclosed subject matter utilizes RNAi to at least partially inhibit expression of one or more proteins of interest, for example, COMT, ADRB2, or ADRB3, or combinations thereof. Inhibition is preferably at least about 10% of normal expression amounts. In some embodiments, the method comprises introducing an RNA to a target cell in an amount sufficient to inhibit expression of, for example, COMT, ADRB2, or ADRB3, or combinations thereof, wherein the RNA comprises a ribonucleotide sequence which corresponds to a coding strand of a gene of interest. In some embodiments, the target cell is present in a subject, and the RNA is introduced into the subject.

The RNA can have a double-stranded region comprising a first strand comprising a ribonucleotide sequence that corresponds to the coding strand of the gene encoding the target protein (for example, COMT, ADRB2, or ADRB3) and a second strand comprising a ribonucleotide sequence that is complementary to the first strand. The first strand and the second strand hybridize to each other to form the double-stranded molecule. The double stranded region can be at least 15 basepairs in length, and in some embodiments, between 15 and 50 basepairs in length, and in some embodiments the double stranded region is between 15 and 30 basepairs in length.

In some embodiments, the RNA comprises one strand that forms a double-stranded region by intramolecular self-hybridization, which is preferably complementary over at least 19 bases. In some embodiments, the RNA comprises two separate strands that form a double-stranded region by intermolecular hybridization that is complementary over at least 19 bases.

One skilled in the art will recognize that any number of suitable common techniques can be used to introduce the RNAs into a target cell. In some embodiments, a vector encoding the RNA is introduced to the target cell. For example, the vector encoding the RNA can be transfected into the target cell and the RNA is then transcribed by cellular polymerases.

In some embodiments, a recombinant virus comprising nucleic acid encoding the RNA can be produced. Introducing the RNA into a target cell then comprises infecting the target cell with the recombinant adenovirus. Cellular polymerases transcribe the RNA resulting in expression of the RNA within the target cell. Engineering recombinant viruses is well known to those having ordinary skill in the art. One of skill would readily appreciate the multiple factors involved in selecting the appropriate virus and vector components needed to optimize recombinant virus production for use with the presently disclosed subject matter without the necessity of further detailed discussion herein. As one non-limiting example, a recombinant adenovirus can be engineered comprising DNA encoding an siRNA. The virus can be engineered to be replication deficient such that hepatocytes can be infected by the recombinant adenovirus, the siRNA transcribed, and transiently expressed in the infected target cell. Details of recombinant virus production and use can be found in published PCT Patent Application No. PCT/US02/22010, herein incorporated by reference in their entireties. Alternatively, a commercial kit for producing recombinant viruses can be used, such as for example, the pSILENCER ADENO 1.0-CMV SYSTEM™ (Ambion, Austin, Tex., USA).

The presently disclosed subject matter further comprises an isolated siRNA molecule, which inhibits expression of a target protein, for example COMT, ADRB2, or ADRB3.

The siRNA molecule can comprise a sense region and an antisense region, wherein the antisense region comprises a nucleic acid sequence complementary to an RNA sequence encoding the target protein and the sense region comprises a nucleic acid sequence complementary to the antisense region. The siRNA molecule is assembled from the sense region and the antisense region of the siRNA molecule. In a representative embodiment, the sense region comprises a contiguous 19-30 nucleotide sequence and the antisense region comprises the reverse-complement of the sense region. The sense region and the antisense region can further comprise a 3'-terminal overhang, which is preferably 2 to 8 nucleotides in length. The 3'-terminal nucleotide overhang can further contain one or more chemically modified nucleotides.

In some embodiments, the sense region and the antisense region are covalently connected via a linker molecule. In some embodiments, the linker molecule is a polynucleotide linker, for example, a polynucleotide linker of from 5 to 9 nucleotides. In some embodiments, the linker molecule is a non-nucleotide linker. A carrier comprising an siRNA is also provided. Representative carriers include, for example, water, saline, dextrose, glycerol, ethanol or the like, and combinations thereof. The carrier can further include auxiliary substances such as wetting or emulsifying agents, pH buffering agents and the like.

III.D. Formulations

A therapeutic composition as described herein preferably comprises a composition that includes a pharmaceutically acceptable carrier. Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions used in the methods can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

III.E. Doses

The term "effective amount" is used herein to refer to an amount of the therapeutic composition (e.g., a composition comprising an ADRB2, ADRB3, and/or COMT modulator) sufficient to produce a measurable biological response (e.g., a modulation in a biological activity of an ADRB2, ADRB3, and/or COMT polypeptide). Actual dosage levels of active ingredients in a therapeutic composition of the presently disclosed subject matter can be varied so as to administer an amount of the active compound(s) that is effective to achieve the desired therapeutic response for a particular subject and/or application. The selected dosage level will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of a therapeutically effective dose, as well as evaluation of when and how to make such adjustments, are known to those of ordinary skill in the art of medicine.

For administration of a therapeutic composition as disclosed herein, conventional methods of extrapolating human dosage based on doses administered to a murine animal model can be carried out using the conversion factor for converting the mouse dosage to human dosage: Dose Human per kg=Dose Mouse per kg×12 (Freireich et al., (1966)). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich et al. (Freireich et al., (1966)). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

For oral administration, a satisfactory result can be obtained employing the therapeutic compound in an amount ranging from about 0.01 mg/kg to about 100 mg/kg and preferably from about 0.1 mg/kg to about 30 mg/kg. A preferred oral dosage form, such as tablets or capsules, will contain an active ingredient in an amount ranging from about 0.1 to about 500 mg, preferably from about 2 to about 50 mg, and more preferably from about 10 to about 25 mg.

For parenteral administration, the therapeutic composition can be employed in an amount ranging from about 0.005 mg/kg to about 100 mg/kg, preferably about 10 to 50 or 10 to 70 mg/kg, and more preferably from about 10 mg/kg to about 30 mg/kg.

For additional guidance regarding formulation and dose, see U.S. Pat. Nos. 5,326,902; 5,234,933; PCT International Publication No. WO93/25521; Berkow et al. (1997); Goodman et al. (1996); Ebadi (1998); Katzunq (2001); Remington et al. (1975); Speight et al. (1997); and Ouch et al. (1998).

III.F. Routes of Administration

Suitable methods for administering to a subject a compound in accordance with the methods of the presently disclosed subject matter include but are not limited to systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

The particular mode of drug administration used in accordance with the methods of the presently disclosed subject matter depends on various factors, including but not limited to the vector and/or drug carrier employed, the severity of the condition to be treated, and mechanisms for metabolism or removal of the drug following administration.

IV. Subjects

A "subject" as the term is used herein generally refers to an animal. In some embodiments, a preferred animal subject is a vertebrate subject. Further, in some embodiments, a preferred vertebrate is warm-blooded and a preferred warm-blooded vertebrate is a mammal. A preferred mammal is most preferably a human. However, as used herein, the term "subject" includes both human and animal subjects. Thus, veterinary therapeutic uses are provided in accordance with the presently disclosed subject matter.

As such, the presently disclosed subject matter provides for the analysis and treatment of mammals such as humans, as well as those mammals of importance due to being endangered, such as Siberian tigers; of economical importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars;

ruminants and/or ungulates such as cattle, oxen, sheep, giraffes, deer, goats, bison, and camels; and horses: A "subject" as the term is used herein can further include birds, such as for example those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, "subject" further includes livestock, including, but not limited to, domesticated swine, ruminants, ungulates, horses (including race horses), poultry, and the like.

V. Animal Models

It is within the scope of the presently disclosed subject matter to provide a non-human animal possessing modulated protein activity levels and methods of producing the non-human animal. In some embodiments, the non-human animal possesses modulated COMT activity, modulated ADRB2 activity, modulated ADRB3 activity, or combinations thereof. In embodiments where the non-human animal possesses modulated activity of one or more of these proteins, the animal exhibits characteristics of a somatosensory disorder. That is, the animal manifests a measurable biological or psychological characteristic that is comparable to one or more characteristics observed in human subjects suffering from a somatosensory disorder. A characteristic can, but need not necessarily be, a symptom of a somatosensory disorder, such as for example increased sensitivity to painful stimulation, fever, psychological disturbances, measurable electrical and chemical changes in the neurochemistry of the brain, and changes in blood chemistry. As such, the animal can serve as a model of a human somatosensory disorder, either as a complete model of a somatosensory disorder, or as a model of one aspect of a somatosensory disorder.

The presently disclosed subject matter further provides methods of producing a non-human animal model of a human somatosensory disorder. In some embodiments, the method comprises modulating COMT activity, ADRB2 activity, ADRB3 activity, or combinations thereof in the non-human animal model to produce the non-human animal model of the human somatosensory disorder. In some embodiments, COMT activity in the animal is inhibited by administering a COMT inhibitor to the animal. In some embodiments, the nonhuman animal model exhibits an increase in production of proinflammatory, propain producing cytokines, such as for example IL-6, IL-1β, TNF-α, IL-1α and combinations thereof, as a result of modification of a protein activity, such as for example inhibition of COMT activity in the animal. The presently disclosed subject matter provides for modulating protein activity in the non-human animal not only pharmacologically, but also through genetic modification techniques.

In some embodiments, the non-human animal is a genetically modified animal. The genetically modified animal can be a rodent, such as for example a mouse. Further, in some embodiments, the genetically modified animal is a transgenic animal that overexpresses a protein, such as for example ADRB2 and/or ADRB3. In some embodiments, the genetically modified animal is a knockout animal. That is, the genetically modified animal has had a targeted disruption of one or more genes such that substantially no functional gene product is produced from the one or more genes. In some embodiments, the knockout animal is a COMT knockout. In some embodiments, the genetically modified animal is a knockdown animal. That is, the genetically modified animal has had a targeted disruption of one or more genes such that substantially less functional gene product is produced from the one or more genes. In some embodiments, the knockdown animal is a COMT knockdown.

Techniques for the preparation of transgenic animals, including knockout animals, are known in the art. Exemplary techniques are described in U.S. Pat. No. 5,489,742 (transgenic rats); U.S. Pat. Nos. 4,736,866; 5,550,316; 5,614,396; 5,625,125; and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), the entire contents of each of which are herein incorporated by reference.

With respect to a representative method for the preparation of a transgenic mouse, cloned recombinant or synthetic DNA sequences or DNA segments encoding a polypeptide gene product from a different species are injected into fertilized mouse eggs. The injected eggs are implanted in pseudo pregnant females and are grown to term to provide transgenic mice whose cells express the foreign polypeptide.

EXAMPLES

Materials and Methods for Examples 1-6

Study Population

Subjects for the baseline analysis were 202 healthy pain-free females aged 18-34 years who provided a blood sample and consent for genotyping from among a larger cohort of 244 females who volunteered for a research project. Volunteers were recruited between April 1998 and March 2000 using advertisements placed in local newspapers in the Raleigh-Durham-Chapel Hill area of central North Carolina, U.S.A. (Table 1). The advertisements explained that healthy females were sought for an ongoing prospective study designed to examine and identify factors that influence sensory perception. No treatment was offered.

Females who responded to advertisements completed a comprehensive medical history to rule out any previous or current history of pain-related disorder or other medical related conditions that might alter their pain perception. Participants completed a series of pain perception assessments and underwent a physical examination at the University of North Carolina School of Dentistry. All subjects underwent pain perception assessments as described herein.

The study was conducted with both written and verbal informed consent using protocols reviewed and approved by the UNC School of Dentistry's Committee on Investigations Involving Human Subjects. Subjects were paid up to $300 for their participation on a sliding scale depending on the number of visits they completed.

TABLE 1

Baseline characteristics of the cohort and percentage genotyped

| Group | | No. in cohort* | No. genotyped* | % genotyped | P-value[†] |
|---|---|---|---|---|---|
| Age: | 18-22 yrs | 129 | 109 | 84.5 | 0.46 |
| | 23-34 yrs | 115 | 93 | 80.9 | |
| Race: | White | 205 | 171 | 83.4 | 0.55 |
| | Other | 39 | 31 | 79.5 | |
| Highest level of education | High school | 50 | 41 | 82.0 | 0.48 |
| | College | 134 | 114 | 85.1 | |
| | Post-grad | 89 | 46 | 78.0 | |
| Marital status | Single | 198 | 164 | 82.8 | 0.97 |
| | Other | 46 | 38 | 82.6 | |
| Baseline pain z-score | <-4.5 | 81 | 73 | 90.1 | 0.07 |
| | -4.5-3.0 | 82 | 63 | 76.8 | |
| | >3.0 | 81 | 66 | 81.5 | |
| Total | | 244 | 202 | 82.8 | |

*Numbers that do not add to total have missing values for socio-demographic variables
[†]Chi-square test Baseline Characteristics of Subjects and Consent for Genotyping At baseline, 244 females volunteered to take part in the study and completed baseline assessments. 202 (83%) of them also provided a blood sample and written consent for genotyping. The percentage genotyped did not differ among sociodemographic subgroups of age, race, education or marital status (Table 1). There were marginal differences (P=0.07) in the percent genotyped among tertiles of baseline summary pain z-score (see below), although the trend was uniform: those who were least pain responsive were most likely to be genotyped (90% of subjects in the lowest quartile) followed by the most pain responsive (81% of subject in the highest quartile) while those with the mid-tertile of pain responsiveness were least likely to be genotyped (77%).

Pain Sensitivity Assessments

All pain measurements, with the exception of pressure pain measures, were performed during the follicular phase of the subject's menstrual cycle between days 3-10 where day 0 represents the onset of menstruation. The reason for this was to control for the modest effects of menstrual cycle on pain sensitivity. Pressure pain thresholds were taken at a separate session approximately 1 week prior to thermal and ischemic pain assessments. All subjects were asked to refrain from consuming over-the-counter pain relieving medications for at least 48 hours before visiting the laboratory and all subjects were free of prescription pain medications for at least two weeks prior to sensory testing.

Pressure Pain Thresholds

Pressure pain thresholds were assessed over the right and left temporalis muscles, masseter muscles, temporomandibular joints, and ventral surfaces of the wrists with a hand-held pressure algometer (Pain Diagnosis and Treatment, Great Neck, N.Y., U.S.A.) using methods similar to those described by Jaeger and Reeves (1986). The algometer's tip consisted of a flat 10 mm diameter rubber pad. Pressure stimuli were delivered at an approximate rate of 1 kg/sec. Participants were instructed to signal either verbally or by a hand movement when the pressure sensation first became painful. When this occurred, the stimulus was removed. The pressure pain threshold was defined as the amount of pressure (kg) at which the subjects first perceived to be painful. The pressure application was not allowed to exceed 6 kg for the wrists and 4 kg for other sites. When those values were attained, the trials were terminated and these values were entered into the calculation for the subject's pressure pain thresholds. One pre-trial assessment was performed at each site followed by two additional assessments. The two values from the right and left sides were then averaged to obtain one pressure pain threshold value per test site, yielding a total of four measures.

Assessment of Thermal Pain Thresholds and Tolerances

A modified "Marstock" procedure (Fagius & Wahren (1981); Fruhstorfer et al. (1976)) was used to measure thermal pain thresholds and tolerances with a 10 mm diameter computer (486 DOS-based PC) controlled contact thermal stimulator. Thermal stimuli were applied to the skin overlying the right masseter muscle, the skin overlying the right hairy forearm, and the skin overlying the dorsal surface of the right foot. Thermal pain threshold was defined as the temperature (° C.) at which the subjects perceived the thermal stimuli as painful, whereas thermal pain tolerance was defined as the temperature (° C.) at which the subjects can no longer tolerate the thermal stimulus.

Two separate procedures were used to assess thermal pain thresholds and a third procedure assessed thermal pain tolerance, each at three anatomical sites. The first set of thermal stimuli was delivered from a neutral adapting temperature of 32° C. at a rate of 3° C./sec which has been proposed to produce a relatively selective activation of Aδ-fibers. During this procedure, subjects were instructed to depress a mouse key when they first perceived thermal pain. This caused the thermode to return to the baseline temperature and the reversal temperature was defined as the Aδ mediated thermal pain threshold temperature. This procedure was repeated six times and the values from these six trials were averaged to obtain the temperature value of Aδ mediated thermal pain threshold. The same procedure was repeated with a second set of thermal stimuli delivered at a rate of 0.5° C./sec. This procedure has been proposed to produce a relatively selective activation of C-fibers. Finally, C-fiber thermal pain tolerance was determined by using a third set of thermal stimuli delivered at the rate of 0.5° C./sec. Subjects were instructed to depress the mouse key when the probe temperature achieved a level that they could no longer tolerate. The probe temperature was not allowed to exceed 53° C. When value approximating 53° C. was attained, the trial was terminated and this value was entered into the calculation for the subject's tolerance value. The values obtained from six repeated thermal trials were averaged to obtain a subject's C-fiber thermal pain tolerance value. This yielded nine measures: two threshold measures and one tolerance measure, each at three anatomical sites.

Assessment of Temporal Summation of C fiber Mediated Thermal Pain

A procedure similar to that described in Price et al. (1977) was used to examine the temporal summation of C fiber mediated thermal pain. A total of fifteen 53° C. heat pulses were applied to skin overlying the thenar region of the right hand. Each heat pulse was 1.5 sec in duration and was delivered at a rate of 10° C./sec from a 40° C. base temperature with an inter-trial interval of 1.5 sec. In effect, this produced a transient 53° C. heat pulse with a peak-to-peak inter-pulse interval of 3 seconds. Subjects were instructed to verbally rate the intensity of each thermal pulse using a 0 to 100 numerical scale with '0' representing 'no sensation', '20' representing 'just painful', and '100' representing 'the most intense pain imaginable'. Subjects were informed that the procedure would be terminated when they reported a value of '100' or when trials had elapsed. For subjects who terminated the procedure prior to the completion of 15 trials, a value of 100 was assigned to the subsequent missing trials. Each subject's ability to summate C-fiber pain was quantified by adding values of all 15 verbal responses. This value was used as a single measurement of the temporal summation of C fiber mediated thermal pain.

Assessment of Ischemic Pain Threshold and Tolerance

A modified submaximal effort tourniquet procedure (Maixner et al. (1990)) was used to evoke ischemic pain. The subject's right arm was elevated and supported in a vertical position for 30 sec to promote venous drainage. Then, a blood pressure arm cuff positioned above the elbow was inflated to 220 mmHg to abolish arterial blood supply and to render the arm hypoxic. A stopwatch was started at the time of cuff inflation and the subject's arm was then lowered to a horizontal position. Immediately afterwards, the subject started squeezing a handgrip dynamometer at 30% of maximum force of grip for 20 repetitions. Prior to the procedure, the subject's maximum grip strength was determined by having each subject squeeze the dynamometer with 'as much force as possible'. The onset, duration, and magnitude of each handgrip squeeze were signaled by computer-controlled signal lights to ensure standardized compression and relaxation periods. Ischemic pain threshold was determined by recording the time (seconds) when subjects first reported hand or forearm discomfort. Ischemic pain tolerance was determined by recording the time (seconds) when subjects could no longer endure their ischemic arm pain. The tourniquet remained in place for 25 minutes or until pain tolerance had been achieved. This procedure yielded two measures: ischemic pain threshold and ischemic pain tolerance.

Summary Measure of Sensitivity to Experimental Pain

A single measure of pain sensitivity was computed for each subject from the sixteen experimental pain procedures. The inventors first reversed the direction of measurement (by subtracting from zero) fifteen of the measures that quantified threshold or tolerance to experimental pain: four measures of pressure pain threshold, nine measures of thermal threshold/tolerance, and two measures of ischemic threshold/tolerance. The sixteenth measure of temporal summation of C fiber mediated thermal pain was retained in its original value. All sixteen measures were standardized to unit normal deviates (z-scores) by subtracting the sample mean, then dividing by the sample standard deviation. Three of the 202 genotyped subjects had a single missing pain measure, one subject had two missing pain measure and one subject had 10 missing pain measures, and we imputed the mean value of zero in each instance. Each subject's summary z-score was then computed by adding together all sixteen unit normal deviates. This yielded an approximately normal distribution (FIG. 9), which satisfied assumptions for homogeneity of variance in all subsequent t-tests and ANOVA models.

Genotyping

Genomic DNA was purified from 202 subjects using QIAAMP™ 96 DNA Blood Kit (Qiagen, Valencia, Calif., U.S.A.) and used for either 5'exonuclease or duplex-specific nuclease assays.

5' Exonuclease Assay

Five COMT SNPs (rs2097903, rs6269, rs4633; rs4818; rs4680 (val$^{158}$met) were genotyped using the 5' exonuclease assay. Probes and primers were chosen using PROBEITY™ (Celadon Laboratories, College Park, Md., U.S.A.) (Table 2) and were synthesized by Applied Biosystems (Foster City, Calif., U.S.A.). The PCR reaction mixture consisted of 2.5 µl PCR Master Mix (Applied Biosystems), 100 nM detection probe for each allele, 900 nM forward and 900 nM reverse amplification primers, and 20 ng genomic DNA in a total reaction volume of 25 µl. Amplification and detection were performed with an ABI PRISM® 7700 Sequence Detection System (Applied Biosystems). General conditions for TAQMAN® (Applied Biosystems) PCR were as described in Shi et al. (1999). The optimized temperatures varied from 60° C. to 63.5° C. The primers and detection probes for each locus are listed in Table 2. Genotype determination was conducted manually using the ABI PRISM® 7700 Sequence Detection System (Applied Biosystems). A verification plate consisting of 17% of the AN probands and control group samples was genotyped in order to assess the reproducibility of the assay. Genotyping error rate was directly determined and was <0.005. Genotype completion rate was 95%.

TABLE 2

Sequences for the primer and probes used in 5'exonuclease and DSN assays

| SNP | Sequence | SEQ ID NO |
|---|---|---|
| rs2097903 | gcc gtg tct gga ctg tga gt | 1 |
|  | ggg ttc aga atc acg gat gtg | 2 |
|  | aac aga cag aaa agT ttc ccc ttc cca | 3 |
|  | cag aca gaa aag Ctt ccc ctt ccc ata | 4 |
| rs6269 | agg cac aag gct ggc att t | 5 |
|  | cca cac gcc cct ttg ct | 6 |
|  | tgc ccc tct gcG aac aca agg | 7 |
|  | acc ttg ccc ctc tgc Aaa cac aag | 8 |
| rs4633 | tgc tca tgg gtg aca cca a | 9 |
|  | gcc tcc agc acg ctc tgt | 10 |
|  | atc ctg aac caT gtg ctg cag cat | 11 |
|  | atc ctg aac caC gtg ctg cag c | 12 |
| rs4818 | ggg ggc cta ctg tgg cta ct | 13 |
|  | tca ggc atg cac acc ttg tc | 14 |
|  | cga ggc tCa tca cca tcg aga tca | 15 |
|  | cga ggc tGa tca cca tcg aga tca | 16 |
| rs4680 (val158met) | tcg aga tca acc ccg act gt | 17 |
|  | aac ggg tca ggc atg ca | 18 |
|  | cct tgt cct tca Cgc cag cga | 19 |
|  | acc ttg tcc ttc aTg cca gcg aaa | 20 |
| rs165599 | cagccacagtggtgcagag | 21 |
|  | gtccacctgtccccagcg | 22 |
|  | tgccAgcctg | 23 |
|  | tgccGgcctg | 24 |

Duplex-Specific Nuclease (DSN) Assay

SNP rs165599 was genotyped using the DSN technique of Shagin et al. (2002). PCR was carry out in 96 well plates using a HYBAID thermocycler. PCR reactions were performed with the ADVANTAGE™ 2 PCR Kit (Ciontech, Palo Alto, Calif., U.S.A.). Each PCR reaction (25 µl) contained 1×ADVANTAGE™ 2 Polymerize mix (Ciontech), 1× reaction buffer, 200 µM dNTPs, 0.3 µM each gene-specific primer (Table 2) and 10 ng of genomic DNA. The following PCR conditions and gene-specific primers were employed: 30 PCR cycles (95° C. for 7 s; 65° C. for 20 s; 72° C. for 30 s). A 7 µl aliquot of PCR products containing about 150 ng DNA was mixed with 1.5 µl 10×DSN buffer (500 mM Tris-HCl, pH8.0, 50 mM MgCl2, 10 mM DTT), probes (to a final concentration of 0.3 µM) (Table 2), 0.75 Kunitz unit DSN nuclease, and milliQ water (to a final volume of 15 µl), and incubated for 20 min at 65° C., 40 min 35° C. Normalized emission spectra of these samples were obtained on a photofluorometer FFM-01 (Kortek, Moscow, Russia) at 538 nm for green fluorescence, FAM (with excitation at 482 nm) and 607 nm for red fluorescence, TAMRA (with excitation at 546 nm). Genotyping results for rs165599 were confirmed by restriction analysis. Restriction analysis was carried out on the 500 ng of PCR products using 10 units of Nae I restriction enzyme (New England Biolabs, Beverly, Mass., U.S.A.). The restricted products were analyzed on 2.5% agarose/ethydium bromide get. One DNA fragment (150 bp) was observed for the homozygous for the alleles A, two DNA fragments (76 and 74 bp)—for the homozygous for allele G and all three fragments for the heterozygous.

Assessment of COMT Activity in Different Haplotypes

A. Transient Transfection of COMT cDNA Clones

Full-length S-COMT cDNA clones corresponding to HPS, APS and LPS haplotypes were obtained from the IMAGE™ clone collection (Open Biosystems, Huntsville, Ala., USA). Clones BG290167 and BG818517 represented LPS haplotype; clones B1821094 and F037202 represented APS haplotype; and clones B1759217 and BF035214 represented HPS haplotype. All clones contained the first ATG codon and were available in the mammalian expression vector pCMV-SPORT6. Plasmid DNA was purified using the ENDOFREE™ Plasmid Maxi purification kit (Qiagen, Germantown, Md., U.S.A.). Once plasmids were isolated, DNA sequences were confirmed by double sequencing at the UNC Core Sequencing Facility.

Human embryonic kidney cells (HEK 293) were transiently transfected into six-well plates using SUPERFECT™ Reagent (Qiagen) in accordance with the manufacture's recommendations. The amount of IMAGE clones was kept at 2 µg/well and to control for the efficiency of transfection pSV-βGalactosidase vector (Promega, Madison, Wis., U.S.A.) was kept at 0.1 µg. Transfection with a vector with no insert was done for each experiment. Cells lysates were collected approximately 24 hours post-transfection. After removing the media, cells were washed twice with 0.9% saline solution (1 ml/35 mm well) and then covered with deionized water containing 10 mM CDTA (500 µl/35 mm well). The wells were frozen at −80° C. overnight. In order to complete the lysing process, HEK 293 cells were pulled into a syringe and passed through a 30½ gauge needle into 1.5 ml tubes. The tubes were centrifuged at 2000 g for 10 min and filtrate removed.

B. Enzymatic Assay

The enzymatic COMT assay was based on the method described by Masuda et al. (2002). Purified lysates (8 µl) were incubated with 200 µM S-adenosyl-L-methionine (SAME™; ICN Chemicals (Aurora, Ohio, U.S.A.)), 7.5 mM L-norepinephrine (Sigma Chemical Co. (St. Louis, Mo., U.S.A.) and 2 mM $MgCl_2$ in 50 mM phosphate buffered saline for 60 min in the final volume of 22 µl. The reaction was terminated using 20 µl of 0.4 M hydrocholoric acid and 1 µl of 330 mM EDTA. The same reaction in the presence of 15 mM EDTA was carried out in parallel for each lysate to bind $Mg^{+2}$ ions that are required for COMT activity. COMT activity was measured with a Normetanephrine (NMN) ELISA kit (IBL, Hamburg, Germany; distributed by IBL-America, Minneapolis, Minn., U.S.A.) in accordance with the manufacture's recommendations using 10 µl of the above reaction mixture. COMT activity was determined after subtracting the amount of NMN produced by endogenous enzymatic activity (transfection with empty vector) as well as the amount of NMN in transfected cells produced by exogenous COMT activity (enzymatic reaction in the presence of EDTA). COMT activity was then normalized for transfection efficiency by measuring the β-galactosidase activity for each lysate. β-galactosidase activity was determined using a β-galactosidase enzyme systems (Promega), according to the supplier's protocol.

C. RT-PCR

Total RNA was isolated using TRIZOL® reagent (Invitrogen, Carlsbad, Calif., U.S.A.). The isolated RNA was treated with RNase free-DNase I (Promega) and reverse transcribed by M-MLV reverse transcriptase (Invitrogen). As a control for transfection efficiency, 200 ng of pSEAP-control plasmid (Ciontech) was co-transfected with each COMT clones. The cDNA was amplified with DYNAMA™-SYBRGreen qPCR kit (MJ Research, Reno, Nev., U.S.A.) using forward and reverse PCR primers, specific for COMT cDNA (TGAACGTGGGCG ACA AGAAAGGCAAGAT (SEQ ID NO: 25) and TGACC TTGTCCTTCACGCCAGCGAAAT (SEQ ID NO:26), respectively) or for SEAP cDNA (GCCGACCACTCC-CACGTCTT and CCCGCTCTCGCTCTCGGTAA, respectively). OPTICON-2™ Real Time Fluorescence Detection System (MJ Research) was used for measuring fluorescence.

Animal Behavior

A. Subjects

Sixteen adult male Sprague-Dawley rats (285-325 g; Charles River Laboratories, Wilmington, Mass., U.S.A.) were used in these experiments. All procedures were approved by the University of North Carolina Animal Care and Use Committee and followed the guidelines for the treatment of animals of the International Association for the Study of Pain.

B. Drugs and Chemicals

OR486, a potent peripheral and central COMT inhibitor, and lambda carrageenan were obtained from Sigma Aldrich (St. Louis, Mo.). OR486 was dissolved in dimethylsulfoxide and saline (3:2 ratio) for systemic administration. Carrageenan (3%) was dissolved in saline and administered in a volume of 100 µl.

C. Assessment of Responsiveness to Mechanical and Thermal Stimulation

Rats were placed in plexiglass cages positioned over an elevated perforated stainless steel platform and habituated to the environment for 15-25 min prior to testing. Paw withdrawal threshold to punctate mechanical stimulation was assessed using the up-down method of Chaplan et al. (1994). A series of nine calibrated filaments (with bending forces of 0.40, 0.68, 1.1, 2.1, 3.4, 5.7, 8.4, 13.2, and 25.0 g; Sammons Preston Rolyan, Bolingbrook, Ill., U.S.A.) with approximately equal logarithmic spacing between stimuli (Mean±SEM: 0.232±0.04 units) were presented to the hind paw in successive order, whether ascending or descending. Filaments were positioned in contact with the hind paw for a duration of 3 s or until a withdrawal response occurred. Testing was initiated with the middle hair of the series (3.4 g). In the absence of a paw withdrawal response, an incrementally stronger filament was presented and in the event of a paw withdrawal, an incrementally weaker filament was presented. After the initial response threshold was crossed, this procedure was repeated four times in order to obtain a total of six responses in the immediate vicinity of the threshold. The presence of paw withdrawal (X) and absence of withdrawal (O) was noted together with the terminal filament used in the series of six responses. The 50% g threshold=$(10^{[Xf+k\delta]})/10,000$, where $X_f$=value (in log units) of the final von Frey hair used; k=tabular value of pattern of positive (X) and negative (O) responses, and $\delta$=mean difference (in log units) between stimuli.

Immediately following determination of the response threshold, paw withdrawal frequency (%) to punctate mechanical stimulation was assessed. A von Frey monofilament with a calibrated bending force of 25 g was presented to the hind paw 10 times for a duration of 1 s with an interstimulus interval of approximately 1 s. Mechanical hyperalgesia was defined as an increase in the percentage frequency ([# of paw withdrawals/10]×100) of paw withdrawal evoked by stimulation with von Frey monofilaments.

Thermal hyperalgesia was evaluated using the radiant heat method of Hargreaves et al. (1988) in the same animals evaluated for responsiveness to von Frey monofilaments. Radiant heat was presented through the floor of a finely perforated stainless steel platform to the midplantar region of the hind paw. Stimulation was terminated upon paw withdrawal or after 20 s if the rat failed to withdraw from the stimulus.

D. Assessment of Effect of COMT Inhibitors

After establishing stable baseline responsiveness to mechanical and thermal stimuli, separate groups of rats received intraperitoneal injections of OR486 (30 mg/kg i.p.; N=8) or vehicle (N=8) one hour prior to behavioral testing. Responsiveness to von Frey filaments was reassessed at 30 min intervals for 2 hours. Paw withdrawal latencies to radiant heat were subsequently assessed at 2.5 hours into the testing procedure. Twenty-four hours later, baseline responsiveness to mechanical and thermal stimuli were reestablished. Animals received OR486 (30 mg/kg i.p.) or vehicle (consistent with the previous day). Thirty minutes following administration of drug or vehicle, separate groups of rats received intraplantar carrageenan (N=4 per group) or saline (N=4 per group). Responsiveness to von Frey filaments was reassessed at 30 min intervals for 2 hours following the induction of inflammation. Paw withdrawal latencies to radiant heat were subsequently assessed at 2.5 hours post carrageenan.

Statistical Evaluation of Associations Between SNPs, Haplotypes and Pain Responsiveness Statistical evaluation began with analysis of variance (ANOVA) models for each of six SNPs and Student's t-test to contrast homozygotes (FIG. 10). The independent effects of SNPs were then evaluated in a multivariable generalized linear model in which each SNP was entered as a separate pair of dummy variables (with two degrees of freedom). SNPs were entered in the following sequence of steps: first, rs4680 (met[158]val), second rs4818, rs4633, and rs6269, and third rs2097903 and rs165599. This sequence was nominated on the following theoretical grounds: first the inventors controlled for the one SNP in the coding region that caused a synonymous change in COMT amino acid sequence; second the inventors examined the effects of SNPs that are associated with a non-synonymous change in the amino acid sequence; and third the inventors evaluated any additional effects of SNPs in the promoter and untranslated regions. SNPs entered in the third step contributed less than one percent each to the total variation (R-squared) of the model. In addition, eight subjects had missing values for the two SNPs in this third block, so those SNPs were eliminated from further analysis. The four SNPs from the coding region accounted for 10.6 percent of R-squared (Table 3).

TABLE 3

Generalized linear model of effects of four SNPs on pain sensitivity*

| SNP locus | Degrees of freedom | Sum of squares | Sequential R-squared | F | P-value |
|---|---|---|---|---|---|
| rs4680 (val/met) | 2 | 383.5 | 0.017 | 1.8 | 0.17 |
| rs4818 | 2 | 1535.1 | 0.068 | 7.3 | <0.01 |
| rs4633 | 2 | 466.4 | 0.021 | 2.2 | 0.11 |
| rs6269 | 2 | 18.5 | <0.001 | 0.1 | 0.91 |
| Error | 193 | 20324.5 | | | |

*Model uses data from n = 202 subjects who were genotyped. For full model $FF_{3,193} = 2.8$, $P < 0.01$, R-squared = 0.106

Associations between haplotypes and pain responsiveness were assessed first by classifying the 186 subjects whose two COMT haplotypes were among the three most prevalent haplotypes: GCGG (which were labeled as low pain sensitive—LPS), ATCA (which were labeled as average pain sensitive—APS), ACCG (which were labeled as high pain sensitive—HPS). This yielded five possible combinations that were evaluated in a factorial analysis of variance model (Table 4). The F-tests were used for each term in this model to first determine that each haplotype in the subjects' pairs had independent effects. Least squares means were then computed to test three hypotheses about haplotypes (using Dunnett's post-hoc adjustment): For the first haplotype, APS had higher adjusted mean summary z-score than LPS subjects (P=0.01, adjusting for the other haplotype—Table 4).

For the second haplotype, HPS had higher adjusted mean summary z-score than APS subjects (P=0.04, adjusting for the other haplotype) and HPS had higher adjusted mean summary z-score than LPS (P<0.01—adjusting for the other haplotype—Table 4).

TABLE 4

Factorial ANOVA model of effects of three major haplotypes on pain sensitivity

| Source | Degrees of freedom | Sum of squares | Sequential R-squared | F | P-value |
|---|---|---|---|---|---|
| Haplotype 1 (LPS, HPS) | 1 | 466.1 | 0.022 | 4.5 | 0.04 |
| Haplotype 2 (LPS, APS, HPS) | 2 | 1730.5 | 0.082 | 8.3 | <0.01 |
| Error | 182 | 18900.5 | | | |

Summary z-score least squares means from model:

| | | mean | (se) | P-value |
|---|---|---|---|---|
| Haplotype 1: | LPS | −2.1 | (1.7) | 0.01 |
| | APS | 2.8 | (1.0) | (reference) |
| Haplotype 2: | LPS | −3.5 | (1.1) | <0.01 |
| | APS | −0.7 | (1.7) | 0.04 |
| | HPS | 5.3 | (1.9) | (reference) |

*Model uses data from n = 186 subjects who were genotyped. For full model $F_{3,182} = 7.05$, $P < 0.01$, R-squared = 0.104

Stratification by Race

There were too-few non-white subjects (n=31) genotyped from this volunteer sample to permit meaningful statistical analyses of them as separate strata. However, the percentage of subjects classified as HPS/APS was virtually identical between whites (35%) and non-whites (36%—Chi-square test, P=0.89) and the two race groups did not differ significantly in mean values of experimental pain z-scores (t-test, P=0.30). Furthermore, when the preceding factorial analyses of COMT haplotypes were restricted to whites, the results remained virtually identical. Specifically, P-values for the effect of each haplotype were significant (P<0.03), and the pairwise effects were significant for ATCA vs GCGG (P=0.03) and for ACCG vs. GCGG (P<0.001).

Linkage Disequilibrium (LD) Analysis

LD between SNPs was estimated with SAS Proc Allele software or PHASE software using default parameters.

Incidence of Newly-Diagnosed TMD

Among the 186 subjects who had the five major haplotype combinations, 170 completed one or more follow-up evaluations when fifteen new cases of TMD were diagnosed (cumulative incidence=8.8%). New cases were diagnosed at periods ranging from nine months to three years, and the duration of follow-up for all subjects ranged from seven months to 43 months. Because of this variation in follow-up periods, we computed the average incidence rate for TMD and contrasted the rates for two subgroups of haplotypes, the first comprising subjects with APS/HPS haplotype (n=58 people with A_C_C_G/A_T_C_A or A_T_C_A/A_T_C_A) and the second comprising subjects with at least one LPS haplotype (n=112 people with A_T_C_A/G_C_G_G, A_C_C_G/G_C_G_G or G_C_G_G/G_C_G_G). Lifetable methodology was used to compute incidence rates. The numerator for the incidence rate was the number of subjects who developed TMD and the denominator was TMD-free-time-in-study, expressed in years. For subjects who developed TMD, their TMD-free-time-in-study was computed as the period from recruitment to the halfway point between their penultimate three monthly screening interviews and their diagnosis examination. For subjects who did not develop TMD but who withdrew from the study before the final annual assessment, their TMD-free-time-in-study was computed as the period from recruitment to the halfway point between their penultimate three monthly screening interview and date of withdrawal. For all remaining subjects, their TMD-free-time-in-study was computed at as the period from recruitment to the final examination. Results were expressed as the rate of new TMD diagnoses per 100-person-years of follow-up, equivalent to the average number of new TMD cases that would be expected in an initially TMD-free cohort of female volunteers who were followed each for one year.

For the complete cohort of n=170 subjects, cumulative incidence was 8.8 percent and the incidence rate was 3.5 cases per 100-person-years (Table 4). Cumulative incidence was compared between the HPS/APS group and the LPS group using the Mantel-Haenszel test, yielding a relative risk of 2.2 (95% confidence interval [95% CI]=0.8-5.8—Table 4). Differences in incidence rates between the same two groups were determined in a Poisson regression model in which the numerator was number of TMD cases and the offset was the log of person-years of follow-up, yielding an incidence density ratio of 2.3 (95% CI=1.1-4.8).

Analysis of Rat Behavioral Data

Behavioral data were analyzed by ANOVA for repeated measures and post hoc comparisons were performed using the Bonferroni test. P<0.05 was considered to be statistically significant.

Example 1

Measuring Variations in Pain Sensitivity in a Population of Subjects

Data for this study were collected from 202 healthy female volunteers. The subjects participated in a three-year prospective cohort study that was designed to identify risk factors for a particular exemplary somatosensory disorder, TMD. Only females were included in this study as they exhibit a higher prevalence for the condition relative to males (Carlsson & Le Resche, (1995)). During an initial screening exam, the sensitivity of subjects to experimental noxious stimuli was assessed, and peripheral blood samples were collected for genetic analyses. Subjects were subsequently followed for up to three years, by both trimonthly interviews and annual physical examinations, to identify newly developed cases of TMD.

In order to evaluate each participant's pain sensitivity, a unique approach was used to derive a unitary measure of pain sensitivity for both cutaneous and deep muscle pain, which are transmitted and modulated by different neural mechanisms (Yu et al. (1991); Mense (1993)). To accomplish this, each of 16 measures of pain sensitivity was normalized to a mean of zero and standard deviation of one, producing a unit normal deviate (z-score) for each test procedure. A sum of these 16 scores produced a normalized single score of pain sensitivity (integral z-score) for each individual. As shown in FIG. 9, measures of individual pain sensitivity (integral z-scores) were distributed approximately normally (skewness=0.3 and kurtosis=−0.1), ranging from −22.4 (least responsive to painful stimuli) to 28.0 (most responsive to painful stimuli); although the majority of individuals display average pain sensitivity, the individual variability in pain sensitivity between people is substantial and spans a range greater than that produced by therapeutic doses of morphine.

Example 2

Genotyping the COMT Locus

Genomic DNA from peripheral blood samples was genotyped for SNPs within the COMT gene locus. Six SNPs were chosen that display high polymorphism frequency in the human population (>40% prevalence). FIG. 6A shows the positions of the SNPs within the COMT locus that codes for two major forms of COMT enzyme: membrane bound (MB-COMT) and soluble (SCOMT). The first SNP (rs2097903) is located at position −1217 in the estrogen sensitive portion of the MB-COMT promoter region (Xie et al. (1999); DeMille et al (2002)), while the second SNP (rs6269) is located in the promoter region of S-COMT (Xie et al. (1999); Shifman et al. (2002)). The next three SNPs (rs4633, rs4818 and rs4680 (val$^{158}$met)) are located within the coding region for both S- and MB-COMT (Li et al. (2000); NCBI genome database). Variations in SNP rs4633 and rs4818 are synonymous (i.e., do not produce a change in amino acid composition). In contrast, SNP rs4680 is non-synonymous and codes for a substitution of valine (val) to methionine (met) at codon 158. The last SNP (rs165599) is situated in the very end of the 3'UTR of the gene and its G allele has been reported to be associated with schizophrenia (Shifman et al. (2002)). Importantly, the COMT SNP map has been thoroughly constructed (see NCBI database). In the coding region of the gene, there are no other SNPs with frequencies greater than 0.15. This was further confirmed by comparing over 300 COMT EST sequences from the NCBI database using the CLUSTALW program for multiple sequence alignments. As disclosed in Risch (2000), alleles with polymorphic frequencies <0.15 are very unlikely to have significant impact on common population-based diseases/disorders such as TMD.

Statistically significant associations were found between the summed z-score and two SNPs (Table 5 and FIG. 10). The SNP rs6269 accounted for 6% of variation in pain sensitivity as determined by analysis of variance (ANOVA, P<0.01), while rs4818 SNP accounted for 7% of the variation (ANOVA, P<0.01). For both SNPs, the homozygous genotypes were associated with significant differences in mean pain sensitivity (t-test, P<0.01). The val$^{158}$met SNP (rs4680) showed a marginal, but not statistically significant, relationship with pain sensitivity, accounting for 2% of the variation in the summary pain measure (ANOVA, P=0.18). Individuals homozygous for met/met tended to be more pain responsive than those homozygous for val/val, but again the association was marginal (t-test, P=0.06). SNPs A—rs2097903, rs4633 and rs16559 were not significantly associated with pain sensitivity (see Table 5 and FIG. 10). Multivariate analysis revealed that all possible combinations of the four SNPs in the coding region accounted for 10.6% of variation in the summary measure of pain sensitivity. In this model, we first controlled for rs4680 (accounting for 2% of variance) then rs4818 (7% of variance); the remaining SNPs did not individually contribute significantly (P>0.10) to the variance in pain sensitivity (see Table 3).

Example 3

COMT Haplotypes Determine Sensitivity to Pain

It was next determined which combinations of alleles (haplotypes) were formed by the 6 COMT SNPs. It has been shown that alleles form associations (haploblocks) of variable length with the average span of 18 kb in populations of European descent and only a few common haplotypes are observed Gabriel et al. (2002). Three haploblocks were determined in the study sample by linkage disequilibrium (LD) analysis (Table 6). Because the association with pain sensitivity was observed only for SNPs rs6269, rs4818, located in the central COMT locus haploblock (see Table 5 and FIG. 6A), analysis was focused on this haploblock.

TABLE 6

Linkage disequilibrium between paired SNP markers

| Marker 1 | Marker 2 | R² | D' |
|---|---|---|---|
| rs2097903 | rs6269 | 0.05 | 0.35 |
|  | rs4633 | 0.08 | 0.34 |
|  | rs4818 | 0.03 | 0.28 |
|  | rs4680 | 0.08 | 0.34 |
|  | rs165599 | 0.00 | 0.00 |
| rs6269 | rs4633 | 0.59 | 0.99 |
|  | rs4818 | 0.88 | 0.94 |
|  | rs4680 | 0.59 | 1.00 |
|  | rs165599 | 0.00 | 0.11 |
| rs4633 | rs4818 | 0.59 | 0.99 |
|  | rs4680 | 0.91 | 0.96 |
|  | rs165599 | 0.01 | 0.14 |
| rs4818 | rs4680 | 0.60 | 1.00 |
|  | rs165599 | 0.00 | 0.04 |
| Met/val | rs165599 | 0.00 | 0.10 |

With reference to Table 6, data were analyzed for significance using the PHASE 2.0 program. D' is the normalized linkage disequilibrium statistic, which lies in the range from

TABLE 5

Variation in pain sensitivity (summed z-score) among tested SNPs and diplotypes of COMT gene

| SNP | Genotype | No. of subjects | genotypes frequencies | Mean (sd) z-score | | ANOVA* | | t-test† |
|---|---|---|---|---|---|---|---|---|
| | | | | | | R² | P-value | P-value |
| rs2097903 | A/A | 68 | 0.340 | −1.4 | (10.1) | 0.012 | 0.3 | 0.1 |
|  | A/G | 104 | 0.520 | 0.2 | (11.4) |  |  |  |
|  | G/G | 28 | 0.140 | 2.2 | (8.0) |  |  |  |
|  | G/G | 31 | 0.153 | −4.7 | (9.1) | 0.061 | 0.002 | 0.006 |
| rs6269 | A/G | 97 | 0.480 | −0.7 | (10.5) |  |  |  |
|  | A/A | 74 | 0.366 | 3.0 | (10.7) |  |  |  |
|  | C/C | 52 | 0.257 | −2.0 | (10.5) | 0.013 | 0.26 | 0.09 |
| rs4633 | C/T | 98 | 0.485 | 0.4 | (10.9) |  |  |  |
|  | T/T | 52 | 0.267 | 1.3 | (10.2) |  |  |  |
|  | G/G | 28 | 0.139 | −5.2 | (8.0) | 0.07 | 0.0007 | 0.0003 |
| rs4818 | G/C | 100 | 0.495 | −0.9 | (10.5) |  |  |  |
|  | C/C | 74 | 0.366 | 3.2 | (10.7) |  |  |  |
|  | G/G | 51 | 0.252 | −2.1 | (10.3) | 0.017 | 0.18 | 0.066 |
| rs4680 | A/G | 102 | 0.505 | 0.2 | (10.9) |  |  |  |
|  | A/A | 49 | 0.243 | 1.7 | (10.3) |  |  |  |
| rs165599 | G/G | 27 | 0.138 | −2.4 | (8.5) | 0.008 | 0.48 | 0.27 |
|  | A/G | 87 | 0.446 | 0.4 | (11.4) |  |  |  |
| Haplotype | A/A | 81 | 0.415 | −0.2 | (10.3) |  |  |  |
| combination | ATCA_ACCG | 15 | 0.081 | 8.9 | (11.4) | 0.107 | 0.0004 |  |
|  | ATCA_ATCA | 49 | 0.263 | 1.7 | (10.3) |  |  |  |
|  | ATCA_GCGG | 80 | 0.430 | −1.3 | (10.2) |  |  |  |
|  | GCGG_ACCG | 14 | 0.075 | 1.5 | (12.3) |  |  |  |
|  | GCGG_GCGG | 28 | 0.151 | −5.2 | (8.0) |  |  |  |

*ANOVA = Analysis of variance testing null hypothesis of equality of means among three alleles;
†t-test for SNPs is Student's t-test testing null hypothesis of equality of means between homozygotes.

0 to 1 with greater values indicating stronger linkage. Four SNPs, rs6269, rs4633, rs4818 and rs4680 (val$^{158}$met), which occur within the coding region of the COMT gene, were found to exhibit strong LOs. This means that these SNPs are forming one haploblock within the COMT gene locus. In contrast, SNPs rs2097903, which is located in the 5' promoter region, and rs165599, which is a 3' UTR SNP, did not show strong LOs. These SNPs are within two haploblocks adjusted to the first one.

Whether there are additional SNPs that modulate COMT enzymatic activity is of importance. There are several dozen identified SNPs within the COMT gene locus in the NCBI and CELERA databases. Importantly, all of the known common SNPs located in the central haploblock of the COMT gene were tested. There are several common SNPs located in the 5' and 3' parts of the gene locus that may influence COMT activity. These SNPs also form haploblocks but the observation that the 5' SNP rs2097903 and 3' SNP rs165599 do not significantly correlate with pain sensitivity (FIG. 10) suggests that these regions are unlikely to contain other frequently found SNPs that impact pain sensitivity.

Seven haplotypes with a frequency greater than 0.5% were detected, three of them representing 95.9% of all haplotypes observed in this study (FIG. 6C). Five combinations of these three haplotypes were present in 92% of subjects and were associated with marked gradients in pain responsiveness (FIG. 11). Subjects homozygous for the G_C_G_G haplotype had the lowest pain responsiveness (mean summed z-score=−5.23±1.5; FIG. 11 and Table 1); thus, G_C_C_G is designated as the "low pain sensitivity" (LPS) haplotype. Intermediate pain responsiveness was observed for individuals homozygous for A_T_C_A, which we refer to as the "average pain sensitivity" (APS) haplotype (mean summed z-score=1.75±1.47; FIG. 11 and Table 1). The greatest pain responsiveness was observed for individuals heterozygous for A_T_C_A (APS) and A_C_C_G haplotypes (mean summed z-score=8.9±2.9; FIG. 11 and Table 1). The A_C_C_G haplotype is referred to herein as the "high pain sensitivity" (HPS) haplotype. Differences among the five combinations of haplotypes were significant (Table 5, overall ANOVA, P=0.0004) and factorial analysis demonstrated that each haplotype had independent effects on pain sensitivity (Table 2, factorial ANOVA model, P≤0.01). These haplotypes accounted for 10.4% of the variation (P<0.01) in pain sensitivity, representing virtually all of the variation (10.6%) explained by combinations of the four individual SNPs in the central haploblock.

Example 4

COMT Haplotypes Determine Enzyme Activity

Functional polymorphism in the COMT gene has been described only for SNP rs4680 (val$^{158}$met) (Zubieta et al. (2003); Mannisto et al. (1999); Lotta et al. (1995)), which codes for a substitution of val to met. The met substitution produces a COMT enzyme with lower thermostability, resulting in decreased enzyme activity (Lotta et al. (1995).

While it appears that the val$^{158}$met amino acid substitution in COMT can explain the greater pain responsiveness observed for individuals with the APS haplotype compared to the LPS haplotype, because the APS haplotype codes for the less stable met variant, it cannot explain the greater pain responsiveness found and disclosed herein for subjects with the HPS haplotype compared to the LPS haplotype. This is because both the HPS and LPS haplotypes possess the G allele that codes for the more stable val variant (FIG. 6C). Thus, the val$^{158}$met SNP alone cannot account for the observed variations in pain perception. Furthermore, even though polymorphism in SNPs rs6269 and rs4818 are significantly associated with pain z-scores, both pain sensitive haplotypes HPS and APS contain the A allele of rs6269 and the C allele of rs4818. Consequently, variations in these SNPs cannot explain why the HPS and APS haplotypes are associated with different levels of pain sensitivity. Instead, the interaction of the val$^{158}$met SNP with other SNPs determines the functional outcomes. The other SNPs are either synonymous (i.e., code for the same amino acid), or are located in the promoter region of S-COMT. A haplotype-dependent regulation of mRNA expression is also unlikely because SNP rs6269, which is located in the promoter region of S-COMT, does not independently contribute to pain sensitivity (Table 3). Therefore, haplotype specific secondary structures of mRNA can possibly affect COMT mRNA stability and/or efficiency of protein translation (Duan et al. (2003)).

To test these possibilities, HEK 293 cells were transiently transfected with full-length COMT cDNA clones that corresponded to the three major haplotypes. The expression of COMT protein was assessed by measuring COMT enzymatic activity in the lysate of transfected cells. FIG. 12A shows that the LPS haplotype provides 4.8 times higher COMT activity compared to the APS haplotype (P<0.01). However, the finding disclosed herein showing the HPS haplotype provides 11.4 times lower COMT activity compared to LPS (P<0.01) can be attributed to the lower amount of protein produced by the HPS haplotype since these two haplotypes code for COMT protein with exactly the same amino acid composition. No differences in COMT RNA abundance were detected in the transfected cells as measured by real-time PCR (FIG. 12B); therefore, the three major haplotypes affect the efficiency of protein synthesis, but not RNA stability.

Example 5

Inhibition of COMT Enhances Sensitivity to Noxious Stimuli

The Examples above strongly suggest that reductions in COMT enzymatic activity enhances pain sensitivity. To directly test whether decreased COMT activity enhances pain sensitivity, the COMT inhibitor OR486 was administered to naive rats. OR486 decreased paw withdrawal thresholds to mechanical and thermal stimuli (P<0.0001 and P<0.0007, respectively) and increased paw withdrawal frequency to noxious punctate mechanical stimuli (P<0.0001) (FIGS. 13A-13C). The degree of mechanical and thermal hyperalgesia produced by OR486 was comparable to that produced by carrageenan-induced inflammation in the hindpaw.

Example 6

High Activity COMT Haplotype (LPS) Protects from Developing TMD

To determine the clinical relevance of these findings, the inventors examined whether COMT polymorphism is related to the incidence of TMD onset among 170 subjects with the five most common haplotype combinations who completed one or more follow-up visits. Fifty-eight of the participants had only "low COMT activity" haplotypes (HPS and/or APS) and the remaining 112 subjects had at least one "high activity" haplotype (LPS). It was first confirmed that HPS and/or APS subjects were more sensitive to experimental pain at their baseline assessment compared with LPS subjects (P=0.02; FIG. 14A). During the three-year observational period, 15 new cases of TMD were diagnosed at varying time periods ranging from nine months to three years after recruitment, yielding an average incidence rate of 3.5 cases per 100 person-years of followup. The incidence rate was more than twice as high among individuals having only HPS and/or APS haplotypes (5.6 cases per 100 person-years) compared with individuals with at least one LPS haplotype (2.5 cases per 100 person-years—FIG. 14B). The derived incidence density ratio of 2.3 was significant (95% confidence interval=1.1-4.8), suggesting that the HPS and/or APS haplotypes represent significant risk factors for TMD onset. FIG. 14C is a graph of paw withdrawal latency.

Materials and Methods for Examples 7-12

Subject Recruitment

Data for these Examples were collected from 210 healthy female Caucasian volunteers. Enrollees participated in a three-year prospective cohort study that was designed to identify risk factors for TMD onset. Only females were included in this study as they exhibit a higher prevalence for the condition relative to males (Carlsson et al. (1995)). Enrollees completed a baseline assessment comprised of psychological questionnaires (described herein below), resting arterial blood pressure assessment, and a clinical examination of the head and neck. Subjects were subsequently followed for up to three years, by both quarterly interviews and annual physical examinations, to identify newly developed cases of the somatosensory disorder TMD.

Psychological Questionnaires

Five psychological questionnaires, which assessed a broad range of psychological characteristics, including affective factors, perceived stress, and somatization/hypervigilance were administered. The questionnaires do not provide diagnoses of any psychiatric conditions, and endeavors to make such diagnoses were not made. The Profile of Mood States—Bi-Polar (POMS-Bi) consists of 72 mood-related items assessing both positive and negative affective dimensions (Lorr & McNair (1988)). The Brief Symptom Inventory (BSI), a short form of the Symptom Checklist 90 Revised, consists of 53 items designed to assess nine aspects of psychological function (Deroaatis (1983)). The State-Trait Anxiety Inventory (STAI) contains 20 statements evaluating levels state and trait anxiety (Spielbemer et al. (1983)). The Perceived Stress Scale (PSS) provides a global assessment of major sources of life stress such as overall stress, financial stress, occupational stress, significant other stress, parental stress, and stress within friendships (Cohen et al. (1983)). The Beck Depression Inventory (BDI) is a 21-item instrument that assesses both cognitive/affective and vegetative signs of depression (Beck et al. (1961)). The BDI has demonstrated adequate reliability and validity and has been used widely in a variety of clinical populations, including patients with chronic pain. Each of these instruments is widely used in clinical research and has good psychometric properties.

Blood Pressure Measurements

Resting systolic and diastolic blood pressures were assessed on the right arm with an automatic blood pressure monitor. Five measures obtained at 2 minute intervals after a 15 minute rest period were averaged.

Genotyping

Genomic DNA was Purified from 198 Subjects Using QIAAMP™ 96 DNA

Blood Kit (Qiagen, Valencia, Calif., U.S.A.) and used for a 5'exonuclease assay as disclosed in Shi et al. (1999). The primer and probes were used as described in Belfer et al. (2004). Genotyping error rate was directly determined and was <0.005. Genotype completion rate was 95%.

Searching of EST Database

Computer analysis of all SNP combinations in the human EST database dbEST (release 030405, U.S. Pat. No. 6,053,112—human entries) was performed using the BLAST program. The complete nucleotide sequence of ADRB2 gene was analyzed (length—2015 nucleotides, accession number—NM_000024). A combination of the C programming language and the Bash shell scripting language was used to perform the statistical analysis of the BLAST program output files. The program produces a complete list of nucleotide variation (SNPs) and their combinations for analyzed gene in the EST database as an output file (*.csv) in Excel format. The inventors then restricted out analysis of nucleotide variations to reported common SNPs with the frequency >10%. Only hits with >95% of similarity to the original sequence were considered. A Chitest was used for statistical analysis of ESTs distribution (Excel, Microsoft, Inc., Redmond, Wash., U.S.A.).

Statistical Analyses

Distributions of phenotype scores in the sample were evaluated to assess normality. All examined variables appeared to be approximately normal with the exception of the BDI, BSI depression, and BSI somatization scores. The distribution of the BDI variable was noticeably skewed, so a transformed version of this variable was analyzed. Data were transformed using the equation log (BDI+$\lambda$). In accordance with the recommendations by Box and Cox (Box & Cox (1964)), $\lambda$ was set at 1.53 because this value yielded the maximum profile likelihood for the full linear model that contained all interactions between haplotypes. Once this transformation had been made, the BDI variable appeared to be approximately normal.

The distributions of the BSI variables were bimodal. For both BSI variables, approximately one third of the individuals in the study answered every question in the negative and hence received a score of 30. The remaining individuals had scores that seemed to be approximately normally distributed between the values of 49 and 75. In order to analyze the BSI data, each of the BSI variables were reduced to a binary form and recorded whether or not each individual had a score above 30.

For all normally distributed variables (including the transformed BDI scores) a one-way ANOVA was used to analyze the dosage effects of each haplotype on the psychological variable. The question addressed in these analyses was whether the mean trait value varied significantly between individuals with 0, 1, or 2 copies of a given haplotype. In these analyses, the number of copies of each haplotype was treated as a factor and a separate analysis was performed for each haplotype. Our protocol was to first perform the overall F-test for each haplotype-phenotype combination, then, if the F-test was significant, we used Tukey's Honestly Significant Difference post hoc test to determine which pairs of haplotype dosages yielded significantly different mean trait values. To adjust for the fact that each phenotype was tested for the dosage of each of the three haplotypes, we also assessed significance using Simes' test ((Simes (1986)).

An analogous analysis of the binary BSI variables was performed using simple logistic regression. In this case, instead of using an F-test to evaluate the fit of the model, we used a likelihood ratio test. Pairwise differences between different haplotype dosages were also investigated using likelihood ratio tests, with significance assessed using a Bonferroni correction.

In addition to looking at dosage effects, in which it was examined how the number of copies of each haplotype contributed to the trait value without reference to the identities of the other haplotypes, also investigated was how the various haplotypes interacted with each other. To assess, for example, the relationship between haplotype H1 and each of the other haplotypes, a linear model based on the number of copies of each haplotype an individual carried was considered. $t_{ij}$ was defined to be the number of copies of haplotype i possessed by individual j. So, for example, if individual j was heterozygous with haplotypes H1 and H2, we would have $t_{1j}=1$, $t_{2j}=1$, and $t_{3j}=0$. Similarly, if individual j was homozygous for haplotype H1, we would have $t_{1j}=2$, $t_{2j}=0$, and $t_{3j}=0$.

The linear model was parameterized as follows:

$$y_j = \gamma_1 + \gamma_2 t_{2j} + \gamma_3 t_{3j} + \gamma_{12} t_{1j} t_{2j} + \gamma_{13} t_{1j} t_{3j} + \gamma_{23} t_{2j} t_{3j} + \varepsilon_j, \quad (1)$$

where, for the normal phenotypes, $y_j$ is the trait value for individual j. For BDI depression, $y_j$ is the transformed trait value $\log(BDI_j+1.53)$. For the binary BSI variables, these analyses were performed according to the analogous logistic model.

The mean trait values for each diplotype, using the parameterization in Equation 1 are given in Table 7. Of note is that haplotype H1 plays a different role in this parameterization than the other two haplotypes. The mean trait value for H1/H1 individuals is given by a single parameter, $\gamma_1$, which serves as a baseline value in this parameterization of the model. This parameterization was chosen because it permits interactions (additivity, dominance, etc.) between H1 and the other haplotypes to be easily tested (see below). A second aspect of this model is that departures from additivity between the haplotypes are captured in the interaction parameters $\gamma_{12}$, $\gamma_{13}$, and $\gamma_{23}$. When these are all zero, a strictly additive model in which the mean heterozygous trait values fall exactly midway between the mean homozygous trait values is achieved.

TABLE 7

Haplotypes Interactions: Mean trait values

| Diplotype | Mean trait value |
|---|---|
| H1/H1 | $\gamma_1$ |
| H1/H2 | $\gamma_1 + \gamma_2 + \gamma_{12}$ |
| H1/H3 | $\gamma_1 + \gamma_3 + \gamma_{13}$ |
| H2/H2 | $\gamma_1 + 2\gamma_2$ |
| H2/H3 | $\gamma_1 + \gamma_2 + \gamma_3 + \gamma_{23}$ |
| H3/H3 | $\gamma_1 + 2\gamma_3$ |

It was assumed in the analyses that the default model should be an additive model, so interactions were first tested for using an F-test (likelihood ratio test for the BSI variables) in which the fit of the full model given in Equation 1 was compared to the additive model in which $\gamma_{12}$, $\gamma_{13}$, and $\gamma_{23}$ were constrained to be equal to zero. If this test showed insufficient evidence for non-additivity, that is, if the full model did not show a significantly better fit to the data than the additive model, analysis was halted at this point.

For the variables that showed evidence of non-additivity, the analyses continued. The Akaike Information Criterion (Akaike (1974)) was used to find the best fitting model of the form shown in Equation 1. The form of this "best-fit" model depended upon the trait being examined, but generally looked like Equation 1 with one or more of the $\gamma_{ij}$ parameters set to zero.

Once the "best-fit" model had been obtained, the relationship between those pairs of variables that had an interaction term that was significantly different than zero was investigated. The parameterization shown in Equation 1 is well suited for this type of testing. For example, interactions between haplotypes H1 and H2 are captured in the parameter $\gamma_{12}$, as can be seen by comparing the mean trait values for H1/H1, H1/H2, and H2/H2 in Table 7. When $\gamma_{12}=0$, the relationship between H1 and H2 is additive. When $\gamma_{12}=-\gamma_2$, H1 is dominant to H2. When $\gamma_{12}=\gamma_2$, H1 is recessive to H2. Overdominance and underdominance occur when $|\gamma_{12}|>|\gamma_2|$. Thus, with this parameterization, relationships such as additivity, dominance, recessiveness, and over/underdominance are hypotheses that can be expressed in terms of the model's parameters and hence can be easily tested. The relationship that was of particular interest was that of over/underdominance and this type of relationship was tested for using a likelihood ratio test in which the maximum obtainable likelihood under the best-fit model was compared with that under the constraint that $|\gamma_{12}| \leq |\gamma_2|$.

Investigations of the relationship between haplotypes H1 and H3 proceeded with this model analogously to the procedure for testing relationships between H1 and H2. Interactions between H2 and H3 are less neatly summarized by the parameters in Equation 1. For those comparisons, the model was reparameterized, exchanging the roles of H1 and H2 so that H2/H2 individuals served as the baseline.

In order to investigate the molecular mechanisms by which the three ADRB2 haplotypes affect psychological and blood pressure, omnibus statistical tests using analysis of variance (ANOVA) to determine associations between ADRB2 haplotype variants and phenotype scores (i.e., psychological scales and average blood pressure measurements) were first conducted. There was more concern for controlling Type II than Type I error. Therefore, follow-up contrasts between specific haplotypes were conducted if the omnibus test was significant at $p \leq 0.10$.

TMD Incidence Cases

From the initial 202 enrolled subjects that were genotyped, 181 completed 3 years observation period and 15 of those developed TMD. The incidence of how TMD in the study varied between individuals with different diplotypes by calculating relative risks was studied. Specifically, under the hypothesis that haplotype 1 (H1) coded for lower levels of RNA expression (see EST data analysis in the Examples below) and that the other haplotypes (H2 and H3) coded for higher levels of expression, individuals were grouped into three categories based on the number of low-expressing haplotypes (0, 1, or 2 copies of H1) each subject possessed. Because individuals with 1 copy of H1 showed the lowest level of TMD incidence, relative risks of TMD for the other groups compared to this group were computed. Since the sample sizes were small compared to the TMD incidence levels, confidence intervals were calculated for relative risks using Koopman's method (Koopman (1984)).

Example 7

Analysis of Haplotypes of ADRB2

Genomic DNA from peripheral blood samples was genotyped for SNPs within the ADRB2 gene locus. Eight SNPs were chosen that display a high frequency of polymorphism in the human population (>20% prevalence), and form one haploblock (Belfer et al. (2004)). See FIGS. 4A-4B. The first five examined SNPs (G-7127A, rs11958940, rs1432622, rs1432623 and r52400707) are located in the promoter region of the gene. The next three SNPs (rs1042713, rs1042714 and rs1042717) are located within the coding region for gene. Variations Arg$^{16}$Gly (rs1042713) and Gln$^{27}$Glu (rs1042714) are known nonsynonymous polymorphisms. SNP Leu$^{84}$Leu (rs1042714) is a synonymous polymorphism. The known functional SNP Thr$^{164}$Ile was also assessed, however none of the examined subjects possessed the minor allele. The PHASE program (Stephens et al. (2001); Stephens et al. (2003)) was used for haplotypes reconstruction. Three major haplotypes were determined, representing 97.4% of all haplotypes observed in this study (FIG. 4B). Only five subjects carried haplotypes that were different from the three major ones. Each of these five haplotypes was different from one of the major haplotypes at only one or two SNP positions and was considered in subsequent analyses as one of the major corresponding haplotypes.

Example 8

ADRB2 Polymorphism and Psychological Traits

Descriptive statistics for phenotype variables that differed significantly in omnibus testing among haplotypes are presented in FIGS. 2A-2C. Subjects bearing two copies of haplotype 1 (H1) had higher BDI depression scores than those who had only one copy of H1 (FIG. 2A). Consistent with this observation, H1 homozygotes displayed the highest BDI depression score compared to the other diplotypes. Subjects who were heterozygotes for H1 with either haplotype 2 (H2) or haplotype 3 (H3) displayed the lowest BDI depression scores (Table 8). Subjects bearing two copies of H2 had significantly higher levels of somatization (both PILL and BDI scores) than subjects possessing only one or no copies of H2 (FIG. 2B). H2 homozygotes displayed the highest somatization score among all diplotypes (Table 8). H2 also had a significant effect on Trait Anxiety: subjects with no H2 reported higher trait anxiety levels than those bearing one copy of H2 (FIG. 2B). Consistent with this, homozygotes for H1 and homozygotes for H3 had the highest trait anxiety scores while H2 heterozygotes had the lowest scores (Table 8). H3 was strongly associated with mood (POMS agreeable-hostile and composed anxious; lower scores correspond to more negative characteristics) and depression (BDI). H3 homozygotes had significantly higher state-dependent anxiety (POMS composed-anxious) and hostility (POMS agreeable-hostile) and lower BDI depression scores (Table 8).

TABLE 8

Estimated means of psychological scores and blood pressure by diplotypes

| Trait[1] | haplotypeX | | | haplotypeY |
|---|---|---|---|---|
| | H1 | H2 | H3 | |
| Depression (BDI) (lower bound-upper bound) | 4.75 (4.09-5.51) (n = 38) | 3.01 (2.58-3.48) (n = 50) 4.06 (3.32-4.91) (n = 24) | 3.51 (2.86-4.26) (n = 24) 3.17 (2.63-3.79) (n = 32) 4.31 (3.15-5.75) (n = 10) | H1 H2 H3 |
| Systolic blood pressure (mmHg ± SEM) | 108.2 ± 1.26 (n = 36) | 109.6 ± 1.06 (n = 51) 106.2 ± 1.58 (n = 24) | 111.6 ± 1.55 (n = 25) 104.9 ± 1.78 (n = 32) 108.4 ± 2.45 (n = 10) | H1 H2 H3 |
| Diastolic blood pressure (mmHg ± SEM) | 59.7 ± 1.03 (n = 38) | 60.0 ± 0.89 (n = 51) 56.7 ± 1.3 (n = 24) | 63.2 ± 1.27 (n = 25) 58.1 ± 1.12 (n = 33) 59.0 ± 2.01 (n = 10) | H1 H2 H3 |
| Somatization (pill) (score ± SEM) | 104.9 ± 3.2 (n = 37) | 103.1 ± 2.76 (n = 49) 116.7 ± 3.9 (n = 25) | 103.8 ± 3.9 (n = 25) 101.7 ± 3.45 (n = 32) 102.7 ± 6.16 (n = 10) | H1 H2 H3 |
| Somatization (BSI) (% (lower bound-upper bound) | 57.9 (49.8-65.6) (n = 38) | 68.0 (61.1-74.2) (n = 50) 92.0 (84.5-96.0) (n = 25) | 76.0 (66.5-83.5) (n = 25) 68.8 (60.0-76.3) (n = 32) 66.7 (47.7-80.2) (n = 9) | H1 H2 H3 |
| Trait anxiety (stai) (score ± SEM) | 38.6 ± 1.37 (n = 36) | 34.9 ± 1.2 (n = 50) 37.4 ± 1.73 (n = 24) | 36.2 ± 1.59 (n = 25) 34.0 ± 1.5 (n = 32) 37.9 ± 2.68 (n = 10) | H1 H2 H3 |
| POMS Agreeable-hostile (score ± SEM) | 30.6 ± 0.69 (n = 38) | 30.6 ± 0.59 (n = 51) 30.6 ± 0.85 (n = 25) | 31.8 ± 0.85 (n = 25) 31.2 ± 0.75 (n = 32) 26.4 ± 1.34 (n = 10) | H1 H2 H3 |
| POMS composed-anxious (score ± SEM) | 28.6 ± 0.95 (n = 36) | 29.2 ± 0.82 (n = 51) 28.4 ± 1.17 (n = 25) | 29.0 ± 1.17 (n = 25) 28.8 ± 1.04 (n = 32) 23.1 ± 1.86 (n = 10) | H1 H2 H3 |
| Depression (BSI) (% (lower bound-upper bound) | 76.3 (68.8-82.5) (n = 38) | 72.0 (65.2-77.9) (n = 50) 83.3 (74.3-89.6) (n = 24) | 92.0 (84.6-96.0) (n = 25) 68.8 (60.0-76.3) (n = 32) 40.0 (25.9-55.97) (n = 10) | H1 H2 H3 |

Regarding Table 8, each value represents the estimated mean of the variable with associated SEM for one of six diplotype groups (combination of haplotype X and haplotype Y, where X and Y are H1 or H2 or H3). Greater positive values for BDI, PILL, BSI and Trait Anxiety scores reflect more negative psychological characteristics. The greater values for measures obtained from the POMS scale reflect more positive psychological characteristics: agreeable or composed. BDI, PILL, STAI and POMS scores were measured in relative units, blood pressure was measured in mm of mercury (mm HG), BSI depression and somatization are presented as the percent of subjects that show the trait. The values in this table came from oneway ANOVAs on the variables, with the exceptions of the BDI and BSI variables. For the BDI variables we performed the ANOVA analysis on a log-translated version of the variable and the results were then translated back into the original units. For the BSI variables, the results are displayed as a logistic regression.

Example 9

Analysis of ADRB2 Polymorphism and Blood Pressure

An association of H1 with both resting systolic and diastolic blood pressure and an effect of H2 on resting diastolic blood pressure was found (FIG. 2A). Subjects who carried no copies of H1 had significantly lower resting blood pressure than those who had one copy (Table 8, FIG. 2A). Consistent with this observation, subjects who carried two copies of H2 showed significantly lower resting diastolic blood pressure than those who carried no H1 (Table 8; FIG. 2A). H1 heterozygotes, with either H2 or H3, displayed the highest systolic and diastolic blood pressure, while H2 homozygotes and H2/H3 heterozygotes had the lowest diastolic blood pressure (Table 8). Thus, H1 heterozygotes showed a significant overdominance: subjects with one copy of H1 had higher systolic and diastolic blood pressure than subjects homozygous for either haplotype (FIG. 2A and Table 8), while H2 showed codominant relationships between gene dosage and diastolic blood pressure (FIG. 2A).

Example 10

Haplotype Interactions

Table 9 summarizes findings from assessments of interactions between haplotypes. For systolic blood pressure and diastolic blood pressure, BSI depression, POMS agreeable-hostile, a comparison between the additive model and the full model (which included all possible interactions) indicated that the model with interactions provided a better fit to the data. There was some indication that this is also the case for somatization PILL (P=0.1042), and POMS composed-anxious (P=0.1133).

Systolic and diastolic blood pressure variables had a best-fit to the model that included significant interactions between H1 and H2 and between H1 and H3. Further analyses did not support the hypothesis that H1 and H2 showed over/underdominance (P=0.341, P=0.862) for either of the blood pressure phenotypes. However, the interaction between haplotypes H 1 and H3 was significant (P=0.0316) for diastolic blood pressure and tend to support an overdominance effect for systolic blood measure (P=0.082).

For BSI depression, the best-fit model included a significant interaction between H1 and H3. A likelihood ratio test for over/underdominance in the relationship between H1 and H3 gave a p-value of 0.044, supporting an overdominant relationship. The POMS agreeable-hostile variable had a best-fit that included significant interactions between H1 and H2 and between H2 and H3. Neither of these haplotype pairs showed evidence for over/underdominance (P=0.250 and P=0.645, respectively).

TABLE 9

Haplotypes interactions: linear model analysis

| Trait | FMP* | FAP* | Model Pval | Parameter | Best-fit model Parameter Estimate | Standard Error | Pval $H_0: = 0$ | Pval**** |
|---|---|---|---|---|---|---|---|---|
| Log (Depression (BDI) + 1.53) | 0.315 | | | | | | | |
| Systolic blood pressure | 0.016 | 0.022 | 0.013 | $\gamma_1$ | 108.22 | 1.26 | 0 | |
| | | | | $\gamma_2$ | −1.39 | 0.960 | 0.150 | |
| | | | | $\gamma_3$ | −0.81 | 1.15 | 0.484 | |
| | | | | $\gamma_{12}$ | 2.95 | 1.44 | 0.043 | 0.341 |
| | | | | $\gamma_{13}$ | 4.24 | 1.83 | 0.030 | 0.082 |
| Diastolic blood pressure | 0.012 | 0.088 | 0.005 | $\gamma_1$ | 59.73 | 1.027 | 0 | |
| | | | | $\gamma_2$ | −1.49 | 0.785 | 0.062 | |
| | | | | $\gamma_3$ | −0.28 | 0.943 | 0.768 | |
| | | | | $\gamma_{12}$ | 1.71 | 1.18 | 0.151 | 0.862 |
| | | | | $\gamma_{13}$ | 3.75 | 1.58 | 0.019 | 0.032 |
| Somatization (PILL) | 0.064 | 0.104 | 0.033 | $\gamma_1$ | 104.94 | 3.04 | 0 | |
| | | | | $\gamma_2$ | 5.89 | 2.47 | 0.018 | |
| | | | | $\gamma_3$ | −1.13 | 3.20 | 0.725 | |
| | | | | $\gamma_{12}$ | −7.73 | 3.71 | 0.039 | |
| | | | | $\gamma_{13}$ | −8.046 | 4.66 | 0.087 | |
| Somatization (BSI) logistic | 0.065 | 0.196 | | | | | | |
| Trail Anxiety (STAI) | 0.213 | | | | | | | |
| Agreeable-hostile (POMS) | 0.030 | 0.012 | 0.015 | $\gamma_1$ | 30.65 | 0.620 | 0 | |
| | | | | $\gamma_2$ | 0.049 | 0.539 | 0.928 | |
| | | | | $\gamma_3$ | −2.12 | 0.738 | 0.004 | |
| | | | | $\gamma_{12}$ | 3.31 | 1.12 | 0.004 | 0.250 |
| | | | | $\gamma_{13}$ | 2.55 | 1.064 | 0.014 | 0.645 |
| Composed-anxious (POMS) | 0.100 | 0.113 | 0.064 | $\gamma_1$ | 28.83 | 0.860 | 0 | |
| | | | | $\gamma_2$ | −0.045 | 0.748 | 0.95259 | |
| | | | | $\gamma_3$ | −2.66 | 1.02 | 0.00562 | |
| | | | | $\gamma_{12}$ | 3.076 | 1.55 | 0.0496 | |
| | | | | $\gamma_{13}$ | 2.66 | 1.48 | 0.05429 | |
| Depression (BSI) logistic | 0.032 | 0.016 | 0.054 | $\gamma_1$ | −1.00 | 0.333 | 0.0028 | |
| | | | | $\gamma_2$ | −0.212 | 0.289 | 0.46354 | |
| | | | | $\gamma_3$ | 0.582 | 0.292 | 0.0461 | |
| | | | | $\gamma_{13}$ | −2.029 | 0.802 | 0.01144 | 0.044 |

*Full model Pvalue
**Pvalue for the full model vs additive model comparison
***For testing over/underdominance

Example 11

AADRB2 Polymorphism and RNA Expression

Many published studies that have examined ADRB2 polymorphism describe associations with the nonsynonymous Arg$^{16}$Gly (rs1042713) and Gln$^{27}$Glu (rs1042714) SNPs. It has been consistently observed that Arg$^{16}$Gly polymorphism is associated with agonist-induced internalization of the receptor (Small et al. (2003)). Although several phenotypes have been associated with Gln$^{27}$Glu polymorphism, the functional effects of this SNP remain unclear Small et al. (2003)). Without being bound by theory, it is hypothesized that since Gln$^{27}$Glu polymorphism is in strong linkage disequilibrium (LD) with SNPs in the promoter region (rs11958940, rs14326222, rs14326223, rs2400707; FIGS. 4A-4B), a set of these SNPs may define the efficiency of RNA transcription. The allelic combination of H1 in the promoter region of the gene and Gln$^{27}$Glu SNPs is opposite to the allelic combination associated with H2 and H3 (haplotype AAAGG versus TGGAC for rs11958940, rs14326222, rs14326223, and rs2400707, Gln$^{27}$Glu, respectively; FIGS. 4A-4B). Based on the outcomes of the association studies disclosed herein, and the known physiology of ADRB2, it is possible that H1 codes for a lower efficiency of transcription while H2 and H3 code for high efficiency of transcription.

In order to examine if there is a significant difference in the expression of ADRB2 mRNA driven by allelic combinations at the promoter region of three haplotypes, existing expressed sequence tag (EST) databases were analysed. Since sequencing of each EST clone is a random nonselective process and there are substantial numbers of EST sequences in the NCBI EST database, the frequency of gene-specific ESTs is correlated to the RNA expression level (Bortoluzzi & Danieli (1999)). This approach has been used previously to estimate the relative abundance of specific RNA transcripts, as well as its tissue or stage-specific levels. It has also been shown that the relative RNA expression values between SAGE, EST and microarray databases are comparable (Cameron (2004)).

The relative expression level of ADRB2 mRNAs were estimated on the basis of the relative abundance of ESTs in a manner described by Castilo-Davis and co-workers (2002). Each EST in available EST libraries was assigned to one of the three identified haplotypes based on their EST sequence (FIG. 25). If each haplotype codes at similar transcription efficiencies, it is expected that the haplotype-specific ESTs would appear in the databases in proportion to the population haplotype frequencies, whereas, if transcription efficiencies vary between the different haplotypes, it is expected those haplotypes that produce more transcript would be over-represented.

Fifty-three ADRB2 ESTs were found. Twenty-four of these had a sequence in the 5' region of the gene that permitted the identification of the corresponding haplotype. Five ESTs corresponded to H1, 8 ESTs corresponded to H2, and 11 ESTs corresponded to H3 haplotypes (FIG. 25). Haplotype-specific EST frequencies were compared with the haplotypes frequencies in the cohort (FIGS. 4A-4B), as well as haplotype frequencies reported by others (Belfer et al. (2004)). The distribution of EST frequencies was statistically different from the distribution of haplotype frequencies in both cohorts ($x^2$ analysis; P's<0.05). After normalization to haplotype frequencies, the amount of H2- and H3-specific ESTs relative to H1 were 1.8 and 4.4 respectively (FIG. 25), which supports the hypothesis that H1 codes for a lower efficiency of transcription compared to H2 and H3.

Example 12

ADRB2 Haplotypes and Risk of TMD

The clinical significance of ADRB2 genetic variants was determined by examining whether ADRB2 polymorphism is related to the incidence of TMD onset. Genotypes associated with decreased levels of somatization, depression, trait anxiety, and negative mood or high blood pressure level, should be protective against TMD development. Taken together, the preceding ANOVA analysis of phenotypic associations, analysis of haplotypes interactions and EST analysis of RNA expression provided the basis for grouping subjects based on the level of ADRB2 expression. Based on this model, subjects homozygous for H1 are predicted to have the lowest ADRB2 function (low ADRB2 expression, "Lo"), while people with only H2 and H3 (i.e., H2/H2, H2/H3 or H3/H3 haplotypes, high ADRB2 expression, "Hi") are predicted to have the highest ADRB2 function. Subjects caring one copy of haplotype H1 (i.e. heterozygous for H1-H2 or H1-H3, "Hi/Lo" group) display evidences for overdominance effect of H1, when coupled with either H2 or H3 haplotypes, show positive psychological characteristic, have higher resting blood pressure, and are predicted to have the lowest TMD incidence.

Of 181 subjects followed for three years, 15 were diagnosed with first onset TMD at some point during follow-up, yielding an overall incidence of 8.3%. TMD incidence was highest among the 25 H2/H2 homozygotes (5/25=20% (0.200), Table 10). Although the "Hi/Lo" reference group of H1 heterozygotes represented almost half of the initially tested cohort (n=76) only one TMD case was observed in this group, yielding a TMD incidence of 1.3%.

Compared with the reference group of "Hi/Lo" H1 heterozygotes, there was a significantly elevated risk of developing TMD for "Lo" homozygotes (relative risk [RR]=8.0, 95% confidence interval [CI]=2.0-67.9) and a significantly elevated risk for the "Hi" homozygotes (RR=11.3, 95% CI=2.0-67.9). If the "Lo/Lo" and "Hi/Hi" homozygotes were combined into one group, the risk of TMD development was 9.02 higher in this group compared to the reference "Hi/Lo" H1 heterozygotes group ([CI]=1.2-66.9). These results confirmed the pattern of overdominance in genetic influences on this clinical condition, with "Hi" homozygotes and "Lo" homozygotes showing a significantly greater risk for TMD development than the heterozygous groups.

TABLE 10

Relative risk of TMD development among different ADRB2 diplotype groups

| Haplotype Combination | TMD Incidence | Groups* | Groups TMD Incidence | Group Estimated RR | 95% lower bound | 95% upper bound |
|---|---|---|---|---|---|---|
| H1/H1 | 4/38 (0.105) | Lo/Lo | 4/38 (0.105) | 8.0 | 1.2 | 52.2 |
| H2/H2 | 5/25 (0.200) | Hi/Hi | 10/67 (0.149) | 11.3 | 2.0 | 67.9 |
| H3/H3 | 1/10 (0.100) | | | | | |
| H2/H3 | 4/32 (0.125) | | | | | |
| H1/H2 | 1/51 (0.020) | Hi/Lo | 1/76 (0.013) | 1 (reference) | NA | NA |
| H1/H3 | 0/25 (0.000) | | | | | |
| All subjects | 15/181 (0.083) | | | | | |

*H1 was considered to code for low levels of RNA expression (Lo) and H2 and H3 to code for high levels of RNA expression (Hi).

Materials and Methods for Example 13

Mechanical and Thermal Pain Testing

Rats were handled and habituated to the testing environment 2-3 days prior to establishing baseline responsiveness. On test days, rats were placed in plexiglass cages positioned over an elevated perforated stainless steel platform and habituated to the environment for 15-20 minutes prior to testing. Paw withdrawal threshold to punctate mechanical stimulation was assessed using the up-down method of Chaplan (Chaplan et al. (1994)). A series of nine calibrated filaments (with bending forces of 0.40, 0.68, 1.1, 2.1, 3.4, 5.7, 8.4, 13.2, and 25.0 g; Stoelting) with approximately equal logarithmic spacing between stimuli (Mean±SEM: 0.232±0.04 units) were presented to the hind paw in successive order, whether ascending or descending. Filaments were positioned in contact with the hindpaw for a duration of 3 seconds or until a withdrawal response occurred. Testing was initiated with the middle hair of the series (3.4 g). In the absence of a paw withdrawal response, an incrementally stronger filament was presented and in the event of a paw withdrawal, an incrementally weaker filament was presented. After the initial response threshold was crossed, this procedure was repeated in order to obtain a total of six responses in the immediate vicinity of the threshold. The pattern of withdrawals (X) and absence of withdrawals (0) was noted together with the terminal filament used in the series of six responses. The 50% g threshold=$(10^{[Xf+k\delta]})/10,000$, where $X_f$=value (in log units) of the final von Frey hair used; k=tabular value of pattern of positive (X) and negative (O) responses, and δ=mean difference (in log units) between stimuli.

Immediately following determination of the response threshold, paw withdrawal frequency (%) to punctate mechanical stimulation was assessed. A von Frey monofilament with a calibrated bending force of 25 g was presented to the hind paw ten times for a duration of 1 s with an interstimulus interval of approximately 1 second. Mechanical hyperalgesia was defined as an increase in the percentage frequency ([# of paw withdrawals/10]×100) of paw withdrawal evoked by stimulation with von Frey monofilaments. Responsiveness to von Frey filaments was reassessed at 30 min intervals for 2 h post-OR486.

Thermal hyperalgesia was evaluated using the radiant heat method (Hargreaves et al. (1988)) in the same animals evaluated for responsiveness to von Frey filaments. Radiant heat was presented through the floor of the stainless steel platform to the midplantar region of the hind paw. Stimulation was terminated upon paw withdrawal or after 20 seconds if the rat failed to withdraw from the stimulus. Paw withdrawal latencies to the thermal stimulus were recorded prior to experimental manipulations and reassessed in triplicate at 2.25 hours following OR486.

In Vitro Cytokine Measurement

Cell Maintenance:

Cell growth media consisted of Dulbecco's modified Eagle's medium supplemented with 10% heat-inactivated fetal bovine serum (Sigma, St. Louis, Mo., U.S.A.) and 1× penicillin-streptomycin (Gibco, Carlsbad, Calif., U.S.A.). Cells were maintained in a humidified atmosphere of 95% air and 5% $CO_2$.

Differentiation of 3T3-L1:

Two days after reaching confluence in growth media, adipogenesis was induced by incubating cells in growth media containing 0.25 μM dexamethasone (Sigma), 0.5 mM IBMX (Sigma), and 1 μM insulin (Sigma). After an additional 2 days in growth media containing 1 μM insulin, cells were grown for 6-8 days in normal growth media.

RNA Extraction and cDNA Synthesis:

Total RNA was isolated using the RNeasy Mini Kit (Qiagen, Valencia, Calif., U.S.A.). RNA was then treated with 2 units of DNase I (Ambion, Austin, Tex., U.S.A.) at 37° C. for 30 min. Reverse transcription was performed according to the manufacturer's instructions. Briefly, the reverse transcription reaction mixture consisted of 1 μg DNase 1-treated RNA, 500 ng oligo-$dT_{12-18}$, 10 mM dNTP, 40 units RNasin (Promega, Madison, Wis., U.S.A.), and 200 units of reverse transcriptase SUPERSCRIPT III™ (Invitrogen, Carlsbad, Calif., U.S.A.). cDNA synthesis was carried out at 50° C. for 1 hr followed by inactivation of reverse transcriptase at 70° C. for 15 min.

Subjects

Two-hundred and twenty-eight adult male Sprague-Dawley rats (250-320 g; Charles River Laboratories, Raleigh, N.C., USA) were used in these experiments. All procedures were approved by the University of North Carolina Animal Care and Use Committee.

Drugs and Chemicals

In Vivo: OR486 and RO41-0960 were dissolved in dimethylsulfoxide (DMSO) and diluted in 0.9% saline pH 7.5 (3:2). Phentolamine, propranolol, SCH23390, and spiperone were dissolved in ethanol and diluted in 0.9% saline pH 3.5 (1:4). Betaxolol, ICI118,551, and SR59230A were dissolved in DMSO and diluted in 0.9% saline (1:4). Lambda carrageenan (3%) was dissolved in 0.9% saline and administered in a volume of 100 μl. In Vitro: Betaxolol, ICI118,551, SR59230A, salmeterol, and CL316243 were dissolved in water. OR486, RO41-0960, phentolamine, propranolol, and carrageenan were obtained from Sigma Aldrich (St. Louis, Mo., U.S.A.), while SCH23390, betaxolol, ICI118,551, SR59230A, salmeterol, and CL316243 were purchased from Tocris (Ellisville, Mo., U.S.A.).

Mechanical and Thermal Pain Behavior Testing

50% paw withdrawal threshold to punctate mechanical stimulation was assessed using the method of limits. Immediately following determination of the response threshold, paw withdrawal frequency (%) to punctate mechanical stimulation was assessed. Responsiveness to von Frey filaments was measured prior to experimental manipulations and reassessed at 30 minute intervals for 2 hours following administration of a COMT inhibitor or vehicle. Thermal hyperalgesia was evaluated using the radiant heat method in the same animals evaluated for responsiveness to von Frey monofilaments. Paw withdrawal latencies to the thermal stimulus were recorded prior to experimental manipulations and reassessed in triplicate at 2.25 hours following OR486. A further description is described herein below.

In Vivo Plasma Cytokine Measurement

Upon termination of behavioral experiments, rats were euthanized and blood drawn from the inferior vena cava into heparinized syringes. Blood was centrifuged and plasma separated from red blood cells. Plasma IL-6 was measured in duplicate using enzyme-linked immunosorbant assay (ELISA) kits from R&D systems (Minneapolis, Minn., U.S.A.). Plasma TNFα and IL-1β were measured in duplicate by the University of North Carolina Proteomics Ilmmunotechnologies Core using ELISA kits from Biosource (Camarillo, Calif., U.S.A.) and the National Institute for Biological Standards and Control (UK), respectively.

In Vitro Cytokine Measurement

Mouse macrophages (RAW 264.7) and human preadipocytes (3T3-L1) were obtained from the University of North Carolina Tissue Culture Facility. Cell maintenance and 3T3-L1 preadipocyte differentiation is described herein below. For pharmacological experiments, cells were seeded at a density of $5 \times 10^5$ cells/well in a 12-well plate (Corning). Total RNA was isolated and reverse transcribed as described in the supplementary materials. TNFα, IL-1β, and IL-6 transcripts were quantitated in quadruplicate by real time polymerase chain reaction using TAQMAN® Gene Expression Assays (Applied Biosystems, Foster City, Calif., U.S.A.) in an ABI PRISM 7000 Sequence Detection System. TNFα, IL-1β, and IL-6 transcript levels were normalized to Glyceraldehyde-3-phosphate dehydrogenase (GAPDH).

Statistical Analysis

When comparing more than two groups, mechanical behavioral data were analyzed by analysis of variance (ANOVA) for repeated measures, while thermal behavioral data and cytokine data were analyzed by ANOVA. Post hoc comparisons were performed using the Bonferroni's test. When comparing two groups, behavioral and cytokine data were analyzed by paired and unpaired t-tests, respectively. $P \leq 0.05$ was considered to be statistically significant.

Example 13

30 COMT Modulation of Pain Sensitivity and Cytokine Production Via ADRB2 and ADRB3 Adrenergic Mechanisms The purpose of the present Example was to determine the mechanisms whereby elevated catecholamime levels, resulting from low COMT activity, lead to increased pain sensitivity. In order to evaluate the degree of pain sensitivity produced by depressed levels of COMT, the COMT inhibitor OR486 was administered to rats and its effects on pain behavior were compared to those produced in the carrageenan model of inflammation. OR486 administration significantly decreased paw withdrawal threshold to mechanical stimuli (FIG. 15A) and increased paw withdrawal frequency to a noxious punctate stimuli (FIG. 15B). OR486 administration also decreased paw withdrawal latency to thermal stimuli (FIG. 15C). The degree of mechanical and thermal hyperalgesia produced by OR486 was remarkable as it was comparable to that produced by carrageenan-induced inflammation of the hindpaw (see FIGS. 16A-16C for comparisons in contralateral non-injected paws). Levels of the prototypical proinflammatory and pro-pain cytokines TNFα, IL-1β, and IL-6 (Cunha, et al. (2005); Kress, et al. (2004)) were evaluated in animals receiving OR486 or carrageenan. Similar to carrageenan, administration of OR486 elevated plasma levels of TNFα, IL-1β, and IL-6 (FIG. 15D-15F). To verify that the effects of OR486 on the development of enhanced pain sensitivity and cytokine production were specific to COMT inhibition, a second COMT inhibitor with a different chemical structure was employed. Similar to OR486, administration of the COMT inhibitor RO41-0960 decreased mechanical and thermal pain sensitivity (FIGS. 15G-15I) and increased cytokine production (FIGS. 17A-17C), suggesting that pain sensitivity is COMT-dependent.

COMT acts peripherally and centrally to metabolize epinephrine, norepinephrine, and dopamine. Thus, pharmacological methods were used to establish which receptor class mediates the COMT-dependent increases in pain behavior and cytokine production. OR486-induced hyperalgesia was completely blocked by the β-adrenergic antagonist propranolol, which normalized paw withdrawal threshold (FIG. 18A) and paw withdrawal frequency (FIG. 18B) to mechanical stimuli and paw withdrawal latency to thermal stimuli (FIG. 18C). Propranolol also normalized plasma levels of TNFα, IL-1β, and IL-6 (FIG. 18D-18F). The α-adrenergic antagonist phentolamine, the D1-like dopaminergic antagonist SCH23390, and the D2-like dopaminergic antagonist spiperone failed to block the hyperalgesic effects of OR486. Antagonists administered in the absence of OR486 did not alter pain sensitivity (FIGS. 19A-19C).

Propranolol is a nonselective ADRB antagonist. Doses similar to that used in the present Example block activity of ADRB1s and ADRB2s (O'Donnell et al. (1994)) and reduce the activity of ADRB3s (Tsujii et al. (1998)). Thus additional studies were conducted in order to identify the ADRB subtype(s) that mediate the development of OR486-induced elevations in pain sensitivity and cytokine production. Administration of the ADRB2 antagonist ICI118,551 or the ADRB3 antagonist SR59230A, but not the ADRB1 antagonist betaxolol, partially blocked the heightened pain sensitivity produced by OR486 in a dose-dependent fashion (FIGS. 20A-20L). Selective ADRB antagonists administered in the absence of OR486 did not alter pain sensitivity (FIGS. 21A-21C). ADRB2 and ADRB3 antagonists also blocked the development of the OR486-induced increase in plasma levels of TNFα, IL-1β, and IL-6 (FIGS. 20G-20L).

Administration of ADRB2 or ADRB3 antagonists reduced the development of increased pain sensitivity and cytokine production produced by COMT inhibition; however, only a partial blockade of OR486-induced mechanical pain sensitivity was achieved. These results suggest that the combined activation of ADRB2s and ADRB3s can produce the maximum degree of COMT-dependent pain sensitivity. To test this hypothesis, ICI118,551 and SR59230A were administered together prior to administration of OR486. Coadministration of ADRB2 and ADRB3 antagonists completely normalized paw withdrawal threshold (FIG. 22A) and paw withdrawal frequency (FIG. 22B) to mechanical stimuli and paw withdrawal latency to thermal stimuli (FIG. 22C). Additionally, coadministration of ICI118,551 and SR59230A prior to OR486 decreased plasma levels of TNFα, IL-1β, and IL-6 (FIGS. 22D-22F) relative to animals receiving vehicle prior to OR486. Thus, COMT-dependent pain sensitivity is mediated exclusively through coincident ADRB2 and ADRB3 adrenergic signaling processes.

The blockade of COMT-dependent increases in TNFα, IL-1β, and IL-6 by $β_{2/3}$AR antagonists further suggests that proinflammatory cytokine production is regulated by ADRB2s and ADRB3s. To determine if proinflammatory cytokine production results from the direct stimulation of $β_{2/3}$ARs, a series of in vitro cell culture studies was performed.

Macrophages, rich in ADRB2s, and adipocytes, rich in ADRB2s and ADRB3s, were chosen as they are the primary producers of TNFα and IL-1β (Kiefer et al. (2001)) and TNFα and IL-6 (Coppack, S. W. (2001)), respectively. Activation of ADRB2s on macrophages and ADRB3s on adipocytes has been shown to increase cAMP production (Liggett, et al. (1989), Strosberg, A. D. (1997)) and cAMP-dependent IL-6 transcription (Elenkov et al. (2000), Zhanq et al. (1988)). A functional cAMP response element has been mapped within the promoter region of TNFα (Roach et al. (2005)) and IL-1β (Chandra et al. (1995)), however there is no direct evidence, to date, that activation of ADRB2s and ADRB3s stimulates TNFα or IL-1β transcription. Non-primed macrophagelike cells line RAW 264.7 and 3T3-L 1 adipoctyes were treated with ADRB2 or ADRB3 agonists and cytokine mRNA level was measured. The dose-response curves were established first and drug doses within one log unit of the ED50 or ID50 were selected. In macrophages, stimulation of ADRB2s by the specific ADRB2 agonist salmeterol produced a 38-fold increase in IL-1β (FIG. 23A) and a 6.5-fold increase in IL-6 (FIG. 23B) mRNA levels. In adipocytes, stimulation of ADRB2s by salmeterol produced a 6-fold increase in TNFα (FIG. 23C) and an 8-fold increase in IL-6 (FIG. 23E) mRNA levels. The salmeterol-induced increase in macrophage IL-1β and IL-6 transcript levels and adipocyte TNFα and IL-6 transcript levels was completely blocked by ICI118,551, but not by betaxolol or SR59230A. Stimulation of ADRB3s in adipocytes by the specific ADRB3 agonist CL316243 produced a 28-fold increase in IL-6 mRNA levels (FIG. 23E) that was completely blocked by SR59230A, but not by betaxolol or ICI118,551. Remarkably, for the high doses of agonists the stimulation of transcription of IL-1β on macrophages and IL-6 on adipocytes reached 150 fold. The immediate (45 minute) response produced by ADRB2 and ADRB3 activation suggests direct stimulation of cytokine transcription occurs. Treatment of cells with antagonists alone failed to produce meaningful changes in cytokine mRNA level (FIGS. 24A-24D). These findings are in line with the view that activation of ADRB2s and ADRB3s located on adipocytes as well as ADRB2s located on macrophages increases the production of proinflammatory cytokines, which enhance pain sensitivity (Cunha et al. (2005); Kress et al. (2004)). Together, these data provide evidence that COMT inhibition can result in proinflammatory cytokine production and increased pain sensitivity comparable to that produced by carrageenan, via ADRB2 and ADRB3 adrenergic mechanisms.

Previous studies have shown that activation of ADRB2s located on nociceptors increases pain sensitivity via protein kinase A-, protein kinase C-, or mitogen activated kinase-dependent pathways (Khasar et al. (1999); Aley et al. (2001)). Norepinephrine and epinephrine can also modulate pain through the activation of ADRBs located on immune cells (Elenkov et al. (2000)) and other cells (e.g., adipocytes) that release proinflammatory cytokines. Elevated levels of TNFα, IL-1β, and IL-6 are associated with increased pain behavior in animal models (Cunha et al. (2005); Kress et al. (2004)) and painful inflammatory and musculoskeletal disorders in humans (Kress et al. (2004)). Proinflammatory cytokines can modulate pain via direct receptor-mediated actions or through the recruitment of additional mediators (Sommer et al. (2004)). IL-1β and IL-6 can act directly on sensory neurons to produce mechanical and thermal hyperalgesia via a PKC-dependent mechanism. Additionally, IL-6 can elicit the release of CGRP from nociceptors. TNFα can act directly or through p38 MAPK to sensitize nociceptors.

Cytokines are able to induce their own production and that of other cytokines. For example, TNFα and IL-1β activate NF-kB, which in turn stimulates the transcription of TNFα, IL-1β, and IL-6 (Kress et al. (2004)). This cascade ultimately results in norepinephrine and epinephrine release from sympathetic efferents. Thus, a great deal of redundancy exists in the cytokine network as it relates to adrenergic signaling. A cycle forms, in which the production and release of catecholamines and cytokines is potentiated.

Disclosed herein is the first demonstration that ADRB2 and ADRB3 activation stimulates TNFα and IL-1β production as well as that of IL-6. Moreover, this is the first study to depict a critical role for ADRB3s and adipocytes in pain transmission. Until now, ADRB3s, which are expressed primarily on adipocytes, have almost exclusively been implicated in energy exchange and lipid metabolism (Strosberg, A. D. (1997)).

The present results suggest that in noninflammatory pain states, activation of ADRB2s stimulates proinflammatory cytokine production via a cAMP-dependent mechanism. These findings are in contrast to those of previous studies showing that ADRB2s have anti-inflammatory actions in models of inflammation by inhibiting NF-kB-dependent transcription of proinflammatory cytokines (Elenkov et al. (2000)). Thus, ADRB2s may play a different role in noninflammatory versus inflammatory pain states. Furthermore, the present results suggest that the same set of cytokines modulate pain evoked in the absence and the presence of peripheral inflammation, likely through different transduction mechanisms. Thus, different therapeutic interventions may be required for pain occurring in the absence versus the presence of inflammation. Specifically, persistent pain conditions or somatosensory disorders, which are frequently associated with enhanced pain sensitivity in the absence of other signs of inflammation (e.g. idiopathic pain conditions, TMD, fibromyalgia syndrome, myofascial pain conditions, chronic pelvic pain, and irritable bowel syndrome), can be treated with novel pharmacological agents that block the function of ADRB2s and ADRB3s.

Further elucidating the factors that impact pain sensitivity will advance understanding of the mechanisms that underlie persistent pain states and somatosensory disorders. This will promote the development of novel pharmacotherapies and behavioral therapies. As disclosed herein above, the presently disclosed subject matter identifies polymorphisms in the COMT gene that are associated with low COMT enzymatic activity and somatosensory disorders and elucidates the mechanism whereby low levels of COMT lead to exacerbated pain states, which can lead to one or more somatosensory disorders. Elevated levels of norepinephrine and epinephrine, resulting from depressed COMT activity, activate ADRB2s and ADRB3 to produce proinflammatory cytokine production and heightened pain sensitivity (FIG. 8). Combined application of antagonists for ADRB2s and ADRB3s, should alleviate selective clinical pain states and somatosensory disorders by reducing catecholamine activity and the subsequent release of cytokines that sensitize nociceptors. Taken together, these results indicate that $\beta_{2/3}$ antagonist therapy can benefit patients suffering from somatosensory disorders resulting from low COMT activity and/or elevated catecholamine levels. These findings also suggest that therapies targeted towards activation of COMT will also benefit patients suffering from somatosensory disorders associated with low COMT activity.

Example 14

Effects of ADRB3 Polymorphism on Pain Perception

Common Haplotypes of ADRB3

Genomic DNA from peripheral blood samples of 210 healthy female Caucasian volunteers was genotyped for SNPs within the ADRB3 gene locus. Nine SNPs were chosen that were evenly spaced among the locus and potentially form one haploblock (Belfer et al. (2004)) (FIGS. 7A-7B). The first two examined SNPs (rs13258937 and rs802162) are located in the promoter region of the gene. The next two SNPs (rs4993 and rs4994) are located within the first exon: rs4993 is in the 5'untranslated region (UTR) and rs4994 is in the coding region. SNP rs4994 codes for the nonsynonomous change Trp64Arg. The next two SNPs (rs4997 and rs2071493) are located in the intron of the gene. SNPs rs4998 and rs4999 are in the 3'UTR of the gene and rs9694197 is the 3' intragenec region. The first three examined SNPs (rs13258937, rs802162 and rs4993) were found to be monomorphic in the study population and were not considered in further analyses. The minor allele of SNP rs4999 also displayed low frequency. Only 6 subjects carried one copy of this minor allele, and thus this SNP was not included in further analyses. The PHASE program (Stephens et al. (2001); Stephens & Donnelly (2003)) was used for haplotype reconstruction from the remaining five SNPs that were present in the test population with a frequency of at least 10% for the minor allele. Three major haplotypes were found, representing 97.3% of all haplotypes observed in this study (FIGS. 7A-7B) and one haplotype was found to be the most abundant in the population with a frequency of 78.5%. Only 10 subjects carried at least one haplotype that was different from the three major ones.

ADRB3 Polymorphism and Pain Responsiveness

Based on the animal experiments results disclosed in the Examples herein above, it was hypothesized that ADRB3 genotypes are also associated with individual variations in pain sensitivity, risk of development of somatosensory disorders, and are predictive of the responsiveness or efficacy of pharmacological treatments for pain conditions. It is further hypothesized that there is interaction between specific COMT and ADRB3 genotypes and identification of both COMT and ADRB3 genotypes can be a better predictor of pain states than that predicted by assessing either COMT or ADRB3 genotypes alone. The association between pain responsiveness and ADRB3 genotypes, as well as pain responsiveness and COMT and ADRB2 genotypes combined were further studied.

TABLE 11

Summed z-scores for Caucasian subjects with COMT-ADRB3 combinations

| | COMT diplotype | | | | | | | |
|---|---|---|---|---|---|---|---|---|
| | HPS/APS gdssumz | | | LPS gdssumz | | | All gdssumz | | |
| | N | Mean | Std | N | Mean | Std | N | Mean | Std |
| ADRB3_diplotype | | | | | | | | | |
| H1/H1 | 38 | 4.9 | (09.0) | 72 | −0.8 | (08.0) | 110 | 1.1 | (08.7) |
| H1/H2 | 14 | −2.1 | (09.9) | 19 | −2.6 | (07.9) | 33 | −2.4 | (08.7) |
| H1/H3 | 5 | 4.5 | (11.1) | 11 | −3.5 | (08.5) | 16 | −1.0 | (09.7) |
| H2/H2 | 1 | 1.2 | . | 5 | −5.4 | (11.9) | 6 | −4.3 | (11.0) |
| other | 2 | 3.7 | (15.6) | 5 | −5.5 | (11.9) | 7 | −2.9 | (12.5) |
| All | 60 | 3.1 | (09.7) | 112 | −1.8 | (08.4) | 172 | −0.1 | (09.1) |

Table 11 presents the summed z-scores for Caucasian subjects grouped according to COMT haplotypes and all possible ADRB3 diplotypes. Data include the number of subjects, mean and standard deviation of the summed z-score, which aggregates responses from 16 experimental pain procedures (for details see Material and Methods disclosed in the Examples herein above). Higher mean z-scores denote individuals who show relatively greater pain responsiveness (i.e., greater sensitivity), while lower mean z-score denote individuals who show relatively lower pain responsiveness (i.e. less sensitivity). In Table 11, diplotypes of COMT have been dichotomized to contrast subjects with only HPS/APS haplotypes (labeled HPS/APS group) versus subjects with at least one LPS haplotypes (labeled LPS group). COMT haplotypes are based on four SNPs: rs6269 rs4633 rs4818 rs4680. Subjects with COMT haplotypes other than HPS, APS or LPS are excluded from the table.

The results demonstrate generally independent effects of COMT and ADRB3 haplotypes. Specifically, the two less frequent genetic variants of ADRB3 both were associated with relatively lower responsiveness to experimental pain (mean z-scores=−2.4 for H1/H2 and −1.0 for H1/H3) compared to the more frequent variant of ADRB3. The observed effects of COMT haplotype groups (HPS/APS vs LPS) are consistent across each ADRB3 haplotype, with higher levels of pain responsiveness observed for the HPS/APS groups compared to the LPS groups. These results suggest that COMT and ADRB3 haplotypes exerted independent effects on pain responsiveness, with an apparent dominant effect of the H2 haplotype of ADRB3 when coupled with H1.

TABLE 12

Summed z-scores for Caucasian subjects with aggregated COMT-ADRB3 combinations

| | COMT Haplotype Groups | | | | | | | |
|---|---|---|---|---|---|---|---|---|
| | HPS/APS Pain z-score | | | LPS Pain z-score | | | All Pain z-score | |
| | N | Mean | Std | N | Mean | Std | N | Mean | Std |
| ADRB3_diplotype | | | | | | | | | |
| H1/H1 | 38 | 4.9 | (09.0) | 72 | −0.8 | (08.0) | 110 | 1.1 | (08.7) |
| H1/H2 or H2/H2 | 15 | −1.9 | (09.6) | 24 | −3.2 | (08.7) | 39 | −2.7 | (08.9) |
| H1/H3 | 5 | 4.5 | (11.1) | 11 | −3.5 | (08.5) | 16 | −1.0 | (09.7) |
| All | 58 | 3.1 | (09.6) | 107 | −1.6 | (08.2) | 165 | 0.0 | (09.0) |

The results shown in Table 11 were further evaluated by regrouping to produce three categories of ADRB3 diplotypes, as shown in Table 12. This regrouping excluded the rare diplotypes, which occurred in only one or two subjects. Statistical evaluation was undertaken using a factorial least squares regression model, in which the summed z-score was the dependent variable. COMT diplotype (1 degree of freedom) formed one first-order independent variable, and ADRB3 haplotype (2 degrees of freedom) formed the other first-order independent variable. An interaction (2 degrees of freedom) was also included. The overall model was statistically significant (F(5,159)=3.9, P=0.0021). There was a statistically significant effect for COMT haplotype group, F(1,59)=11.2, P=0.001 and ADRB3 haplotype groups F(2, 159)=3.15, P=0.046. The interaction term was not statistically significant [F(2,159)=1.1, P=0.33] demonstrating that the effects of each diplotype were independent. Importantly, pain responsiveness of the subjects carrying H1/H2 diplotype was low in both LPS and APS/HPS COMT groups.

These data demonstrate that predictions of treatment responses to chronic pain states based on ADRB3 genotype can be made. For example, subjects carrying H2 or H3 ADRB3 haplotypes will be poor responders to therapies that block or reduce ADRB3 function, especially when they also carry high COMT activity diplotypes (e.g., LPS group).

ADRB3 Polymorphism and Somatization

Somatization, which is a measure of one's ability to perceive bodily sensations, is elevated and highly associated with several somatosensory disorders. As shown in FIG. 5, a derived measure of somatization (PILL somatization score; see Diatchenko et al. (2005) and Examples herein above) is statistically associated with ADRB3 diplotypes. Subjects bearing an H3 haplotype have a lower PILL somatization score than those who do not carry an H3 allele (FIG. 5). Consistent with this observation, H1/H3 heterozygous also have low pain responsiveness (Table 11).

ADRB3 Polymorphism and Risk of TMD Onset

Based on the determined association analysis of ADRB3 haplotypes with pain responsiveness and somatization score, it is evident that subjects bearing H2 or H3 haplotypes of ADRB3 can be predicted to have lower risk for developing somatosensory disorders, including TMD.

TABLE 13

Cumulative incidence of TMD among ADRB3 diplotype groups for Caucasians
tmdcase (TMD case status)

| | Cases n % | Non case n % | Total |
|---|---|---|---|
| H1/H1 | 99.38 | 8790.63 | 96 |
| H1/H2 or H2/H2 | 25.41 | 3594.59 | 37 |

TABLE 13-continued

Cumulative incidence of TMD among ADRB3 diplotype groups for Caucasians
tmdcase (TMD case status)

| | Cases n % | Non case n % | Total |
|---|---|---|---|
| H1/H3 | 16.67 | 1493.33 | 15 |
| Other | 333.33 | 666.67 | 9 |
| Total | 15 | 142 | 157 |

Table 13 presents the number and percentage of subjects who, during a three-years prospective cohort study (for details see Examples herein above and Diatchenko et al. (2005)) were diagnosed clinically with temporomandibular disorder (TMD). Subjects are classified according to their ADRB3 diplotype and subjects who developed TMD during the 3-year observational period were labeled as 'cases'. Among the 96 subjects who had the most prevalent H1/H1 diplotype, 9 became cases, with a 3-year cumulative incidence of 9.38%. Incidence was lowest for H1/H2 and H1/H3 subjects (5.41% and 6.67%, respectively). The 9 subjects with other, infrequent (also referred to herein as "Uncommon" haplotypes/diplotypes), diplotypes of ADRB3 had a strikingly high incidence rate of 33.33%. These data are consistent with the results shown in Tables 11 and 12 and suggest that H1/H2 or H2/H2 subjects (who have the lowest pain sensitivity in Table 11) and H1/H3 subjects (who have low pain sensitivity in Table 11 and the lowest somatization scores in FIG. 5) have a very low risk of developing a somatosensory disorder.

Example 15

Uncommon Haplotypes of ADRB2 and ADRB3 and Risk of TMD Development

The genomic structure of adrenergic receptors ADRB2 and ADRB3 has several striking features. These are rather short genes, each comprising less than 5 kb on genomic DNA, however, the density of SNPs common in the human population is higher than one for each 1 kb. Furthermore, in spite of the high density of common SNPs there are only three common haplotypes (H1, H2, H3) that can be reconstructed for each gene. Among 212 Caucasian subjects in the tested cohort (see Examples herein above), only 5 subjects carried one ADRB2 haplotype that was one or two SNPs different from one of the three common haplotypes for ADRB2, and only 10 subjects carried at least one ADRB3 haplotype that was one SNP different from one of three common haplotypes for ADRB3. It is hypothesized that allelic combinations in adrenergic receptors have gone through evolutionary selection, resulting in haplotypes that possess strong self-compensatory, self-balanced features. It is proposed that allelic combinations that are different from common allelic combinations ("Uncommon" haplotypes) produce phenotypic disadvantages for carriers and increase the risk for the development of maladaptive conditions such as somatosensory disorders.

ADRB2 Polymorphism and Risk of Development of TMD

Tables 14 and 15 present the number and percentage of subjects who, during 3-years of follow-up, were diagnosed clinically with TMD. Subjects are classified according to their ADRB2 (Table 14) or ADRB3 (Table 15) diplotypes. Subjects who were diagnosed with TMD are labeled as 'cases'.

TABLE 14

Cumulative incidence of TMD among ADRB2 diplotype groups for Caucasians
tmdcase (TMD case status)

| | Cases n % | Non case n % | Total |
|---|---|---|---|
| H1/H1 | 310.00 | 2790.00 | 30 |
| H1/H2 | 12.13 | 4697.87 | 47 |
| H1/H3 | 00.00 | 18100.00 | 18 |
| H2/H2 | 421.05 | 1578.95 | 19 |
| H2/H3 | 413.33 | 2686.67 | 30 |
| H3/H3 | 111.11 | 888.89 | 9 |
| Other (uncommon) | 111.11 | 250.00 | 4 |
| Total | 15 | 142 | 157 |

TABLE 15

Cumulative incidence of TMD among ADRB3 diplotype groups for Caucasians
tmdcase (TMD case status)

| | Cases n % | Non case n % | Total |
|---|---|---|---|
| H1/H1 | 99.38 | 8790.63 | 96 |
| H1/H2 or H2/H2 | 25.41 | 3594.59 | 37 |
| H1/H3 | 16.67 | 1493.33 | 15 |
| Other (uncommon) | 333.33 | 666.67 | 9 |
| Total | 15 | 142 | 157 |

Among the numerically largest group of subjects with the H1/H2 diplotype of ABDRB2, there was only one case of TMD onset, hence representing a 3-year cumulative incidence of 2.13%. TMD incidence was lowest (0%) for the 18 subjects with the H1/H3 diplotype. The highest TMD incidence was observed among subjects who carried at least one of the rare haplotypes (i.e., a haplotype different than one of the three common haplotypes, and referred to herein collectively as "Uncommon" haplotype) for ADRB2 haplotype (50.0%).

Among the 109 subjects who had the most prevalent H1/H1 diplotype of ADRB3 (Table 15), 9 were cases, hence representing a 3-year cumulative incidence of 9.38%. The highest TMD incidence was observed among subjects carried at least one Uncommon ADRB3 haplotype (33.3%).

The results strongly suggest that subjects carrying Uncommon haplotypes of ADRB2 or ADRB3 are under higher risk of developing somatosensory disorders.

Example 16

Analysis of COMT/ADRB2 Genotype Combinations as a Predictor of Pain Sensitivity and Risk for Developing Somatosensory Disorders Based on the experimental animal subject results disclosed herein in the above Examples and the clinical studies that have shown associations between ADRB2 haplotypes (H1, H2, H3) and psychological variables, ADRB2 genotypes are predictive of human pain sensitivity, risk of developing somatosensory disorders, and responses to pharmacological treatments for somatosensory disorders.

Based on the knowledge that COMT and ADRB2 are part of the same biological pathway (e.g., COMT→Epinephrine→ADRB2) that influences pain sensitivity and proinflammatory cytokine responses in animals (see Khasar, et al. (2003) and data disclosed herein in the Examples) and humans (see data disclosed in Examples herein above) it is hypothesized that specific combinations of COMT and ADRB2 genotypes interact to influence pain sensitivity, psychological variables associated with pain perception, and the risk of developing chronic pain conditions. As such, the presently disclosed subject matter discloses that specific combinations of COMT and ADRB2 genotypes can better predict human pain sensitivity, risk of developing somatosensory disorders, and responses to pharmacological treatments for somatosensory disorders than either COMT or ADRB2 genotype alone.

The associations between specific combinations of COMT and ADRB2 genotypes on human pain sensitivity (Table 16) have been examined. The results on association between ADRB2 haplotypes, psychological profile and blood pressure noted significant overdominance effect of H1 haplotype when combined with H2 or H3 haplotypes (see Examples herein above). Because of this observation, the association of the number of copies of H1 haplotype with pain z-score (a measure of human pain sensitivity) was examined.

TABLE 16

Summed z-scores for Caucasian subjects with COMT diplotypes and differing numbers of ADRB2 haplotypes

| | COMT halotypes groups | | | | | | | | |
|---|---|---|---|---|---|---|---|---|---|
| | HPS/APS pain z-score | | | LPS pain z-score | | | All pain z-score | | |
| | N | Mean | Std | N | Mean | Std | N | Mean | Std |
| ADRB2diplotype | | | | | | | | | |
| 2 copies of H1 | 14 | 4.0 | (09.2) | 19 | −1.9 | (09.5) | 33 | 0.6 | (09.7) |
| 1 copy of H1* | 24 | 2.3 | (10.6) | 47 | −3.6 | (07.5) | 71 | −1.6 | (09.0) |
| 0 copies of H1† | 20 | 3.9 | (09.4) | 43 | 0.1 | (08.7) | 63 | 1.3 | (09.1) |
| All | 58 | 3.3 | (09.7) | 109 | −1.9 | (08.5) | 167 | −0.1 | (09.2) |

*Subjects with H1/H2 or H1/H3 diplotypes
†Subjects with H2/H2, H2/H3 or H3/H3 diplotypes Table 16 presents summed z-scores for subjects grouped according to COMT diplotype group and number of copies of ADRB2 haplotype H1. The analysis has been restricted by only Caucasian subjects to increase genetic homogeneity of analyzed cohort and eliminate the possibility of false associations due to population stratification. Data include number of subjects, mean and standard deviation of the summed z-score, which aggregates responses from 16 experimental pain procedures. Higher mean z-scores represent groups with relatively greater responsiveness (i.e. greater sensitivity) to experimental pain, while lower mean z-scores represent relatively lower pain responsiveness (i.e. less sensitivity). Diplotypes of COMT have been dichotomized to contrast subjects with only HPS and APS haplotypes (labeled HPS/APS group) versus subjects with at least one LPS haplotype (labeled LPS) (See Examples herein above). COMT haplotypes are based on four SNPs: rs6269 rs4633 rs4818 rs4680. Diplotypes of ADRB2 represent all possible combinations of three major haplotypes (H1, H2, H3) formed by eight SNPS: G-7127A, rs11958940, rs1432622, rs1432623, rs2400707, rs1042713, rs1042714 and rs1042717 (for details see data of Examples herein above). Subjects with other, infrequent COMT or ADRB2 haplotypes that differ from the ones shown here are excluded from the table.

The results in Table 16 show a consistent pattern of diminished pain response among subjects with only one copy of the H1 haplotype compared with subjects who have either two copies or no copies of the H1 haplotype. This effect was observed for all subjects of the study described herein and separately for subjects with the HPS/APS COMT haplotype and with the LPS COMT haplotype. This pattern, in which pain responsiveness is similar for subjects with no copies of the H1 haplotypes and with two copies of a haplotype, is consistent with the concept of overdominance, in which homozygous subjects have similar phenotypes, while heterozygotes have a markedly different phenotype.

The independent effects of COMT and ADRB2 receptor genotype on human pain sensitivity was evaluated statistically in a factorial least squares regression model, in which the summed z-score was the dependent variable. Explanatory variables were COMT diplotype groups (1 degree of freedom) and two categories of ADRB2: a single copy of the H1 haplotype, versus zero or two copies of the H1 haplotype. Again, subjects with rare haplotypes were excluded from the analysis. The overall model was statistically significant ($F(2,165)=7.8$, $P=0.0006$) and there were independent effects of both COMT ($F1,165)=11.8$, $P=0.0007$) and ADRB2 ($F(1,165)=3.4$, $P=0.066$). Their independent effects were confirmed by a lack of significance of the interaction term in the model ($P=0.69$).

The association between summed z-scores for subjects grouped according to COMT diplotype and all possible ADRB2 diplotypes (Table 17) was next analyzed.

TABLE 17

Summed z-scores for subjects with COMT-ADRB2 combinations

| | comt_halotypes group | | | | | | | | |
|---|---|---|---|---|---|---|---|---|---|
| | HPS/APS Pain z-score | | | LPS Pain z-score | | | All Pain z-score | | |
| | N | Mean | Std | N | Mean | Std | N | Mean | Std |
| ADRB2_ diplotype | | | | | | | | | |
| H1/H1 | 13 | 2.6 | (08.0) | 18 | −1.6 | (09.8) | 31 | 0.1 | (09.2) |
| H1/H2 | 17 | 3.6 | (10.1) | 26 | −4.1 | (07.7) | 43 | −1.0 | (09.4) |

TABLE 17-continued

Summed z-scores for subjects with COMT-ADRB2 combinations

| | comt_halotypes group | | | | | | | | |
|---|---|---|---|---|---|---|---|---|---|
| | HPS/APS Pain z-score | | | LPS Pain z-score | | | All Pain z-score | | |
| | N | Mean | Std | N | Mean | Std | N | Mean | Std |
| H1/H3 | 6 | 0.1 | (12.6) | 11 | −2.7 | (08.1) | 17 | −1.7 | (09.6) |
| H2/H2 | 6 | 4.2 | (10.0) | 13 | −3.5 | (08.8) | 19 | −1.1 | (09.6) |
| H3/H2 | 10 | 3.3 | (09.5) | 18 | 3.3 | (09.2) | 28 | 3.3 | (09.1) |
| H3/H3 | 3 | 4.2 | (13.6) | 6 | 2.4 | (07.2) | 9 | 3.0 | (06.9) |
| All | 57 | 2.9 | (09.5) | 95 | −1.4 | (08.7) | 152 | 0.2 | (09.2) |

The results demonstrate that subjects who carry only HPS/APS diplotypes of COMT have higher pain sensitivity (mean z-score=2.9) than subjects with LPS diplotypes (mean z-score=−1.4). The net difference of 4.3 z-score units between APS/HPS and LPS is repeated within most groupings of ADRB2 diplotype. However, there is some indication that the difference between APS/HPS and LPS is dependent upon ADRB2 diplotype. Specifically, subjects with H2/H2 diplotypes of ADRB2 have a much larger difference of 7.7 z-score units when HPS/APS (mean=4.2) and LPS (mean=−3.5) are contrasted. In contrast, among subjects with H3/H3 or H3/H2 diplotypes, z-scores do not differ between HPS/APS and LPS groups and have a much smaller difference of 1.2 z-score units for H3/H3 and no difference of z-score units for H2/H3, making diplotypes H3/H3 and H2/H3 associated with higher pain responsiveness regardless of COMT genotype. In summary, among subjects within HPS/APS COMT haplotype group, the H3/H3 and H2/H3 homozygotes for ADRB2 are associated with highest pain responsiveness; and among subjects within LPS COMT group, the H3/H3 and H2/H3 carriers are associated with highest pain responsiveness.

The data strongly suggest that the effect of COMT haplotypes on pain perception can be modulated by specific ADRB2 haplotypes but not by others (Table 17). This observation is consistent with the known cell biology of ADRB2. Epinephrine, an agonist of ADRB2, regulates activity of ADRB2 at several levels (Small et al. (2003)). First, ADRB2 is internalized inside the cell in response to agonist (e.g., epinephrine) stimulation. Second epinephrine-dependent stimulation of ADRB2 leads to an activation of its own transcription through a functional cAMP-response element in the promoter region of ADRB2 (Gaiddon et al. (2003)). Since the concentration of epinephrine in the human body is influenced by the COMT activity, ADRB2 density on the cell surface should be substantially influenced by COMT haplotypes. Given this understanding of the cell biology, an interaction between specific ADRB2 and COMT haplotypes on ADRB2 mediated biological responses (i.e., pain sensitivity, psychological state and trait, and inflammatory state) can be expected. Since ADRB2 coded by different ADRB2 haplotypes can be regulated by epinephrine differently, it is very likely that there are specific interactions between ADRB2 haplotypes and COMT haplotypes, which is supported by the results presented in Table 16.

Based on the data presented herein the presently disclosed subject matter provide that ADRB2 and COMT haplotypes can be used to guide pharmacological treatment decisions regarding the treatment of somatosensory disorders, persistent pain conditions, and inflammatory conditions. Specifically, subjects with low COMT activity (HPS/APS group)

can be predicted to benefit from pharmacological therapy with ADRB2 antagonists or procedures that block or reduce ADRB2 function, with the best therapeutic effect observed for individuals who are either H2 or H3 homozygous. In contrast, subjects with high COMT activity (LPS group) can be predicted to be poor responders to ADRB2-antagonist therapy, except for subjects carrying H3/H3 and H2/H3 diplotypes.

REFERENCES

All references cited herein and those provided in the list below are herein incorporated by reference in their entireties.

Abiola, O., Angel, J. M., Avner, P., Bachmanov, A. A., Belknap, J. K., Bennett, B., Blankenhorn, E. P., Blizard, D. A., Bolivar, V., Brockmann, G. A., Buck, K. J., Bureau, J. F., Casley, W. L., Chesler, E. J., Cheverud, J. M., Churchill, G. A., Cook, M., Crabbe, J. C., Crusio, W. E., Darvasi, A., de Haan, G., Dermant, P., Doerge, R. W., Elliot, R. W., Farber, C. R., Flaherty, L., Flint, J., Gershenfeld, H., Gibson, J. P., Gu, J., Gu, W., Himmelbauer, H., Hitzemann, R., Hsu, H. C., Hunter, K., Iraqi, F. F., Jansen, R. C., Johnson, T. E., Jones, B. C., Kempermann, G., Lammert, F., Lu, L., Manly, K. F., Matthews, D. B., Medrano, J. F., Mehrabian, M., Mittlemann, G., Mock, B. A., Mogil, J. S., Montagutelli, X., Morahan, G., Mountz, J. D., Nagase, H., Nowakowski, R. S., O'Hara, B. F., Osadchuk, A. V., Paigen, B., Palmer, A. A., Peirce, J. L., Pomp, D., Rosemann, M., Rosen, G. D., Schalkwyk, L. C., Seltzer, Z., Settle, S., Shimomura, K., Shou, S., Sikela, J. M., Siracusa, L. D., Spearow, J. L., Teuscher, C., Threadgill, D. W., Toth, L. A., Toye, A. A., Vadasz, C., Van Zant, G., Wakeland, E., Williams, R. W., Zhang, H. G., and Zou, F. (2003) The nature and identification of quantitative trait loci: a community's view. *Nat. Rev. Genet.,* 4, 911-916.

Akaike, H., (1974) A new look at statistical model identification. *IEEE Trans. Biomed. Engin.,* AU-19, 716-722.

Aley, K. O. et al. Nociceptor sensitization by extracellular signal-regulated kinases. *J Neurosci* 21, 6933-9 (2001).

Aston-Jones, G., Rajkowski, J., and Cohen, J. (1999) Role of locus coeruleus in attention and behavioral flexibility. *Bioi. Psychiatry,* 46, 1309-1320.

Beck, A. T., Ward, C. H., Mendelson, M., Mock, J. E., and Erbaugh, J. (1961) An inventory for measuring depression. *Arch. Gen. Psychiatry,* 4, 561-571.

Belfer, I., Buzas, B., Evans, C., Hipp, H., Phillips, G., Taubman, J., Lorincz, I., Lipsky, R. H., Enoch, M. A., Max, M. B., and Goldman, D. (2004) Haplotype structure of the beta adrenergic receptor genes in US Caucasians and African Americans. *Eur. J. Hum. Genet.*

Berkow et al., (1997) *The Merck Manual of Medical Information,* Home ed. Merck Research Laboratories, Whitehouse Station, N.J.

Bortoluzzi, S., Danieli, G. A. (1999) Towards an in silica analysis of transcription patterns. *Trends Genet.,* 15, 118-119.

Box, J. E. P., Cox, D. R. (1964) An analysis of transformations. *Journal of the Royal Statistical Society,* 26, 211-252.

Bray, M. S., Krushkai, J., Li, L., Ferrell, R., Kardia, S., Sing, C. F., Turner, S. T., and Boerwinkle, E. (2000) Positional genomic analysis identifies the beta(2)adrenergic receptor gene as a susceptibility locus for human hypertension. *Circulation,* 101, 2877-2882.

Brodde, O. E., Michel, M. C. (1992) Adrenergic receptors and their signal transduction mechanisms in hypertension. *J. Hypertens. Suppl,* 10, S133-5145.

Bruehi, S., Chung, O. Y. (2004) Interactions between the cardiovascular and pain regulatory systems: an updated review of mechanisms and possible alterations in chronic pain. *Neurosci. Biobehav. Rev.,* 28, 395-414.

Busjahn, A., Freier, K., Faulhaber, H. D., Li, G. H., Rosenthai, M., Jordan, J., Hoehe, M. R., Timmermann, B., and Luft, F. C. (2002) Beta-2 adrenergic receptor gene variations and coping styles in twins. *Bioi. Psychol.,* 61, 97-109.

Carlsson, G. E., Le Resche, L. (1995) In Sessle, B. J., Bryant, P. S., and Dionne, R. A. (eds), Temporomandibular Disorders and Related Pain Conditions. IASP Press, Seattle, Vol. 4, pp. 211-226.

Chandra, G. et al. Cyclic AMP signaling pathways are important in IL-1 beta transcriptional regulation. *J Immunol* 155, 4535-43 (1995).

Chaplan, S. R., Bach, F. W., Pogrel, J. W., Chung, J. M. & Yaksh, T. L. Quantitative assessment of tactile allodynia in the rat paw. *J Neurosci Methods* 53, 55-63 (1994).

Chaplan, S. R., Pogrel, J. W., and Yaksh, T. L. (1994) Role of voltage dependent calcium channel subtypes in experimental tactile allodynia. *J. Pharmacoi. Exp. Ther.,* 269, 1117-1123.

Cohen, S., Kamarck, T., and Mermelstein, R. (1983) Aglobal measure of perceived stress. *J Health Soc. Behav.,* 24, 385-396.

Coppack, S. W. Pro-inflammatory cytokines and adipose tissue. *Proc Nutr Soc* 60, 349-56 (2001).

Comeron, J. M. (2004) Selective and mutational patterns associated with gene expression in humans: influences on synonymous composition and intron presence. *Genetics,* 167, 1293-1304.

Cunha, T. M. et al. A cascade of cytokines mediates mechanical inflammatory hypernociception in mice. *Proc Natl Acad Sci USA* 102, 1755-60 (2005).

DeMille, M. M., Kidd, J. R., Ruggeri, V., Palmatier, M. A., Goldman, D., Odunsi, A., Okonofua, F., Grigorenko, E., Schulz, L. O., Bonne-Tamir, B., Lu, R. B., Parnas, J., Pakstis, A. J., and Kidd, K. K. (2002) Population variation in linkage disequilibrium across the COMT gene considering promoter region and coding region variation. *Hum. Genet.,* 111, 521-537.

Derogatis, L. R., Melisaratos, N. (1983) The Brief Symptom Inventory: an introductory report. *Psychoi. Med.,* 13, 595-605.

Diatchenko, L. et al. Genetic basis for individual variations in pain perception and the development of a chronic pain condition. *Hum Mol Genet* 14, 135-43 (2005).

Drysdale, C. M., McGraw, D. W., Stack, C. B., Stephens, J. C., Judson, R. S., Nandabalan, K., Arnold, K., Ruano, G., and Liggett, S. B. (2000) Complex promoter and coding region beta 2-adrenergic receptor haplotypes alter receptor expression and predict in vivo responsiveness. *Proc. Nati. Acad. Sci. U.S.A,* 97, 10483-10488.

Duan, J., Wainwright, M. S., Comeron, J. M., Saitou, N., Sanders, A. R., Gelernter, J., and Gejman, P. V. (2003) Synonymous mutations in the human dopamine receptor D2 (DRD2) affect mRNA stability and synthesis of the receptor. *Hum. Mol. Genet.,* 12, 205-216.

Ouch et al., (1998) *Toxicol. Lett.* 100-101:255-263.

Easton, J. D., Sherman, D. G. (1976) Somatic anxiety attacks and propranolol. *Arch. Neurol.,* 33, 689-691.

Ebadi, (1998) *CRC Desk Reference of Clinical Pharmacology.* CRC Press, Boca Raton, Fla.

Elenkov, I. J., Wilder, R. L., Chrousos, G. P. & Vizi, E. S. The sympathetic nerve—an integrative interface between two supersystems: the brain and the immune system. *Pharmacal Rev* 52, 595-638 (2000).

Fagius, A. N., Wahren, L. K. (1981) Variability of sensory threshold determination in clinical use. *J. Neurai. Sci.,* 51, 11-27.

Fillingim, R. B., Maixner, W. (1996) The influence of resting blood pressure and gender on pain responses. *Psychosomatic Med.,* 58, 326-332.

Fillingim, R. B., Maixner, W., Bunting, S., and Silva, S. (1998) Resting blood pressure and thermal pain responses among females: effects on pain unpleasantness but not pain intensity. *International Journal of Psychophysiology,* 30, 313-318.

Freireich et al., (1966) *Cancer Chemother Rep.* 50:219-244

Fruhstorfer, H., Lindblom, U., and Schmidt, W. G. (1976) Method for quantitative estimation of thermal thresholds in patients. *J. Neurol. Neurosurg.,&Psych.,* 39, 1071-1075.

Gabriel, S. B., Schaffner, S. F., Nguyen, H., Moore, J. M., Roy, J., Blumenstiel, B., Higgins, J., DeFelice, M., Lochner, A., Faggart, M., LiuCordero, S. N., Rotimi, C., Adeyemo, A., Cooper, R., Ward, R., Lander, E. S., Daly, M. J., and Altshuler, D. (2002) The structure of haplotype blocks in the human genome. *Science,* 296, 2225-2229.

Gaiddon, C., Larmet, Y., Trinh, E., Boutillier, A. L., Sommer, B., and Loeffler, J. P. (1999) Brain-derived neurotrophic factor exerts opposing effects on beta2-adrenergic receptor according to depolarization status of cerebellar neurons. *J. Neurochem.,* 73, 1467-1476.

Goodman et al., (1996) *Goodman & Gilman's the Pharmacological Basis of Therapeutics,* 9th ed. McGraw-Hill Health Professions Division, New York.

Gratze, G., Fortin, J., Labugger, R., Binder, A., Kotanko, P., Timmermann, B., Luft, F. C., Hoehe, M. R., and Skrabal, F. (1999) beta-2 Adrenergic receptor variants affect resting blood pressure and agonist-induced vasodilation in young adult Caucasians. *Hypertension,* 33, 1425-1430.

Hagen, K., Zwart, J. A., Holmen, J., Svebak, S., Bovim, G., and Stovner, L. J. (2005) Does hypertension protect against chronic musculoskeletal complaints? The Nord-Trondelag Health Study. *Arch. Intern. Med.,* 165, 916-922.

Hargreaves, K., Dubner, R., Brown, F., Flores, C., and Joris, J. (1988) A new and sensitive method for measuring thermal nociception in cutaneous hyperalgesia. *Pain,* 32, 77-88.

Hoit, B. D., Suresh, D. P., Craft, L., Walsh, R. A., and Liggett, S. B. (2000) beta2-adrenergic receptor polymorphisms at amino acid 16 differentially influence agonist-stimulated blood pressure and peripheral blood flow in normal individuals. *Am. Heart J.,* 139, 537-542.

Iaccarino, G., Cipolletta, E., Fiorillo, A., Annecchiarico, M., Ciccarelli, M., Cimini, V., Koch, W. J., and Trimarco, B. (2002) Beta(2)-adrenergic receptor gene delivery to the endothelium corrects impaired adrenergic vasorelaxation in hypertension. *Circulation,* 106, 349-355.

Jaeger, B., Reeves, J. L. (1986) Quantification of changes in myofascial trigger point sensitivity with the pressure algometer following passive stretch. *Pain,* 27, 203-210.

John, M. T., Miglioretti, D. L., LeResche, L., Von Korif, M., and Critchlow, C. W. (2003) Widespread pain as a risk factor for dysfunctional temporomandibular disorder pain. *Pain,* 102, 257-263.

Katzung, (2001) *Basic & Clinical Pharmacology,* 8th ed. Lange Medical Books/McGraw-Hill Medical Pub. Division, New York.

Khasar, S. G., McCarter, G. & Levine, J. D. Epinephrine produces a betaadrenergic receptor-mediated mechanical hyperalgesia and in vitro sensitization of rat nociceptors. *J Neurophysiol* 81, 1104-12 (1999).

Khasar, S. G., Green, P. G., Miao, F. J., and Levine, J. D. (2003) Vagal modulation of nociception is mediated by adrenomedullary epinephrine in the rat. *Eur. J Neurosci.,* 17, 909-915.

Kiefer, R., Kieseier, B. C., Stoll, G. & Hartung, H. P. The role of macrophages in immune-mediated damage to the peripheral nervous system. *Prog Neurobiol* 64, 109-27 (2001).

Koopman, P. A. R. (1984) Confidence intervals for the ratio of two binomial proportions. *Biometrics,* 40, 513-517.

Kopin, I. J. (1984) Avenues of investigation for the role of catecholamines in anxiety. *Psychopathology,* 17 Suppl1, 83-97.

Kotanko, P., Binder, A., Tasker, J., DeFreitas, P., Kamdar, S., Clark, A. J., Skrabal, F., and Caulfield, M. (1997) Essential hypertension in African Caribbeans associates with a variant of the beta2-adrenoceptor. *Hypertension,* 30, 773-776.

Kress, M. a. S., C. Neuroimmunology and Pain: Peripheral Effects of Proinflammatory Cytokines. in *Hyperalgesia: Molecular Mechanisms and Clinical Implications, Progress in Pain Research Management,* Vol. 30 (ed. Brune, K. a. H., H. O.) 57-65 (IASP Press, Seattle, 2004).

Lader, M. (1988) Beta-adrenoceptor antagonists in neuropsychiatry: an update. *J. Ciin. Psychiatry,* 49, 213-223.

Li, T., Ball, D., Zhao, J., Murray, R. M., Liu, X., Sham, P. C., and Collier, D. A. (2000) Family-based linkage disequilibrium mapping using SNP marker haplotypes: application to a potential locus for schizophrenia at chromosome 22q11. *Moi. Psychiatry,* 5, 452.

Liggett, S. B. Identification and characterization of a homogeneous population of beta 2-adrenergic receptors on human alveolar macrophages. *Am Rev Respir Dis* 139, 552-5 (1989).

Lorr, M., McNair, D. M. (1988) *Profile of Mood States: Bipolar Form.* Educational and Industrial Testing Service, San Diego, Calif.

Lotta, T., Vidgren, J., Tilgmann, C., Ulmanen, I., Melen, K., Julkunen, I., and Taskinen, J. (1995) Kinetics of human soluble and membrane-bound catechol 0-methyltransferase: a revised mechanism and description of the thermolabile variant of the enzyme. *Biochem.,* 34, 4202-4210.

Magliozzi, J. R., Gietzen, D., Maddock, R. J., Haack, D., Doran, A. R., Goodman, T., and Weiler, P. G. (1989) Lymphocyte beta-adrenoreceptor density in patients with unipolar depression and normal controls. *Biol. Psychiatry,* 26, 15-25.

Maixner, W., Gracely, R. H., Zuniga, J. R., Humphrey, C. B., and Bloodworth, G. R. (1990) Cardiovascular and sensory responses to forearm ischemia and dynamic hand exercise. *Am J Physiol,* 259, R1156-R1163.

Maixner, W. (1991) Interactions between cardiovascular and pain modulatory systems: physiological and pathophysiological implications. *J. Cardiovas. Eiectrophysiol.,* (Supplement) 2, S2-S 12.

Maixner, W., Fillingim, R. B., Kincaid, S., Sigurdsson, A., and Harris, M. B. (1997) Relationship between pain sensitivity and resting arterial blood pressure in patients with painful temporomandibular disorders. *Psychosomatic Med.,* 59, 503-511.

Mannisto, P. T., Kaakkola, S. (1999) Catechol-O-methyltransferase (COMT): biochemistry, molecular biology, pharmacology, and clinical efficacy of the new selective COMT inhibitors. *Pharmacol. Rev.,* 51, 593-628.

Masuda, M., Tsunoda, M., Yusa, Y., Yamada, S., and Imai, K. (2002) Assay of catechol-O-methyltransferase activity in human erythrocytes using norepinephrine as a natural substrate. *Ann. Clin. Biochem.,* 39, 589-594.

McGraw, D. W., Forbes, S. L., Kramer, L. A., and Liggett, S. B. (1998) Polymorphisms of the 5' leader cistron of the human beta2-adrenergic receptor regulate receptor expression. *J. Clin. Invest,* 102, 1927-1932.

Mense, S. (1993) Nociception from skeletal muscle in relation to clinical muscle pain. *Pain,* 54, 241-289.

Mogil, J. S. The genetic mediation of individual differences in sensitivity to pain and its inhibition. Proc. Natl. Acad. Sci. 96, 7744-7751.1999.

Mogil, J. S., Wilson, S. G., Chesler, E. J., Rankin, A. L., Nemmani, K. V., Lariviere, W. R., Groce, M. K., Wallace, M. R., Kaplan, L., Staud, R., Ness, T. J., Glover, T. L., Stankova, M., Mayorov, A., Hruby, V. J., Grisel, J. E., and Fillingim, R. B. (2003) The melanocortin-1 receptor gene mediates female-specific mechanisms of analgesia in mice and humans. *Proc. Nati. Acad. Sci. U.S.A,* 100, 4867-4872.

O'Donnell, J. M., Frith, S. & Wilkins, J. Involvement of beta-1 and beta-2 adrenergic receptors in the antidepressant-like effects of centrally administered isoproterenol. *J Pharmacol Exp Ther* 271, 246-54 (1994).

PCT International Publication No. WO 93/25521.

Pfleeger, M., Straneva, P., Fillingim, R. B., Maixner, W., and Girdler, S. S. (1997) Menstrual cycle, blood pressure and ischemic pain sensitivity in women. *Int. J. Beh. Med., Submitted.*

Price, D. D., Hu, J. W., Dubner, R., and Gracely, R. H. (1977) Peripheral suppression of first pain and central summation of second pain evoked by noxious heat pulses. *Pain,* 3, 57-68.

Randich, A., Maixner, W. (1984) Interactions between cardiovascular and pain regulatory systems. *Neurosci. Biobehay. Rev.,* 8, 343-367.

Remington et al., (1975) *Remington's Pharmaceutical Sciences,* 15th ed. Mack Pub. Co., Easton, Pa.

Risch, N. J. (2000) Searching for genetic determinants in the new millennium. *Nature,* 405, 847-856.

Roach, S. K., Lee, S. B. & Schorey, J. S. Differential activation of the transcription factor cyclic AMP response element binding protein (CREB) in macrophages following infection with pathogenic and nonpathogenic mycobacteria and role for CREB in tumor necrosis factor alpha production. *Infect Immun* 73, 514-22 (2005).

Rockman, M. V., Wray, G. A. (2002) Abundant raw material for cisregulatory evolution in humans. *Mol. Biol. Evol.,* 19, 1991-2004.

Routledge, C., Marsden, C. A. (1987) Adrenaline in the CNS: in vivo evidence for a functional pathway innervating the hypothalamus. *Neuropharmacology,* 26, 823-830.

Shagin, D. A., Rebrikov, D. V., Kozhemyako, V. B., Altshuler, I. M., Shcheglov, A. S., Zhulidov, P. A., Bogdanova, E. A., Staroverov, D. B., Rasskazov, V. A., and Lukyanov, S. (2002) A novel method for SNP detection using a new duplex-specific nuclease from crab hepatopancreas. *Genome Res.,* 12, 1935-1942.

Sheps, D. S., Bragdon, E. E., Gray, T. F., Ballenger, M., Usedom, J. E., and Maixner, W. (1992) Relationship between systemic hypertension and pain perception. *Am. J. Cardiol.,* 70, 3F-5F.

Shi, M. M., Bleavins, M. R., and de la iglesia, F. A. (1999) Technologies for detecting genetic polymorphisms in pharmacogenomics. *Mol. Diagn.,* 4, 343-351.

Shifman, S., Bronstein, M., Sternfeld, M., Pisante-Shalom, A., Lev-Lehman, E., Weizman, A., Reznik, I., Spivak, B., Grisaru, N., Karp, L., Schiffer, R., Kotler, M., Strous, R. D., Swartz-Vanetik, M., Knobler, H. Y., Shinar, E., Beckmann, J. S., Yakir, B., Risch, N., Zak, N. B., and Darvasi, A. (2002) A highly significant association between a COMT haplotype and schizophrenia. *Am. J Hum. Genet.,* 71, 1296-1302.

Speight et al., (1997) *Avery's Drug Treatment: A Guide to the Properties,* Choice. Therapeutic Use and Economic Value of Drugs in Disease Management, 4th ed. Adis International, Auckland/Philadelphia.

Simes, R. J. (1986) An improved Bonferroni procedure for multiple tests of signi_cance. *Biometrika,* 73, 751-754.

Small, K. M., McGraw, D. W., and Liggett, S. B. (2003) Pharmacology and physiology of human adrenergic receptor polymorphisms. *Annu. Rev. Pharmacol. Toxicol.,* 43, 381-411.

Snapir, A., Koskenvuo, J., Toikka, J., Orho-Melander, M., Hinkka, S., Saraste, M., Hartiala, J., and Scheinin, M. (2003) Effects of common polymorphisms in the alpha1A-, alpha2B-, beta1- and beta2-adrenoreceptors on haemodynamic responses to adrenaline. *Clin. Sci.* (*Lond*), 104, 509-520.

Spielberger, C. D., Gorusch, R. L., Lushene, R., Vagg, P. R., and Jacobs, G. A. (1983) *Manual for the State-Trait Anxiety Inventory (Form Y*1). Consulting Psychologists Press, Palo Alto, Calif.

Stephens, M., Smith, N. J., and Donnelly, P. (2001) A new statistical method for haplotype reconstruction from population data. *Am. J. Hum. Genet.,* 68, 978-989.

Stephens, M., Donnelly, P. (2003) A comparison of bayesian methods for haplotype reconstruction from population genotype data. *Am. J. Hum. Genet.,* 73, 1162-1169.

Strosberg, A. D. Structure and function of the beta 3-adrenergic receptor. *Annu Rev Pharmacal Toxicol* 37, 421-50 (1997).

Sommer, C. & Kress, M. Recent findings on how proinflammatory cytokines cause pain: peripheral mechanisms in inflammatory and neuropathic hyperalgesia. *Neurosci Lett* 361, 184-7 (2004).

Syed, N. H., Chen, Z. J. (2004) Molecular marker genotypes, heterozygosity and genetic interactions explain heterosis in *Arabidopsis thaliana. Heredity.*

Tattersfield, A. E., Hall, I. P. (2004) Are beta2-adrenoceptor polymorphisms important in asthma—an unravelling story. *Lancet,* 364, 1464-1466.

Thiessen, B. Q., Wallace, S. M., Blackburn, J. L., Wilson, T. W., and Bergman, U. (1990) Increased prescribing of antidepressants subsequent to beta-blocker therapy. *Arch. Intern. Med.,* 150, 2286-2290.

Tsujii, S. & Bray, G. A. A beta-3 adrenergic agonist (BRL-37,344) decreases food intake. *Physiol Behav* 63, 723-8 (1998).

Von Korff, M., Le Resche, L., and Dworkin, S. F. (1993) First onset of common pain symptoms: a prospective study of depression as a risk factor. *Pain,* 55, 251-258.

U.S. Pat. No. 4,736,866.
U.S. Pat. No. 5,162,215.
U.S. Pat. No. 5,234,933.

U.S. Pat. No. 5,326,902.
U.S. Pat. No. 5,489,742.
U.S. Pat. No. 5,550,316.
U.S. Pat. No. 5,573,933.
U.S. Pat. No. 5,614,396.
U.S. Pat. No. 5,625,125.
U.S. Pat. No. 5,648,061.
U.S. Pat. No. 5,741,957.
U.S. Pat. No. 6,180,082.

Ward-Routledge, C., Marshaii, P., and Marsden, C. A. (1988) Involvement of central alpha- and beta-adrenoceptors in the pressor response to electrical stimulation of the rostral ventrolateral medulla in rats. *Br. J. Pharmacol.*, 94, 609-619.

Xie, T., Ho, S. L., and Ramsden, D. (1999) Characterization and implications of estrogenic down-regulation of human catechol-O-methyltransferase gene transcription. *Mol. Pharmacol.*, 56, 31-38.

Yu, X.-M., Hua, M., and Mense, S. (1991) The effects of intracerebroventricular injection of naloxone, phentolamine, methysergide on the transmission of nociceptive signals in the rat dorsal horn neurones with convergent cutaneous-deep input. *Neuroscience*, 715-723.

Zhang, H. T., Huang, Y., and O'Donneii, J. M. (2003) Antagonism of the antidepressant-like effects of clenbuterol by central administration of beta-adrenergic antagonists in rats. *Psychopharmacology (Bert)*, 170, 102-107.

Zhang, Y., Lin, J. X. & Vilcek, J. Synthesis of interleukin 6 (interferon-beta 2/B cell stimulatory factor 2) in human fibroblasts is triggered by an increase in intracellular cyclic AMP. *J Biol Chem* 263, 6177-82 (1988).

Zubieta, J. K., Heitzeg, M. M., Smith, Y. R., Bueller, J. A., Xu, K., Xu, Y., Koeppe, R. A., Stohler, C. S., and Goldman, D. (2003) COMTval158metgenotype affects mu-opioid neurotransmitter responses to a pain stressor. *Science*, 299, 1240-1243.

It will be understood that various details of the subject matter disclosed herein can be changed without departing from the scope of the presently disclosed subject matter. Furthermore, the foregoing description is for the purpose of illustration only, and not for the purpose of limitation, as the presently disclosed subject matter is defined by the claims as set forth hereinafter.

What is claimed is:

1. A method of treating a somatosensory disorder in a subject having an elevated pain sensitivity, comprising:
   (a) obtaining a DNA sample from the subject having a somatosensory disorder;
   (b) determining from the DNA sample a genotype of the subject with respect to a COMT gene, by detecting either a G or A nucleotide at the rs6269 SNP, detecting either a C or T nucleotide at the rs4633 SNP, detecting either a G or C nucleotide at the rs4818 SNP, and detecting either an A or G nucleotide at the rs4680 SNP, wherein the COMT genotype is selected from a low pain sensitive haplotype (LPS), average pain sensitive haplotype (APS), high pain sensitive haplotype (HPS), or a combination thereof; and
   (c) identifying subjects with an elevated pain sensitivity based on the COMT genotype, wherein subjects with a APS or HPS haplotype have an elevated pain sensitivity, and subjects without a APS or HPS haplotype do not have an elevated pain sensitivity;
   (d) administering to subjects with an elevated pain sensitivity an effective amount of an ADRB2 modulator that is an antagonist; and thereby
   (e) treating the somatosensory disorder in the subjects having an elevated pain sensitivity,
   wherein the somatosensory disorder is temporomandibular joint disorder, and wherein the subject has a genotype that is HPS/HPS, and the ADRB2 modulator is propranolol.

2. The method of claim 1, wherein administering to the subject an effective amount of an ADRB2 modulator reduces the concentration of one or more cytokines.

3. The method of claim 1, wherein the ADRB2 modulator is a pharmaceutical that blocks or reduces ADRB2 function.

* * * * *

UNITED STATES PATENT AND TRADEMARK OFFICE
CERTIFICATE OF CORRECTION

PATENT NO. : 11,085,081 B2
APPLICATION NO. : 15/968438
DATED : August 10, 2021
INVENTOR(S) : Diatchenko et al.

It is certified that error appears in the above-identified patent and that said Letters Patent is hereby corrected as shown below:

In the Specification

Column 9, Line 1: Please correct "IG. 7A" to read -- FIG. 7A --

Column 12, Line 3: Please correct "Meant±SEM" to read -- Mean±SEM --

Column 13, Line 25: Please correct "$\mu_1$" to read -- $\beta_1$ --

Column 13, Line 27: Please correct "$\mu_3$" to read -- $\beta_3$ --

Column 20, Line 66: Please correct "Zhanq" to read -- Zhang --

Column 24, Line 29: Please correct "IID." to read -- II.D. --

Column 32, Line 43: Please correct "IIIA." to read -- III.A. --

Column 61, Line 48: Please correct "Deroaatis" to read -- Derogatis --

Column 65, Line 3: Please correct "r52400707" to read -- rs2400707 --

Column 71, Line 44: Please correct "(0)" to read -- (O) --

Column 75, Line 24: Please correct "Zhanq" to read -- Zhang --

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*

Column 81, Lines 16-30: Please replace Table 14 with the following:

Table 14

Cumulative incidence of TMD among ADRB2 diplotype groups for Caucasians

|  | tmdcase (TMD case status) | | Total |
|---|---|---|---|
|  | Cases n % | Non case n % |  |
| H1/H1 | 3 10.00 | 27 90.00 | 30 |
| H1/H2 | 1 2.13 | 46 97.87 | 47 |
| H1/H3 | 0 0.00 | 18 100.00 | 18 |
| H2/H2 | 4 21.05 | 15 78.95 | 19 |
| H2/H3 | 4 13.33 | 26 86.67 | 30 |
| H3/H3 | 1 11.11 | 8 88.89 | 9 |
| Other (Uncommon) | 2 50.00 | 2 50.00 | 4 |
| Total | 15 | 142 | 157 |

CERTIFICATE OF CORRECTION (continued)
U.S. Pat. No. 11,085,081 B2

Column 81, Lines 32-43: Please replace Table 15 with the following:

Table 15

Cumulative incidence of TMD among ADRB3 diplotype groups for Caucasians

|  | tmdcase (TMD case status) | | Total |
|---|---|---|---|
|  | Cases n % | Non case n % |  |
| H1/H1 | 9<br>9.38 | 87<br>90.63 | 96 |
| H1/H2 or H2/H2 | 2<br>5.41 | 35<br>94.59 | 37 |
| H1/H3 | 1<br>6.67 | 14<br>93.33 | 15 |
| Other (Uncommon) | 3<br>33.33 | 6<br>66.67 | 9 |
| Total | 15 | 142 | 157 |

SEQUENCE LISTING

```
<160> NUMBER OF SEQ ID NOS: 330

<210> SEQ ID NO 1
<211> LENGTH: 20
<212> TYPE: DNA
<213> ORGANISM: Homo sapiens

<400> SEQUENCE: 1
gccgtgtctg gactgtgagt                                              20

<210> SEQ ID NO 2
<211> LENGTH: 21
<212> TYPE: DNA
<213> ORGANISM: Homo sapiens

<400> SEQUENCE: 2
gggttcagaa tcacggatgt g                                            21

<210> SEQ ID NO 3
<211> LENGTH: 27
<212> TYPE: DNA
<213> ORGANISM: Homo sapiens

<400> SEQUENCE: 3
aacagacaga aaagtttccc cttccca                                      27

<210> SEQ ID NO 4
<211> LENGTH: 27
<212> TYPE: DNA
<213> ORGANISM: Homo sapiens

<400> SEQUENCE: 4
cagacagaaa agcttcccct tcccata                                      27

<210> SEQ ID NO 5
<211> LENGTH: 19
<212> TYPE: DNA
<213> ORGANISM: Homo sapiens

<400> SEQUENCE: 5
```
aggcacaagg ctggcattt                        19

<210> SEQ ID NO 6
<211> LENGTH: 17
<212> TYPE: DNA
<213> ORGANISM: Homo sapiens

<400> SEQUENCE: 6
ccacacgccc ctttgct                          17

<210> SEQ ID NO 7
<211> LENGTH: 21
<212> TYPE: DNA
<213> ORGANISM: Homo sapiens

<400> SEQUENCE: 7
tgcccctctg cgaacacaag g                     21

<210> SEQ ID NO 8
<211> LENGTH: 24
<212> TYPE: DNA
<213> ORGANISM: Homo sapiens

<400> SEQUENCE: 8
accttgcccc tctgcaaaca caag                  24

<210> SEQ ID NO 9
<211> LENGTH: 19
<212> TYPE: DNA
<213> ORGANISM: Homo sapiens

<400> SEQUENCE: 9
tgctcatggg tgacaccaa                        19

<210> SEQ ID NO 10
<211> LENGTH: 18
<212> TYPE: DNA
<213> ORGANISM: Homo sapiens

<400> SEQUENCE: 10
gcctccagca cgctctgt                         18

<210> SEQ ID NO 11
<211> LENGTH: 24
<212> TYPE: DNA
<213> ORGANISM: Homo sapiens

<400> SEQUENCE: 11
atcctgaacc atgtgctgca gcat                  24

<210> SEQ ID NO 12
<211> LENGTH: 22
<212> TYPE: DNA
<213> ORGANISM: Homo sapiens

<400> SEQUENCE: 12
atcctgaacc acgtgctgca gc                    22

<210> SEQ ID NO 13
<211> LENGTH: 20
<212> TYPE: DNA
<213> ORGANISM: Homo sapiens

<400> SEQUENCE: 13
gggggcctac tgtggctact                                               20

<210> SEQ ID NO 14
<211> LENGTH: 20
<212> TYPE: DNA
<213> ORGANISM: Homo sapiens

<400> SEQUENCE: 14
tcaggcatgc acaccttgtc                                               20

<210> SEQ ID NO 15
<211> LENGTH: 24
<212> TYPE: DNA
<213> ORGANISM: Homo sapiens

<400> SEQUENCE: 15
cgaggctcat caccatcgag atca                                          24

<210> SEQ ID NO 16
<211> LENGTH: 24
<212> TYPE: DNA
<213> ORGANISM: Homo sapiens

<400> SEQUENCE: 16
cgaggctgat caccatcgag atca                                          24

<210> SEQ ID NO 17
<211> LENGTH: 20
<212> TYPE: DNA
<213> ORGANISM: Homo sapiens

<400> SEQUENCE: 17
tcgagatcaa ccccgactgt                                               20

<210> SEQ ID NO 18
<211> LENGTH: 17
<212> TYPE: DNA
<213> ORGANISM: Homo sapiens

<400> SEQUENCE: 18
aacgggtcag gcatgca                                                  17

<210> SEQ ID NO 19
<211> LENGTH: 21
<212> TYPE: DNA
<213> ORGANISM: Homo sapiens

<400> SEQUENCE: 19
ccttgtcctt cacgccagcg a                                             21

<210> SEQ ID NO 20
<211> LENGTH: 24
<212> TYPE: DNA
<213> ORGANISM: Homo sapiens

<400> SEQUENCE: 20
accttgtcct tcatgccagc gaaa                                          24

<210> SEQ ID NO 21
<211> LENGTH: 19
<212> TYPE: DNA
<213> ORGANISM: Homo sapiens

<400> SEQUENCE: 21
cagccacagt ggtgcagag                                                   19

<210> SEQ ID NO 22
<211> LENGTH: 18
<212> TYPE: DNA
<213> ORGANISM: Homo sapiens

<400> SEQUENCE: 22
gtccacctgt ccccagcg                                                    18

<210> SEQ ID NO 23
<211> LENGTH: 10
<212> TYPE: DNA
<213> ORGANISM: Homo sapiens

<400> SEQUENCE: 23
tgccagcctg                                                             10

<210> SEQ ID NO 24
<211> LENGTH: 10
<212> TYPE: DNA
<213> ORGANISM: Homo sapiens

<400> SEQUENCE: 24
tgccggcctg                                                             10

<210> SEQ ID NO 25
<211> LENGTH: 28
<212> TYPE: DNA
<213> ORGANISM: Homo sapiens

<400> SEQUENCE: 25
tgaacgtggg cgacaagaaa ggcaagat                                         28

<210> SEQ ID NO 26
<211> LENGTH: 27
<212> TYPE: DNA
<213> ORGANISM: Homo sapiens

<400> SEQUENCE: 26
tgaccttgtc cttcacgcca gcgaaat                                          27

<210> SEQ ID NO 27
<211> LENGTH: 20
<212> TYPE: DNA
<213> ORGANISM: Homo sapiens

<400> SEQUENCE: 27
gccgaccact cccacgtctt                                                  20

<210> SEQ ID NO 28
<211> LENGTH: 20
<212> TYPE: DNA
<213> ORGANISM: Homo sapiens

<400> SEQUENCE: 28
cccgctctcg ctctcggtaa                                                  20

<210> SEQ ID NO 29
<211> LENGTH: 51
<212> TYPE: DNA
<213> ORGANISM: Homo sapiens

```
<400> SEQUENCE: 29
gcatttctga accttgcccc tctgcraaca caaggggggcg atggtggcac t         51

<210> SEQ ID NO 30
<211> LENGTH: 51
<212> TYPE: DNA
<213> ORGANISM: Homo sapiens

<400> SEQUENCE: 30
ccaaggagca gcgcatcctg aaccaygtgc tgcagcatgc ggagcccggg a          51

<210> SEQ ID NO 31
<211> LENGTH: 51
<212> TYPE: DNA
<213> ORGANISM: Homo sapiens

<400> SEQUENCE: 31
gcctgctgtc accaggggcg aggctbatca ccatcgagat caaccccgac t          51

<210> SEQ ID NO 32
<211> LENGTH: 51
<212> TYPE: DNA
<213> ORGANISM: Homo sapiens

<400> SEQUENCE: 32
ccagcggatg gtggatttcg ctggcrtgaa ggacaaggtg tgcatgcctg a          51

<210> SEQ ID NO 33
<211> LENGTH: 51
<212> TYPE: DNA
<213> ORGANISM: Homo sapiens

<400> SEQUENCE: 33
tggactgtga gtatgggaag gggaarcttt tctgtctgtt gtccccacta c         51

<210> SEQ ID NO 34
<211> LENGTH: 51
<212> TYPE: DNA
<213> ORGANISM: Homo sapiens

<400> SEQUENCE: 34
tgttagcccc atggggacga ctgccrgcct gggaaacgaa gaggagtcag c         51

<210> SEQ ID NO 35
<211> LENGTH: 51
<212> TYPE: DNA
<213> ORGANISM: Homo sapiens

<400> SEQUENCE: 35
aaaggagcaa ggtggaaagt tctggmtgct tcaggtctgc atggtccctc t         51

<210> SEQ ID NO 36
<211> LENGTH: 51
<212> TYPE: DNA
<213> ORGANISM: Homo sapiens

<400> SEQUENCE: 36
acgggggtct catgagcttg cgagcygatg gccaggcagc cggtgcagaa g         51

<210> SEQ ID NO 37
<211> LENGTH: 51
<212> TYPE: DNA
```

<213> ORGANISM: Homo sapiens

<400> SEQUENCE: 37
cgagcagaag gagtgggcca tgaacrtggg cgacaagaaa ggtggggtcc g         51

<210> SEQ ID NO 38
<211> LENGTH: 51
<212> TYPE: DNA
<213> ORGANISM: Homo sapiens

<400> SEQUENCE: 38
cctagcaggg cgagggcagt gcttcrcctt tccggcctca gaagagacag c         51

<210> SEQ ID NO 39
<211> LENGTH: 51
<212> TYPE: DNA
<213> ORGANISM: Homo sapiens

<400> SEQUENCE: 39
gaccactgga aggaccggta cctgcyggac acgcttctct tggaggtgag c         51

<210> SEQ ID NO 40
<211> LENGTH: 51
<212> TYPE: DNA
<213> ORGANISM: Homo sapiens

<400> SEQUENCE: 40
agacaaggca cccagcccca gtttcyccac ctgggaaggg ggctacttgt g         51

<210> SEQ ID NO 41
<211> LENGTH: 51
<212> TYPE: DNA
<213> ORGANISM: Homo sapiens

<400> SEQUENCE: 41
cacgctgggc agaaagtgga aacctrgccc caggggctag gcacaggcgt g         51

<210> SEQ ID NO 42
<211> LENGTH: 51
<212> TYPE: DNA
<213> ORGANISM: Homo sapiens

<400> SEQUENCE: 42
tggccccagg ggctaggcac aggcgyggtg ccgtggccta gtgaggagca c         51

<210> SEQ ID NO 43
<211> LENGTH: 51
<212> TYPE: DNA
<213> ORGANISM: Homo sapiens

<400> SEQUENCE: 43
tggccaggat ggtcttgagc tctctytttt tttttttttt tttttttga g         51

<210> SEQ ID NO 44
<211> LENGTH: 51
<212> TYPE: DNA
<213> ORGANISM: Homo sapiens

<400> SEQUENCE: 44
tcccccttaa aaaaaaaaaa aaaaaragaa aaagacagag tcttgctctg t         51

<210> SEQ ID NO 45
<211> LENGTH: 51

```
<212> TYPE: DNA
<213> ORGANISM: Homo sapiens

<400> SEQUENCE: 45
ctgccctgca gagcccagtg agacamtagt taatgcagaa aaaacagatt t         51

<210> SEQ ID NO 46
<211> LENGTH: 51
<212> TYPE: DNA
<213> ORGANISM: Homo sapiens

<400> SEQUENCE: 46
ttttgtgtcc tgttgctttt tattgwttaa agtgaccctc caagcctgag g         51

<210> SEQ ID NO 47
<211> LENGTH: 51
<212> TYPE: DNA
<213> ORGANISM: Homo sapiens

<400> SEQUENCE: 47
cacaactcac tagtttatat aagagytagt tctcactttt tttttttactc t        51

<210> SEQ ID NO 48
<211> LENGTH: 51
<212> TYPE: DNA
<213> ORGANISM: Homo sapiens

<400> SEQUENCE: 48
ctcctgagta gctgggacta acaggkgctt gccaccaagc ctggctaatt t         51

<210> SEQ ID NO 49
<211> LENGTH: 51
<212> TYPE: DNA
<213> ORGANISM: Homo sapiens

<400> SEQUENCE: 49
gcaacctctg cctcccaggt tcaggstatt ctcctgcctc agcctcctga g         51

<210> SEQ ID NO 50
<211> LENGTH: 51
<212> TYPE: DNA
<213> ORGANISM: Homo sapiens

<400> SEQUENCE: 50
ggcctccgga taactgtggg caaacytgac actccacaag aggtggttga g         51

<210> SEQ ID NO 51
<211> LENGTH: 51
<212> TYPE: DNA
<213> ORGANISM: Homo sapiens

<400> SEQUENCE: 51
ggcagatgcc tgtagtccca gctacycggg aggctgaggc aggagaatgg c         51

<210> SEQ ID NO 52
<211> LENGTH: 51
<212> TYPE: DNA
<213> ORGANISM: Homo sapiens

<400> SEQUENCE: 52
tggcagatgc ctgtagtccc agctamtcgg gaggctgagg caggagaatg g         51

<210> SEQ ID NO 53
```

<211> LENGTH: 51
<212> TYPE: DNA
<213> ORGANISM: Homo sapiens

<400> SEQUENCE: 53
ttgagcccag gagtttgaga ccagcytgag aaacatgctg aggccctgtc t    51

<210> SEQ ID NO 54
<211> LENGTH: 51
<212> TYPE: DNA
<213> ORGANISM: Homo sapiens

<400> SEQUENCE: 54
tctcgagaca gtctctcgct ctgtcrccca ggctggagtg cagtggcgcg a    51

<210> SEQ ID NO 55
<211> LENGTH: 51
<212> TYPE: DNA
<213> ORGANISM: Homo sapiens

<400> SEQUENCE: 55
gggagcggtg gctcacgcct gtaatyccag cactttggga ggccgaggcg g    51

<210> SEQ ID NO 56
<211> LENGTH: 51
<212> TYPE: DNA
<213> ORGANISM: Homo sapiens

<400> SEQUENCE: 56
ggctgaggca ggagaatggt gtgaayccgg gaggtggagc ttgcaatgag c    51

<210> SEQ ID NO 57
<211> LENGTH: 51
<212> TYPE: DNA
<213> ORGANISM: Homo sapiens

<400> SEQUENCE: 57
tttggccttg agcacttccc catccyccat ggctcttggc cgttggggcc c    51

<210> SEQ ID NO 58
<211> LENGTH: 51
<212> TYPE: DNA
<213> ORGANISM: Homo sapiens

<400> SEQUENCE: 58
tcccccatgg ctcttggccg ttgggsccca gttggccgca gagcctttgg c    51

<210> SEQ ID NO 59
<211> LENGTH: 51
<212> TYPE: DNA
<213> ORGANISM: Homo sapiens

<400> SEQUENCE: 59
tccccatccc ccatggctct tggccrttgg ggcccagttg ccgcagagc c    51

<210> SEQ ID NO 60
<211> LENGTH: 51
<212> TYPE: DNA
<213> ORGANISM: Homo sapiens

<400> SEQUENCE: 60
ttctcaacca gtggagatcc tggctyagtg cagtcatgtg atctcaaagt t    51

```
<210> SEQ ID NO 61
<211> LENGTH: 51
<212> TYPE: DNA
<213> ORGANISM: Homo sapiens

<400> SEQUENCE: 61
aaactaatga ttaacaatat tcatayataa tcatatctat gatctatatc t          51

<210> SEQ ID NO 62
<211> LENGTH: 51
<212> TYPE: DNA
<213> ORGANISM: Homo sapiens

<400> SEQUENCE: 62
tggccggagt gtgatggggg agtctytgtc caggctgctg ccacggtggg c          51

<210> SEQ ID NO 63
<211> LENGTH: 51
<212> TYPE: DNA
<213> ORGANISM: Homo sapiens

<400> SEQUENCE: 63
gtggcatggg cctatagttc cagctrcttg ggaggctgag gtgaaaagat c          51

<210> SEQ ID NO 64
<211> LENGTH: 51
<212> TYPE: DNA
<213> ORGANISM: Homo sapiens

<400> SEQUENCE: 64
tttcttttct tttttttttt tttttytttt tctgtagaga caaggtcttg c          51

<210> SEQ ID NO 65
<211> LENGTH: 51
<212> TYPE: DNA
<213> ORGANISM: Homo sapiens

<400> SEQUENCE: 65
ttttcttttc ttttcttttc tttttyttt tttttttttt ttctgtagag a           51

<210> SEQ ID NO 66
<211> LENGTH: 51
<212> TYPE: DNA
<213> ORGANISM: Homo sapiens

<400> SEQUENCE: 66
atctggaatc cttatattaa catttmccaa tatgcatgta actcaaggaa g          51

<210> SEQ ID NO 67
<211> LENGTH: 51
<212> TYPE: DNA
<213> ORGANISM: Homo sapiens

<400> SEQUENCE: 67
ctgtgggcag ggagggcatg cgcackttgt cctccccacc aggtgttcac a          51

<210> SEQ ID NO 68
<211> LENGTH: 51
<212> TYPE: DNA
<213> ORGANISM: Homo sapiens

<400> SEQUENCE: 68
gaagaagttt ccttgtgtcc ttcccrtttt agggtctgtg acctgaaccc c          51
```

<210> SEQ ID NO 69
<211> LENGTH: 51
<212> TYPE: DNA
<213> ORGANISM: Homo sapiens

<400> SEQUENCE: 69
ccccacgagg tacactgttg tgggcrgcag ggctggcctt tctcatctgg g        51

<210> SEQ ID NO 70
<211> LENGTH: 51
<212> TYPE: DNA
<213> ORGANISM: Homo sapiens

<400> SEQUENCE: 70
ggttcccagg ctacctgcct ggaggrtcac accaggagga tttcaaacag g        51

<210> SEQ ID NO 71
<211> LENGTH: 51
<212> TYPE: DNA
<213> ORGANISM: Homo sapiens

<400> SEQUENCE: 71
cccctgggtg tcctctaagc cagctsggag acaacagcct gagtccgtgt c        51

<210> SEQ ID NO 72
<211> LENGTH: 51
<212> TYPE: DNA
<213> ORGANISM: Homo sapiens

<400> SEQUENCE: 72
tccgtgtctg cttctgtatt ttgtgyggtt ttagaggatc cctgggctgc c        51

<210> SEQ ID NO 73
<211> LENGTH: 51
<212> TYPE: DNA
<213> ORGANISM: Homo sapiens

<400> SEQUENCE: 73
cacagaaata acatctgctt tgctgscgag ctcagaggag accccagacc c        51

<210> SEQ ID NO 74
<211> LENGTH: 51
<212> TYPE: DNA
<213> ORGANISM: Homo sapiens

<400> SEQUENCE: 74
ttcaggagca ccagccctcc gtgctsctgg agctgggggc ctactgtggc t        51

<210> SEQ ID NO 75
<211> LENGTH: 51
<212> TYPE: DNA
<213> ORGANISM: Homo sapiens

<400> SEQUENCE: 75
agaagtcatg attgagtctt aaaaargaac aatccagtgt tgcagttcag a        51

<210> SEQ ID NO 76
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this c may be missing

<400> SEQUENCE: 76
ggatggatac tcctgagatg gataccagga gttgatgaga gaaaggtccc t       51

<210> SEQ ID NO 77
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this t may be missing

<400> SEQUENCE: 77
gtcttgagct ctctttttt tttttttttt tttttttgag acggagtctc g       51

<210> SEQ ID NO 78
<211> LENGTH: 51
<212> TYPE: DNA
<213> ORGANISM: Homo sapiens

<400> SEQUENCE: 78
ggagtctttg tccaggctgc tgccayggtg ggcctcagga ctcatggcct g       51

<210> SEQ ID NO 79
<211> LENGTH: 51
<212> TYPE: DNA
<213> ORGANISM: Homo sapiens

<400> SEQUENCE: 79
aaaacacaac tcactagttt atatargagc tagttctcac ttttttttt a        51

<210> SEQ ID NO 80
<211> LENGTH: 51
<212> TYPE: DNA
<213> ORGANISM: Homo sapiens

<400> SEQUENCE: 80
tttctttctt tttttctttt ttttcyttt tttttttttt ttttttttt g         51

<210> SEQ ID NO 81
<211> LENGTH: 51
<212> TYPE: DNA
<213> ORGANISM: Homo sapiens

<400> SEQUENCE: 81
gctgggatta caggtgtgag ccaccwccca gccctatttt atatttttat c       51

<210> SEQ ID NO 82
<211> LENGTH: 51
<212> TYPE: DNA
<213> ORGANISM: Homo sapiens

<400> SEQUENCE: 82
gcctttggcc ttgagcactt ccccakcccc catggctctt ggccattgga c       51

<210> SEQ ID NO 83
<211> LENGTH: 51
<212> TYPE: DNA
<213> ORGANISM: Homo sapiens

<400> SEQUENCE: 83
cttttctttt tttttttttt tttttkttct gtagagacaa ggtcttgctg t       51

<210> SEQ ID NO 84
<211> LENGTH: 51
<212> TYPE: DNA
<213> ORGANISM: Homo sapiens

<400> SEQUENCE: 84
aaaaaaaatt taggctgggt gcagcrgctc acgcctataa tcccagcatt t                51

<210> SEQ ID NO 85
<211> LENGTH: 51
<212> TYPE: DNA
<213> ORGANISM: Homo sapiens

<400> SEQUENCE: 85
ctccccgtgt gcagagatga gagatygtag aaataaagac acaagacaaa g                51

<210> SEQ ID NO 86
<211> LENGTH: 51
<212> TYPE: DNA
<213> ORGANISM: Homo sapiens

<400> SEQUENCE: 86
aaggccaggc aggtgcggtg gctcaygcct gtaatcccag cactttggga g                51

<210> SEQ ID NO 87
<211> LENGTH: 51
<212> TYPE: DNA
<213> ORGANISM: Homo sapiens

<400> SEQUENCE: 87 gggggcccctt ccctgtttgg cagccraggc ggacagcgag aggagacagc t               51

<210> SEQ ID NO 88
<211> LENGTH: 51
<212> TYPE: DNA
<213> ORGANISM: Homo sapiens

<400> SEQUENCE: 88
tgaggcagga aatggcgtg aacccrggag gcggagcttg cagtgagctg a                 51

<210> SEQ ID NO 89
<211> LENGTH: 51
<212> TYPE: DNA
<213> ORGANISM: Homo sapiens

<400> SEQUENCE: 89
gcccatgagt gaggatgcag tgctgktttc tgtccaccta cacctagagc t                51

<210> SEQ ID NO 90
<211> LENGTH: 51
<212> TYPE: DNA
<213> ORGANISM: Homo sapiens

<400> SEQUENCE: 90
taagaatcta aatatttaga tataastcga cttagtacat ccttctcaac t                51

<210> SEQ ID NO 91
<211> LENGTH: 51
<212> TYPE: DNA
<213> ORGANISM: Homo sapiens

<400> SEQUENCE: 91
cctgacatgc taacctctct gaactrcaac actggattgt tctttttaa g                 51

<210> SEQ ID NO 92
<211> LENGTH: 51
<212> TYPE: DNA
<213> ORGANISM: Homo sapiens

<400> SEQUENCE: 92
cccatgttct gaaggtggca cccaastctt gtacagtcct ttcctgcagg a            51

<210> SEQ ID NO 93
<211> LENGTH: 51
<212> TYPE: DNA
<213> ORGANISM: Homo sapiens

<400> SEQUENCE: 93
aacccctctc cttgggtgcc tctccytcat aggcctgagt tcctggcact g            51

<210> SEQ ID NO 94
<211> LENGTH: 51
<212> TYPE: DNA
<213> ORGANISM: Homo sapiens

<400> SEQUENCE: 94
cagctgcaag ccctgtggga ctctcsaggc ccatcccaga ggcatgtggg g            51

<210> SEQ ID NO 95
<211> LENGTH: 51
<212> TYPE: DNA
<213> ORGANISM: Homo sapiens

<400> SEQUENCE: 95
ccctgacctc actgaccttg cagccrtgtg gtgtccatac tgtcacatga a            51

<210> SEQ ID NO 96
<211> LENGTH: 51
<212> TYPE: DNA
<213> ORGANISM: Homo sapiens

<400> SEQUENCE: 96
tgtcacctgc tcctctgaca ctgtcscttc tccatggcat tagattttca g            51

<210> SEQ ID NO 97
<211> LENGTH: 51
<212> TYPE: DNA
<213> ORGANISM: Homo sapiens

<400> SEQUENCE: 97
ggagtacagg tgtgtgcttg gtctgmggct ccaactttt gttgttgttt c            51

<210> SEQ ID NO 98
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this t may be missing

<400> SEQUENCE: 98
agctaggact aaaggcatgc accactacac ctggctaatt taaaaatttt t            51

<210> SEQ ID NO 99
<211> LENGTH: 51
<212> TYPE: DNA

<213> ORGANISM: Homo sapiens

<400> SEQUENCE: 99
ccacctcagc tcctgagta gctagsacta aaggcatgca ccactacacc t    51

<210> SEQ ID NO 100
<211> LENGTH: 51
<212> TYPE: DNA
<213> ORGANISM: Homo sapiens

<400> SEQUENCE: 100
ggctgctttg aggaggcctc tccacygggc tgctgtagtc accaagtcca g    51

<210> SEQ ID NO 101
<211> LENGTH: 51
<212> TYPE: DNA
<213> ORGANISM: Homo sapiens

<400> SEQUENCE: 101
agcaaagtca tgaagtggga agtcaygaat tgggaatggg tgtccttgtt a    51

<210> SEQ ID NO 102
<211> LENGTH: 51
<212> TYPE: DNA
<213> ORGANISM: Homo sapiens

<400> SEQUENCE: 102
caggccaaga cagggtagct ggaggrgggc tcacccctga caaaggagca t    51

<210> SEQ ID NO 103
<211> LENGTH: 51
<212> TYPE: DNA
<213> ORGANISM: Homo sapiens

<400> SEQUENCE: 103
ggtagggccg ctggaccctg dacacrgatt ggaaggaacc agcactagca g    51

<210> SEQ ID NO 104
<211> LENGTH: 51
<212> TYPE: DNA
<213> ORGANISM: Homo sapiens

<400> SEQUENCE: 104
ctaagggacc atgggagctc caagcrcgct cacagtgggg accaggtcct g    51

<210> SEQ ID NO 105
<211> LENGTH: 51
<212> TYPE: DNA
<213> ORGANISM: Homo sapiens

<400> SEQUENCE: 105
gcacaggatg tgttaccggg ctcackgagt gactcaggga actagtgccg c    51

<210> SEQ ID NO 106
<211> LENGTH: 51
<212> TYPE: DNA
<213> ORGANISM: Homo sapiens

<400> SEQUENCE: 106
acaggttctc ctgggcccgc ctcccrcttg aacttcagcc tggggcacag g    51

<210> SEQ ID NO 107
<211> LENGTH: 51

```
<212> TYPE: DNA
<213> ORGANISM: Homo sapiens

<400> SEQUENCE: 107
cactgttgtg ggcggcaggg ctggcmtttc tcatctggga catgccacgt t          51

<210> SEQ ID NO 108
<211> LENGTH: 51
<212> TYPE: DNA
<213> ORGANISM: Homo sapiens

<400> SEQUENCE: 108
tgggtgtgcc tttctaaaat ggagcrtcca gcagagagtg ggatctccta t          51

<210> SEQ ID NO 109
<211> LENGTH: 51
<212> TYPE: DNA
<213> ORGANISM: Homo sapiens

<400> SEQUENCE: 109 cccccctaggg cggagcctct gcttcyctgt tctcttctgc tctgtcctct g         51

<210> SEQ ID NO 110
<211> LENGTH: 51
<212> TYPE: DNA
<213> ORGANISM: Homo sapiens

<400> SEQUENCE: 110 aaatcccta gaagcctggt gtccgyatga cctcccccta gggcggagcc t           51

<210> SEQ ID NO 111
<211> LENGTH: 51
<212> TYPE: DNA
<213> ORGANISM: Homo sapiens

<400> SEQUENCE: 111
ccagggtggg tacagattcc ggcccrgtgc atgggcacag gtctgctgag c          51

<210> SEQ ID NO 112
<211> LENGTH: 51
<212> TYPE: DNA
<213> ORGANISM: Homo sapiens

<400> SEQUENCE: 112
aacggaagcc ggggcagtgc cagggygggt acagattccg gcccggtgca t          51

<210> SEQ ID NO 113
<211> LENGTH: 51
<212> TYPE: DNA
<213> ORGANISM: Homo sapiens

<400> SEQUENCE: 113
gcacaacctg aggtctcctg agcttkctgt gcagcccagt ctttctctcc g          51

<210> SEQ ID NO 114
<211> LENGTH: 51
<212> TYPE: DNA
<213> ORGANISM: Homo sapiens

<400> SEQUENCE: 114
atttcagagc acaacctgag gtctcytgag cttgctgtgc agcccagtct t          51

<210> SEQ ID NO 115
```

```
<211> LENGTH: 51
<212> TYPE: DNA
<213> ORGANISM: Homo sapiens

<400> SEQUENCE: 115
cgcatgttgg ccctctgtgg agaacrgagg atgcacagcc atttcagagc a            51

<210> SEQ ID NO 116
<211> LENGTH: 51
<212> TYPE: DNA
<213> ORGANISM: Homo sapiens

<400> SEQUENCE: 116
cctttccgag ggtcactgca gccgcrtgtt ggccctctgt ggagaacgga g            51

<210> SEQ ID NO 117
<211> LENGTH: 52
<212> TYPE: DNA
<213> ORGANISM: Homo sapiens
<220> FEATURE:
<221> NAME/KEY: misc_feature
<222> LOCATION: (26)..(27)
<223> OTHER INFORMATION: these two nucleotides (ca) may be missing

<400> SEQUENCE: 117
ccaagccaca gtggctctca gtgtgcatgc aggtgctgt tagcattggt tc            52

<210> SEQ ID NO 118
<211> LENGTH: 52
<212> TYPE: DNA
<213> ORGANISM: Homo sapiens
<220> FEATURE:
<221> NAME/KEY: misc_feature
<222> LOCATION: (26)..(27)
<223> OTHER INFORMATION: these two nucleotides (gt) may be missing

<400> SEQUENCE: 118
cacgtccaag ccacagtggc tctcagtgtg catgcagggt gctgttagca tt            52

<210> SEQ ID NO 119
<211> LENGTH: 51
<212> TYPE: DNA
<213> ORGANISM: Homo sapiens

<400> SEQUENCE: 119
gcaggatgag gcacgtccaa gccacrgtgg ctctcagtgt gcatgcaggg t            51

<210> SEQ ID NO 120
<211> LENGTH: 51
<212> TYPE: DNA
<213> ORGANISM: Homo sapiens

<400> SEQUENCE: 120
cctgtgtgcc gagcagagct gccccrtgtg taaacgctta gaactggcct c            51

<210> SEQ ID NO 121
<211> LENGTH: 51
<212> TYPE: DNA
<213> ORGANISM: Homo sapiens

<400> SEQUENCE: 121
ccaaagggca gggcttcttg cagcarttcc agcctttgct ggggtttcc a             51

<210> SEQ ID NO 122
<211> LENGTH: 51
```

<210> SEQ ID NO 122
<211> LENGTH: 51
<212> TYPE: DNA
<213> ORGANISM: Homo sapiens

<400> SEQUENCE: 122
gaatcctggt ccccctttat cacacyggat cagccccaaa gggcagggct t          51

<210> SEQ ID NO 123
<211> LENGTH: 51
<212> TYPE: DNA
<213> ORGANISM: Homo sapiens

<400> SEQUENCE: 123
gacagtggca ggaggggac actccyagag tgctgccaga aagaggcgag g           51

<210> SEQ ID NO 124
<211> LENGTH: 51
<212> TYPE: DNA
<213> ORGANISM: Homo sapiens

<400> SEQUENCE: 124
ggtcaggctg ttcttgaact cctgamctca ggtgatccac ccgcctcagc c          51

<210> SEQ ID NO 125
<211> LENGTH: 51
<212> TYPE: DNA
<213> ORGANISM: Homo sapiens

<400> SEQUENCE: 125
ttttaataga gactggggtt tcaccdtgtt ggtcaggctg ttcttgaact c          51

<210> SEQ ID NO 126
<211> LENGTH: 51
<212> TYPE: DNA
<213> ORGANISM: Homo sapiens

<400> SEQUENCE: 126
ggctggagtg taatggcacc atctcrgctc actgcaacct ccacctcccg a          51

<210> SEQ ID NO 127
<211> LENGTH: 51
<212> TYPE: DNA
<213> ORGANISM: Homo sapiens

<400> SEQUENCE: 127
cactgtatgg cctggtttct cctagrttat aattgtagag cgaagattat t          51

<210> SEQ ID NO 128
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this nucleotide may be missing

<400> SEQUENCE: 128
cacttctcac cgtgtccctt cagcttctta tcactgtatg gcctggtttc t          51

<210> SEQ ID NO 129
<211> LENGTH: 51
<212> TYPE: DNA
<213> ORGANISM: Homo sapiens

<400> SEQUENCE: 129

```
tattggatac aagacaaggg ggcagrgtaa ggagtgtgag ccatctccag t              51

<210> SEQ ID NO 130
<211> LENGTH: 51
<212> TYPE: DNA
<213> ORGANISM: Homo sapiens

<400> SEQUENCE: 130
ccagcctggg caacacagtg agactscatc tcaaaaaaag aaataaggaa a              51

<210> SEQ ID NO 131
<211> LENGTH: 51
<212> TYPE: DNA
<213> ORGANISM: Homo sapiens

<400> SEQUENCE: 131
gcagacgcct gtaatcccaa ctactyggga ggctgaagtg ggagaatcgc t              51

<210> SEQ ID NO 132
<211> LENGTH: 51
<212> TYPE: DNA
<213> ORGANISM: Homo sapiens

<400> SEQUENCE: 132
caccattctc ctgcctcagc ctcccragta gctgggacta caggtgcctg c              51

<210> SEQ ID NO 133
<211> LENGTH: 51
<212> TYPE: DNA
<213> ORGANISM: Homo sapiens

<400> SEQUENCE: 133
agctcactgc aagctccgcc tcctgrgttt acaccattct cctgcctcag c              51

<210> SEQ ID NO 134
<211> LENGTH: 51
<212> TYPE: DNA
<213> ORGANISM: Homo sapiens

<400> SEQUENCE: 134
gtgatctcag ctcactgcaa gctcckcctc ctgggtttac accattctcc t              51

<210> SEQ ID NO 135
<211> LENGTH: 51
<212> TYPE: DNA
<213> ORGANISM: Homo sapiens

<400> SEQUENCE: 135
aaactgggaa gggagggttg gccccygtga aaccaactga tctgggtttg c              51

<210> SEQ ID NO 136
<211> LENGTH: 51
<212> TYPE: DNA
<213> ORGANISM: Homo sapiens

<400> SEQUENCE: 136
ctgacaacat gagaaaaagc tggctycatg ctgatttgtc tagatgtgcc t              51

<210> SEQ ID NO 137
<211> LENGTH: 51
<212> TYPE: DNA
<213> ORGANISM: Homo sapiens

<400> SEQUENCE: 137
```

```
ctccttttga tgccgaatcc cctttyatgg gactccgcca gcacgggtgc a        51
```

<210> SEQ ID NO 138
<211> LENGTH: 51
<212> TYPE: DNA
<213> ORGANISM: Homo sapiens

<400> SEQUENCE: 138

```
agataagggc attatccccc taagtytcgt atgatattcc ccattctgag t        51
```

<210> SEQ ID NO 139
<211> LENGTH: 51
<212> TYPE: DNA
<213> ORGANISM: Homo sapiens

<400> SEQUENCE: 139

```
tttgttctttt cccttaaaat aggaarataa gggcattatc cccctaagtc t       51
```

<210> SEQ ID NO 140
<211> LENGTH: 51
<212> TYPE: DNA
<213> ORGANISM: Homo sapiens

<400> SEQUENCE: 140

```
gcccatccca gaggcatgtg gggtcrgata ccagtgtttc aaggcacctg c        51
```

<210> SEQ ID NO 141
<211> LENGTH: 51
<212> TYPE: DNA
<213> ORGANISM: Homo sapiens

<400> SEQUENCE: 141

```
gtattccagc tttcaaaaca acaaamaaca acaaaaactt ttctggaaag a        51
```

<210> SEQ ID NO 142
<211> LENGTH: 51
<212> TYPE: DNA
<213> ORGANISM: Homo sapiens

<400> SEQUENCE: 142

```
gggcccagga ctccccaggg tcgggsggat gtgtggtgtg caggaccacg t        51
```

<210> SEQ ID NO 143
<211> LENGTH: 51
<212> TYPE: DNA
<213> ORGANISM: Homo sapiens

<400> SEQUENCE: 143

```
aaggggccca ggactcccca gggtckgggg gatgtgtggt gtgcaggacc a        51
```

<210> SEQ ID NO 144
<211> LENGTH: 51
<212> TYPE: DNA
<213> ORGANISM: Homo sapiens

<400> SEQUENCE: 144

```
tgctccacca ggaaggggcc caggastccc cagggtcggg gggatgtgtg g        51
```

<210> SEQ ID NO 145
<211> LENGTH: 51
<212> TYPE: DNA
<213> ORGANISM: Homo sapiens

```
<400> SEQUENCE: 145
agtctcgtat gatattcccc attctragtc cagaatacct agaaatttgg a           51

<210> SEQ ID NO 146
<211> LENGTH: 51
<212> TYPE: DNA
<213> ORGANISM: Homo sapiens

<400> SEQUENCE: 146
ccatcgagat caaccccgac tgtgcygcca tcacccagcg gatggtggat t           51

<210> SEQ ID NO 147
<211> LENGTH: 51
<212> TYPE: DNA
<213> ORGANISM: Homo sapiens

<400> SEQUENCE: 147
ttcaataact atattgccat gaaaakagaa tactcaataa tagtttctga t           51

<210> SEQ ID NO 148
<211> LENGTH: 51
<212> TYPE: DNA
<213> ORGANISM: Homo sapiens

<400> SEQUENCE: 148
atctttcttt ctttttttc tttttytctt tttttttttt tttttttttt t           51

<210> SEQ ID NO 149
<211> LENGTH: 51
<212> TYPE: DNA
<213> ORGANISM: Homo sapiens

<400> SEQUENCE: 149
caggtcctgg gggctgggga caccasggag gtgaaatacc cctccagcgg g           51

<210> SEQ ID NO 150
<211> LENGTH: 51
<212> TYPE: DNA
<213> ORGANISM: Homo sapiens

<400> SEQUENCE: 150
ctttctttct tttttttctt tttttyttt tttttttttt tttttttttt t            51

<210> SEQ ID NO 151
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: y may be c or t, or may be missing

<400> SEQUENCE: 151
ctagttatct ttctttcttt tttttyttt tttctttttt tttttttttt t            51

<210> SEQ ID NO 152
<211> LENGTH: 51
<212> TYPE: DNA
<213> ORGANISM: Homo sapiens

<400> SEQUENCE: 152
taaaaataca aaacattagc cgggcrtggt ggtgcactca ggaggctgag g           51
```

```
<210> SEQ ID NO 153
<211> LENGTH: 51
<212> TYPE: DNA
<213> ORGANISM: Homo sapiens

<400> SEQUENCE: 153
gtagctgcag ctataggcac accacsatgc ctggctcaat gggtattttg t          51

<210> SEQ ID NO 154
<211> LENGTH: 51
<212> TYPE: DNA
<213> ORGANISM: Homo sapiens

<400> SEQUENCE: 154
gctgaggcgg gataatcgct tgaacyggga ggtgggggc tgcagtaagc c          51

<210> SEQ ID NO 155
<211> LENGTH: 51
<212> TYPE: DNA
<213> ORGANISM: Homo sapiens

<400> SEQUENCE: 155
gggaggccga ggtgggcaaa tcaccygagt ccagaagttc gagaccagcc t          51

<210> SEQ ID NO 156
<211> LENGTH: 51
<212> TYPE: DNA
<213> ORGANISM: Homo sapiens

<400> SEQUENCE: 156
gtaagcaaac cctttctga tagcakagat aggcaagcat cctatgaggt t          51

<210> SEQ ID NO 157
<211> LENGTH: 51
<212> TYPE: DNA
<213> ORGANISM: Homo sapiens

<400> SEQUENCE: 157
ctcctgacct cgtgatctgc ccgccycggc ctcccaaagt gctgggatta c          51

<210> SEQ ID NO 158
<211> LENGTH: 51
<212> TYPE: DNA
<213> ORGANISM: Homo sapiens

<400> SEQUENCE: 158
aagttagccg ggcgtgctgg cgggckcctg tagtcccagc tactgggagg c          51

<210> SEQ ID NO 159
<211> LENGTH: 51
<212> TYPE: DNA
<213> ORGANISM: Homo sapiens

<400> SEQUENCE: 159
tttttctttt cttttcttt cttttyttt tttttttttt tttctgtaga g          51

<210> SEQ ID NO 160
<211> LENGTH: 51
<212> TYPE: DNA
<213> ORGANISM: Homo sapiens

<400> SEQUENCE: 160
gttgaaagtt actgaaaaca tcttgkaagc tttttaggc caatatatta t          51
```

<210> SEQ ID NO 161
<211> LENGTH: 51
<212> TYPE: DNA
<213> ORGANISM: Homo sapiens

<400> SEQUENCE: 161
aaagttacgc ttaataatga atgttkcagc actttcttct cttcaggtat t    51

<210> SEQ ID NO 162
<211> LENGTH: 51
<212> TYPE: DNA
<213> ORGANISM: Homo sapiens

<400> SEQUENCE: 162
taaaaataca aaaattagct gggcgyggtg ccatgtgcct gtggtcccag c    51

<210> SEQ ID NO 163
<211> LENGTH: 51
<212> TYPE: DNA
<213> ORGANISM: Homo sapiens

<400> SEQUENCE: 163
agaccagtag tggccccgaa tgccargctg cgctgttatt tattggatac a    51

<210> SEQ ID NO 164
<211> LENGTH: 51
<212> TYPE: DNA
<213> ORGANISM: Homo sapiens

<400> SEQUENCE: 164
cactgtgtta gcaaggatgg tctcgmtctc cagacctcgt gatccacccg c    51

<210> SEQ ID NO 165
<211> LENGTH: 51
<212> TYPE: DNA
<213> ORGANISM: Homo sapiens

<400> SEQUENCE: 165
agcccctggg tccagagatg agcgcrgggc ctggctgcag cctgtggggt c    51

<210> SEQ ID NO 166
<211> LENGTH: 51
<212> TYPE: DNA
<213> ORGANISM: Homo sapiens

<400> SEQUENCE: 166
tgccatggtc ggatgagagc agccayggac aatgtctgtg caattgtgcg t    51

<210> SEQ ID NO 167
<211> LENGTH: 51
<212> TYPE: DNA
<213> ORGANISM: Homo sapiens

<400> SEQUENCE: 167
aaaaaagcct tcccctgagc ctgggkgcct ggccccactg aggataccag g    51

<210> SEQ ID NO 168
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this nucleotide may be missing -continued

<400> SEQUENCE: 168
gtggcatgca ggagctggag gggggtctt cctgggcggc ctgtgtagca g         51

<210> SEQ ID NO 169
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this nucleotide may be missing

<400> SEQUENCE: 169
gagcatgtgg catgcaggag ctggaggggg ggtcttcctg gcggcctgt g          51

<210> SEQ ID NO 170
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this nucleotide may be missing

<400> SEQUENCE: 170
agcctgaggg accgtaggag ctgccctgca gagcccagtg agacactagt t         51

<210> SEQ ID NO 171
<211> LENGTH: 51
<212> TYPE: DNA
<213> ORGANISM: Homo sapiens

<400> SEQUENCE: 171
aacatctgct ttgctgccga gctcakagga daccccagac ccctcccgca g         51

<210> SEQ ID NO 172
<211> LENGTH: 51
<212> TYPE: DNA
<213> ORGANISM: Homo sapiens

<400> SEQUENCE: 172
tacaggtgcc tgccaccacg cccggmtaat tttttgtgtt tttagtagag a         51

<210> SEQ ID NO 173
<211> LENGTH: 51
<212> TYPE: DNA
<213> ORGANISM: Homo sapiens

<400> SEQUENCE: 173
gatgccctga actcacgagg aggcaytgaa ccctggccgt ggagagggag g         51

<210> SEQ ID NO 174
<211> LENGTH: 51
<212> TYPE: DNA
<213> ORGANISM: Homo sapiens

<400> SEQUENCE: 174 cccttttatca caccggatca gccccraagg gcagggcttc ttgcagcagt t        51

<210> SEQ ID NO 175
<211> LENGTH: 51
<212> TYPE: DNA
<213> ORGANISM: Homo sapiens

<400> SEQUENCE: 175
accctgcaca ggcaagatcg tggacrccgt gattcaggag caccagccct c    51

<210> SEQ ID NO 176
<211> LENGTH: 51
<212> TYPE: DNA
<213> ORGANISM: Homo sapiens

<400> SEQUENCE: 176
accatcgaga tcaaccccga ctgtgycgcc atcacccagc ggatggtgga t    51

<210> SEQ ID NO 177
<211> LENGTH: 51
<212> TYPE: DNA
<213> ORGANISM: Homo sapiens

<400> SEQUENCE: 177
actggaaggc agccgccctg ctcaargcct aggccattgt cctcctcccg g    51

<210> SEQ ID NO 178
<211> LENGTH: 51
<212> TYPE: DNA
<213> ORGANISM: Homo sapiens

<400> SEQUENCE: 178
caaggagatg gggtggggaa gggccrctct gggcccagcc tgctctcccc c    51

<210> SEQ ID NO 179
<211> LENGTH: 51
<212> TYPE: DNA
<213> ORGANISM: Homo sapiens

<400> SEQUENCE: 179
cccagaccag acaccagggc agaaayggca caggaccaag agatggggt g    51

<210> SEQ ID NO 180
<211> LENGTH: 51
<212> TYPE: DNA
<213> ORGANISM: Homo sapiens

<400> SEQUENCE: 180
ttcagtcagc ctcagcctct ccaaasagcc aggcattcca gtagagccct g    51

<210> SEQ ID NO 181
<211> LENGTH: 51
<212> TYPE: DNA
<213> ORGANISM: Homo sapiens

<400> SEQUENCE: 181
ggctcctgct ctttgggaga ggtggkgggc cgtgcctggg gatccaagtt c    51

<210> SEQ ID NO 182
<211> LENGTH: 51
<212> TYPE: DNA
<213> ORGANISM: Homo sapiens

<400> SEQUENCE: 182
ggaggggctc ctgctctttg ggagargtgg ggggccgtgc ctggggatcc a    51

<210> SEQ ID NO 183
<211> LENGTH: 51
<212> TYPE: DNA
<213> ORGANISM: Homo sapiens

<400> SEQUENCE: 183
tggtttgtgt atgttcttgg taaacyagcc cttggtctta cacatcattt c              51

<210> SEQ ID NO 184
<211> LENGTH: 51
<212> TYPE: DNA
<213> ORGANISM: Homo sapiens

<400> SEQUENCE: 184
aggcacccag ccccagtttc cccacytggg aaggggggcta cttgtggcta g              51

<210> SEQ ID NO 185
<211> LENGTH: 51
<212> TYPE: DNA
<213> ORGANISM: Homo sapiens

<400> SEQUENCE: 185
ttcttcaggg gctccaggag gacgartgtg tatcctccca ttgctctgtg c              51

<210> SEQ ID NO 186
<211> LENGTH: 56
<212> TYPE: DNA
<213> ORGANISM: Homo sapiens
<220> FEATURE:
<221> NAME/KEY: misc_feature
<222> LOCATION: (26)..(31)
<223> OTHER INFORMATION: this group of 6 a nucleotides may be missing

<400> SEQUENCE: 186
aggtattgag tcaaaaaaaa aaaaaaaaaa agccttcccc tgagcctggg ggcctg          56

<210> SEQ ID NO 187
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this nucleotide may be missing

<400> SEQUENCE: 187
gaagcagggc cctgactgcc cccccggcc ccctctcgg gctctctcac c                 51

<210> SEQ ID NO 188
<211> LENGTH: 51
<212> TYPE: DNA
<213> ORGANISM: Homo sapiens

<400> SEQUENCE: 188
caggtctggc ccatggaagg gagggraggg ggccccggcg gggccacagt a              51

<210> SEQ ID NO 189
<211> LENGTH: 51
<212> TYPE: DNA
<213> ORGANISM: Homo sapiens

<400> SEQUENCE: 189
cccatggccc ggagttgggg gtagtsacgg gtggccaaag gagaggctgt a              51

<210> SEQ ID NO 190
<211> LENGTH: 51
<212> TYPE: DNA
<213> ORGANISM: Homo sapiens

<400> SEQUENCE: 190
tctccaacag gctccctgtt ggaggmcttg gggtacccca gggcctttcc c          51

<210> SEQ ID NO 191
<211> LENGTH: 51
<212> TYPE: DNA
<213> ORGANISM: Homo sapiens

<400> SEQUENCE: 191
gagggccttg gtgacttctc caacargctc cctgttggag gccttggggt a          51

<210> SEQ ID NO 192
<211> LENGTH: 51
<212> TYPE: DNA
<213> ORGANISM: Homo sapiens

<400> SEQUENCE: 192
gtgaagtgat ctgacgttgg gtgggrgtct ccggacttgg ggtggggaat c          51

<210> SEQ ID NO 193
<211> LENGTH: 51
<212> TYPE: DNA
<213> ORGANISM: Homo sapiens

<400> SEQUENCE: 193
cgtgggcgac aagaaaggtg gggtcygggc cagcaggtgc tcagctctgg g          51

<210> SEQ ID NO 194
<211> LENGTH: 51
<212> TYPE: DNA
<213> ORGANISM: Homo sapiens

<400> SEQUENCE: 194
cctccactcc tttactgtgg ccccgycggg gccccctccc ctcccttcca t          51

<210> SEQ ID NO 195
<211> LENGTH: 52
<212> TYPE: DNA
<213> ORGANISM: Homo sapiens
<220> FEATURE:
<221> NAME/KEY: misc_feature
<222> LOCATION: (26)..(27)
<223> OTHER INFORMATION: this group of 2 a nucleotides may be missing

<400> SEQUENCE: 195
ttccttaaaa aaaaaaaaaa aaaaaaagcc agctgggcac ggtggctcat gc         52

<210> SEQ ID NO 196
<211> LENGTH: 53
<212> TYPE: DNA
<213> ORGANISM: Homo sapiens
<220> FEATURE:
<221> NAME/KEY: misc_feature
<222> LOCATION: (26)..(28)
<223> OTHER INFORMATION: this group of 3 t nucleotides may be missing

<400> SEQUENCE: 196
agcatgttta attttttttt tttttttga cacggggtct tgctctgttg ccc         53

<210> SEQ ID NO 197
<211> LENGTH: 52
<212> TYPE: DNA
<213> ORGANISM: Homo sapiens
<220> FEATURE:
<221> NAME/KEY: misc_feature

```
<222> LOCATION: (26)..(27)
<223> OTHER INFORMATION: one or both of these 2 a nucleotides may be
      missing

<400> SEQUENCE: 197
tgtctcaaaa aaaaaaaaaa aaaaaaagcc tgggactctt agcgcctcag ag          52

<210> SEQ ID NO 198
<211> LENGTH: 51
<212> TYPE: DNA
<213> ORGANISM: Homo sapiens

<400> SEQUENCE: 198
cagactagga gcacgagggg cacagscccc atgcctggct aggtagggcc g           51

<210> SEQ ID NO 199
<211> LENGTH: 51
<212> TYPE: DNA
<213> ORGANISM: Homo sapiens

<400> SEQUENCE: 199
ttacaggaga agctgttatc accccrtttc caggggctg gaaccctgg g             51

<210> SEQ ID NO 200
<211> LENGTH: 51
<212> TYPE: DNA
<213> ORGANISM: Homo sapiens

<400> SEQUENCE: 200
ctggggagaa gttgggaagt ctggcyagtg gggccggtgc ctggtgacct c           51

<210> SEQ ID NO 201
<211> LENGTH: 51
<212> TYPE: DNA
<213> ORGANISM: Homo sapiens

<400> SEQUENCE: 201
ccaggctttt tttttttttt tttttkgaga cagagtcttg ctctgtcgcc c           51

<210> SEQ ID NO 202
<211> LENGTH: 51
<212> TYPE: DNA
<213> ORGANISM: Homo sapiens

<400> SEQUENCE: 202
caccgccatt gccgccatcg tcgtgsggct tctggggcag ctagggctgc c           51

<210> SEQ ID NO 203
<211> LENGTH: 51
<212> TYPE: DNA
<213> ORGANISM: Homo sapiens

<400> SEQUENCE: 203
tctttcaaag cttcttggct gcatgygtca ggtgggcaag ctcagaagtt a           51

<210> SEQ ID NO 204
<211> LENGTH: 51
<212> TYPE: DNA
<213> ORGANISM: Homo sapiens

<400> SEQUENCE: 204
gagacaaatt agaaatgtca gtctgragag agtggtaggt agccagatac t           51
```

<210> SEQ ID NO 205
<211> LENGTH: 51
<212> TYPE: DNA
<213> ORGANISM: Homo sapiens

<400> SEQUENCE: 205
tgcaattcaa aatcaagggc tgcttygagg aggcctctcc accgggctgc t            51

<210> SEQ ID NO 206
<211> LENGTH: 51
<212> TYPE: DNA
<213> ORGANISM: Homo sapiens

<400> SEQUENCE: 206
aagggagggr aggggccccc grcggrgcca cagtaaagga gtggaggggc c            51

<210> SEQ ID NO 207
<211> LENGTH: 51
<212> TYPE: DNA
<213> ORGANISM: Homo sapiens

<400> SEQUENCE: 207
gtggttactt tctggagaga gcatgyggca tgcaggagct ggagggggggg t           51

<210> SEQ ID NO 208
<211> LENGTH: 51
<212> TYPE: DNA
<213> ORGANISM: Homo sapiens

<400> SEQUENCE: 208
gagagcccct atctttaaaa aaaaawaata ataataaaat aaaaaaataa a            51

<210> SEQ ID NO 209
<211> LENGTH: 51
<212> TYPE: DNA
<213> ORGANISM: Homo sapiens

<400> SEQUENCE: 209
gaaaagatcg tttgagcctg ggaggyggag gctgccatga gccatgatct t            51

<210> SEQ ID NO 210
<211> LENGTH: 51
<212> TYPE: DNA
<213> ORGANISM: Homo sapiens

<400> SEQUENCE: 210
accactggaa ggaccggtac ctgccrgaca cgcttctctt ggaggtgagc c            51

<210> SEQ ID NO 211
<211> LENGTH: 51
<212> TYPE: DNA
<213> ORGANISM: Homo sapiens

<400> SEQUENCE: 211
tggcccgcct gctgtcacca ggggcraggc tcatcaccat cgagatcaac c            51

<210> SEQ ID NO 212
<211> LENGTH: 51
<212> TYPE: DNA
<213> ORGANISM: Homo sapiens

<400> SEQUENCE: 212
tgtgaggcac tgaggatgcc ctcacrcgtg catctgcatg tggcgtgcat g            51

<210> SEQ ID NO 213
<211> LENGTH: 51
<212> TYPE: DNA
<213> ORGANISM: Homo sapiens

<400> SEQUENCE: 213
agcatgcgga gcccgggaac gcacaragcg tgctggaggc cattgacacc t        51

<210> SEQ ID NO 214
<211> LENGTH: 51
<212> TYPE: DNA
<213> ORGANISM: Homo sapiens

<400> SEQUENCE: 214
aacacagagc tgccctctct gaatcmccga accgcccacc ttggggccct g        51

<210> SEQ ID NO 215
<211> LENGTH: 51
<212> TYPE: DNA
<213> ORGANISM: Homo sapiens

<400> SEQUENCE: 215
tgggaaccac catccgatca accctyggat gcaacaaccg gagcacacag t        51

<210> SEQ ID NO 216
<211> LENGTH: 51
<212> TYPE: DNA
<213> ORGANISM: Homo sapiens

<400> SEQUENCE: 216
caggacacaa aaatccctgg ctggaraaat ccaaaaagca ggtctgttag c        51

<210> SEQ ID NO 217
<211> LENGTH: 51
<212> TYPE: DNA
<213> ORGANISM: Homo sapiens

<400> SEQUENCE: 217
aataaaaagc aacaggacac aaaaayccct ggctggaaaa atccaaaaag c        51

<210> SEQ ID NO 218
<211> LENGTH: 51
<212> TYPE: DNA
<213> ORGANISM: Homo sapiens

<400> SEQUENCE: 218
ctcctacggt ccctcaggct tgagrgtca ctttaaacaa taaaaagcaa c         51

<210> SEQ ID NO 219
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this nucleotide may be missing

<400> SEQUENCE: 219
aaagctgctg ctgcttcatt ttatttattt atttatttat ttatttattt a        51

<210> SEQ ID NO 220
<211> LENGTH: 51
<212> TYPE: DNA
<213> ORGANISM: Homo sapiens

```
<220> FEATURE:
<221> NAME/KEY: misc_feature
<222> LOCATION: (26)..(26)
<223> OTHER INFORMATION: this nucleotide may be missing

<400> SEQUENCE: 220
gagcccgaga ggggggccgg gggggcagt cagggccctg cttcgctgcc t              51

<210> SEQ ID NO 221
<211> LENGTH: 52
<212> TYPE: DNA
<213> ORGANISM: Homo sapiens
<220> FEATURE:
<221> NAME/KEY: misc_feature
<222> LOCATION: (26)..(27)
<223> OTHER INFORMATION: one or both of these t nucleotides may be
      missing

<400> SEQUENCE: 221 tcttttctt ttttttttt tttttttaag ggggaactca ttcctcttcc tt              52

<210> SEQ ID NO 222
<211> LENGTH: 52
<212> TYPE: DNA
<213> ORGANISM: Homo sapiens
<220> FEATURE:
<221> NAME/KEY: misc_feature
<222> LOCATION: (26)..(27)
<223> OTHER INFORMATION: these 2 a nucleotides may be missing

<400> SEQUENCE: 222
gaccccgtct caaaaaaaaa aaaaaaatta aacatgctat gcacccacaa at            52

<210> SEQ ID NO 223
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this nucleotide may be missing

<400> SEQUENCE: 223
tcaggggaag gctttttttt tttttgact caatacctaa tagctaaagg g              51

<210> SEQ ID NO 224
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this nucleotide may be missing

<400> SEQUENCE: 224
gctggctttt tttttttttt tttttaagg aaataacaa gtgttagcaa g               51

<210> SEQ ID NO 225
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this nucleotide may be missing

<400> SEQUENCE: 225
ccagcttttt tttttttttt tttttggta gagatggagt ggaggtgggg t              51
```

<210> SEQ ID NO 226
<211> LENGTH: 51
<212> TYPE: DNA
<213> ORGANISM: Homo sapiens

<400> SEQUENCE: 226
ctcctctgac actgtcgctt ctccayggca ttagattttc agtcctgctc a      51

<210> SEQ ID NO 227
<211> LENGTH: 51
<212> TYPE: DNA
<213> ORGANISM: Homo sapiens

<400> SEQUENCE: 227
ttctcgagac agtctctcgc tctgtygccc aggctggagt gcagtggcgc g      51

<210> SEQ ID NO 228
<211> LENGTH: 51
<212> TYPE: DNA
<213> ORGANISM: Homo sapiens

<400> SEQUENCE: 228
gggttctgtg agcatcggag gcacgrgggg tgaggggctc aggagcaggt t      51

<210> SEQ ID NO 229
<211> LENGTH: 51
<212> TYPE: DNA
<213> ORGANISM: Homo sapiens

<400> SEQUENCE: 229
ctgcgtccgg ccgtattcca gctttyaaaa caacaaaaaa caacaaaaac t      51

<210> SEQ ID NO 230
<211> LENGTH: 51
<212> TYPE: DNA
<213> ORGANISM: Homo sapiens

<400> SEQUENCE: 230
gggacaggcg ggcactgggt gcctcyttgc accagccagg cccagcctgc a      51

<210> SEQ ID NO 231
<211> LENGTH: 119
<212> TYPE: DNA
<213> ORGANISM: Homo sapiens
<220> FEATURE:
<221> NAME/KEY: misc_feature
<222> LOCATION: (26)..(92)
<223> OTHER INFORMATION: n can be a, c, g, or t
<220> FEATURE:
<221> NAME/KEY: misc_feature
<222> LOCATION: (93)..(94)
<223> OTHER INFORMATION: one of both of these nucleotides can be
      missing, with the proviso that both are not present together

<400> SEQUENCE: 231
gcctttggcc ttgagcactt ccccannnnn nnnnnnnnnn nnnnnnnnnn nnnnnnnnnn      60
nnnnnnnnnn nnnnnnnnnn nnnnnnnnnn nngtccccca tggctcttgg ccattggac     119

<210> SEQ ID NO 232
<211> LENGTH: 51
<212> TYPE: DNA
<213> ORGANISM: Homo sapiens

<400> SEQUENCE: 232

```
cttggccatt ggaccccagt tggccrcaga gcctttggcc ttgagcactt c          51
```

<210> SEQ ID NO 233
<211> LENGTH: 51
<212> TYPE: DNA
<213> ORGANISM: Homo sapiens

<400> SEQUENCE: 233

```
aacacaaaaa agttagccgg gcgtgstggc gggcgcctgt agtcccagct a          51
```

<210> SEQ ID NO 234
<211> LENGTH: 51
<212> TYPE: DNA
<213> ORGANISM: Homo sapiens

<400> SEQUENCE: 234

```
ggagtttaag accagcctgg gcaacrtagc aagacgctgt ctctacaaaa a          51
```

<210> SEQ ID NO 235
<211> LENGTH: 51
<212> TYPE: DNA
<213> ORGANISM: Homo sapiens

<400> SEQUENCE: 235

```
ctgggagaca ggggcccccat cttcargtgt tggccagaac acaggaaatt c          51
```

<210> SEQ ID NO 236
<211> LENGTH: 51
<212> TYPE: DNA
<213> ORGANISM: Homo sapiens

<400> SEQUENCE: 236

```
aagggagggt tagccttggg aaaccratct gggtttgcca cggggctta c          51
```

<210> SEQ ID NO 237
<211> LENGTH: 51
<212> TYPE: DNA
<213> ORGANISM: Homo sapiens

<400> SEQUENCE: 237

```
ctgggcgaca gagcaagact ctgtcycaaa aaaaaaaaaa aaaaaagcct g          51
```

<210> SEQ ID NO 238
<211> LENGTH: 51
<212> TYPE: DNA
<213> ORGANISM: Homo sapiens

<400> SEQUENCE: 238

```
acggagcttg caatgagccg agattrtgcc actgcactcc agcctgggcg a          51
```

<210> SEQ ID NO 239
<211> LENGTH: 51
<212> TYPE: DNA
<213> ORGANISM: Homo sapiens

<400> SEQUENCE: 239

```
atcctggcta acacggtgaa accccwtctc tactaaaaat acaaaaaatt a          51
```

<210> SEQ ID NO 240
<211> LENGTH: 51
<212> TYPE: DNA
<213> ORGANISM: Homo sapiens

<400> SEQUENCE: 240
ggctggccaa catggcaaaa ccccayctgt actaaaaata caaaaattag c        51

<210> SEQ ID NO 241
<211> LENGTH: 51
<212> TYPE: DNA
<213> ORGANISM: Homo sapiens

<400> SEQUENCE: 241
aggccctgtc tctacaaaac aaaaarttga aaaattagct gggcatggtg g        51

<210> SEQ ID NO 242
<211> LENGTH: 51
<212> TYPE: DNA
<213> ORGANISM: Homo sapiens

<400> SEQUENCE: 242
actttgggag tccgaggagg gaggaytcct tgagcccagg agtttgagac c        51

<210> SEQ ID NO 243
<211> LENGTH: 51
<212> TYPE: DNA
<213> ORGANISM: Homo sapiens

<400> SEQUENCE: 243
gattattata atattggaat aaagaktaat tgctacaaac taatgattaa c        51

<210> SEQ ID NO 244
<211> LENGTH: 51
<212> TYPE: DNA
<213> ORGANISM: Homo sapiens

<400> SEQUENCE: 244
ttaggcctcc ggataactgt gggcaracct gacactccac aagaggtggt t        51

<210> SEQ ID NO 245
<211> LENGTH: 51
<212> TYPE: DNA
<213> ORGANISM: Homo sapiens

<400> SEQUENCE: 245 aggggggcagg gtaaggagtg tgagcyatct ccagtgacag gtaaggtcac a        51

<210> SEQ ID NO 246
<211> LENGTH: 51
<212> TYPE: DNA
<213> ORGANISM: Homo sapiens

<400> SEQUENCE: 246
tgcagagatg agagatcgta gaaatraaga cacaagacaa agagatagaa g        51

<210> SEQ ID NO 247
<211> LENGTH: 51
<212> TYPE: DNA
<213> ORGANISM: Homo sapiens

<400> SEQUENCE: 247
gtatttttag tagagatggg gtttcrccac actggccagg ctggtcttga a        51

<210> SEQ ID NO 248
<211> LENGTH: 51
<212> TYPE: DNA
<213> ORGANISM: Homo sapiens

<400> SEQUENCE: 248
tttttttttt ttgagacaga gtcccrctgt gttgctcagg ctggagtgca g          51

<210> SEQ ID NO 249
<211> LENGTH: 51
<212> TYPE: DNA
<213> ORGANISM: Homo sapiens

<400> SEQUENCE: 249
agcattaaaa aaattttttt tttagkttt tttttttttt tttttttga g            51

<210> SEQ ID NO 250
<211> LENGTH: 51
<212> TYPE: DNA
<213> ORGANISM: Homo sapiens

<400> SEQUENCE: 250
gaaatgctgt cagaagccta ccccayggta cctgtcatgg gccttttcat t          51

<210> SEQ ID NO 251
<211> LENGTH: 51
<212> TYPE: DNA
<213> ORGANISM: Homo sapiens

<400> SEQUENCE: 251
gactccatct caaaaaaaga aataargaaa tgctgtcaga agcctacccc a          51

<210> SEQ ID NO 252
<211> LENGTH: 51
<212> TYPE: DNA
<213> ORGANISM: Homo sapiens

<400> SEQUENCE: 252
taatcccaac actttgggag gccaasgtgg ctatatcact tgaagtcagg a          51

<210> SEQ ID NO 253
<211> LENGTH: 51
<212> TYPE: DNA
<213> ORGANISM: Homo sapiens

<400> SEQUENCE: 253
ttttgtagtt tagtagagat ggggtytcac cacattggcc aggatggtct c          51

<210> SEQ ID NO 254
<211> LENGTH: 51
<212> TYPE: DNA
<213> ORGANISM: Homo sapiens

<400> SEQUENCE: 254
gctcattttt tgcattttta gtggaracag agtttcacca tgttggccag g          51

<210> SEQ ID NO 255
<211> LENGTH: 51
<212> TYPE: DNA
<213> ORGANISM: Homo sapiens

<400> SEQUENCE: 255
aaactggaca ctgctgttag cagccrgact aggagcacga ggggcacagc c          51

<210> SEQ ID NO 256
<211> LENGTH: 51
<212> TYPE: DNA

<213> ORGANISM: Homo sapiens

<400> SEQUENCE: 256
gtgatctcgg ctcactgcaa gctccrcctc tggggttcac gccattctcc t    51

<210> SEQ ID NO 257
<211> LENGTH: 51
<212> TYPE: DNA
<213> ORGANISM: Homo sapiens

<400> SEQUENCE: 257
ttgggacacc caccctcacg gcctcyccac ctggtgctcg ctcacctgca g    51

<210> SEQ ID NO 258
<211> LENGTH: 51
<212> TYPE: DNA
<213> ORGANISM: Homo sapiens

<400> SEQUENCE: 258
agtgaggatg cagtgctggt ttctgyccac ctacacctag agctgtcccc a    51

<210> SEQ ID NO 259
<211> LENGTH: 51
<212> TYPE: DNA
<213> ORGANISM: Homo sapiens

<400> SEQUENCE: 259
cttccctgtt ctcttctgct ctgtcytctg gtgccctgag gctggcctcc a    51

<210> SEQ ID NO 260
<211> LENGTH: 51
<212> TYPE: DNA
<213> ORGANISM: Homo sapiens

<400> SEQUENCE: 260
cagtgccagg gtgggtacag attccsgccc ggtgcatggg cacaggtctg c    51

<210> SEQ ID NO 261
<211> LENGTH: 51
<212> TYPE: DNA
<213> ORGANISM: Homo sapiens

<400> SEQUENCE: 261
accggtacct gccggacacg cttctyttgg aggtgagccc caaccaggat g    51

<210> SEQ ID NO 262
<211> LENGTH: 51
<212> TYPE: DNA
<213> ORGANISM: Homo sapiens

<400> SEQUENCE: 262
ctctgaactg caaacactgga ttgttytttt ttaagactca atcatgactt c    51

<210> SEQ ID NO 263
<211> LENGTH: 51
<212> TYPE: DNA
<213> ORGANISM: Homo sapiens

<400> SEQUENCE: 263
cccggccccc ctctcgggct ctctcwccca gcctggtact gaaggtgcca g    51

<210> SEQ ID NO 264
<211> LENGTH: 51

```
<212> TYPE: DNA
<213> ORGANISM: Homo sapiens

<400> SEQUENCE: 264
ctgaggcact ggggctggrg cctgtscctt atcggctgga acgagttcat c          51

<210> SEQ ID NO 265
<211> LENGTH: 51
<212> TYPE: DNA
<213> ORGANISM: Homo sapiens

<400> SEQUENCE: 265
gcaccagagg gcacgagaag gctggytccc tggcgctgac acgtcaggca a          51

<210> SEQ ID NO 266
<211> LENGTH: 51
<212> TYPE: DNA
<213> ORGANISM: Homo sapiens

<400> SEQUENCE: 266
gctgcagcat gcggagcccg ggaackcaca gagcgtgctg gaggccattg a          51

<210> SEQ ID NO 267
<211> LENGTH: 136
<212> TYPE: DNA
<213> ORGANISM: Homo sapiens

<400> SEQUENCE: 267
caagttgttg tgtaggatat tggcaatttt tgcttgtcag ctccatggta cttcttccga    60
atcaraaatt tatctcctca gtggccctca aagcactttc ttcccactat aggcttgttc   120
agtttagagt agacag                                                   136

<210> SEQ ID NO 268
<211> LENGTH: 51
<212> TYPE: DNA
<213> ORGANISM: Homo sapiens

<400> SEQUENCE: 268
actctctaag gtcatgtgaa cagtawgcag tgctactcga actcctctgc t           51

<210> SEQ ID NO 269
<211> LENGTH: 51
<212> TYPE: DNA
<213> ORGANISM: Homo sapiens

<400> SEQUENCE: 269
gaaaactatg tgaatataat agatcyttaa ttcatatttg tggattttat g           51

<210> SEQ ID NO 270
<211> LENGTH: 51
<212> TYPE: DNA
<213> ORGANISM: Homo sapiens

<400> SEQUENCE: 270
ttatgtaaac ttcgcttaca aactayactt gtgtgacact tatatgagca a           51

<210> SEQ ID NO 271
<211> LENGTH: 51
<212> TYPE: DNA
<213> ORGANISM: Homo sapiens

<400> SEQUENCE: 271
```

```
ccagatggtg gcaatttcac atggcrcaac ccgaaagatt aacaaactat c         51

<210> SEQ ID NO 272
<211> LENGTH: 51
<212> TYPE: DNA
<213> ORGANISM: Homo sapiens

<400> SEQUENCE: 272
cagcgccttc ttgctggcac ccaatrgaag ccatgcgccg gaccacgacg t         51

<210> SEQ ID NO 273
<211> LENGTH: 51
<212> TYPE: DNA
<213> ORGANISM: Homo sapiens

<400> SEQUENCE: 273
tgcgccggac cacgacgtca cgcagsaaag ggacgaggtg tgggtggtgg g         51

<210> SEQ ID NO 274
<211> LENGTH: 51
<212> TYPE: DNA
<213> ORGANISM: Homo sapiens

<400> SEQUENCE: 274
cctgtgctga tctggtcatg ggcctrgcag tggtgccctt tggggccgcc c         51

<210> SEQ ID NO 275
<211> LENGTH: 51
<212> TYPE: DNA
<213> ORGANISM: Homo sapiens

<400> SEQUENCE: 275
caaagacacc actaatacat gggaawtcaa accctgaaaa ttaatttcac t         51

<210> SEQ ID NO 276
<211> LENGTH: 51
<212> TYPE: DNA
<213> ORGANISM: Homo sapiens

<400> SEQUENCE: 276
tcccgagtag ctgggactac aggtaygtgc caccacacct ggctaatttt t         51

<210> SEQ ID NO 277
<211> LENGTH: 51
<212> TYPE: DNA
<213> ORGANISM: Homo sapiens

<400> SEQUENCE: 277
ttctatagct tcaaaatgtt cttaawgtta agacattctt aatactctga a         51

<210> SEQ ID NO 278
<211> LENGTH: 51
<212> TYPE: DNA
<213> ORGANISM: Homo sapiens

<400> SEQUENCE: 278
tgacagcgag tgtgctgagg aaatcrgcag ctgttgaagt cacctcctgt g         51

<210> SEQ ID NO 279
<211> LENGTH: 51
<212> TYPE: DNA
<213> ORGANISM: Homo sapiens

<400> SEQUENCE: 279
```
cctccaagcc agcgtgtgtt tacttkctgt gtgtgtcacc atgtctttgt g    51

<210> SEQ ID NO 280
<211> LENGTH: 51
<212> TYPE: DNA
<213> ORGANISM: Homo sapiens

<400> SEQUENCE: 280
tatggctgtg gttcggtata agtctragca tgtctgccag ggtgtatttg t    51

<210> SEQ ID NO 281
<211> LENGTH: 51
<212> TYPE: DNA
<213> ORGANISM: Homo sapiens

<400> SEQUENCE: 281
aaaagctccc gggttggctg gtaagsacac cacctccagc tttagccctc t    51

<210> SEQ ID NO 282
<211> LENGTH: 51
<212> TYPE: DNA
<213> ORGANISM: Homo sapiens

<400> SEQUENCE: 282
cagttgggcc ccgcccgggc cagccycagg agaaggaggg cgaggggagg g    51

<210> SEQ ID NO 283
<211> LENGTH: 51
<212> TYPE: DNA
<213> ORGANISM: Homo sapiens

<400> SEQUENCE: 283
cgcagagccc cgccgtgggt ccgccygctg aggcgccccc agccagtgcg c    51

<210> SEQ ID NO 284
<211> LENGTH: 51
<212> TYPE: DNA
<213> ORGANISM: Homo sapiens

<400> SEQUENCE: 284
ctgaggcgcc cccagccagt gcgctyacct gccagactgc gcgccatggg g    51

<210> SEQ ID NO 285
<211> LENGTH: 51
<212> TYPE: DNA
<213> ORGANISM: Homo sapiens

<400> SEQUENCE: 285
atggtgtgga ttgtgtcagg ccttayctcc ttcttgccca ttcagatgca c    51

<210> SEQ ID NO 286
<211> LENGTH: 51
<212> TYPE: DNA
<213> ORGANISM: Homo sapiens

<400> SEQUENCE: 286
cttgcccatt cagatgcact ggtacmgggc cacccaccag gaagccatca a    51

<210> SEQ ID NO 287
<211> LENGTH: 51
<212> TYPE: DNA
<213> ORGANISM: Homo sapiens

<400> SEQUENCE: 287
ctggtgatca tggtcttcgt ctactscagg gtctttcagg aggccaaaag g       51

<210> SEQ ID NO 288
<211> LENGTH: 51
<212> TYPE: DNA
<213> ORGANISM: Homo sapiens

<400> SEQUENCE: 288
gcaggtcttc tttgaaggcc tatggsaatg gctactccag caacggcaac a       51

<210> SEQ ID NO 289
<211> LENGTH: 51
<212> TYPE: DNA
<213> ORGANISM: Homo sapiens

<400> SEQUENCE: 289
caggcacgga agactttgtg ggccaycaag gtactgtgcc tagcgataac a       51

<210> SEQ ID NO 290
<211> LENGTH: 51
<212> TYPE: DNA
<213> ORGANISM: Homo sapiens

<400> SEQUENCE: 290
aagactttgt gggccatcaa ggtacygtgc ctagcgataa cattgattca c       51

<210> SEQ ID NO 291
<211> LENGTH: 51
<212> TYPE: DNA
<213> ORGANISM: Homo sapiens

<400> SEQUENCE: 291
attgtagtac aaatgactca ctgctdtaaa gcagttttc tacttttaaa g        51

<210> SEQ ID NO 292
<211> LENGTH: 51
<212> TYPE: DNA
<213> ORGANISM: Homo sapiens

<400> SEQUENCE: 292
tttttctact tttaaagacc cccccsccca acagaacact aaacagacta t       51

<210> SEQ ID NO 293
<211> LENGTH: 52
<212> TYPE: DNA
<213> ORGANISM: Homo sapiens
<220> FEATURE:
<221> NAME/KEY: misc_feature
<222> LOCATION: (26)..(26)
<223> OTHER INFORMATION: r is a or g or absent
<220> FEATURE:
<221> NAME/KEY: misc_feature
<222> LOCATION: (27)..(27)
<223> OTHER INFORMATION: this nucleotide may be missing

<400> SEQUENCE: 293
tttctacttt taaagacccc cccccrccca acagaacact aaacagacta tt      52

<210> SEQ ID NO 294
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this nucleotide may be missing

<400> SEQUENCE: 294
ggtaataaac ttagaataaa attgtaaaaa ttgtatagag atatgcagaa g    51

<210> SEQ ID NO 295
<211> LENGTH: 51
<212> TYPE: DNA
<213> ORGANISM: Homo sapiens

<400> SEQUENCE: 295
tattttttta agctgtaaaa agagaraaaa cttatttgag tgattatttg t    51

<210> SEQ ID NO 296
<211> LENGTH: 51
<212> TYPE: DNA
<213> ORGANISM: Homo sapiens

<400> SEQUENCE: 296
tatctgaagg agattttcct tcctamaccc ttggacttga ggattttgag t    51

<210> SEQ ID NO 297
<211> LENGTH: 51
<212> TYPE: DNA
<213> ORGANISM: Homo sapiens

<400> SEQUENCE: 297
ctgaaggaga ttttccttcc tacacycttg gacttgagga ttttgagtat c    51

<210> SEQ ID NO 298
<211> LENGTH: 51
<212> TYPE: DNA
<213> ORGANISM: Homo sapiens

<400> SEQUENCE: 298
ccccactcct cttatttgct cacacrgggt attttaggca gggatttgag g    51

<210> SEQ ID NO 299
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this nucleotide may be missing

<400> SEQUENCE: 299
agcttcagtt gttttcccga gcaaaggtct aaagtttaca gtaaataaaa t    51

<210> SEQ ID NO 300
<211> LENGTH: 51
<212> TYPE: DNA
<213> ORGANISM: Homo sapiens

<400> SEQUENCE: 300
aagtctaaag tttacagtaa ataaawtgtt tgaccatgcc ttcattgcac c    51

<210> SEQ ID NO 301
<211> LENGTH: 51
<212> TYPE: DNA
<213> ORGANISM: Homo sapiens

<400> SEQUENCE: 301
aggtctaaag tttacagtaa ataaawtgtt tgaccatgaa aaaaaaaaaa a          51

<210> SEQ ID NO 302
<211> LENGTH: 51
<212> TYPE: DNA
<213> ORGANISM: Homo sapiens

<400> SEQUENCE: 302
cctgctggtc atcgtggcca tcgccyggac tccgagactc cagaccatga c          51

<210> SEQ ID NO 303
<211> LENGTH: 51
<212> TYPE: DNA
<213> ORGANISM: Homo sapiens

<400> SEQUENCE: 303
acggctcgac gggtaggtaa ccgggkcaga gggaccggcg gctcagggtc g          51

<210> SEQ ID NO 304
<211> LENGTH: 51
<212> TYPE: DNA
<213> ORGANISM: Homo sapiens

<400> SEQUENCE: 304
gtgccctggc gttttgtgt aactaratat gcgttccagg gtctctgatc t          51

<210> SEQ ID NO 305
<211> LENGTH: 51
<212> TYPE: DNA
<213> ORGANISM: Homo sapiens

<400> SEQUENCE: 305
ctcctccctc agtggtagtg tccagstgcc gtggagcagc aggctggctt t          51

<210> SEQ ID NO 306
<211> LENGTH: 51
<212> TYPE: DNA
<213> ORGANISM: Homo sapiens

<400> SEQUENCE: 306
ccaagaaatc ttgcacacct cagacrccag agatctcacc ctgccctggt t          51

<210> SEQ ID NO 307
<211> LENGTH: 51
<212> TYPE: DNA
<213> ORGANISM: Homo sapiens

<400> SEQUENCE: 307
ctcagtgcat tcagaggccc acagaygctg cctgcttcca agggcacaga a          51

<210> SEQ ID NO 308
<211> LENGTH: 51
<212> TYPE: DNA
<213> ORGANISM: Homo sapiens

<400> SEQUENCE: 308
gagagctccc ctggttccat tccttytgcc acccaaaccc tgatgagacc t          51

<210> SEQ ID NO 309
<211> LENGTH: 51
<212> TYPE: DNA
<213> ORGANISM: Homo sapiens

<400> SEQUENCE: 309
gagacgaggc tggttctttt tccttsggga taattttagg ttctgaattc c       51

<210> SEQ ID NO 310
<211> LENGTH: 51
<212> TYPE: DNA
<213> ORGANISM: Homo sapiens

<400> SEQUENCE: 310
ctttaagcgt cgctactcct ccccragag cggtggcacc gagggagttg g       51

<210> SEQ ID NO 311
<211> LENGTH: 51
<212> TYPE: DNA
<213> ORGANISM: Homo sapiens

<400> SEQUENCE: 311
taagaggata atacagattt ttgtasctgg ggaaggtgag tgggaaggta g       51

<210> SEQ ID NO 312
<211> LENGTH: 52
<212> TYPE: DNA
<213> ORGANISM: Homo sapiens
<220> FEATURE:
<221> NAME/KEY: misc_feature
<222> LOCATION: (26)..(27)
<223> OTHER INFORMATION: this ca dinucleotide may be missing

<400> SEQUENCE: 312
acacacacgc acacacacac acacacacca tgtaaggcac cactggatta ta       52

<210> SEQ ID NO 313
<211> LENGTH: 51
<212> TYPE: DNA
<213> ORGANISM: Homo sapiens

<400> SEQUENCE: 313
ttcatcctcg gcccccttc cctccrtttg ttttcttttc ataatccact t       51

<210> SEQ ID NO 314
<211> LENGTH: 51
<212> TYPE: DNA
<213> ORGANISM: Homo sapiens

<400> SEQUENCE: 314
tttcacccca gggtctatta tctccrcttt ttttcccagg gcttcttggg g       51

<210> SEQ ID NO 315
<211> LENGTH: 51
<212> TYPE: DNA
<213> ORGANISM: Homo sapiens

<400> SEQUENCE: 315
gtgcagatgt gtgccctccc gctccmtggg ctgggttgga gtagggatgg g       51

<210> SEQ ID NO 316
<211> LENGTH: 52
<212> TYPE: DNA
<213> ORGANISM: Homo sapiens
<220> FEATURE:
<221> NAME/KEY: misc_feature
<222> LOCATION: (26)..(27)
<223> OTHER INFORMATION: this gg dinucleotide may be missing
<220> FEATURE:
<221> NAME/KEY: misc_feature
<222> LOCATION: (28)..(28)

<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 316
gacctggctc ggacttgaag ggcagggnct agtgcccccc cnacccgccc cc      52

<210> SEQ ID NO 317
<211> LENGTH: 51
<212> TYPE: DNA
<213> ORGANISM: Homo sapiens

<400> SEQUENCE: 317
tgtcgcccac gcgggaatgc agtggygcga tctcagctca ctgcagtctt g       51

<210> SEQ ID NO 318
<211> LENGTH: 50
<212> TYPE: DNA
<213> ORGANISM: Homo sapiens
<220> FEATURE:
<221> NAME/KEY: misc_feature
<222> LOCATION: (26)..(26)
<223> OTHER INFORMATION: this nucleotide may be missing

<400> SEQUENCE: 318
cagagacgaa accctgtctc tatttaaaaa aaaaaaaaat ccctaaagcc         50

<210> SEQ ID NO 319
<211> LENGTH: 51
<212> TYPE: DNA
<213> ORGANISM: Homo sapiens

<400> SEQUENCE: 319
gggacaccgc agcgctttcc ggtggmgcac cttgggtcct tgggtgagga a       51

<210> SEQ ID NO 320
<211> LENGTH: 51
<212> TYPE: DNA
<213> ORGANISM: Homo sapiens

<400> SEQUENCE: 320
ctccggagcc ctgcgccgcc gcccgyccgg ccctcttccc ctcgggcgtt c       51

<210> SEQ ID NO 321
<211> LENGTH: 51
<212> TYPE: DNA
<213> ORGANISM: Homo sapiens

<400> SEQUENCE: 321
ccggccccgg tggggacgtg cgctcygccc gaaggggtgc ccgcctgcgg c       51

<210> SEQ ID NO 322
<211> LENGTH: 51
<212> TYPE: DNA
<213> ORGANISM: Homo sapiens

<400> SEQUENCE: 322
tctctggccc cggccccggt ggggaygtgc gctccgcccg aaggggtgcc c       51

<210> SEQ ID NO 323
<211> LENGTH: 51
<212> TYPE: DNA
<213> ORGANISM: Homo sapiens

```
<400> SEQUENCE: 323
cgccggcgcc gtcgcgctct ctggcyccgg ccccggtggg gacgtgcgct c             51

<210> SEQ ID NO 324
<211> LENGTH: 51
<212> TYPE: DNA
<213> ORGANISM: Homo sapiens

<400> SEQUENCE: 324
gccagagagc gcgacggcgc cggcgkagac tcctcgggcg gaaagcggcc c             51

<210> SEQ ID NO 325
<211> LENGTH: 51
<212> TYPE: DNA
<213> ORGANISM: Homo sapiens

<400> SEQUENCE: 325
cctcgggcgg aaagcggccc agctcyccgc gcagcaagcg cagctggcgc g             51

<210> SEQ ID NO 326
<211> LENGTH: 51
<212> TYPE: DNA
<213> ORGANISM: Homo sapiens

<400> SEQUENCE: 326
cgcagccgac ctggtgatgg gactcytggt ggtgccgccg gcggccacct t             51

<210> SEQ ID NO 327
<211> LENGTH: 51
<212> TYPE: DNA
<213> ORGANISM: Homo sapiens

<400> SEQUENCE: 327
agctgcccct ttaagcgtcg ctactyctcc cccaagagcg gtggcaccga g             51

<210> SEQ ID NO 328
<211> LENGTH: 51
<212> TYPE: DNA
<213> ORGANISM: Homo sapiens

<400> SEQUENCE: 328
gtcttttcct ttttcttttt cttttycttt tcttttttt ttttttttg a               51

<210> SEQ ID NO 329
<211> LENGTH: 54
<212> TYPE: DNA
<213> ORGANISM: Homo sapiens
<220> FEATURE:
<221> NAME/KEY: misc_feature
<222> LOCATION: (26)..(29)
<223> OTHER INFORMATION: this tetranucleotide (cttt) may be missing
<220> FEATURE:
<221> NAME/KEY: misc_feature
<222> LOCATION: (27)..(29)
<223> OTHER INFORMATION: 2 of these t nucleotides may be missing

<400> SEQUENCE: 329
ttcttttcct ttttcttttt cttttctttt tttttttttt tttttgaga cggc           54

<210> SEQ ID NO 330
<211> LENGTH: 51
<212> TYPE: DNA
<213> ORGANISM: Homo sapiens
```

```
<400> SEQUENCE: 330 ggctaattttt tttttttttt ttttgkattt ttagtagaga cagggtttct c        51
```